United States Patent
Rabizadeh et al.

(10) Patent No.: US 10,487,078 B2
(45) Date of Patent: Nov. 26, 2019

(54) COMPOSITIONS AND METHODS OF TARGETING MUTANT K-RAS

(71) Applicants: NantBio, Inc., Culver City, CA (US); NantOmics, LLC, Culver City, CA (US); Nant Holdings IP, LLC, Culver City, CA (US)

(72) Inventors: Shahrooz Rabizadeh, Agoura Hills, CA (US); Kayvan Niazi, Encino, CA (US); Oleksandr V. Buzko, Oak Park, CA (US); Paul Weingarten, Anaheim, CA (US); Heather McFarlane, Los Angeles, CA (US); Anna Juncker-Jensen, Irvine, CA (US); Justin Golovato, Los Angeles, CA (US); Patrick Soon-Shiong, Culver City, CA (US); Chunlin Tao, Newport Coast, CA (US); David Ho, Los Angeles, CA (US)

(73) Assignees: NantBio, Inc., Culver City, CA (US); NantOmics, LLC, Culver City, CA (US); Nant Holdings IP, LLC, Culver City, CA (US)

( * ) Notice: Subject to any disclaimer, the term of this patent is extended or adjusted under 35 U.S.C. 154(b) by 0 days.

(21) Appl. No.: 15/563,813

(22) PCT Filed: Apr. 1, 2016

(86) PCT No.: PCT/US2016/025697
§ 371 (c)(1),
(2) Date: Oct. 2, 2017

(87) PCT Pub. No.: WO2016/161361
PCT Pub. Date: Oct. 6, 2016

(65) Prior Publication Data
US 2018/0086752 A1 Mar. 29, 2018

Related U.S. Application Data

(60) Provisional application No. 62/142,974, filed on Apr. 3, 2015.

(51) Int. Cl.
C07D 417/12 (2006.01)
C07D 417/14 (2006.01)
(Continued)

(52) U.S. Cl.
CPC .......... C07D 417/14 (2013.01); A61K 31/427 (2013.01); A61P 35/00 (2018.01);
(Continued)

(58) Field of Classification Search
CPC .......................... C07D 417/12; C07D 417/14
See application file for complete search history.

(56) References Cited

U.S. PATENT DOCUMENTS

2018/0201610 A1 7/2018 Tao

FOREIGN PATENT DOCUMENTS

CN 103784450 A 5/2014
WO WO/2009/121535 A2 10/2009
(Continued)

OTHER PUBLICATIONS

PCT Notification of Transmittal of the International Search Report and Written Opinion, PCT International Search Report and PCT Written Opinion issued for the corresponding PCT application No. PCT/US16/25697, dated Sep. 6, 2016 (17 pages).
(Continued)

Primary Examiner — Brian E McDowell
(74) Attorney, Agent, or Firm — Lucas & Mercanti, LLP

(57) ABSTRACT

Compounds and compositions are presented that inhibit K-ras, and especially mutant K-ras. Certain compounds
(Continued)

preferentially or even selectively inhibit specific forms of mutant K-Ras, and particularly the G12D mutant form.

7 Claims, 76 Drawing Sheets

(51) Int. Cl.
  *A61K 31/427* (2006.01)
  *C07D 417/04* (2006.01)
  *C07D 277/46* (2006.01)
  *C07D 471/06* (2006.01)
  *C07F 9/6558* (2006.01)
  *A61P 35/00* (2006.01)

(52) U.S. Cl.
  CPC ......... *C07D 277/46* (2013.01); *C07D 417/04* (2013.01); *C07D 417/12* (2013.01); *C07D 471/06* (2013.01); *C07F 9/65583* (2013.01)

(56) References Cited

FOREIGN PATENT DOCUMENTS

| WO | WO 2012/161879 A1 | 11/2012 |
| WO | WO/2013/155233 A1 | 10/2013 |
| WO | WO 2014/063167 A1 | 4/2014 |

OTHER PUBLICATIONS

Grant BJ, Lukman S, Hocker HJ, Sayyah J, Brown JH, McCammon JA, et al. (2011) Novel Allosteric Sites on Ras for Lead Generation. PLoS One 6(10): e25711. https://doi.org/10.1371/journal.pone.0025711.

European Patent Office, Extended European Search Report, Issued in connection with EP Application No. 16774366.5-1116/Patent No. 3277678. EPO Reference P116924EP00, dated Jul. 12, 2018, pp. 1-9.

Substance Record for SID 145041270, PubChem, Source AKos Consulting & Solutions, External ID AKOS008730007, dated Oct. 18, 2017.

Substance Record for SID 133265758, PubChem, Source AKos Consulting & Solutions, External ID AKOS006983131, dated Jan. 25, 2012.

Substance Record for SID 29748996, PubChem, Source ChemSpider, External ID 16950112, dated Dec. 4, 2007.

Chemical Abstract Compound, STN Express. RN 1090021-13-8, dated Dec. 25, 2008.

Chemical Abstract Compounds, STN Express. RN 1356747-40-4, dated Feb. 14, 2012; and RN 1301208-15-0, dated May 26, 2011.

Chemical Abstract Compounds, STN Express. RN 1374548-73-8, dated May 25, 2012; RN 1317826-78-0, dated Aug. 15, 2011; RN 1316792-31-0 and RN 1316539-20-4, dated Aug. 12, 2011; and RN 1296040-37-3, dated May 17, 2011.

Chemical Abstract Compound, STN Express. RN 1288357-24-3, dated May 1, 2011.

Chemical Abstract Compounds, STN Express. RN 1625469-37-5, dated Sep. 24, 2014; RN 1387153-90-3, dated Aug. 7, 2012; RN 1356638-27-1, dated Feb. 14, 2012; and RN 1320842-60-1, dated Aug. 21, 2011.

Chemical Abstract Compounds, STN Express. RN 1294872-06-2, dated May 15, 2011; and RN 1061592-74-2, dated Oct. 25, 2008.

Healthline "What is Neoplastic Disease" dowloaded from https://www.healthline.com/health/neoplastic-disease on Jun. 21, 2018, 4 pages. (Year: 2018).

Bos; "ras Oncogenes in Human Cancer: A Review"; Cancer Res 1989, 49, 4682-4689. (Year: 1989).

Hobbs; "RAS isoforms and mutations in cancer at a glance"; Journal of Cell Science 2016, 129, 1287-1292. (Year: 2016).

Chemical Abstracts STN Registry Database, record for RN 878115-07-2, first entered into STN database on Mar. 27, 2006, with commercial source information, 2 pages. (Year: 2006).

Chemical Abstracts STN Registry Database record for RN 1296462-10-6, Entered into STN on May 18, 2011. (Year 2011).

Chemical Abstracts STN Registry Database record for RN 949229-29-2, Entered into STN on Oct. 5, 2007. (Year: 2007).

Chemical Abstracts STN Registry Database record for RN 1386202-88-5, Entered into STN on Aug. 3, 2012. (Year: 2012).

4734

4735

4747

4748

4749

4800

4801

4802

4803

4805

4824

4825

4826
 4827
 4828
 4829
 4855
 4856
 4874
 4875
 4876
 4877
 4878
 4888

4888

4889

4891

4892

4893

4894

4895

4896

COMPOSITIONS AND METHODS OF TARGETING MUTANT K-RAS

CROSS-REFERENCE TO RELATED APPLICATIONS

This application is a 371 of PCT/US2016/025697, filed Apr. 1, 2016, which claims the benefit of U.S. Provisional Patent Application NO. 62/142,974, filed Apr. 3, 2015.

FIELD OF THE INVENTION

The field of the invention is pharmaceutical compounds, compositions, and methods, and uses thereof in treatment of diseases associated with mutant KRAS proteins.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and applications referred to herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

K-Ras (or Ki-Ras or Kirsten-Ras) is a 21 kD member of the Ras family of GTPase proteins and a necessary component in cell signaling. Activated K-Ras typically activates downstream kinases necessary for the propagation of growth factor and other receptors signals (e.g., c-Raf and PI3-kinase). Unfortunately, genetic alterations in the gene encoding K-Ras are associated with development of neoplasias, and the mechanism of activation is relatively well understood.

Cancer-associated mutant K-Ras is constitutively active, with prolonged stabilization of its GTP-bound (active) state, and is thus able to constitutively activate downstream effectors such as Raf kinase and phosphoinositide-3 kinase (PI3K). Both of these kinases play important roles in proliferation/survival/anti-apoptotic signaling pathways. These mutations have been implicated in insensitivity to EGFR-targeted anti-cancer therapies as mutations in K-Ras predispose cancer cells to be significantly less responsive to EGFR targeting therapies (e.g., Panitumumab, Cetuximab, etc.). Interaction with the Ras GTPase activating protein (Ras-GAP) is vital to the timely inactivation of K-Ras, resulting in more efficient hydrolysis of GTP to GDP. The conformational changes in K-Ras structure due to the GTP hydrolysis result in the elimination of K-Ras' affinity for effector proteins, thereby inactivating downstream proliferation and anti-death pathways. Cancer-associated mutations in K-Ras have been shown to interact poorly with RasGAP, therefore remaining in the "on" or constitutively active position.

Approximately 33% of all human tumors express mutant Ras, and these mutations often stabilize Ras in GTP-bound (active) state. Mutations found in K-Ras associate strongly with pancreatic cancer (90%), biliary tract cancer (33%), colorectal cancer (32%), and lung cancer (20%), among others. Approximately 20-25% of all human tumors harbor an activating mutation in gene encoding K-Ras.

Examples of cancer-associated mutations are found at glycine-12 (Gly12), Gly13, and glutamine-61 (Gln61), with Gly12 being the predominant site of mutagenesis (88%). Most notably, while the most common Gly12 mutations are defects in the same position, different mutations have their own different characteristics. For example, expression of G12C is often associated with a reduced response to cisplatin and an increased sensitivity to taxol and pemetrexed, whereas the expression of G12D mutant typically results in resistance to taxol treatment and sensitivity to sorafenib. The G12V mutant shows a strong sensitivity to cisplatin when compared with the wild type variant and is slightly more resistant to pemetrexed. Such diversity in treatment response is compounding difficulties in finding adequate treatment with drugs that are specific to K-Ras, and also highlight that specific mutant forms of K-Ras may require specific drugs for inhibition of the K-Ras activity.

More recently, specific drugs have been proposed to target a particular mutant form of K-Ras. For example, WO2013/155223A1 discloses small molecule inhibitors for G12C mutant forms. While promising, issues with restricted use and potential toxicity may limit compounds presented in the '223 reference. To circumvent mutant specific forms, allosteric inhibitors were proposed (PLOS One October 2011, Volume 6, Issue 10, e25711). However, that report did not distinguish among different mutant forms.

In view of the important role mutant K-Ras plays in various neoplastic disease states, it would be advantageous to be able to identify compounds that bind specifically to the mutant K-Ras protein forms associated with cancer diseases states and/or specific mutant forms, and most preferably to a specific mutant type with little or no binding to the wild type.

Thus, even though various forms of inhibitors for K-ras are known in the art, there remains a need for compositions and methods that preferentially or even selectively target mutant K-Ras, and especially a single mutant form.

SUMMARY OF THE INVENTION

The inventive subject matter is directed to compounds, compositions, and methods for inhibiting mutant K-Ras, and especially inhibiting G12V and/or G12D mutant K-Ras. Most preferably, the compounds presented herein inhibit G12V and/or G12D mutant K-Ras with high selectivity over other mutant forms and high specificity over wild type K-Ras.

In one aspect of the inventive subject matter, a compound having a structure according to Formula I

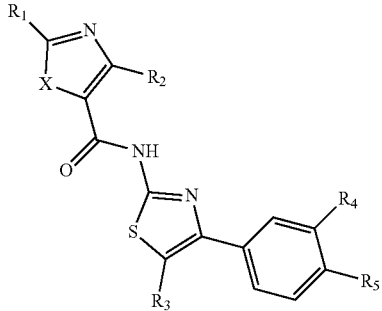

Formula I wherein X is O or S, wherein $R_1$ and $R_2$ are independently H, alkyl, cycloalkyl, heterocycloalkyl, alkenyl, alkynyl, aryl, heteroaryl, alkaryl, haloalkyl, alkoxy, alkylthio, halogen, —OH, —NHC(O)alkyl, or —NHC(O)aryl, wherein $R_3$ is H, $C_1$-$C_4$ alkyl, —$NHR_6$, or —$OR_6$, wherein $R_6$ is H, alkyl, haloalkyl, alkenyl, aryl, or heteroaryl, wherein $R_4$ and $R_5$ together form an optionally substituted heterocyclic 5-, 6-, or 7-membered ring, or $R_4$ is null when $R_5$ is —NHC(O)alkyl or —NHC(O)aryl.

In further preferred aspects, $R_1$ and $R_2$ are independently H, alkyl, heteroaryl, cycloalkyl, or heterocycloalkyl. For example, $R_1$ may be alkyl or cycloalkyl, and $R_2$ may be alkyl. Most preferably, but not necessarily, X is S, and/or $R_3$ is H or $C_1$-$C_4$ alkyl. Additionally, it is generally preferred that the optionally substituted heterocyclic 5-, 6-, or 7-membered ring contains a nitrogen atom, and that the ring further contains an oxo substituent. Therefore, the phenyl group carrying $R_4$ and $R_5$ may form together with the heterocyclic 5-, 6-, or 7-membered ring a two- or three-ringed structure, including

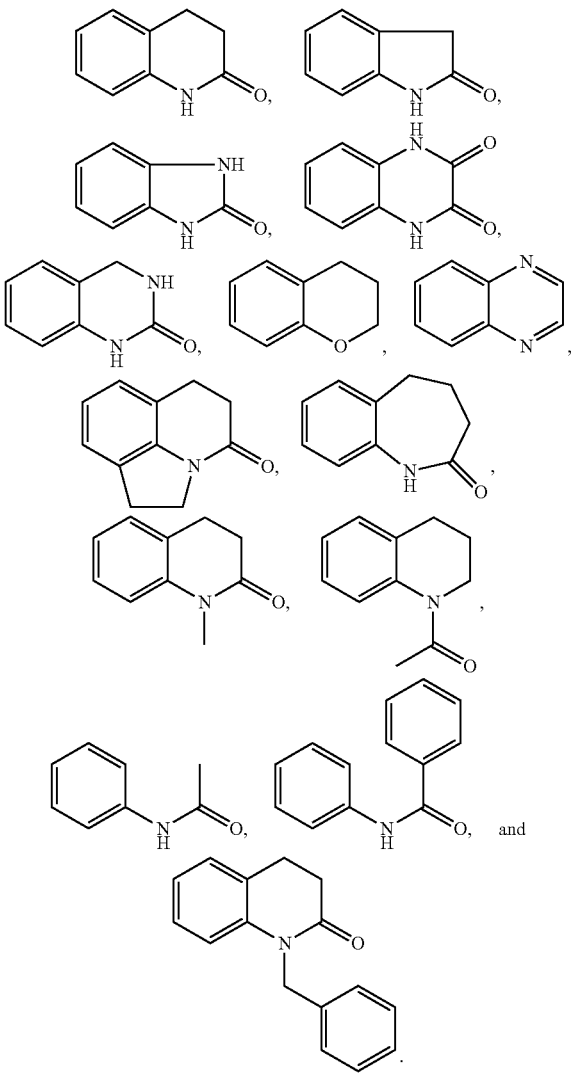

Therefore, and viewed from another perspective, contemplated compounds may have a structure according to Formula II

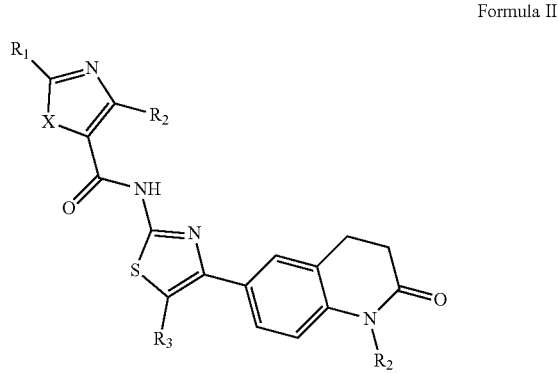

Formula II wherein X is O or S, wherein $R_1$ and $R_2$ are independently H, alkyl, cycloalkyl, heterocycloalkyl, alkenyl, alkynyl, aryl, heteroaryl, alkaryl, haloalkyl, alkoxy, alkylthio, halogen, —OH, —NHC(O)alkyl, or —NHC(O)aryl; wherein $R_3$ is H or $C_1$-$C_4$ alkyl; and wherein $R_7$ is H, alkyl, cycloalkyl, heterocycloalkyl, alkenyl, alkynyl, aryl, heteroaryl, alkaryl or alkheteroaryl. For example, contemplated compounds include those in which $R_1$ is alkyl or cycloalkyl, and in which $R_2$ is alkyl. As before, it is preferred that at least in some compounds X is S, and/or that $R_3$ is H.

For example, especially preferred compounds will have a structure of Formula III or Formula IV where $R_3$ is H, methyl, or halogen.

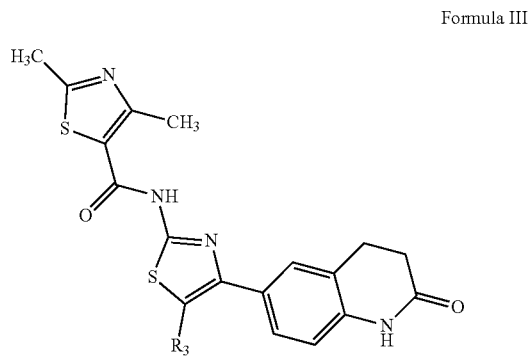

Formula III

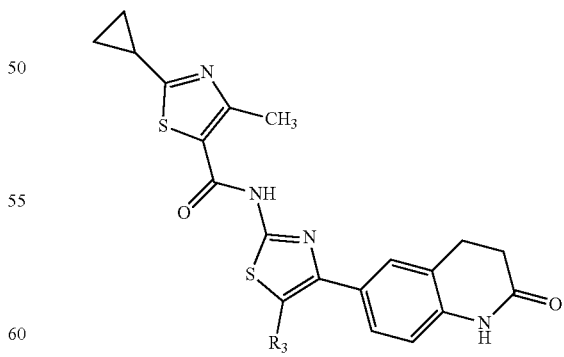

Formula IV

In another aspect of the inventive subject matter, the inventors contemplate a pharmaceutical composition comprising a pharmaceutically acceptable carrier and one or more compounds as presented above. Most preferably, the compound(s) is/are present at a concentration effective to inhibit K-ras in a mammal when administered to the mammal at a dosage effective to inhibit K-ras in the mammal. Moreover, it is generally preferred that the K-ras is a mutant K-ras. For example, especially contemplated composition include those in which the compound preferentially inhibits mutant K-ras G12D relative to mutant K-ras G12V and mutant K-ras G12C.

Consequently, the inventors also contemplate the use of a compound as presented above to inhibit K-ras signaling, and in most preferred uses, the compound has a structure according to Formula II, Formula III, or Formula IV. Thus, it is also contemplated that K-ras signaling is mediated by a mutant K-ras. For example, the mutant K-ras is K-ras G12D, and the compound preferentially inhibits mutant K-ras G12D relative to mutant K-ras G12V and mutant K-ras G12C.

Viewed from another perspective, the inventors therefore also contemplate the use of a compound as presented herein in the manufacture of a medicament to treat a neoplastic disease, and especially where the neoplastic disease is associated with a mutant K-ras (e.g., K-ras G12D). For example, the compounds in such medicament may have a structure according to Formula II, Formula III, or Formula IV.

Alternatively, the inventors also contemplate a method of inhibiting mutant K-ras. Such methods will typically include a step of contacting (in vitro or in vivo) the mutant K-ras with contemplated compounds at a concentration effective to inhibit the mutant K-ras (e.g., where the mutant K-ras is K-ras G12D). For example, especially preferred compounds preferentially inhibit mutant K-ras G12D relative to mutant K-ras G12V and mutant K-ras G12C. Suitable concentrations will be effective to reduce downstream signaling with respect to at least one of MEK signaling and ERK signaling.

In yet a further aspect of the inventive subject matter, the inventors also contemplate a method of treating a neoplastic disease (e.g., colon cancer, pancreatic cancer, and non-small cell lung cancer) in a mammal in need thereof, wherein such methods comprise a step of administering to the mammal contemplated compounds under a protocol effective to inhibit K-ras in the mammal. For example, suitable compound will have a structure according to Formula II, Formula III, or Formula IV, and/or it is contemplated that the step of administering will comprise oral administration or injection.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
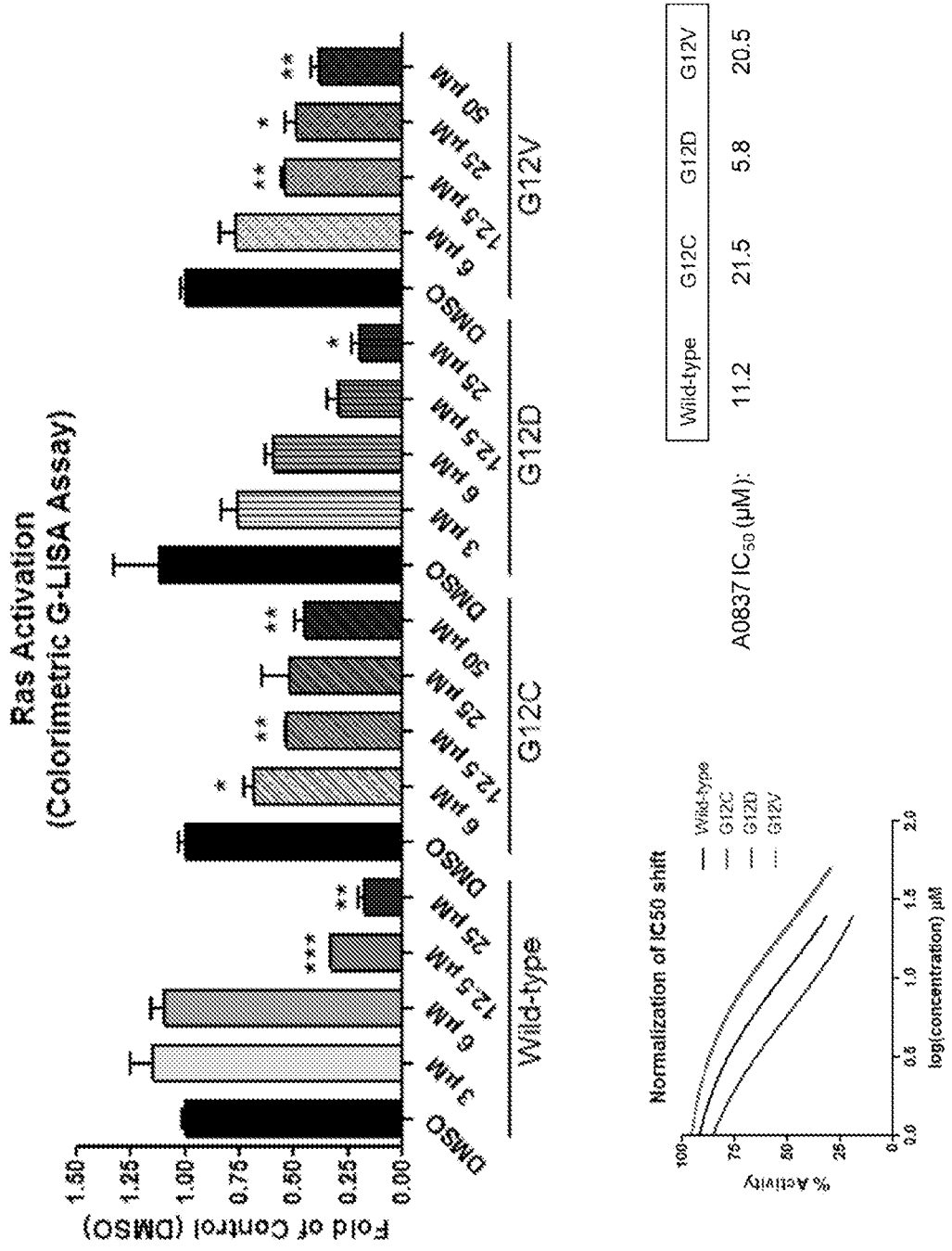
FIG. 1 depicts graphs illustrating Ras inhibition of various mutant forms in recombinant cells using G-LISA assay.

The inventors have now discovered that certain compounds can be prepared that will preferentially or even selectively inhibit mutant K-ras. Such compounds were found to have a scaffold as schematically illustrated in Formula A

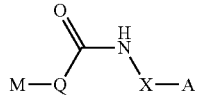

Formula A where X and Q are independently and typically a five-membered heteroaromatic ring (and most typically an optionally substituted thiazole or oxazole), A comprises an aryl, heteroaryl, or heterocyclic moiety (most typically a substituted phenyl or tetrahydroquinoline), and M is one or more substituents such as an alkyl, a cyclocalkyl, an alkenyl, or halogen.

The term "substituted" as used herein refers to a replacement of an atom or chemical group (e.g., H, $NH_2$, or OH) with a functional group, and particularly contemplated functional groups include nucleophilic groups (e.g., —$NH_2$, —OH, SH, —NC, etc.), electrophilic groups (e.g., C(O)OR, C(X)OH, etc.), polar groups (e.g., —OH), non-polar groups (e.g., aryl, alkyl, alkenyl, alkynyl, etc.), ionic groups (e.g., $NH_3^+$), and halogens (e.g., —F, —Cl), and all chemically reasonable combinations thereof. Thus, the term "functional group" as used herein may refer to a nucleophilic group (e.g., —NH2, —OH, SH, —NC, —CN etc.), an electrophilic group (e.g., C(O)OR, C(X)OH, C(Halogen)OR, etc.), a polar group (e.g., —OH), a non-polar group (e.g., aryl, alkyl, alkenyl, alkynyl, etc.), an ionic group (e.g., NH3+), and a halogen.

While not limiting to the inventive subject matter, the inventors discovered that the heterocyclic ring system for Q and X are preferably five-membered heteroaryl systems that may or may not be substituted with one or more substituents. Therefore, and among other suitable heteroaryl systems, especially preferred X and Q group include a thiazole ring, an oxazole ring, am imidazole ring, a trizole ring, a furan ring, and a thophene ring. In still further preferred aspects, and particularly where Q is an oxazole or thiazole, it is preferred that Q one or two hydrogen atoms in Q in the oxazole or thiazole are substituted by a $C_1$-$C_4$ alkyl moiety, which may be cyclic. Thus, especially preferred substituents include methyl, ethyl, trifluoromethyl, propyl, and cyclopropyl for each of the substituents as depicted in the exemplary list of Q moieties having one or two M substituents (here identified as $R_4$ and $R_5$, which may preferably be an alkyl, a cyclocalkyl, an alkenyl, a hydroxy, a trifluoromethyl, or a halogen).

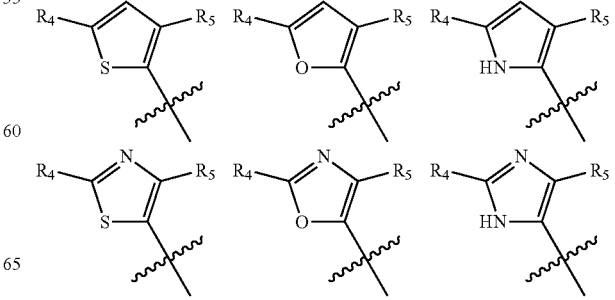

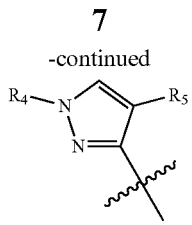

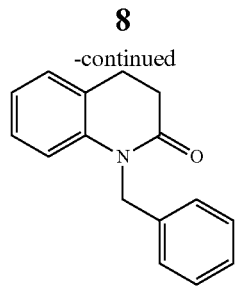

Similarly, it should be appreciated that the X group may vary considerably. However, especially preferred X groups are optionally substituted thiazoles, particularly where the thiazole is substituted with a relatively small substituent (e.g., methyl, hydroxyl, halogen, etc.)

With respect to the A group, it is contemplated that such group will preferably include an aryl, heteroaryl, or heterocyclic moiety that includes an aromatic portion. Most typically, the A group will therefore comprise a phenyl ring that may be fused with one or more other aromatic, saturated, or unsaturated ring systems, which may or may not include a heteroatom. For example, where A is a substituted phenyl ring, the substituent is preferably an amine group that may be coupled to an acyl moiety. On the other hand, where the A group is a fused ring system, at least one of the rings will preferably comprise a phenyl group while the other ring is preferably heterocyclic ring. For example, suitable A groups include those listed below.

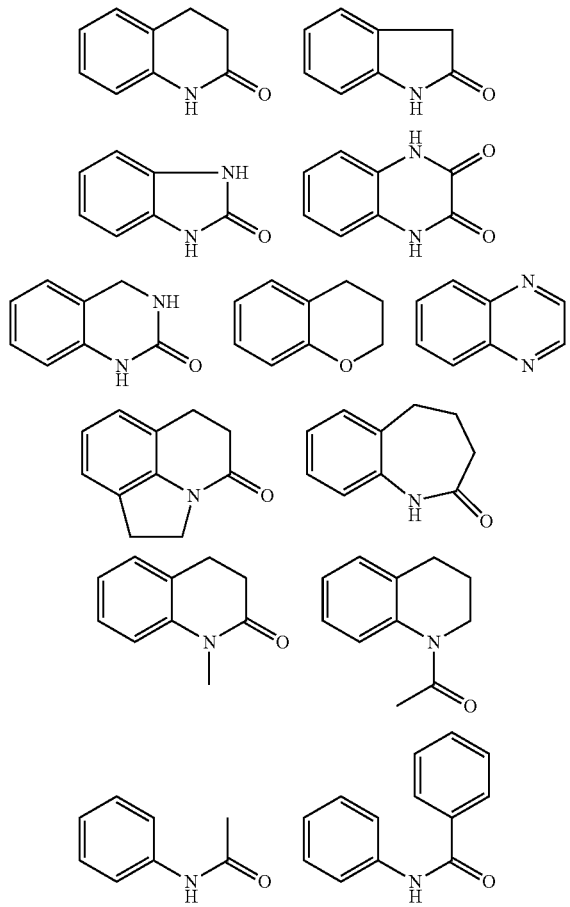

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Therefore, and where the X group is a thiazole and where the Q group is an oxazole or a thiazole, contemplated compounds may have a structure according to Formula II Formula II

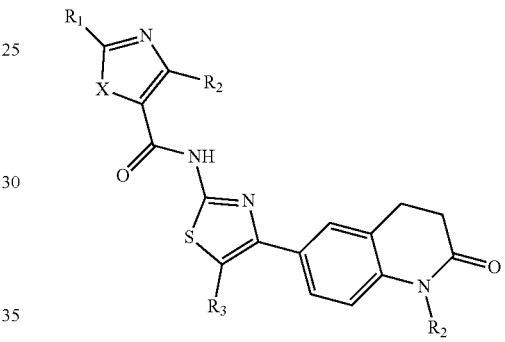

in which X is O or S, and in which $R_1$ and $R_2$ are independently H, alkyl, cycloalkyl, heterocycloalkyl, alkenyl, alkynyl, aryl, heteroaryl, alkaryl, haloalkyl, alkoxy, alkylthio, halogen, —OH, —NHC(O)alkyl, or —NHC(O)aryl. It is preferred that $R_3$ in such compounds is H or $C_1$-$C_4$ alkyl (which may be cyclic), and/or that $R_7$ is H, alkyl, cycloalkyl, heterocycloalkyl, alkenyl, alkynyl, aryl, heteroaryl, alkaryl or alkheteroaryl. Most preferably, however, contemplated compounds include those in which $R_1$ is alkyl or cycloalkyl (and especially cyclopropyl), and in which $R_2$ is alkyl (and especially methyl), particularly where X is S, and where $R_3$ is H.

For example, especially preferred compounds will have a structure of Formula III or Formula IV where $R_3$ is H, methyl, or halogen.

Formula III

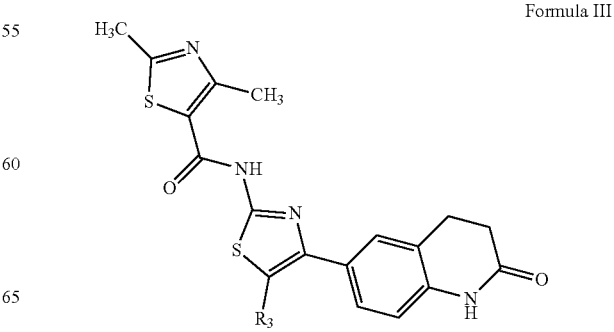

Formula IV

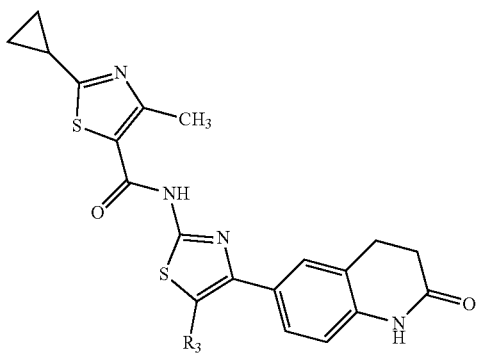

Certain compounds contemplated herein may comprise one or more asymmetric centers, and therefore exist in different enantiomeric forms. It should be recognized that all enantiomeric forms of contemplated compounds are specifically contemplated herein. Similarly, where contemplated compounds exhibit optical activity and/or have stereoisomers, all isomeric forms are contemplated herein. Furthermore, where double bonds distinguish a Z-form from an E-form (or cis- from trans-), both isomers are contemplated.

Still further, it should be recognized that the compounds according to the inventive subject matter may also be isotopically-labeled. Examples of suitable isotopes $^{2}H$, $^{3}H$, $^{13}C$, $^{14}C$, $^{15}N$, $^{18}O$, $^{17}O$, $^{18}F$, or $^{36}Cl$. Certain isotopically-labeled compounds of the inventive subject matter, for example those into which $^{14}C$ or $^{3}H$ is incorporated, may be useful in drug and/or substrate tissue distribution assays. On the other hand, substitution with non-radioactive isotopes (e.g., $^{2}H$ or $^{13}C$) can afford certain therapeutic advantages resulting from greater metabolic stability, for example increased in vivo half-life or reduced dosage requirements and, hence, may be preferred in some circumstances.

Contemplated compounds may be prepared as pharmaceutically acceptable salt(s), which especially include salts of acidic or basic groups which may be present in the contemplated compounds. For example, contemplated compounds that are basic in nature may form a wide variety of salts with various inorganic and organic acids. Suitable acids will provide pharmacologically acceptable anions, including chloride, bromide, iodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate [1,1'-methylene-bis-(2-hydroxy-3-naphthoate)] anions. Similarly, compounds that are acidic in nature may form base salts with various pharmacologically acceptable cations, and especially suitable cations include alkali metal or alkaline earth metal ions (e.g., sodium and potassium cations).

It is still further especially contemplated that compounds according to the inventive subject matter may also be prepared as prodrugs, and all known manners and types of prodrugs are considered suitable for use herein, so long as such prodrug will increase the concentration of the drug (or metabolite of the prodrug) at a target organ or target cell. For example, where the compounds have a free amino, amido, hydroxy, thio, or carboxylic group, it is contemplated that such groups can be employed to covalently and releasably bind a moiety that converts the drug into a prodrug. Therefore, prodrugs particularly include those in which contemplated compounds forms an ester, amide, or disulfide bond with another cleavable moiety. Such moieties may assist in organ or cell-specific delivery of the drug. For instance, a carboxyl group can be derivatized to form an amide or alkyl ester, which may include an ether, amine-, and/or carboxylic acid group. Free hydroxy groups may be derivatized using hemisuccinates, phosphate esters, dimethylaminoacetates, and phosphoryloxymethyloxycarbonyls, as outlined in D. Fleisher, R. Bong, B. H. Stewart, Advanced Drug Delivery 40 Reviews (1996) 19, 115. Carbamate prodrugs of hydroxy and amino groups are also included, as are carbonate prodrugs and sulfate esters of hydroxy groups. Derivatization of hydroxy groups as (acyloxy)methyl and (acyloxy)ethylethers, wherein the acyl group may be an alkyl ester (optionally substituted), or where the acyl group is an amino acid ester are also contemplated (Prodrugs of this type are described in R. P. Robinson et al., J. Medicinal Chemistry (1996) 39:p.10).

Still further, it should also be recognized that contemplated compounds may be metabolized in a cell or extracellular compartment, and that such metabolites may exhibit the same or different pharmacological effect. For example, contemplated compounds may be phosphorylated and thus be more active than the parent compound. On the other hand, reduction or glycosylation may affect bioavailability of contemplated compounds. Consequently, contemplated compounds will not only include those as described above, but also include metabolites thereof.

Viewed from another perspective, it should be thus be appreciated that contemplated compounds and compositions may be used for all conditions and/or disorders that are associated with a dysregulation and/or dysfunction of K-ras, and especially with a mutant form of K-ras (particularly G12D and/or G12V). For example, contemplated conditions and disorders include various cancers, and especially pancreatic cancer, colon cancer, and non-small cell lung cancer.

Viewed from yet another perspective, the present inventive subject matter is directed to various compounds that modulate (e.g., inhibit or reduce) K-ras dependent signaling in a cell, and/or that directly or indirectly affect (mutant) K-ras, GTP binding, and effector protein interaction to so interfere with signal transduction. Exemplary compounds will therefore not only include the compounds as discussed above, but also various derivatives that impart one or another advantageous property.

Based on the inventors' discovery of biological activity of contemplated compounds, it is generally contemplated that the compounds according to the inventive subject matter may be formulated for treatment of various diseases associated with dysregulation and/or dysfunction of K-ras or mutant K-ras. Therefore, and among other contemplated uses, the inventors especially contemplate that pharmaceutical compositions comprising contemplated compounds may be effective for the treatment or prevention of K-ras signaling dependent cancers, and especially colon cancer, pancreactic cancer, and non-small cell lung cancer, wherein contemplated pharmaceutical compositions comprise a therapeutically effective amount of contemplated compounds (or pharmaceutically acceptable salt, hydrate, or prodrug thereof), and a pharmaceutically acceptable carrier. Therefore, it should be recognized that contemplated compounds are suitable for use to inhibit K-ras signaling, and/or for the manufacture of a medicament to treat a neoplastic disease that is associated with a mutation in K-ras, especially where the K-ras has a G12D or G12V mutation. Therefore, the inventors also contemplate a method of inhibiting mutant KRAS, comprising a step of contacting the mutant KRAS with a method of inhibiting K-ras or mutant K-ras using contemplated compounds at a concentration effective to inhibit the (mutant) K-ras. As used herein, the term "inhibit" or "inhibition" in conjunction with K-ras activity means a reduction in activation of downstream signaling components (e.g., MEK, Erk, etc.) as compared to activity of the same (mutant) K-ras without exposure to the inhibitory compound under otherwise identical conditions.

It is therefore particularly preferred that contemplated compounds are included in a composition that is formulated with one or more non-toxic and pharmaceutically acceptable carriers. Preferred pharmaceutical compositions are formulated for oral administration in solid or liquid form, or for parenteral injection. Thus, it should be recognized that the pharmaceutical compositions according to the inventive subject matter may be administered to humans and other animals using various routes, including oral, rectal, parenteral, intraperitoneal, vaginal, or topical administration.

For example, suitable pharmaceutical compositions for injection preferably comprise pharmaceutically acceptable sterile aqueous or nonaqueous solutions, dispersions, emulsions, or suspensions, as well as sterile powders for reconstitution into sterile injectable solutions or dispersions prior to use. Examples of suitable aqueous and nonaqueous carriers, diluents, solvents, or vehicles include water, ethanol, polyols (e.g., glycerol, propylene glycol, polyethylene glycol, etc.), and suitable mixtures thereof, oils, and injectable organic esters (e.g., ethyl oleate). Contemplated compositions may also contain various inactive ingredients, including preservatives, wetting agents, emulsifying agents, and/or dispersing agents. Sterility may be ensured by inclusion of antibacterial and/or antifungal agents (e.g., paraben, phenol sorbic acid, chlorobutanol, etc.). Where appropriate, osmotically active agents may be included (e.g., sugars, sodium chloride, etc.).

Alternatively, contemplated compositions may be formulated into solid dosage forms for oral administration, and may therefore be capsules, tablets, pills, powders, and granules. In preferred solid dosage forms, contemplated compound are mixed with at least one of a pharmaceutically acceptable excipient or carrier (e.g., sodium citrate or dicalcium phosphate), a filler or extender (e.g., starch, lactose, sucrose, glucose, mannitol, or silicic acid), a binder (e.g., carboxymethylcellulose, alginates, gelatin, polyvinylpyrrolidone, sucrose, etc.), a humectant (e.g., glycerol), a disintegrating agent (e.g., agar-agar, calcium carbonate, potato or tapioca starch, alginic acid, certain silicates, or sodium carbonate), a solution retarding agent (e.g., paraffin), an absorption accelerator (e.g., quaternary ammonium compound), a wetting agents (e.g., cetyl alcohol and glycerol monostearate), and absorbents (e.g., kaolin, or bentonite clay), and a lubricant (e.g., talc, calcium stearate, magnesium stearate, solid polyethylene glycols, sodium lauryl sulfate).

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. Contemplated compositions may further be formulated to release the active ingredient(s) only, or preferentially, in a certain part of the intestinal tract, optionally, in a delayed manner. Examples of embedding compositions which can be used include polymeric substances and waxes. Contemplated compounds may also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, liquid dosage forms may contain inert diluents commonly used in the art (e.g., water, or other solvent, solubilizing agents), emulsifiers (e.g., ethyl alcohol, isopropyl alcohol, ethyl carbonate, ethyl acetate, benzyl alcohol, benzyl benzoate, propylene glycol, 1,3-butylene glycol, dimethyl formamide), oils (and in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions may also include adjuvants such as wetting agents, emulsifying and suspending agents, sweetening, flavoring, and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound. Compounds according to the inventive subject matter can also be administered in form of liposomes, which may be unilamellar, oligolamellar, or polylamellar. Contemplated compositions in liposome form may further contain stabilizers, preservatives, excipients, etc. Preferred lipids for liposome formation include phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p. 33 et seq.

Actual dosage levels of contemplated compounds in pharmaceutical compositions according to the inventive subject matter may be varied so as to obtain an amount of contemplated compound(s) that is effective to achieve the desired therapeutic response for a particular patient, composition, and mode of administration. Thus, the selected dosage level will depend upon various factors, including the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. Generally, dosage levels of about 0.01 mg/kg to about 0.1 mg/kg, or about 0.1 mg/kg to about 1 mg/kg, or about 1 mg/kg to about 10 mg/kg, or about 10 mg/kg to about 50 mg/kg of body weight per day. Thus, single dosage units for administration will typically be between 0.1 mg and 1 mg, between 1 mg and 50 mg, between 50 mg and 250 mg, between 250 mg-1,000 mg, between 1,000 mg and 5,000 or even higher when administered orally to a mammalian patient. If desired, it should be appreciated that the effective daily dose may be divided into multiple doses for purposes of administration, e.g., two to four separate doses per day.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary. In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

It should still further be appreciated that contemplated pharmaceutical compositions may also include additional pharmaceutically active compounds, and especially contemplated additional pharmaceutically active compounds include anti-metabolic and/or antineoplastic agents and/or immunologically active agents, which may act upon cell division, apoptosis, T-cell recognition, NK-cell activity, memory cell formation, checkpoint inhibition, and/or immune stimulation. Of course, it should be recognized that additional pharmaceutically active compounds may be included in the same pharmaceutical composition, or may be administered separately, and a person of ordinary skill in the art will readily determine schedule and route of suitable co-administration of the additional pharmaceutically active compounds.

EXAMPLES

Exemplary Compounds

The following examples are intended to provide a non-limiting general protocol for the preparation of various intermediates that can be subsequently used to prepare compounds according to the inventive subject matter. Based on the below exemplary protocols, the person of ordinary skill in the art will be readily able to produce similar compounds starting with similar educts. Likewise, the examples provided for biological activities exemplarily set out systems and methods for ascertaining inhibitory activity and preference/selectivity.

Intermediate 1

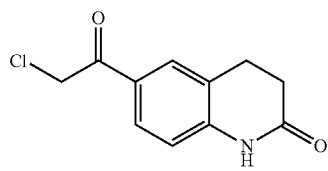 [SMILES: O=C1CCc2cc(C(=O)CCl)ccc2N1]

To a 500 mL round-bottomed flask equipped with condenser and argon inlet were added aluminum chloride (7.93 g, 59.45 mmol), carbon disulfide (40 mL), and chloroacetyl chloride (2.30 g, 20.38 mmol) under ice-bath. The mixture was stirred for 15 mins. To the stirring mixture was added 3,4-dihydro-2(H)-quinolinone (2.50 g, 16.99 mmol) in portions over 5 mins. The mixture was stirred for 10 minutes prior to reflux for 2.5 hours. The reaction mixture was cooled and the solvent was decanted off. Then ice and cold water (50 mL) was slowly added while stirred thoroughly. The beige precipitate filtered, washed with water (3×50 mL) followed by tetrahydrofuran (2×100 mL) and hexanes (1×200 mL). The solid was dried under vacuum to give 6-(2-chloroacetyl)-3,4-dihydroquinolin-2(1H)-one (3.44 g, 90%) as a beige solid. $^1$H NMR (400 MHz, DMSO-d): δ 10.47 (bs, 1H), 7.83 (s, 1H), 7.80 (dd, 1H, J=8.8, 1.6 Hz), 6.94 (d, 1H, J=8.0 Hz), 5.08 (s, 2H), 2.95 (m, 2H), 2.49 (partial masked under d-DMSO, m, 2H). MS (ESI): Calcd. for $C_{11}H_{10}ClNO_2$: 223, found 224 (M+1)$^+$.

Intermediate 2

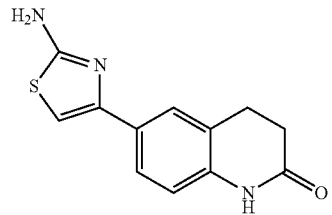

6-(Chloroacetyl)-3,4-dihydroquinolin-2(1H)-one (1.00 g, 4.47 mmol) and thiourea (0.36 g, 4.69 mmol) were suspended in anhydrous ethanol (10 ml) in a sealed tube under argon atmosphere. The sealed tube was microwaved at 120° C. for 30 min. The mixture was diluted with tetrahydrofuran (200 mL) and neutralized with 1N aq. NaOH solution and then extracted with ethyl acetate (2×200 mL). The combined organic layers were dried over anhydrous $Na_2SO_4$ and concentrated in vacuo. The residue was purified by precipitating in dichloromethane and filtration to give 6-(2-aminothiazol-4-yl)-3,4-dihydroquinolin-2(1H)-one (0.920 g, 73%) as a light brown solid. $^1$H NMR (400 MHz, DMSO-d): δ 10.27 (s, 1H), 8.71 (br s, 2H), 7.61 (s, 1H), 7.55 (dd, 1H, J=8.8, 2.0 Hz), 7.05 (s, 1H), 6.91 (d, 1H, J=8.4 Hz), 2.91 (t, 2H, J=7.6 Hz), 2.48 (partial masked under d-DMSO, m, 2H). MS (ESI): Calcd. for $C_{12}H_{11}N_3OS$: 245, found 246 (M+1)$^+$.

Intermediate 3

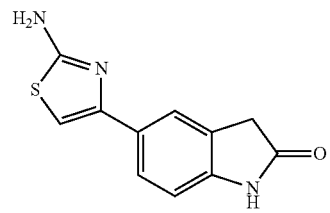 [SMILES: Nc1nc(-c2ccc3c(c2)CC(=O)N3)cs1]

5-chloroacetyloxidole (2.00 g, 9.54 mmol) and thiourea (0.76 g, 10.02 mmol) were suspended in anhydrous ethanol (15 ml) in a sealed tube under argon atmosphere. The sealed tube was microwaved at 120° C. for 35 min. The mixture diluted with tetrahydrofuran (200 mL) and neutralized with 1N aq. NaOH solution and then extracted with ethyl acetate (2×200 mL). The combined organic layers were dried over anhydrous Na₂SO₄ and concentrated in vacuo. The residue was purified by precipitating in dichloromethane and filtration to give 5-(2-aminothiazol-4-yl)indolin-2-one (2.36 g, 92%) as a light brown solid. $^1$H NMR (400 MHz, DMSO-d): δ 10.64 (s, 1H), 8.95 (bs, 1H), 7.62 (s, 1H), 7.60 (dd, 1H, J=8.4, 1.2 Hz), 7.06 (s, 1H), 6.89 (d, 1H, J=8.4 Hz). MS (ESI): Calcd. for C11H10ClN3OS: 267, found 268 (M+1)⁺.

Intermediate 4

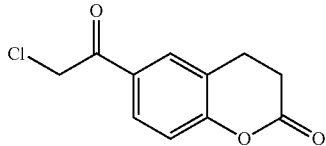 [SMILES: O=C1CCc2cc(C(=O)CCl)ccc2O1]

Preparation: To a 500 mL round-bottomed flask equipped with condenser and argon inlet were added aluminum chloride (6.30 g, 47.25 mmol), carbon disulfide (35 mL), and chloroacetyl chloride (1.83 g, 16.20 mmol) under ice-bath. The mixture was stirred for 15 mins. The mixture was added 3,4-dihydrocoumarin (2.00 g, 13.50 mmol) in portions over 5 mins. The reaction was stirred for 10 minutes prior to reflux for 2.5 hours. The reaction mixture was cooled and the solvent was decanted off. Then ice and cold water (50 mL) was slowly added while stirred thoroughly. The tan precipitate was collected by filtration and washing thoroughly with water. The crude precipitate was suspended and sonicated in diethyl ether (10 mL) and the resulted fine solid was again collected by filtration and dried under vacuum to give 6-(2-chloroacetyl)chroman-2-one (1.60 g, 53%) as a beige solid. $^1$H NMR (400 MHz, DMSO-d): δ 7.96 (d, 1H, J=2.0 Hz), 7.90 (dd, 1H, J=16.0, 8.8 Hz), 7.21 (d, 1H, J=8.0 Hz), 5.16 (s, 2H), 3.08 (t, 2H, J=7.2 Hz), 2.84 (t, 2H, J=7.2 Hz). MS (ESI): Calcd. for C₁₁H₉ClO₃: 224, found 371 (Unstable).

Intermediate 5

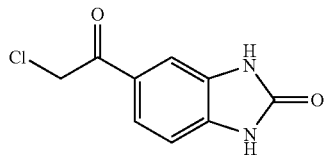 [SMILES: O=C(CCl)c1ccc2[nH]c(=O)[nH]c2c1]

To a 500 mL round-bottomed flask equipped with condenser and argon inlet were added aluminum chloride (6.96 g, 52.19 mmol), carbon disulfide (35 mL), and chloroacetyl chloride (2.02 g, 17.89 mmol) under ice-bath. The mixture was stirred for 15 mins. To the stirring mixture was added 2-hydroxybenzimidazole (2.00 g, 14.91 mmol) in portions over 5 mins. The reaction mixture was stirred for 10 minutes prior to reflux for 2.5 hours. The reaction mixture was cooled and the solvent was decanted off. Then ice and cold water (50 mL) was slowly added while stirred thoroughly. The tan precipitate was collected by filtration and washed thoroughly with water. The precipitate was sonicated in diethyl ether (10 mL) and the resulted fine solid was again collected by filtration. The solid was dried under vacuum to give 5-(2-chloroacetyl)-1,3-dihydro-2H-benzo[d]imidazol-2-one (2.92 g, 93%) as a beige solid. $^1$H NMR (400 MHz, DMSO-d): δ 11.12 (s, 1H), 10.96 (s, 1H), 7.67 (dd, 1H, J=8.8, 2.0 Hz), 7.49 (d, 1H, J=2.0 Hz), 7.03 (d, 1H, J=8.4 Hz), 5.13 (s, 2H). MS (ESI): Calcd. for C₉H₇ClN₂O₂: 210, found 390 (Unstable).

Intermediate 6

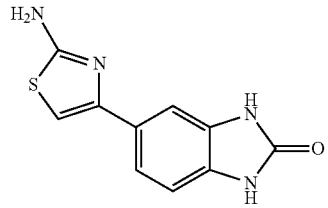 [SMILES: Nc1nc(-c2ccc3[nH]c(=O)[nH]c3c2)cs1]

5-(2-chloroacetyl)-1H-benzo[d]imidazol-2(3H)-one (2.00 g, 9.50 mmol) and thiourea (0.76 g, 9.97 mmol) was suspended in anhydrous ethanol (15 ml) in a sealed tube under argon atmosphere. The sealed tube was microwaved at 120° C. for 40 min. The mixture was diluted with tetrahydrofuran (200 mL) and neutralized with 1N aq. NaOH solution and then extracted with ethyl acetate (2×200 mL). The combined organic layers were dried over anhydrous Na₂SO₄ and concentrated in vacuo. The residue was purified by precipitating in dichloromethane and filtration to give 5-(2-aminothiazol-4-yl)-1,3-dihydro-2H-benzo[d]imidazol-2-one (1.81 g, 22%) as a tan solid. $^1$H NMR (400 MHz, DMSO-d): δ 10.67 (s, 1H), 10.64 (s, 1H), 7.40 (dd, 1H, J=8.4, 1.6 Hz), 7.37 (s, 1H), 7.01 (bs, 2H), 6.88 (d, 1H, d, J=8.0 Hz), 6.80 (s, 1H). MS (ESI): Calcd. for C₁₁H₉N₃OS: 231, found 232 (M+1)⁺.

Intermediate 7

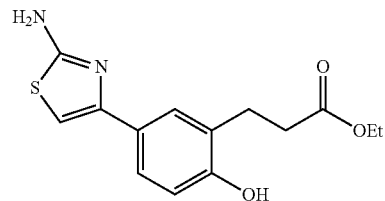 [SMILES: CCOC(=O)CCc1cc(-c2csc(N)n2)ccc1O]

6-(2-chloroacetyl)chroman-2-one (1.30 g, 5.79 mmol) and thiourea (0.46 g, 6.08 mmol) was suspended in anhydrous ethanol (12 ml) in a sealed tube under argon atmosphere. The sealed tube was microwaved at 120° C. for 35 min. The mixture was diluted with tetrahydrofuran (200 mL) and neutralized with 1N aq. NaOH solution and then extracted with ethyl acetate (2×200 mL). The combined organic layers were dried over anhydrous Na₂SO₄ and concentrated in vacuo. The residue was purified by precipitating in dichloromethane and filtration to give ethyl 3-(5-(2-aminothiazol-4-yl)-2-hydroxyphenyl)propanoate (1.50 g, 89%) as a beige solid. $^1$H NMR (400 MHz, DMSO-d): δ 9.50 (s, 1H), 7.51 (d, 1H, J=2.0 Hz), 7.44 (dd, 1H, J=8.2, 2.0 Hz), 6.96 (bs, 2H), 6.74 (d, 1H, J=8.0 Hz), 6.70 (s, 1H), 4.03 (q, 2H, J=7.2 Hz), 2.78 (t, 2H, J=7.8 Hz), 2.55 (t, 2H, J=7.8 Hz), 1.51 (t, 3H, J=7.0 Hz). MS (ESI): Calcd. for C₁₄H₁₆N₂O₃S: 292, found 293 (M+1)⁺.

Intermediate 8

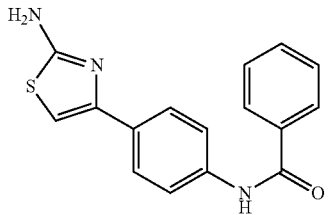 [SMILES: Nc1nc(-c2ccc(NC(=O)c3ccccc3)cc2)cs1]

N-[4-(2-Chloroacetyl)phenyl]benzamide (0.241 g, 0.882 mmol) and thiourea (0.071 g, 0.926 mmol) suspended in anhydrous ethanol (5 ml) in a sealed tube under argon atmosphere. The sealed tube was microwaved at 120° C. for 30 min. The mixture was diluted with tetrahydrofuran (50 mL) and neutralized with 1N aq. NaOH solution and then extracted with ethyl acetate (4×50 mL). The combined organic layers were dried over anhydrous $Na_2SO_4$ and concentrated in vacuo. The residue was purified by precipitating in dichloromethane and filtration to give N-(4-(2-aminothiazol-4-yl)phenyl)benzamide (0.08 g, 33%) as a brown solid. $^1$H NMR (400 MHz, DMSO-d): δ 10.28 (s, 1H), 7.95 (m, 2H), 7.78 (s, 4H), 7.60-7.50 (m, 3H), 7.02 (s, 2H), 6.93 (s, 1H). MS (ESI): Calcd. for $C_{16}H_{13}N_3OS$: 295, found 296 $(M+1)^+$.

Intermediate 9

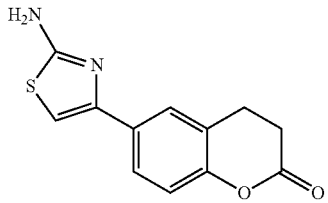 [SMILES: Nc1nc(-c2ccc3c(c2)CCC(=O)O3)cs1]

6-(2-chloroacetyl)chroman-2-one (0.283 g, 1.26 mmol) and thiourea (0.101 g, 1.32 mmol) was dissolved in anhydrous acetonitrile (10 ml) in a sealed tube under argon atmosphere. The sealed tube was microwaved at 80° C. for 30 min. The reaction was quenched with trimethylamine (1 mL), extracted with ethyl acetate (2×200 mL) and washed with sat. $NaHCO_3$ (2×50 mL). The combined organic layers were dried over anhydrous $Na_2SO_4$ and concentrated in vacuo. The residue was purified by precipitating in dichloromethane and filtration to give 6-(2-aminothiazol-4-yl)chroman-2-one (0.26 g, 84%) as a tan solid. $^1$H NMR (400 MHz, DMSO-d): δ 7.10 (d, 1H, J=2.0 Hz), 7.67 (dd, 1H, J=8.4, 2.0 Hz), 7.04 (m, 2H), 6.96 (s, 1H), 3.01 (t, 2H, J=7.6 Hz), 2.80 (t, 2H, J=7.6 Hz). MS (ESI): Calcd. for $C_{12}H_{10}N_2O_2S$: 246, found 247 $(M+1)^+$.

Intermediate 10

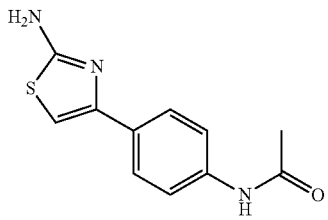 [SMILES: CC(=O)Nc1ccc(-c2csc(N)n2)cc1]

4-Chloroacetylacetanilide (1.00 g, 4.72 mmol) and thiourea (0.378 g, 4.96 mmol) suspended in anhydrous ethanol (8 ml) in a sealed tube under argon atmosphere. The sealed tube was microwaved at 120° C. for 30 min. The sealed tube was microwaved at 120° C. for 40 min. The mixture was diluted with tetrahydrofuran (200 mL) and neutralized with 1N aq. NaOH solution and then extracted with ethyl acetate (2×200 mL). The combined organic layers were dried over anhydrous $Na_2SO_4$ and concentrated in vacuo. The residue was purified by precipitating in dichloromethane and filtration to give N-(4-(2-aminothiazol-4-yl)phenyl)acetamide (1.05 g, 95%) as a yellow solid. $^1$H NMR (400 MHz, DMSO-d): δ 9.95 (s, 1H), 7.70 (d, 2H, J=8.4 Hz), 7.56 (d, 2H, J=8.4 Hz), 7.00 (s, 2H), 6.86 (s, 1H), 2.04 (s, 3H). MS (ESI): Calcd. for $C_{11}H_{11}N_3OS$: 233, found 234 $(M+1)^+$.

Intermediate 11

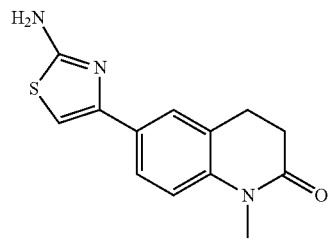 [SMILES: CN1C(=O)CCc2cc(-c3csc(N)n3)ccc21]

6-(2-Chloroacetyl)-1-methyl-1,2,3,4-tetrahydroquinolin-2-one (0.50 g, 2.10 mmol) and thiourea (0.17 g, 2.21 mmol) suspended in anhydrous ethanol (4 ml) in a sealed tube under argon atmosphere. The sealed tube was microwaved at 120° C. for 35 min. The mixture was diluted with tetrahydrofuran (100 mL), neutralized with triethylamine (2 mL), and extracted with ethyl acetate (2×200 mL) followed by washing with saturated sodium bicarbonate (2×100 mL). The combined organic layers were dried over anhydrous $Na_2SO_4$ and concentrated in vacuo. The residue was purified by precipitating in dichloromethane and filtration to give 6-(2-aminothiazol-4-yl)-1-methyl-3,4-dihydroquinolin-2(1H)-one (0.50 g, 92%) as a vanilla solid. $^1$H NMR (400 MHz, DMSO-d): δ 7.67 (dd, 1H, J=8.4, 2.0 Hz), 7.64 (d, 1H, J=1.6 Hz), 7.06 (d, 1H, J=8.4 Hz), 7.02 (s, 2H), 6.91 (s, 1H), 3.26 (s, 3H), 2.88 (t, 2H, J=6.4 Hz), 2.55 (t, 2H, J=6.8 Hz). MS (ESI): Calcd. for $C_{13}H_{13}N_3OS$: 259, found 260 $(M+1)^+$.

Intermediate 12

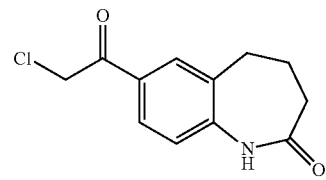 [SMILES: O=C1CCCc2cc(C(=O)CCl)ccc2N1]

To a 500 mL round-bottomed flask equipped with condenser and argon inlet were added aluminum chloride (5.79 g, 43.42 mmol), carbon disulfide (40 mL), and chloroacetyl chloride (1.68 g, 14.89 mmol) under ice-bath. The mixture was stirred for 15 mins. To the stirring mixture was added 4,5-dihydro-1H-benzo[b]azepine-2(3H)-one (2.00 g, 12.41 mmol) in portions over 5 mins. The mixture was stirred for 10 minutes prior to reflux for 2.5 hours. The reaction mixture was cooled and the solvent was decanted off. Then ice and cold water (50 mL) was slowly added while stirred thoroughly. The tan precipitate was collected by filtration and washed thoroughly with water. The precipitate was sonicated in diethyl ether (10 mL) and the resulted fine solid was again collected by filtration. The solid was dried under vacuum to give 7-(2-chloroacetyl)-1,3,4,5-tetrahydro-2H-benzo[b]azepin-2-one (2.68 g, 91%) as a beige solid. $^1$H NMR (400 MHz, DMSO-d): δ 9.90 (s, 1H), 7.90 (d, 1H, J=2.0 Hz), 7.85 (dd, 1H, J=8.0, 2.0 Hz), 7.07 (d, 1H, J=8.4 Hz), 2.76 (t, 2H, J=7.2 Hz), 2.20 (m, 2H), 2.16 (m, 2H). MS (ESI): Calcd. for $C_{12}H_{12}ClNO_2$: 237, found 238 (M+1)$^+$.

Intermediate 13 minutes prior to reflux for 2.5 hours. The reaction mixture was cooled and the solvent was decanted off. Then ice and cold water (50 mL) was slowly added while stirred thoroughly. The tan precipitate was collected by filtration and washed thoroughly with water. The precipitate was sonicated in diethyl ether (10 mL) and the resulted fine solid was again collected by filtration. The solid was dried under vacuum to give 1-(1-acetyl-1,2,3,4-tetrahydroquinolin-6-yl)-2-chloroethan-1-one (1.79 g, 62%) as a beige solid. $^1$H NMR (400 MHz, DMSO-d): δ 7.76 (m, 3H), 5.14 (s, 2H), 3.72 (t, 2H, J=6.4 Hz), 2.78 (t, 2H, J=6.8 Hz), 2.23 (s, 3H), 1.89 (p, 2H, J=6.8 Hz). MS (ESI): Calcd. for $C_{13}H_{14}ClNO_2$: 251, found 252 (M+1)$^+$.

Intermediate 15

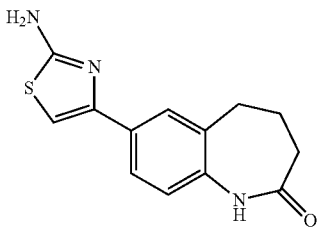 [SMILES: Nc1nc(-c2ccc3c(c2)CCCC(=O)N3)cs1]

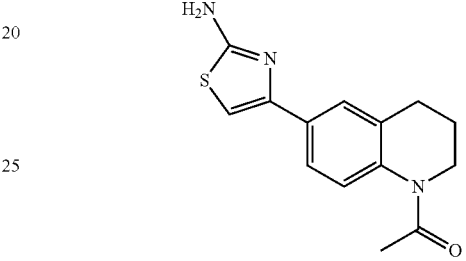

7-(2-chloroacetyl)-4,5-dihydro-1H-benzo[b]azepin-2(3H)-one (1.50 g, 6.31 mmol) and thiourea (0.504 g, 6.63 mmol) suspended in anhydrous ethanol (12 ml) in a sealed tube under argon atmosphere. The sealed tube was microwaved at 120° C. for 40 min. The mixture was diluted with tetrahydrofuran (200 mL), neutralized with triethylamine (5 mL), and extracted with ethyl acetate (2×200 mL) followed by washing with saturated sodium bicarbonate (2×200 mL). The combined organic layers were dried over anhydrous Na$_2$SO$_4$ and concentrated in vacuo. The residue was purified by precipitating in dichloromethane and filtration to give 7-(2-aminothiazol-4-yl)-1,3,4,5-tetrahydro-2H-benzo[b]azepin-2-one (1.25 g, 76%) as a tan solid. $^1$H NMR (400 MHz, DMSO-d): δ 9.52 (s, 1H), 7.67 (d, 1H, J=2.0 Hz), 7.63 (dd, 1H, J=8.4, 2.0 Hz), 7.02 (s, 2H), 6.93 (m, 2H), 2.70 (t, 2H, J=7.2 Hz), 2.13 (m, 4H). MS (ESI): Calcd. for $C_{13}H_{13}N_3OS$: 259, found 260 (M+1)$^+$.

Intermediate 14

1-(1-acetyl-1,2,3,4-tetrahydroquinolin-6-yl)-2-chloroethanone (1.00 g, 3.97 mmol) and thiourea (0.318 g, 4.17 mmol) suspended in anhydrous ethanol (10 ml) in a sealed tube under argon atmosphere. The sealed tube was microwaved at 120° C. for 35 min. The mixture was diluted with tetrahydrofuran (200 mL) and neutralized with triethylamine (3 mL) and then extracted with ethyl acetate (2×200 mL) followed by washing with saturated sodium bicarbonate (2×200 mL). The combined organic layers were dried over anhydrous Na$_2$SO$_4$ and concentrated in vacuo. The residue was purified by precipitating in 1:3 dichloromethane/diethyl ether and filtration to give 1-(6-(2-aminothiazol-4-yl)-3,4-dihydroquinolin-1(2H)-yl)ethan-1-one (0.47 g, 43%) as a tan solid. $^1$H NMR (400 MHz, DMSO-d): δ 7.58 (m, 2H), 7.95 (bs, 1H, 7.02 (s, 2H), 6.93 (s, 1H), 3.68 (t, 2H, J=6.4 Hz), 2.72 (t, 2H, J=6.8 Hz), 2.17 (s, 3H), 1.87 (p, 2H, J=6.8 Hz). MS (ESI): Calcd. for $C_{14}H_{15}N_3OS$: 273, found 274 (M+1)$^+$.

Intermediate 16

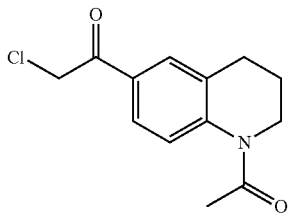 [SMILES: CC(=O)N1CCCc2cc(C(=O)CCl)ccc21]

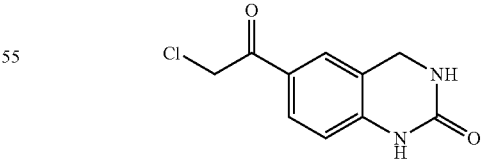

To a 500 mL round-bottomed flask equipped with condenser and argon inlet were added aluminum chloride (5.33 g, 39.95 mmol), carbon disulfide (40 mL), and chloroacetyl chloride (1.55 g, 13.70 mmol) under ice-bath. The mixture was stirred for 15 mins. To the stirring mixture was added 1-acetyl-1,2,3,4-tetrahydroquinoline (2.00 g, 11.41 mmol) in portions over 5 mins. The mixture was stirred for 10

To a 500 mL round-bottomed flask equipped with condenser and argon inlet were added aluminum chloride (3.15 g, 23.62 mmol), carbon disulfide (25 mL), and chloroacetyl chloride (0.92 g, 8.10 mmol) under ice-bath. The mixture was stirred for 15 mins. To the stirring mixture was added 3,4-dihydro-2(H)-quinolinone (1.00 g, 6.75 mmol) in portions over 5 mins. The mixture was stirred for 10 minutes prior to reflux for 2.5 hours. The reaction mixture was cooled and the solvent was decanted off. Then ice and cold water (25 mL) was slowly added while stirred thoroughly. The beige precipitate filtered, washed with water (3×50 mL) followed by tetrahydrofuran (2×100 mL) and hexanes (1×200 mL). The solid was dried under vacuum to give 6-(2-chloroacetyl)-3,4-dihydroquinazolin-2(1H)-one (1.42 g, 94%) as a beige solid. $^1$H NMR (400 MHz, DMSO-d): δ 9.50 (s, 1H), 7.78 (dd, 1H, J=8.8, 1.6 Hz), 7.76 (s, 1H), 7.04 (s, 1H), 6.85 (d, 1H, J=8.0 Hz), 5.04 (s, 2H), 4.38 (s, 2H). MS (ESI): Calcd. for $C_{10}H_9ClN_2O_2$: 224, found 225 (M+1)$^+$.

Intermediate 17

To a 500 mL round-bottomed flask equipped with condenser and argon inlet were added aluminum chloride (1.35 g, 10.10 mmol), carbon disulfide (15 mL), and chloroacetyl chloride (0.39 g, 3.46 mmol) under ice-bath. The mixture was stirred for 15 mins. To the stirring mixture was added 1,2,5,6-tetrahydro-4H-pyrrolo[3,2,1-ij]quinolin-4-one (0.50 g, 3.46 mmol) in portions over 5 mins. The mixture was stirred for 10 minutes prior to reflux for 2.5 hours. The reaction mixture was cooled and the solvent was decanted off. Then ice and cold water (10 mL) was slowly added while stirred thoroughly. The beige precipitate filtered, washed with water (3×50 mL) followed by tetrahydrofuran (2×100 mL) and hexanes (1×200 mL). The solid was dried under vacuum to give 8-(2-chloroacetyl)-1,2,5,6-tetrahydro-4H-pyrrolo[3,2,1-ij]quinolin-4-one (0.71 g, 98%) as a beige solid. $^1$H NMR (400 MHz, DMSO-d): δ 7.74 (s, 2H), 5.07 (s, 2H), 3.99 (t, 2H, J=8.8 Hz), 3.20 (t, 2H, J=8.8 Hz), 2.98 (t, 2H, J=7.6 Hz), 2.60 (t, 2H, J=7.6 Hz). MS (ESI): Calcd. for $C_{13}H_{12}ClNO_2$: 249, found 250 (M+1)$^+$.

Intermediate 18

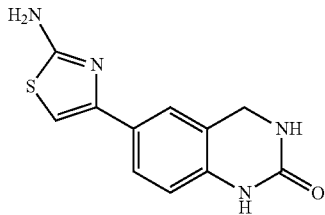 [SMILES: Nc1nc(-c2ccc3c(c2)CNC(=O)N3)cs1]

6-(2-chloroacetyl)-3,4-dihydroquinazolin-2(1H)-one (0.50 g, 2.23 mmol), thiourea (0.178 g, 2.34 mmol) and triethylamine (0.46 mL, 3.34 mmol) suspended in anhydrous ethanol (12 ml) under argon atmosphere. The sealed tube was microwaved at 120° C. for 35 min. The brown precipitate was collected by filtration and washed with cold ethanol. The residue was purified by precipitating in diethyl ether and filtration to give 6-(2-aminothiazol-4-yl)-3,4-dihydroqui- nazolin-2(1H)-one (0.529 g, 96%) as a light brown solid. $^1$H NMR (400 MHz, DMSO-d): δ 9.06 (s, 1H), 7.53 (d, 1H, J=8.4 Hz), 7.50 (s, 1H), 6.97 (s, 2H), 6.81 (s, 1H), 6.77 (s, 1H), 6.73 (d, 1H, J=8.4 Hz), 4.33 (s, 2H). MS (ESI): Calcd. for $C_{11}H_{10}N_4OS$: 246, found 247 (M+1)$^+$.

Intermediate 19

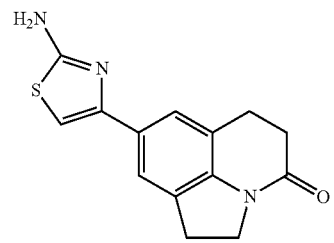 [SMILES: Nc1nc(-c2cc3c4c(c2)CCN4C(=O)CC3)cs1]

8-(2-chloroacetyl)-5,6-dihydro-1H-pyrrolo[3,2,1-ij]qui- nolin-4(2H)-one (0.30 g, 1.20 mmol), thiourea (0.10 g, 1.26 mmol) and triethylamine (0.25 mL, 1.80 mmol) suspended in anhydrous ethanol (12 ml) in a sealed tube under argon atmosphere. The sealed tube was microwaved at 120° C. for 35 min. The brown precipitate was collected by filtration and washed with cold ethanol. The residue was purified by precipitating in diethyl ether and filtration to give 8-(2-aminothiazol-4-yl)-1,2,5,6-tetrahydro-4H-pyrrolo[3,2,1-ij] quinolin-4-one (0.296 g, 91%) as a brown solid. $^1$H NMR (400 MHz, DMSO-d): δ 7.51 (d, 1H, J=8.4 Hz), 6.96 (s, 2H), 6.82 (s, 1H), 3.95 (t, 2H, J=8.8 Hz), 3.14 (t, 2H, J=8.8 Hz), 2.92 (t, 2H, J=7.6 Hz), 2.55 (t, 2H, J=7.6 Hz). MS (ESI): Calcd. for $C_{14}H_{13}N_3OS$: 271, found 272 (M+1)$^+$.

Intermediate 20

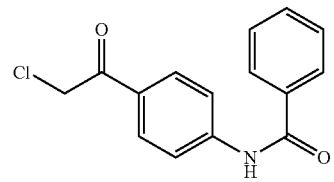 [SMILES: O=C(CCl)c1ccc(NC(=O)c2ccccc2)cc1]

To a 500 mL round-bottomed flask equipped with condenser and argon inlet were added aluminum chloride (7.10 g, 53.24 mmol), carbon disulfide (60 mL), and chloroacetyl chloride (2.06 g, 18.25 mmol) under ice-bath. The mixture was stirred for 15 mins. To the stirring mixture was added benzanilide (3.00 g, 15.21 mmol) in portions over 5 mins. The mixture was stirred for 10 minutes prior to reflux for 2.5 hours. The reaction mixture was cooled and the solvent was decanted off. Then ice and cold water (100 mL) was slowly added while stirred thoroughly. The beige precipitate filtered and washed with water (3×100 mL). The residue was purified by precipitating in diethyl ether and filtration to N-(4-(2-chloroacetyl)phenyl)benzamide (3.75 g, 90%) as a grey solid. $^1$H NMR (400 MHz, DMSO-d): δ 10.60 (s, 1H), 7.99 (m, 6H), 7.62 (m, 1H), 7.56 (m, 2H), 5.15 (s, 2H). MS (ESI): Calcd. for $C_{15}H_{12}ClNO_2$: 273, found 274 (M+1)$^+$.

Intermediate 21

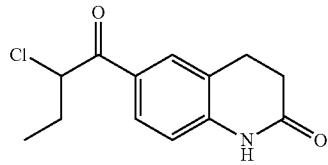 [SMILES: CCC(Cl)C(=O)c1ccc2c(c1)CCC(=O)N2]

To a 500 mL round-bottomed flask equipped with condenser and argon inlet were added aluminum chloride (3.17 g, 23.78 mmol), carbon disulfide (20 mL), and 2-chlorobutyryl chloride (85% tech., 1.53 g, 10.87 mmol) under ice-bath. The mixture was stirred for 15 mins. To the stirring mixture was added 3,4-dihydro-2(H)-quinolinone (1.00 g, 6.79 mmol) in one portion. The mixture was stirred for 10 minutes prior to reflux for 2.5 hours. The reaction mixture was cooled and the solvent was decanted off. Then ice and cold water (30 mL) was slowly added while stirred thoroughly. The beige precipitate filtered, washed with water (3×50 mL). The residue was purified by precipitating in diethyl ether and filtration to 6-(2-chlorobutanoyl)-3,4-dihydroquinolin-2(1H)-one (0.81 g, 48%) as a beige solid. $^1$H NMR (400 MHz, DMSO-d): δ 10.30 (s, 1H), 7.47 (s, 1H), 7.44 (dd, 1H, J=8.8, 1.6 Hz), 6.95 (d, 1H, J=8.0 Hz), 2.97 (t, 1H, J=7.2 Hz), 2.91 (t, 2H, J=7.6 Hz), 2.49 (partial masked under d-DMSO, m, 3H), 2.45 (t, 2H, J=7.2 Hz). MS (ESI): Calcd. for $C_{13}H_{14}ClNO_2$: 251, found 252 (M+1)$^+$.

Intermediate 22

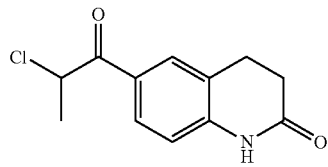 [SMILES: CC(Cl)C(=O)c1ccc2c(c1)CCC(=O)N2]

To a 500 mL round-bottomed flask equipped with condenser and argon inlet were added aluminum chloride (3.17 g, 23.78 mmol), carbon disulfide (20 mL), and 2-chloropropionyl chloride (1.04 g, 8.15 mmol) under ice-bath. The mixture was stirred for 15 mins. To the stirring mixture was added 3,4-dihydro-2(H)-quinolinone (1.00 g, 6.79 mmol) in one portion. The mixture was stirred for 10 minutes prior to reflux for 2.5 hours. The reaction mixture was cooled and the solvent was decanted off. Then ice and cold water (30 mL) was slowly added while stirred thoroughly. The beige precipitate filtered, washed with water (3×50 mL). The residue was purified by precipitating in diethyl ether and filtration to 6-(2-chloropropanoyl)-3,4-dihydroquinolin-2(1H)-one (1.47 g, 91%) as a beige solid. $^1$H NMR (400 MHz, DMSO-d): δ 10.48 (s, 1H), 7.89-7.84 (m, 2H), 6.96 (d, 1H, J=8.4 Hz), 5.70 (q, 1H, J=6.8 Hz), 2.96 (t, 2H, J=7.6 Hz), 2.50 (partial masked under d-DMSO, m, 2H), 1.59 (2, 3H, J=6.8 Hz). MS (ESI): Calcd. for $C_{12}H_{12}ClNO_2$: 237, found 238 (M+1)$^+$.

Intermediate 23

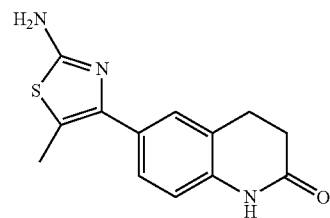 [SMILES: Cc1sc(N)nc1-c1ccc2c(c1)CCC(=O)N2]

6-(2-chloropropanoyl)-3,4-dihydroquinolin-2(1H)-one (1.00 g, 4.21 mmol), thiourea (0.35 g, 4.63 mmol) and triethylamine (0.88 mL, 6.31 mmol) suspended in anhydrous ethanol (12 ml) in a sealed tube under argon atmosphere. The sealed tube was microwaved at 120° C. for 45 min. The brown precipitate was collected by filtration and washed with cold ethanol. The residue was purified by precipitating in diethyl ether and filtration to 6-(2-amino-5-methylthiazol-4-yl)-3,4-dihydroquinolin-2(1H)-one (0.92 g, 84%) as a yellow solid. $^1$H NMR (400 MHz, DMSO-d): δ 10.11 (s, 1H), 7.37 (s, 1H), 7.32 (dd, 1H, J=8.4, 2.0 Hz), 6.84 (d, 1H, J=8.0 Hz), 6.70 (s, 2H), 2.89 (t, 2H, J=7.2 Hz), 2.46 (t, 2H, J=7.6 Hz), 2.30 (s, 3H). MS (ESI): Calcd. for $C_{13}H_{13}N_3OS$: 259, found 260 (M+1)$^+$.

Intermediate 24

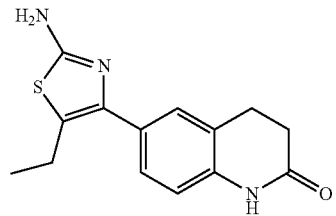 [SMILES: CCc1sc(N)nc1-c1ccc2c(c1)CCC(=O)N2]

6-(2-chlorobutanoyl)-3,4-dihydroquinolin-2(1H)-one (0.80 g, 3.18 mmol), thiourea (0.25 g, 3.34 mmol) and triethylamine (0.66 mL, 4.77 mmol) suspended in anhydrous ethanol (12 ml) in a sealed tube under argon atmosphere. The sealed tube was microwaved at 120° C. for 45 min. The brown precipitate was collected by filtration and washed with cold ethanol. The residue was dried loaded onto silica and purified by flash chromatography over silica gel with $CH_2Cl_2$:MeOH (95:5) to give 6-(2-amino-5-ethylthiazol-4-yl)-3,4-dihydroquinolin-2(1H)-one (0.27 g, 29%) as a light brown solid. $^1$H NMR (400 MHz, DMSO-d): δ 10.11 (s, 1H), 7.30 (s, 1H), 7.26 (dd, 1H, J=8.4, 2.0 Hz), 6.84 (d, 1H, J=8.0 Hz), 6.72 (s, 2H), 2.89 (m, 2H), 2.71 (q, 2H, J=8.0 Hz), 2.46 (t, 2H, J=8.4 Hz), 1.16 (t, 3H, J=7.6 Hz). MS (ESI): Calcd. for $C_{14}H_{15}N_3OS$: 273, found 274 (M+1)$^+$.

Intermediate 25

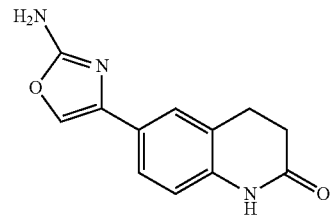 [SMILES: Nc1nc(-c2ccc3c(c2)CCC(=O)N3)co1]

6-(Chloroacetyl)-3,4-dihydroquinolin-2(1H)-one (0.300 g, 1.34 mmol) and urea (1.61 g, 26.82 mmol) dissolve in anhydrous acetonitrile (30 ml) in a flask under argon atmosphere. The mixture refluxed for 15 days. After cooling, the precipitate was filtered away and the filtrate was extracted with 8:2 dichloromethane/isopropanol (3×20 mL) over sat. NaHCO₃ (2×50 mL). The combined organic layers were dried over anhydrous Na₂SO₄ and concentrated in vacuo. The residue was purified by flash chromatography over silica gel using 95:5 dichloromethane/methanol to give 6-(2-aminooxazol-4-yl)-3,4-dihydroquinolin-2(1H)-one (0.058 g, 19%) as a peach solid. ¹H NMR (400 MHz, DMSO-d): δ 10.10 (s, 1H), 7.74 (s, 1H), 7.43 (s, 1H), 7.39 (dd, 1H, J=8.0, 1.6 Hz), 6.82 (d, 1H, J=8.4 Hz), 6.65 (s, 2H), 2.87 (t, 2H, J=7.6 Hz), 2.45 (partial masked under d-DMSO, t, 2H, J=7.2 Hz). MS (ESI): Calcd. for $C_{12}H_{11}N_3O_2$: 229, found 230 (M+1)⁺.

Intermediate 26

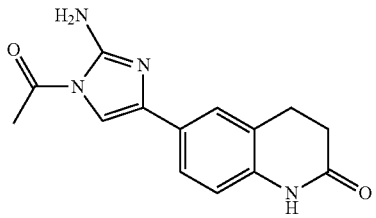 [SMILES: CC(=O)n1cc(-c2ccc3c(c2)CCC(=O)N3)nc1N]

6-(Chloroacetyl)-3,4-dihydroquinolin-2(1H)-one (0.500 g, 2.24 mmol) and N-acetylguanidine (0.678 g, 6.71 mmol) suspended in anhydrous acetonitrile (15 ml) in a sealed tube under argon atmosphere. The sealed tube was microwaved at 100° C. for 120 min. The precipitate was filtered out and the filtrate residue was purified by flash chromatography over silica gel using 95:5 dichloromethane/methanol to give 6-(1-acetyl-2-amino-1H-imidazol-4-yl)-3,4-dihydroquinolin-2(1H)-one (0.044 g, 7%) as a yellow solid. ¹H NMR (400 MHz, DMSO-d): δ 11.52 (s, 1H), 11.19 (s, 1H), 10.04 (s, 1H), 8.71 (br s, 2H), 7.51 (s, 1H), 7.46 (dd, 1H, J=8.4, 1.6 Hz), 7.12 (d, 1H, J=1.6 Hz), 6.79 (d, 1H, J=8.0 Hz), 2.87 (m, 2H), 2.45 (m, 2H), 2.06 (s, 3H). MS (ESI): Calcd. for $C_{14}H_{14}N_4O_2$: 270, found 271 (M+1)⁺.

Intermediate 27

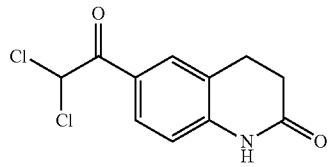 [SMILES: O=C1CCc2cc(C(=O)C(Cl)Cl)ccc2N1]

To a 500 mL round-bottomed flask equipped with condenser and argon inlet were added aluminum chloride (19.02 g, 142.69 mmol), carbon disulfide (100 mL), and dichloroacetyl chloride (7.21 g, 48.92 mmol) under ice-bath. The mixture was stirred for 15 mins. To the stirring mixture was added 3,4-dihydro-2(H)-quinolinone (6.00 g, 40.77 mmol) in one portion. The mixture was stirred for 15 minutes prior to reflux for 3 hours. The reaction mixture was cooled and the solvent was decanted off. Then ice and cold water (250 mL) was slowly added while stirred thoroughly. The beige precipitate filtered and washed with water (3×100 mL). The residue was purified by precipitating in diethyl ether and filtration to give 6-(2,2-dichloroacetyl)-3,4-dihydroquinolin-2(1H)-one (9.54 g, 91%) as a light brown solid. ¹H NMR (400 MHz, DMSO-d): δ 10.56 (bs, 1H), 7.93 (bs, 1H), 7.90 (dd, 1H, J=8.4, 1.6 Hz), 7.82 (s, 1H), 6.98 (d, 1H, J=8.4 Hz), 2.97 (m, 2H), 2.53 (partial masked under d-DMSO, m, 2H). MS (ESI): Calcd. for $C_{11}H_9Cl_2NO_2$: 258, found 258 (M)⁺.

Intermediate 28

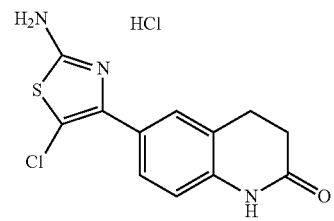 [SMILES: Nc1nc(-c2ccc3c(c2)CCC(=O)N3)c(Cl)s1 ; Cl]

6-(2,2-dichloroacetyl)-3,4-dihydroquinolin-2(1H)-one (1.00 g, 3.87 mmol) and thiourea (0.310 g, 4.07 mmol) suspended in anhydrous acetonitrile (12 ml) in a sealed under argon atmosphere. The sealed tube was heated at 45° C. for 4 days. The yellow precipitate was collected by filtration and washed with cold ethanol. The solid was dried in vacuo to give 6-(2-amino-5-chlorothiazol-4-yl)-3,4-dihydroquinolin-2(1H)-one hydrochloride (0.90 g, 74%) as a yellow solid. ¹H NMR (400 MHz, DMSO-d): δ 10.22 (s, 1H), 7.61 (s, 1H), 6.89 (d, 1H, J=8.4 Hz), 6.30 (bs, 2H), 2.91 (m, 2H), 2.47 (partial masked under d-DMSO, m, 2H). MS (ESI): Calcd. for $C_{12}H_{11}Cl_2N_3OS$: 316, found 280 (M+1-HCl)⁺.

EXEMPLARY COMPOUNDS

Example 1

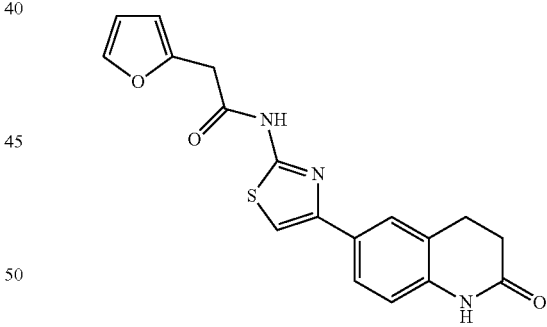

Step 1: Preparation of furan-2-yl-acetyl chloride: Oxalyl chloride (10.5 mL, 124.22 mmol), was added dropwise to a solution of furan-2-yl-acetic acid (0.500 g, 1.77 mmol) in dichloromethane (40 mL) at 0° C., followed by the addition of DMF (1 drop) and the mixture was stirred overnight (15 hrs). The reaction mixture was concentrated in vacuo and the residue was used without further purification.

Step 2: 6-(2-aminothiazol-4-yl)-3,4-dihydroquinolin-2(1H)-one was dissolved in 1:1 acetonitrile/pyridine mixture (10 mL/10 mL) and excess triethylamine (4 mL) was added. The mixture was cool under ice-bath and a solution of furan-2-yl-acetyl chloride in acetonitrile (5 mL) was slowly added. The mixture was then stirred at room temperature overnight (15 hrs). The reaction was quenched with water (20 mL) and concentrated to minimum. The crude was extracted with 8:2 dichloromethane/isopropanol (2×400 mL) mixtures, washed with sat. NH₄Cl (2×400 mL), and dried over anhydrous Na₂SO₄. The concentrated residue was then purified by flash chromatography over silica with CH₂Cl₂/MeOH (95:5). The solid was then sonicated in minimum amount of dichloromethane and the precipitated solid was collected by filtration to give 2-(furan-2-yl)-N-(4-(2-oxo-1,2,3,4-tetrahydroquinolin-6-yl)thiazol-2-yl)acetamide (0.423 g, 68%) as a beige solid. ¹H NMR (400 MHz, DMSO-d): δ 12.46 (bs, 1H), 10.18 (s, 1H), 7.70 (s, 1H), 7.66 (dd, 1H, J=8.8, 1.6 Hz), 7.58 (bs, 1H), 7.46 (bs, 1H), 6.88 (d, 1H, J=8.8 Hz), 6.41 (m, 1H), 6.31 (m, 1H), 3.88 (s, 2H), 2.92 (m, 2H), 2.48 (partial masked under d-DMSO, m, 2H). MS (ESI): Calcd. for $C_{18}H_{15}N_3O_3S$: 353, found 354 (M+1)⁺.

Example 2

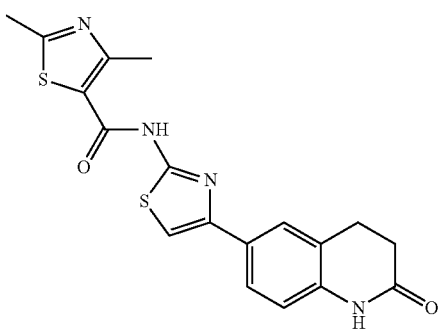 [SMILES: Cc1nc(C)c(C(=O)Nc2nc(-c3ccc4c(c3)CCC(=O)N4)cs2)s1]

To a suspension of 6-(2-aminothiazol-4-yl)-3,4-dihydroquinolin-2(1H)-one (0.050 g, 0.203 mmol) and 2,4-dimethylthiazole-5-carboxylic acid (0.035 g, 0.224 mmol), and pyridine (0.06 mL, 0.713 mmol) in acetonitrile (2 mL) in a sealed tube was added propylphosphonic anhydride solution (50 wt % in ethyl acetate, 0.29 mL, 0.489 mmol). The sealed tube was heated to 48.5° C. for 4 days and the precipitation formed. After cooling, the solid was collected by filtration and washed with cold dichloromethane to give 2,4-dimethyl-N-(4-(2-oxo-1,2,3,4-tetrahydroquinolin-6-yl)thiazol-2-yl)thiazole-5-carboxamide (0.045 g, 58%) as a beige solid. ¹H NMR (400 MHz, DMSO-d): δ 12.58 (bs, 1H), 10.18 (s, 1H), 7.74 (s, 1H), 7.69 (dd, 1H, J=8.4, 1.6 Hz), 7.45 (bs, 1H), 6.88 (d, 1H, J=8.4 Hz), 2.93 (m, 2H), 2.66 (s, 3H), 2.61 (s, 3H), 2.48 (partial masked under d-DMSO, m, 2H). MS (ESI): Calcd. for $C_{18}H_{16}N_4O_2S_2$: 384, found 385 (M+1)⁺.

Example 3

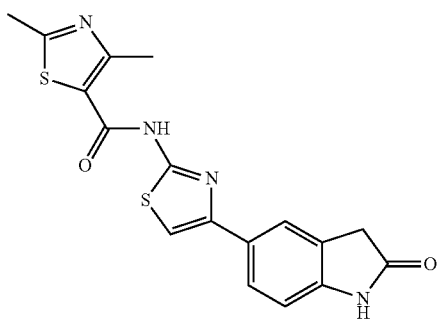 [SMILES: Cc1nc(C)c(C(=O)Nc2nc(-c3ccc4c(c3)CC(=O)N4)cs2)s1]

To a suspension of 5-(2-aminothiazol-4-yl)indolin-2-one (0.050 g, 0.203 mmol) and 2,4-dimethylthiazole-5-carboxylic acid (0.035 g, 0.224 mmol), and pyridine (0.06 mL, 0.713 mmol) in acetonitrile (2 mL) in a sealed tube was added propylphosphonic anhydride solution (50 wt % in ethyl acetate, 0.29 mL, 0.489 mmol). The sealed tube was heated to 48.5° C. for 4 days and the precipitation formed. After cooling, the solid was collected by filtration and washed with cold dichloromethane to give 2,4-dimethyl-N-(4-(2-oxoindolin-5-yl)thiazol-2-yl)thiazole-5-carboxamide (0.045 g, 58%) as a beige solid. ¹H NMR (400 MHz, DMSO-d): δ 12.53 (bs 1H), 10.48 (s, 1H), 7.77 (m, 2H), 7.48 (s, 1H), 6.86 (d, 1H, J=8.8 Hz), 3.54 (s, 2H), 2.67 (s, 3H), 2.61 (s, 3H). MS (ESI): Calcd. for $C_{17}H_{14}N_4O_2S_2$: 370, found 371 (M+1)⁺.

Example 4

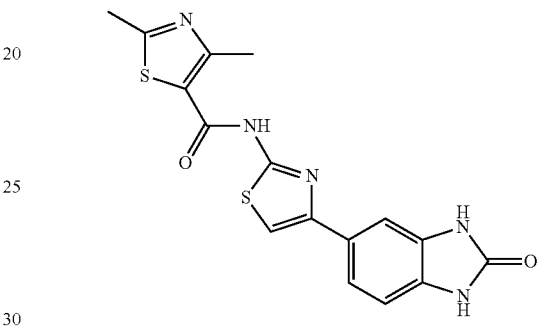

To a suspension of 5-(2-aminothiazol-4-yl)-1H-benzo[d]imidazol-2(3H)-one (0.200 g, 0.861 mmol) and 2,4-dimethylthiazole-5-carboxylic acid (0.149 g, 0.947 mmol), and pyridine (0.31 mL, 3.872 mmol) in acetonitrile (4 mL) in a sealed tube was added propylphosphonic anhydride solution (50 wt % in ethyl acetate, 1.790 mL, 3.012 mmol). The sealed tube was heated to 48.5° C. for 4 days. After cooling, the mixture was quenched with water (50 mL) and extracted with 8:2 dichloromethane/isopropanol (2×50 mL) followed by washing once with sat. NaHCO₃ (200 mL). The combined organic layers were dried over anhydrous Na₂SO₄ and concentrated in vacuo. The residue was purified by precipitating in dichloromethane and filtration to give 2,4-dimethyl-N-(4-(2-oxo-2,3-dihydro-1H-benzo[d]imidazol-5-yl)thiazol-2-yl)thiazole-5-carboxamide (0.035 g, 11%) as a beige solid. ¹H NMR (400 MHz, DMSO-d): δ 12.55 (bs, 1H), 10.76 (s, 1H), 10.70 (s, 1H), 7.51 (m, 3H), 6.96 (d, 1H, J=8.4 Hz), 2.67 (s, 3H), 2.61 (s, 3H). MS (ESI): Calcd. for $C_{16}H_{13}N_5O_2S_2$: 371, found 372 (M+1)⁺.

Example 5

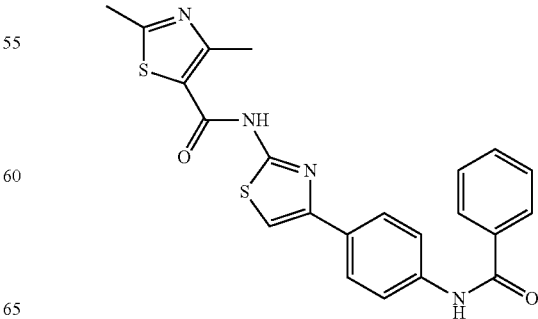

To a suspension of N-(4-(2-aminothiazol-4-yl)phenyl)benzamide (0.041 g, 0.138 mmol) and 2,4-dimethylthiazole-5-carboxylic acid (0.024 g, 0.152 mmol), and pyridine (0.01 mL, 0.623 mmol) in acetonitrile (1.5 mL) in a sealed tube was added propylphosphonic anhydride solution (50 wt % in ethyl acetate, 0.29 mL, 0.485 mmol). The sealed tube was heated to 48.5° C. for 4 days. After cooling, the mixture was quenched with water (10 mL) and extracted with 8:2 dichloromethane/isopropanol (2×25 mL) followed by washing once with sat. NaHCO$_3$ (100 mL). The combined organic layers were dried over anhydrous Na$_2$SO$_4$ and concentrated in vacuo. The residue was purified by precipitating in dichloromethane and filtration to give N-(4-(4-benzamidophenyl)thiazol-2-yl)-2,4-dimethylthiazole-5-carboxamide (0.029 g, 48%) as a beige solid. $^1$H NMR (400 MHz, DMSO-d): δ 10.34 (s, 1H), 7.96 (d, 2H, J=7.2 Hz), 7.89 (m, 4H), 7.57 (m, 4H), 2.67 (s, 3H), 2.62 (s, 3H). MS (ESI): Calcd. for C$_{22}$H$_{18}$N$_4$O$_2$S$_2$: 434, found 435 (M+1)$^+$.

Example 6

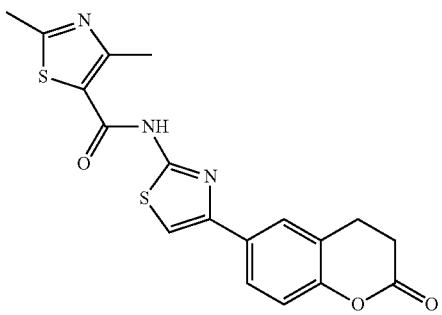 [SMILES: Cc1nc(C)c(C(=O)Nc2nc(-c3ccc4c(c3)CCC(=O)O4)cs2)s1]

To a suspension of 6-(2-aminothiazol-4-yl)chroman-2-one (0.100 g, 0.406 mmol) and 2,4-dimethylthiazole-5-carboxylic acid (0.070 g, 0.447 mmol), and pyridine (0.15 mL, 1.831 mmol) in acetonitrile (4 mL) in a sealed tube was added propylphosphonic anhydride solution (50 wt % in ethyl acetate, 0.95 mL, 1.421 mmol). The sealed tube was heated to 48.5° C. for 5 days. After cooling, the mixture was quenched with water (50 mL) and extracted with 8:2 dichloromethane/isopropanol (2×50 mL) followed by washing once with sat. NaHCO$_3$ (100 mL). The combined organic layers were dried over anhydrous Na$_2$SO$_4$ and concentrated in vacuo. The residue was purified by precipitating in 1:3 dichloromethane/diethyl ether mixture and filtration to give 2,4-dimethyl-N-(4-(2-oxochroman-6-yl)thiazol-2-yl)thiazole-5-carboxamide (0.106 g, 67%) as a beige solid. $^1$H NMR (400 MHz, DMSO-d): δ 12.59 (bs, 1H), 7.86 (d, 1H, J=1.6 Hz), 7.82 (dd, 1H, J=8.4, 1.6 Hz), 7.64 (s, 1H), 7.12 (d, 1H, J=8.4 Hz), 3.05 (t, 2H, J=7.2 Hz), 2.83 (t, 2H, J=7.2 Hz), 2.68 (s, 3H), 2.61 (s, 3H). MS (ESI): Calcd. for C$_{18}$H$_{15}$N$_3$O$_3$S$_2$: 385, found 386 (M+1)$^+$.

Example 7

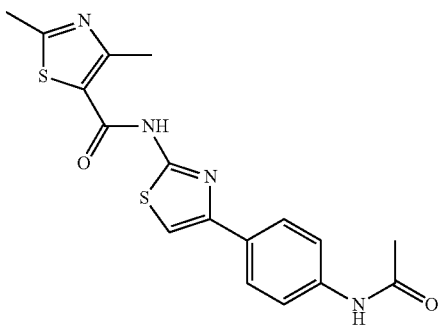 [SMILES: CC(=O)Nc1ccc(-c2csc(NC(=O)c3sc(C)nc3C)n2)cc1]

To a suspension of N-(4-(2-aminothiazol-4-yl)phenyl)acetamide (0.200 g, 0.857 mmol) and 2,4-dimethylthiazole-5-carboxylic acid (0.184 g, 0.943 mmol), and pyridine (0.31 mL, 3.862 mmol) in acetonitrile (8 mL) in a sealed tube was added propylphosphonic anhydride solution (50 wt % in ethyl acetate, 1.79 mL, 3.001 mmol). The sealed tube was heated to 48.5° C. for 5 days. After cooling, the mixture was quenched with water (100 mL) and extracted with 8:2 dichloromethane/isopropanol (2×100 mL) followed by washing once with sat. NaHCO$_3$ (200 mL). The combined organic layers were dried over anhydrous Na$_2$SO$_4$ and concentrated in vacuo. The residue was purified by precipitating in dichloromethane and filtration to give N-(4-(4-acetamidophenyl)thiazol-2-yl)-2,4-dimethylthiazole-5-carboxamide (0.141 g, 44%) as a beige solid. $^1$H NMR (400 MHz, DMSO-d): δ 10.02 (s, 1H), 7.84 (d, 2H, J=8.4 Hz), 7.64 (d, 2H, J=8.4 Hz), 7.54 (s, 1H), 2.67 (s, 3H), 2.61 (s, 3H), 2.06 (s, 3H). MS (ESI): Calcd. for C$_{17}$H$_{16}$N$_4$O$_2$S$_2$: 372, found 373 (M+1)$^+$.

Example 8

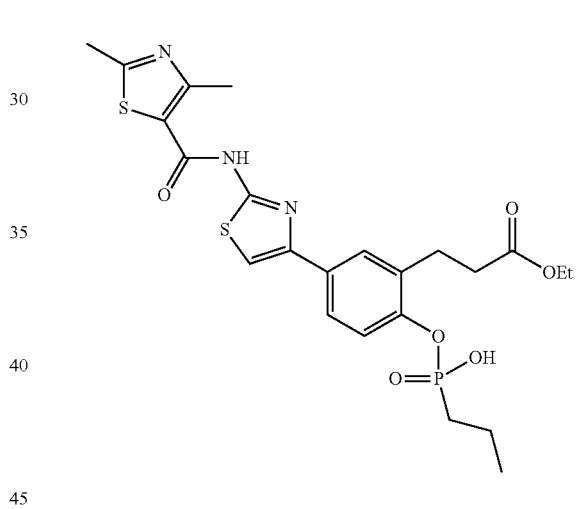

To a suspension of ethyl 3-(5-(2-aminothiazol-4-yl)-2-hydroxyphenyl)propanoate (0.100 g, 0.342 mmol) and 2,4-dimethylthiazole-5-carboxylic acid (0.059 g, 0.376 mmol), and pyridine (0.12 mL, 1.541 mmol) in acetonitrile (4 mL) in a sealed tube was added propylphosphonic anhydride solution (50 wt % in ethyl acetate, 0.71 mL, 1.201 mmol). The sealed tube was heated to 48.5° C. for 5 days. After cooling, the mixture was quenched with water (50 mL) and extracted with 8:2 dichloromethane/isopropanol (2×50 mL) followed by washing once with sat. NaHCO$_3$ (100 mL). The combined organic layers were dried over anhydrous Na$_2$SO$_4$ and concentrated in vacuo. The residue was purified by precipitating in 1:3 dichloromethane/diethyl ether mixture and filtration to give ethyl 3-(5-(2-(2,4-dimethylthiazole-5-carboxamido)thiazol-4-yl)-2-((hydroxy(propyl)phosphoryl)oxy)phenyl)propanoate (0.028 g, 15%) as an orange solid after dried under high vacuum. $^1$H NMR (400 MHz, DMSO-d): δ 7.82-7.10 (m, 6H), 4.05 (q, 2H, J=7.2 Hz), 2.89 (m, 2H), 2.67 (s, 3H), 2.61 (s, 3H), 1.75-1.30 (m, 6H), 1.16 (t, 3H, J=7.2 Hz), 0.96 (t, 3H, J=7.2 Hz). MS (ESI): Calcd. for C$_{23}$H$_{28}$N$_3$O$_6$PS$_2$: 537, found 538 (M+1)$^+$.

Example 9

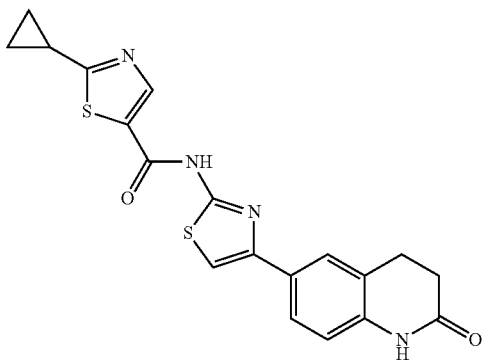 [SMILES: O=C1CCc2cc(-c3csc(NC(=O)c4cnc(C5CC5)s4)n3)ccc2N1]

To a suspension of 6-(2-aminothiazol-4-yl)-3,4-dihydroquinolin-2(1H)-one (0.100 g, 0.408 mmol) and 2-cyclopropyl-1,3-thiazole carboxylic acid (0.076 g, 0.448 mmol), and pyridine (0.15 mL, 1.832 mmol) in acetonitrile (4 mL) in a sealed tube was added propylphosphonic anhydride solution (50 wt % in ethyl acetate, 0.85 mL, 1.432 mmol). The sealed tube was heated to 48.5° C. for 4 days and the precipitation formed. After cooling, the the precipitated solid was collected by filtration and washed with cold dichloromethane to give 2-cyclopropyl-N-(4-(2-oxo-1,2,3,4-tetrahydroquinolin-6-yl)thiazol-2-yl)thiazole-5-carboxamide (0.111 g, 69%) as a beige solid. $^1$H NMR (400 MHz, DMSO-d): δ 12.9 (bs, 1H), 10.19 (s, 1H), 8.65 (s, 1H), 7.75 (s, 1H), 7.70 (dd, 1H, J=8.0, 1.6 Hz), 7.51 (s, 1H), 6.89 (1H, d, J=8.4 Hz), 2.93 (t, 2H, J=6.8 Hz), 2.49 (partial masked under d-DMSO, m, 2H), 2.07 (s, 1H), 1.19 (m, 2H), 1.08 (m, 2H). MS (ESI): Calcd. for $C_{19}H_{16}N_4O_2S_2$: 396, found 397 (M+1)$^+$.

Example 10

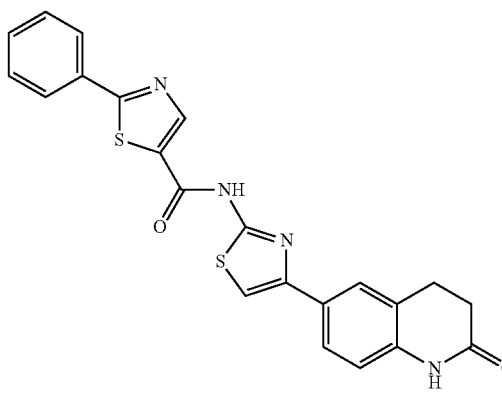

To a suspension of 6-(2-aminothiazol-4-yl)-3,4-dihydroquinolin-2(1H)-one (0.100 g, 0.408 mmol) and 2-phenylthiazole-5-carboxylic acid (0.092 g, 0.448 mmol), and pyridine (0.15 mL, 1.832 mmol) in acetonitrile (4 mL) in a sealed tube was added propylphosphonic anhydride solution (50 wt % in ethyl acetate, 0.85 mL, 1.432 mmol). The sealed tube was heated to 48.5° C. for 4 days and the precipitation formed. After cooling, the precipitated solid was collected by filtration and washed with cold dichloromethane to give N-(4-(2-oxo-1,2,3,4-tetrahydroquinolin-6-yl)thiazol-2-yl)-2-phenylthiazole-5-carboxamide (0.156 g, 88%) as a beige solid. $^1$H NMR (400 MHz, DMSO-d): δ 13.10 (bs, 1H), 10.20 (s, 1H), 8.93 (s, 1H), 8.05 (m, 2H), 7.77 (s, 1H), 7.72 (dd, 1H, J=8.0, 1.6 Hz), 7.57 (m, 4H), 6.90 (d, 1H, J=8.4 Hz), 2.94 (t, 2H, J=6.8 Hz), 2.50 (masked under d-DMSO, m, 2H). MS (ESI): Calcd. for $C_{22}H_{16}N_4O_2S_2$: 432, found 433 (M+1)$^+$.

Example 11

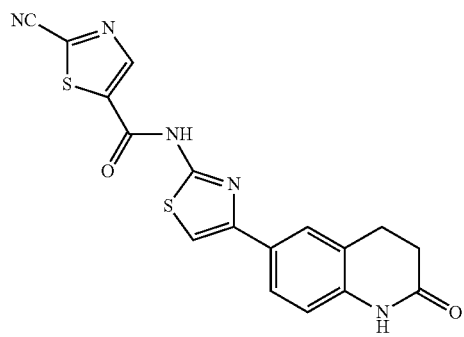 [SMILES: N#Cc1ncc(C(=O)Nc2nc(-c3ccc4c(c3)CCC(=O)N4)cs2)s1]

To a suspension of 6-(2-aminothiazol-4-yl)-3,4-dihydroquinolin-2(1H)-one (0.100 g, 0.408 mmol) and 2-cyano-1,3-thiazole-5-carboxylic acid (0.069 g, 0.448 mmol), and pyridine (0.15 mL, 1.832 mmol) in acetonitrile (4 mL) in a sealed tube was added propylphosphonic anhydride solution (50 wt % in ethyl acetate, 0.85 mL, 1.432 mmol). The sealed tube was heated to 48.5° C. for 4 days and the precipitation formed. After cooling, the precipitated solid was collected by filtration and washed with cold dichloromethane to give 2-cyano-N-(4-(2-oxo-1,2,3,4-tetrahydroquinolin-6-yl)thiazol-2-yl)thiazole-5-carboxamide (0.073 g, 47%) as a yellow solid. $^1$H NMR (400 MHz, DMSO-d): δ 13.43 (bs, 1H), 10.21 (s, 1H), 9.03 (s, 1H), 7.75 (s, 1H), 7.71 (dd, 1H, J=8.0, 1.6 Hz), 7.59 (s, 1H), 6.91 (d, 1H, J=8.4 Hz), 2.94 (t, 2H, J=6.8 Hz), 2.50 (masked under d-DMSO, m, 2H). MS (ESI): Calcd. for $C_{17}H_{11}N_5O_2S_2$: 381, found 382 (M+1)$^+$.

Example 12

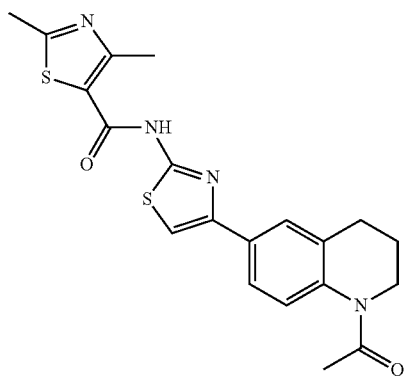 [SMILES: CC(=O)N1CCCc2cc(-c3csc(NC(=O)c4sc(C)nc4C)n3)ccc21]

To a suspension of 1-(6-(2-aminothiazol-4-yl)-3,4-dihydroquinolin-1(2H)-yl)ethanone (0.100 g, 0.366 mmol) and 2,4-dimethylthiazole-5-carboxylic acid (0.063 g, 0.402 mmol), and pyridine (0.13 mL, 1.65 mmol) in acetonitrile (4 mL) in a sealed tube was added propylphosphonic anhydride solution (50 wt % in ethyl acetate, 0.76 mL, 1.281 mmol). The sealed tube was heated to 48.5° C. for 4 days and the precipitation formed. After cooling, the solid was collected by filtration and washed with cold dichloromethane to give N-(4-(1-acetyl-1,2,3,4-tetrahydroquinolin-6-yl)thiazol-2-yl)-2,4-dimethylthiazole-5-carboxamide (0.043 g, 29%) as a beige solid. $^1$H NMR (400 MHz, DMSO-d): δ 12.58 (bs, 1H), 7.75 (s, 1H), 7.70 (dd, 1H, J=8.0, 1.6 Hz), 7.61 (bs, 2H), 3.70 (t, 2H, J=6.4 Hz), 2.77 (t, 2H, J=6.4 Hz), 2.68 (s, 3H), 2.61 (s, 3H), 2.20 (s, 3H0, 1.90 (p, 2H, J=6.4 Hz). MS (ESI): Calcd. for $C_{20}H_{20}N_4O_2S_2$: 412, found 413 (M+1)$^+$.

Example 13

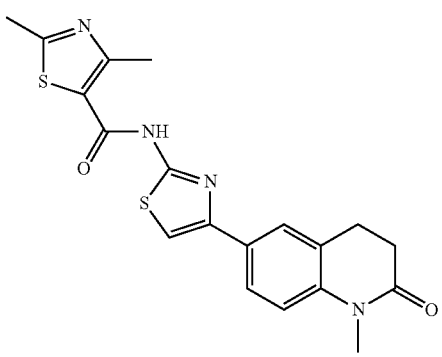 [SMILES: Cc1nc(C)c(C(=O)Nc2nc(-c3ccc4c(c3)CCC(=O)N4C)cs2)s1]

To a suspension of 6-(2-aminothiazol-4-yl)-1-methyl-3,4-dihydroquinolin-2(1H)-one (0.100 g, 0.386 mmol) and 2,4-dimethyl-1,3-thiazole carboxylic acid (0.067 g, 0.424 mmol), and pyridine (0.14 mL, 1.742 mmol) in acetonitrile (4 mL) in a sealed tube was added propylphosphonic anhydride solution (50 wt % in ethyl acetate, 0.80 mL, 1.352 mmol). The sealed tube was heated to 48.5° C. for 4 days. After cooling, the mixture was quenched with water (100 mL) and extracted with 8:2 dichloromethane/isopropanol (2×100 mL) followed by washing once with sat. NaHCO$_3$ (200 mL). The combined organic layers were dried over anhydrous Na$_2$SO$_4$ and concentrated in vacuo. The residue was purified by precipitating in 1:3 dichloromethane/diethyl ether mixture and filtration to give 2,4-dimethyl-N-(4-(1-methyl-2-oxo-1,2,3,4-tetrahydroquinolin-6-yl)thiazol-2-yl)thiazole-5-carboxamide (0.059 g, 39%) as a beige solid. $^1$H NMR (400 MHz, DMSO-d): δ 12.57 (bs, 1H), 7.82 (dd, 1H, J=8.0, 1.6 Hz), 7.79 (s, 1H), 7.56 (s, 1H), 7.15 (d, 1H, J=8.4 Hz), 3.28 (s, 3H), 2.92 (t, 2H, J=6.4 Hz), 2.67 (s, 3H), 2.62 (s, 3H), 2.58 (t, 2H, J=6.4 Hz). MS (ESI): Calcd. for $C_{19}H_{18}N_4O_2S_2$: 398, found 399 (M+1)$^+$.

Example 14

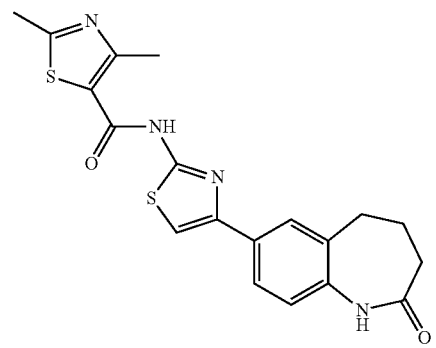 [SMILES: Cc1nc(C)c(C(=O)Nc2nc(-c3ccc4c(c3)CCCC(=O)N4)cs2)s1]

To a suspension of 7-(2-aminothiazol-4-yl)-4,5-dihydro-1H-benzo[b]azepin-2(3H)-one (0.100 g, 0.386 mmol) and 2,4-dimethyl-1,3-thiazole carboxylic acid (0.067 g, 0.424 mmol), and pyridine (0.14 mL, 1.742 mmol) in acetonitrile (4 mL) in a sealed tube was added propylphosphonic anhydride solution (50 wt % in ethyl acetate, 0.80 mL, 1.352 mmol). The sealed tube was heated to 48.5° C. for 4 days. After cooling, the mixture was quenched with water (100 mL) and extracted with 8:2 dichloromethane/isopropanol (2×100 mL) followed by washing once with sat. NaHCO$_3$ (200 mL). The combined organic layers were dried over anhydrous Na$_2$SO$_4$ and concentrated in vacuo. The residue was purified by precipitating in 1:3 dichloromethane/diethyl ether mixture and filtration to give 2,4-dimethyl-N-(4-(2-oxo-2,3,4,5-tetrahydro-1H-benzo[b]azepin-7-yl)thiazol-2-yl)thiazole-5-carboxamide (0.060 g, 39%) as a beige solid. $^1$H NMR (400 MHz, DMSO-d): δ 12.59 (bs, 1H), 9.59 (s, 1H), 7.82 (s, 1H), 7.76 (dd, 1H, J=8.0, 1.6 Hz), 7.59 (s, 1H), 7.01 (d, 1H, J=8.4 Hz), 2.73 (t, 2H, J=6.4 Hz), 2.67 (s, 3H), 2.61 (s, 3H), 2.16 (m, 4H). MS (ESI): Calcd. for $C_{19}H_{18}N_4O_2S_2$: 398, found 399 (M+1)$^+$.

Example 15

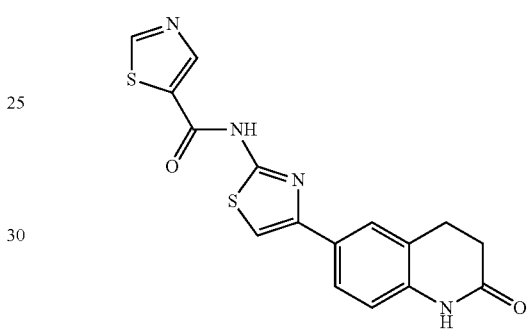

To a suspension of 6-(2-aminothiazol-4-yl)-3,4-dihydroquinolin-2(1H)-one (0.100 g, 0.408 mmol) and 5-thiazole carboxylic acid (0.058 g, 0.448 mmol), and pyridine (0.15 mL, 1.832 mmol) in acetonitrile (4 mL) in a sealed tube was added propylphosphonic anhydride solution (50 wt % in ethyl acetate, 0.85 mL, 1.431 mmol). The sealed tube was heated to 48.5° C. for 4 days and the precipitation formed. After cooling, the solid was collected by filtration and washed with cold dichloromethane to give N-(4-(2-oxo-1,2,3,4-tetrahydroquinolin-6-yl)thiazol-2-yl)thiazole-5-carboxamide (0.132 g, 91%) as a beige solid. $^1$H NMR (400 MHz, DMSO-d): δ 13.01 (bs, 1H), 10.19 (s, 1H), 9.38 (s, 1H), 8.93 (s, 1H), 7.75 (s, 1H), 7.71 (dd, 1H, J=8.4, 1.6 Hz), 7.54 (s, 1H), 6.89 (d, 1H, J=8.4 Hz), 2.93 (m, 2H), 2.48 (partial masked under d-DMSO, m, 2H). MS (ESI): Calcd. for $C_{16}H_{12}N_4O_2S_2$: 356, found 357 (M+1)$^+$.

Example 16

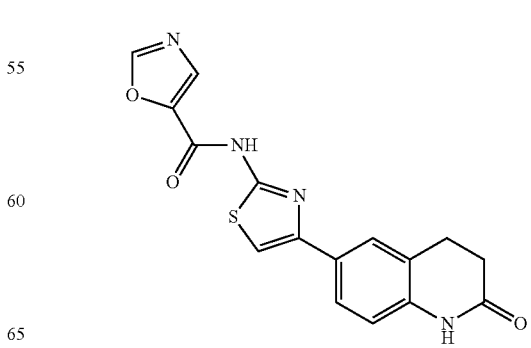

To a suspension of 6-(2-aminothiazol-4-yl)-3,4-dihydroquinolin-2(1H)-one (0.100 g, 0.408 mmol) and oxazole-5-carboxylic acid (0.051 g, 0.448 mmol), and pyridine (0.15 mL, 1.832 mmol) in acetonitrile (4 mL) in a sealed tube was added propylphosphonic anhydride solution (50 wt % in ethyl acetate, 0.85 mL, 1.431 mmol). The sealed tube was heated to 48.5° C. for 4 days and the precipitation formed. After cooling, the solid was collected by filtration and washed with cold dichloromethane to give N-(4-(2-oxo-1,2,3,4-tetrahydroquinolin-6-yl)thiazol-2-yl)oxazole-5-carboxamide (0.121 g, 87%) as a beige solid. $^1$H NMR (400 MHz, DMSO-d): δ 13.03 (bs, 1H), 10.18 (s, 1H), 8.72 (s, 1H), 8.29 (s, 1H), 7.75 (s, 1H), 7.71 (dd, 1H, J=8.4, 1.6 Hz), 7.56 (s, 1H), 6.90 (d, 1H, J=8.4 Hz), 2.93 (m, 2H), 2.48 (partial masked under d-DMSO, m, 2H). MS (ESI): Calcd. for $C_{16}H_{12}N_4O_3S$: 340, found 341 (M+1)$^+$.

Example 17

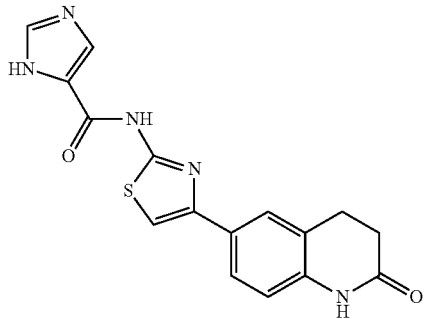 [SMILES: O=C1CCc2cc(-c3csc(NC(=O)c4cnc[nH]4)n3)ccc2N1]

To a suspension of 6-(2-aminothiazol-4-yl)-3,4-dihydroquinolin-2(1H)-one (0.100 g, 0.408 mmol) and 1H-imidazole-4-carboxylic acid (0.050 g, 0.448 mmol), and pyridine (0.15 mL, 1.832 mmol) in acetonitrile (4 mL) in a sealed tube was added propylphosphonic anhydride solution (50 wt % in ethyl acetate, 0.85 mL, 1.431 mmol). The sealed tube was heated to 48.5° C. for 4 days and the precipitation formed. After cooling, the mixture was quenched with water (10 mL) and extracted with 8:2 dichloromethane/isopropanol (2×25 mL) followed by washing once with sat. NaHCO$_3$ (100 mL). The combined organic layers were dried over anhydrous Na$_2$SO$_4$ and concentrated in vacuo. The residue was purified by precipitating in dichloromethane and filtration to give N-(4-(2-oxo-1,2,3,4-tetrahydroquinolin-6-yl)thiazol-2-yl)-1H-imidazole-5-carboxamide (0.013 g, 10%) as a tan solid. $^1$H NMR (400 MHz, DMSO-d): δ 12.73 (bs, 1H), 11.38 (bs, 1H), 10.14 (s, 1H), 8.04 (s, 1H), 7.85 (s, 1H), 7.72 (s, 1H), 7.67 (dd, 1H, J=8.4, 1.6 Hz), 7.44 (s, 1H), 6.85 (d, 1H, J=8.4 Hz), 2.90 (m, 2H), 2.45 (partial masked under d-DMSO, m, 2H). MS (ESI): Calcd. for $C_{16}H_{13}N_5O_2S$: 339, found 340 (M+1)$^+$.

Example 18

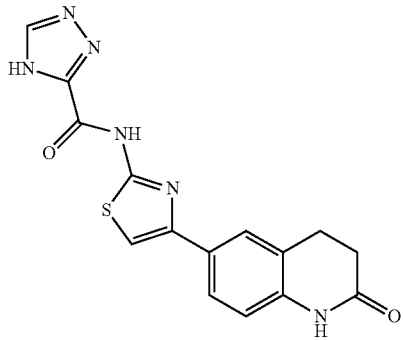 [SMILES: O=C1CCc2cc(-c3csc(NC(=O)c4nnc[nH]4)n3)ccc2N1]

To a suspension of 6-(2-aminothiazol-4-yl)-3,4-dihydroquinolin-2(1H)-one (0.100 g, 0.408 mmol) and 1,2,4-triazole-3-carboxylic acid (0.051 g, 0.448 mmol), and pyridine (0.15 mL, 1.832 mmol) in acetonitrile (4 mL) in a sealed tube was added propylphosphonic anhydride solution (50 wt % in ethyl acetate, 0.85 mL, 1.431 mmol). The sealed tube was heated to 48.5° C. for 4 days and the precipitation formed. After cooling, the solid was collected by filtration and washed with cold dichloromethane to give N-(4-(2-oxo-1,2,3,4-tetrahydroquinolin-6-yl)thiazol-2-yl)-4H-1,2,4-triazole-3-carboxamide (0.099 g, 71%) as a green solid. $^1$H NMR (400 MHz, DMSO-d): δ 12.35 (bs, 1H), 10.17 (s, 1H), 8.74 (s, 1H), 7.76 (s, 1H), 7.71 (dd, 1H, J=8.4, 1.6 Hz), 7.56 (s, 1H), 6.89 (d, 1H, J=8.4 Hz), 2.93 (m, 2H), 2.48 (partial masked under d-DMSO, m, 2H). MS (ESI): Calcd. for $C_{15}H_{12}N_6O_2S$: 340, found 341 (M+1)$^+$.

Example 19

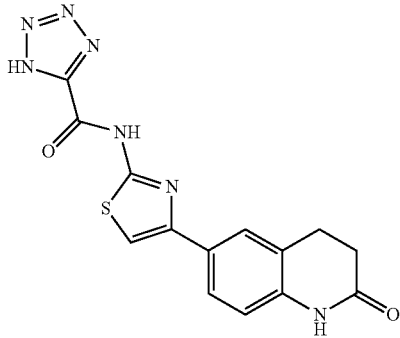 [SMILES: O=C1CCc2cc(-c3csc(NC(=O)c4nnn[nH]4)n3)ccc2N1]

Step 1: Preparation of 1H-tetrazole acid chloride: Thionyl chloride (0.74 mL, 10.191 mmol), was added dropwise to a solution of 1H-tetrazole-5-carboxylic acid (0.069 g, 0.612 mmol) in tetrahydrofuran (2 mL) at 0° C., followed by the addition of DMF (1 drop) and the mixture was stirred overnight (15 hrs). The reaction mixture was concentrated in vacuo and the residue was used without further purification.

Step 2: A solution 6-(2-aminothiazol-4-yl)-3,4-dihydroquinolin-2(1H)-one in pyridine (2 mL) was quickly added to acid chloride under ice-bath. The mixture was vigorously stirred for 10 min and then stirred at room temperature overnight (15 hrs). The reaction was quenched with water (20 mL) and concentrated to minimum. The crude mixture was extracted with 8:2 dichloromethane/isopropanol (3×20 mL) mixtures, washed with sat. NaHCO$_3$ (2×20 mL), and dried over anhydrous Na$_2$SO$_4$. The concentrated residue was purified by precipitation in minimum amount of dichloromethane and filtration to give N-(4-(2-oxo-1,2,3,4-tetrahydroquinolin-6-yl)thiazol-2-yl)-1H-tetrazole-5-carboxamide (0.065 g, 47%) as a greenish-grey solid. $^1$H NMR (400 MHz, DMSO-d): δ 10.21 (s, 1H), 8.11 (bs, 1H), 7.61 (s, 1H), 7.55 (dd, 1H, J=8.4, 1.6 Hz), 6.97 (s, 1H), 7.56 (s, 1H), 6.88 (d, 1H, J=8.4 Hz), 2.90 (m, 2H), 2.47 (partial masked under d-DMSO, m, 2H). MS (ESI): Calcd. for $C_{14}H_{11}N_7O_2S$: 341, found 398 (unstabled, M+56)$^+$.

Example 20

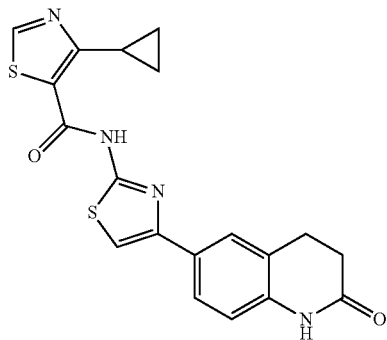 [SMILES: O=C1CCc2cc(-c3csc(NC(=O)c4scnc4C4CC4)n3)ccc2N1]

To a suspension of 6-(2-aminothiazol-4-yl)-3,4-dihydroquinolin-2(1H)-one (0.100 g, 0.408 mmol) and 4-cyclopropyl-1,3-thiazole-5-carboxylic acid (0.079 g, 0.469 mmol), and pyridine (0.15 mL, 1.832 mmol) in acetonitrile (4 mL) in a sealed tube was added propylphosphonic anhydride solution (50 wt % in ethyl acetate, 0.85 mL, 1.431 mmol). The sealed tube was heated to 48.5° C. for 7 days. After cooling, the mixture was quenched with water (10 mL) and extracted with 8:2 dichloromethane/isopropanol (2×25 mL) followed by washing once with sat. NaHCO$_3$ (100 mL). The combined organic layers were dried over anhydrous Na$_2$SO$_4$ and concentrated in vacuo. The crude mixture was purified by precipitation in minium amount of 1:1 dichloromethane/diethyl ether mixture. The obtained solid was collected by filtration and washed with cold dichloromethane to give 4-cyclopropyl-N-(4-(2-oxo-1,2,3,4-tetrahydroquinolin-6-yl)thiazol-2-yl)thiazole-5-carboxamide (0.129 g, 80%) as a green crystalline solid. $^1$H NMR (400 MHz, DMSO-d): δ 12.76 (bs, 1H), 10.20 (s, 1H), 9.07 (s, 1H), 7.74 (s, 1H), 7.70 (dd, 1H, J=8.4, 1.6 Hz), 7.51 (bs, 1H), 6.89 (d, 1H, J=8.4 Hz), 2.93 (m, 2H), 2.49 (partial masked under d-DMSO, m, 2H). MS (ESI): Calcd. for C$_{19}$H$_{16}$N$_4$O$_2$S$_2$: 396, found 397 (M+1)$^+$.

Example 21

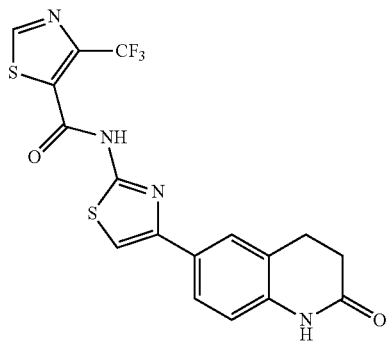 [SMILES: O=C1CCc2cc(-c3csc(NC(=O)c4scnc4C(F)(F)F)n3)ccc2N1]

To a suspension of 6-(2-aminothiazol-4-yl)-3,4-dihydroquinolin-2(1H)-one (0.100 g, 0.408 mmol) and 4-(trifluoromethyl)-1,3-thiazole-5-carboxylic acid (0.088 g, 0.448 mmol), and pyridine (0.15 mL, 1.832 mmol) in acetonitrile (4 mL) in a sealed tube was added propylphosphonic anhydride solution (50 wt % in ethyl acetate, 0.85 mL, 1.431 mmol). The sealed tube was heated to 48.5° C. for 7 days. After cooling, the mixture was quenched with water (10 mL) and extracted with 8:2 dichloromethane/isopropanol (2×25 mL) followed by washing once with sat. NaHCO$_3$ (100 mL). The combined organic layers were dried over anhydrous Na$_2$SO$_4$ and concentrated in vacuo. The crude mixture was purified by precipitation in minium amount of dichloromethane. The obtained solid was collected by filtration and washed with cold dichloromethane to give N-(4-(2-oxo-1,2,3,4-tetrahydroquinolin-6-yl)thiazol-2-yl)-4-(trifluoromethyl)thiazole-5-carboxamide (0.155 g, 90%) as a beige solid. $^1$H NMR (400 MHz, DMSO-d): δ 13.35 (bs, 1H), 10.20 (s, 1H), 9.36 (s, 1H), 7.73 (s, 1H), 7.68 (dd, 1H, J=8.4, 1.6 Hz), 7.59 (bs, 1H), 6.89 (d, 1H, J=8.4 Hz), 2.93 (m, 2H), 2.49 (partial masked under d-DMSO, m, 2H). MS (ESI): Calcd. for C$_{17}$H$_{11}$F$_3$N$_4$O$_2$S$_2$: 424, found 425 (M+1)$^+$.

Example 22

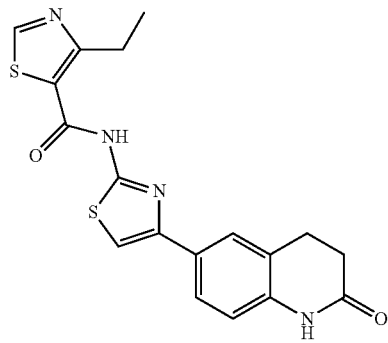 [SMILES: CCc1ncsc1C(=O)Nc1nc(-c2ccc3c(c2)CCC(=O)N3)cs1]

To a suspension of 6-(2-aminothiazol-4-yl)-3,4-dihydroquinolin-2(1H)-one (0.075 g, 0.306 mmol) and 4-ethyl-1,3-thiazole-5-carboxylic acid (0.055 g, 0.351 mmol), and pyridine (0.11 mL, 1.381 mmol) in acetonitrile (4 mL) in a sealed tube was added propylphosphonic anhydride solution (50 wt % in ethyl acetate, 0.64 mL, 1.072 mmol). The sealed tube was heated to 50° C. for 7 days. After cooling, the mixture was quenched with water (10 mL) and extracted with 8:2 dichloromethane/isopropanol (2×25 mL) followed by washing once with sat. NaHCO$_3$ (100 mL). The combined organic layers were dried over anhydrous Na$_2$SO$_4$ and concentrated in vacuo. The crude mixture was purified by precipitation in minium amount of dichloromethane. The obtained solid was collected by filtration and washed with cold dichloromethane to give 4-ethyl-N-(4-(2-oxo-1,2,3,4-tetrahydroquinolin-6-yl)thiazol-2-yl)thiazole-5-carboxamide (0.090 g, 76%) as an off-white solid. $^1$H NMR (400 MHz, DMSO-d): δ 12.74 (bs, 1H), 10.19 (s, 1H), 9.18 (s, 1H), 7.74 (s, 1H), 7.71 (dd, 1H, J=8.4, 1.6 Hz), 7.52 (bs, 1H), 6.89 (d, 1H, J=8.4 Hz), 3.08 (q, 2H, J=7.2 Hz), 2.93 (t, 2H, J=7.2 Hz), 2.49 (partial masked under d-DMSO, m, 2H), 1.25 (t, 3H, J=7.2 Hz). MS (ESI): Calcd. for C$_{18}$H$_{16}$N$_4$O$_2$S$_2$: 384, found 385 (M+1)$^+$.

Example 23

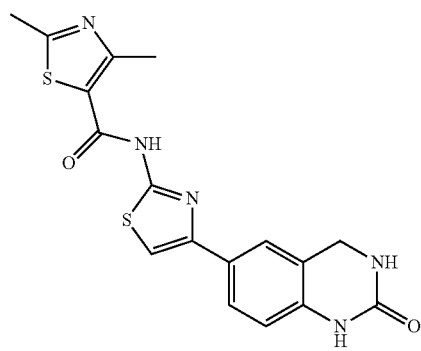

To a suspension of 6-(2-aminothiazol-4-yl)-3,4-dihydroquinazolin-2(1H)-one (0.100 g, 0.406 mmol) and 2,4-dimethylhiazole-5-carboxylic acid (0.073 g, 0.467 mmol), and pyridine (0.15 mL, 1.832 mmol) in acetonitrile (4 mL) in a sealed tube was added propylphosphonic anhydride solution (50 wt % in ethyl acetate, 0.85 mL, 1421 mmol). The sealed tube was heated to 50° C. for 5 days. After cooling, the mixture was quenched with water (10 mL) and extracted with 8:2 dichloromethane/isopropanol (2×25 mL) followed by washing once with sat. NaHCO₃ (100 mL). The combined organic layers were dried over anhydrous Na₂SO₄ and concentrated in vacuo. The crude mixture was purified by precipitation in minium amount of dichloromethane. The obtained solid was collected by filtration and washed with cold dichloromethane to give 2,4-dimethyl-N-(4-(2-oxo-1,2,3,4-tetrahydroquinazolin-6-yl)thiazol-2-yl)thiazole-5-carboxamide (0.129 g, 82%) as a brown solid. $^1$H NMR (400 MHz, DMSO-d): δ 9.15 (s, 1H), 7.66 (dd, 1H, J=8.4, 1.6 Hz), 7.64 (s, 1H), 7.44 (s, 1H), 6.86 (bs, 1H), 6.81 (d, 1H, J=8.4 Hz), 4.37 (s, 2H), 2.67 (s, 3H), 2.61 (s, 3H). MS (ESI): Calcd. for $C_{17}H_{15}N_5O_2S_2$: 385, found 386 (M+1)⁺.

Example 24

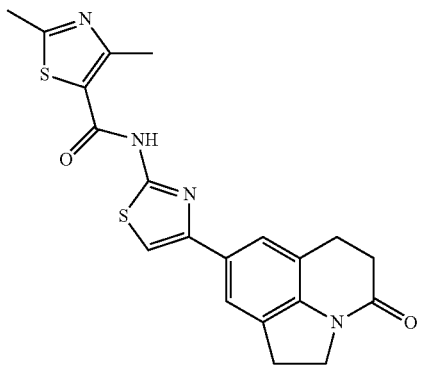 [SMILES: Cc1nc(C)c(C(=O)Nc2nc(-c3cc4c5c(c3)CCN5C(=O)CC4)cs2)s1]

To a suspension of 8-(2-aminothiazol-4-yl)-5,6-dihydro-1H-pyrrolo[3,2,1-ij]quinolin-4(2H)-one (0.075 g, 0.276 mmol) and 2,4-dimethylhiazole-5-carboxylic acid (0.050 g, 0.318 mmol), and pyridine (0.10 mL, 1.121 mmol) in acetonitrile (4 mL) in a sealed tube was added propylphosphonic anhydride solution (50 wt % in ethyl acetate, 0.58 mL, 1.241 mmol). The sealed tube was heated to 50° C. for 5 days. After cooling, the mixture was quenched with water (10 mL) and extracted with 8:2 dichloromethane/isopropanol (2×25 mL) followed by washing once with sat. NaHCO₃ (100 mL). The combined organic layers were dried over anhydrous Na₂SO₄ and concentrated in vacuo. The obtained solid was collected by filtration and washed with cold dichloromethane to give 2,4-dimethyl-N-(4-(4-oxo-1,2,5,6-tetrahydro-4H-pyrrolo[3,2,1-ij]quinolin-8-yl)thiazol-2-yl)thiazole-5-carboxamide (0.089 g, 79%) as a yellow solid. $^1$H NMR (400 MHz, DMSO-d): δ 12.50 (bs, 1H), 7.64 (dd, 1H, J=8.4, 1.6 Hz), 7.49 (s, 1H), 3.97 (t, 2H, J=8.8 Hz), 3.18 (t, 2H, J=8.8 Hz), 2.97 (t, 2H, J=7.6 Hz), 2.67 (s, 3H), 2.61 (s, 3H), 2.58 (t, 2H, J=7.6 Hz). MS (ESI): Calcd. for $C_{20}H_{18}N_4O_2S_2$: 410, found 411 (M+1)⁺.

Example 25

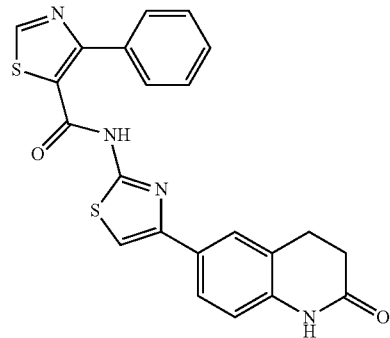 [SMILES: O=C1CCc2cc(-c3csc(NC(=O)c4scnc4-c4ccccc4)n3)ccc2N1]

To a suspension of 6-(2-aminothiazol-4-yl)-3,4-dihydroquinolin-2(1H)-one (0.100 g, 0.408 mmol) and 4-phenylthiazole-5-carboxylic acid (0.092 g, 0.448 mmol), and pyridine (0.15 mL, 1.832 mmol) in acetonitrile (4 mL) in a sealed tube was added propylphosphonic anhydride solution (50 wt % in ethyl acetate, 0.85 mL, 1.432 mmol). The sealed tube was heated to 50° C. for 6 days. After cooling, the mixture was quenched with water (3 mL) and the precitate was collected by filtration washing with cold 1:1 acetonitrile/water mixture. The residue was purified by precipitating in dichloromethane and filtration to give N-(4-(2-oxo-1,2,3,4-tetrahydroquinolin-6-yl)thiazol-2-yl)-4-phenylthiazole-5-carboxamide (0.151 g, 86%) as a yellow solid. $^1$H NMR (400 MHz, DMSO-d): δ 12.82 (bs, 1H), 10.18 (s, 1H), 9.31 (s, 1H), 7.69 (m, 3H), 7.64 (dd, 1H, J=8.4, 2.0 Hz), 7.54 (s, 1H), 7.48-7.38 (m, 3H), 6.87 (d, 1H, J=8.4 Hz), 2.91 (t, 2H, J=7.2 Hz), 2.47 (partial masked under d-DMSO, t, 2H, J=7.2 Hz). MS (ESI): Calcd. for $C_{22}H_{16}N_4O_2S_2$: 432, found 433 (M+1)⁺.

Example 26

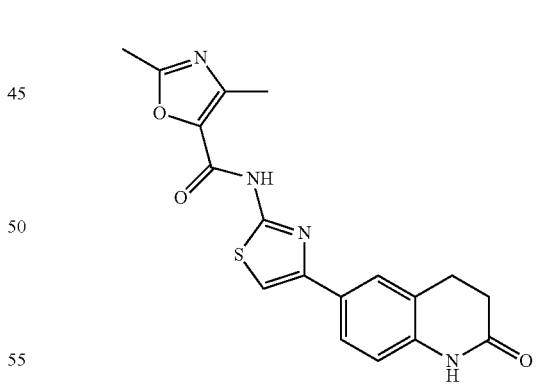

To a suspension of 6-(2-aminothiazol-4-yl)-3,4-dihydroquinolin-2(1H)-one (0.100 g, 0.408 mmol) and dimethyl-1,3-oxazole-5-carboxylic acid (0.063 g, 0.448 mmol), and pyridine (0.15 mL, 1.832 mmol) in acetonitrile (4 mL) in a sealed tube was added propylphosphonic anhydride solution (50 wt % in ethyl acetate, 0.85 mL, 1.432 mmol). The sealed tube was heated to 50° C. for 6 days. After cooling, the mixture was quenched with water (3 mL) and the precitate was collected by filtration washing with cold 1:1 acetonitrile/water mixture. The residue was purified by precipitating in dichloromethane and filtration to give 2,4-dimethyl-N-(4-(2-oxo-1,2,3,4-tetrahydroquinolin-6-yl)thiazol-2-yl)oxazole-5-carboxamide (0.12 g, 83%) as a beige solid. $^1$H NMR (400 MHz, DMSO-d): δ 12.38 (bs, 1H), 10.19 (s, 1H), 7.75 (s, 1H), 7.70 (dd, 1H, J=8.4, 2.0 Hz), 7.52 (s, 1H), 6.89 (d, 1H, J=8.4 Hz), 2.93 (t, 2H, J=7.2 Hz), 2.48 (partial masked under d-DMSO, m, 5H), 2.40 (s, 3H). MS (ESI): Calcd. for $C_{18}H_{16}N_4O_3S$: 368, found 369 (M+1)$^+$.

Example 27

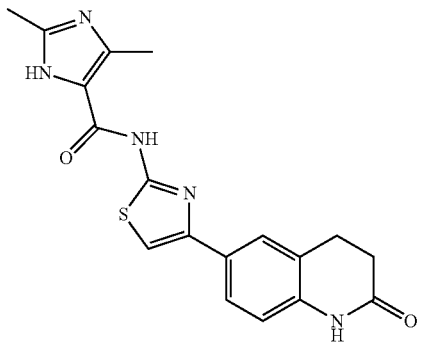 [SMILES: Cc1nc(C)c(C(=O)Nc2nc(-c3ccc4c(c3)CCC(=O)N4)cs2)[nH]1]

To a suspension of 6-(2-aminothiazol-4-yl)-3,4-dihydroquinolin-2(1H)-one (0.100 g, 0.408 mmol) and 2,5-dimethyl-1H-imidazole-4-carboxylic acid (0.063 g, 0.448 mmol), and pyridine (0.15 mL, 1.832 mmol) in acetonitrile (4 mL) in a sealed tube was added propylphosphonic anhydride solution (50 wt % in ethyl acetate, 0.85 mL, 1.432 mmol). The sealed tube was heated to 50° C. for 12 days. After cooling, the mixture was quenched with water (3 mL) and extracted with 8:2 dichloromethane/isopropanol (3×50 mL) followed by washing with sat. NaHCO$_3$ (2×50 mL). The crude solid was dried loaded onto silica and purified by flash chromatography using 95:5 dichloromethane/methanol to give 2,4-dimethyl-N-(4-(2-oxo-1,2,3,4-tetrahydroquinolin-6-yl)-1H-imidazole-5-carboxamide (0.07 g, 47%) as a peach solid. $^1$H NMR (400 MHz, DMSO-d): δ 12.34 (bs, 1H), 10.58 (bs, 1H), 10.16 (s, 1H), 7.74 (s, 1H), 7.69 (dd, 1H, J=8.4, 2.0 Hz), 7.45 (s, 1H), 6.88 (d, 1H, J=8.4 Hz), 2.93 (t, 2H, J=7.2 Hz), 2.49 (partial masked under d-DMSO, m, 5H), 2.31 (s, 3H). MS (ESI): Calcd. for $C_{18}H_{17}N_5O_2S$: 367, found 368 (M+1)$^+$.

Example 28

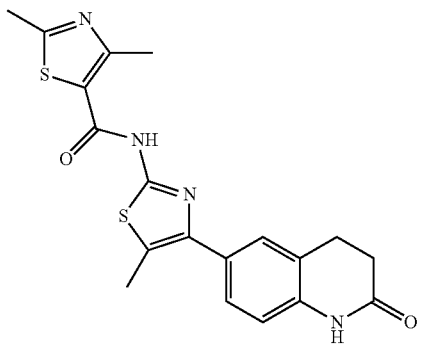 [SMILES: Cc1nc(C)c(C(=O)Nc2nc(-c3ccc4c(c3)CCC(=O)N4)c(C)s2)s1]

To a suspension of 6-(2-amino-5-methylthiazol-4-yl)-3,4-dihydroquinolin-2(1H)-one (0.100 g, 0.386 mmol) and 2,4-dimethylthiazole-5-carboxylic acid (0.067 g, 0.424 mmol), and pyridine (0.14 mL, 1.742 mmol) in acetonitrile (4 mL) in a sealed tube was added propylphosphonic anhydride solution (50 wt % in ethyl acetate, 0.80 mL, 1.352 mmol). The sealed tube was heated to 50° C. for 6 days. After cooling, the mixture was quenched with water (3 mL) and the precitate was collected by filtration washing with cold 1:1 acetonitrile/water mixture. The residue was purified by precipitating in dichloromethane and filtration to give 2,4-dimethyl-N-(5-methyl-4-(2-oxo-1,2,3,4-tetrahydroquinolin-6-yl)thiazol-2-yl)thiazole-5-carboxamide (0.12 g, 78%) as an off-white solid. $^1$H NMR (400 MHz, DMSO-d): δ 12.38 (bs, 1H), 10.19 (s, 1H), 7.46 (s, 1H), 7.41 (dd, 1H, J=8.4, 2.0 Hz), 6.92 (d, 1H, J=8.4 Hz), 2.93 (t, 2H, J=7.2 Hz), 2.65 (s, 3H), 2.61 (s, 3H), 2.49 (partial masked under d-DMSO, m, 2H), 2.43 (s, 3H). MS (ESI): Calcd. for $C_{19}H_{18}N_4O_2S_2$: 398, found 399 (M+1)$^+$.

Example 29

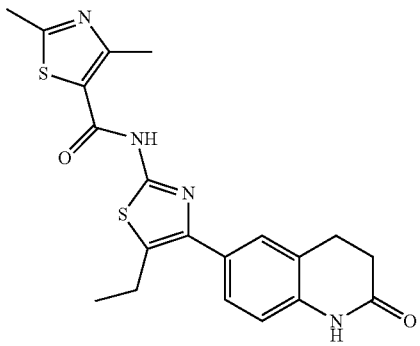 [SMILES: CCc1sc(NC(=O)c2sc(C)nc2C)nc1-c1ccc2c(c1)CCC(=O)N2]

To a suspension of 6-(2-amino-5-ethylthiazol-4-yl)-3,4-dihydroquinolin-2(1H)-one (0.100 g, 0.367 mmol) and 2,4-dimethylthiazole-5-carboxylic acid (0.063 g, 0.402 mmol), and pyridine (0.13 mL, 1.652 mmol) in acetonitrile (4 mL) in a sealed tube was added propylphosphonic anhydride solution (50 wt % in ethyl acetate, 0.76 mL, 1.282 mmol). The sealed tube was heated to 50° C. for 6 days. After cooling, the mixture was quenched with water (3 mL) and the precitate was collected by filtration washing with cold 1:1 acetonitrile/water mixture. The residue was purified by precipitating in dichloromethane and filtration to give N-(5-ethyl-4-(2-oxo-1,2,3,4-tetrahydroquinolin-6-yl)thiazol-2-yl)-2,4-dimethylthiazole-5-carboxamide (0.11 g, 73%) as a beige solid. $^1$H NMR (400 MHz, DMSO-d): δ 12.22 (bs, 1H), 10.20 (s, 1H), 7.40 (s, 1H), 7.35 (dd, 1H, J=8.4, 2.0 Hz), 6.92 (d, 1H, J=8.4 Hz), 2.93 (t, 2H, J=7.2 Hz), 2.86 (q, 2H, J=7.6 Hz), 2.65 (s, 3H), 2.61 (s, 3H), 2.49 (partial masked under d-DMSO, m, 2H), 1.25 (t, 3H, J=7.6 Hz). MS (ESI): Calcd. for $C_{20}H_{20}N_4O_2S_2$: 412, found 413 (M+1)$^+$.

Example 30

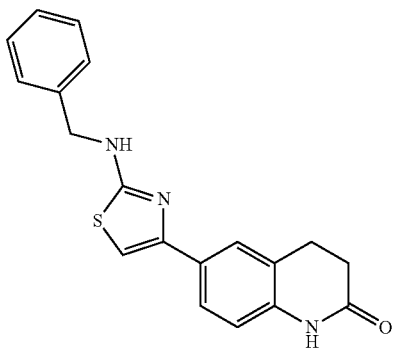 [SMILES: O=C1CCc2cc(-c3csc(NCc4ccccc4)n3)ccc2N1]

To a solution of 6-(2-aminothiazol-4-yl)-3,4-dihydroquinolin-2(1H)-one (0.200 g, 0.815 mmol) and benzaldehyde (0.091 g, 0.856 mmol) in dry tetrahydrofuran (20 mL) with glacial acetic acid (1 mL) in a flamed dried flask. The mixture was stirred for 4 hours prior to addition of excess sodium borohydride (0.070 mg, 1.71 mmol). The mixture was then stirred and monitored by LCMS for completion. Then it was quenced with water and extracted with ethyl acetate (3×20 mL). The combined organic layers were washed once with sat. NaHCO$_3$, dried over anhydrous Na$_2$SO$_4$ and concentrated in vacuo. The residue was purified by flash chromatography over silica gel using 95:5 dichloromethane/methanol to give 6-(2-(benzylamino)thiazol-4-yl)-3,4-dihydroquinolin-2(1H)-one (0.099 g, 36%) as a light yellow solid. $^1$H NMR (400 MHz, DMSO-d): δ 10.10 (s, 1H), 8.12 (t, 1H, J=5.6 Hz), 7.62 (s, 1H), 7.58 (dd, 1H, J=8.4, 1.6 Hz), 7.42-7.30 (m, 4H), 7.25 (t, 1H, J=6.8 Hz), 6.88 (s, 1H), 6.82 (d, 1H, J=8.0 Hz), 4.49 (d, 2H, J=5.6 Hz), 2.89 (t, 2H, J=7.8 Hz), 2.45 (t, 2H, J=7.2 Hz). MS (ESI): Calcd. for C$_{19}$H$_{17}$N$_3$OS: 335, found 336 (M+1)$^+$.

Example 31

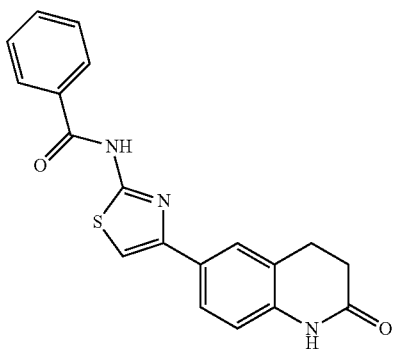 [SMILES: O=C1CCc2cc(-c3csc(NC(=O)c4ccccc4)n3)ccc2N1]

To a suspension of 6-(2-aminothiazol-4-yl)-3,4-dihydroquinolin-2(1H)-one (0.100 g, 0.408 mmol) and benzoic acid (0.055 g, 0.448 mmol), and pyridine (0.15 mL, 1.832 mmol) in acetonitrile (4 mL) in a sealed tube was added propylphosphonic anhydride solution (50 wt % in ethyl acetate, 0.85 mL, 1.432 mmol). The sealed tube was heated to 50° C. for 4 days and the precipitation formed. After cooling, the precipitate was collected by filtration and washed with cold 1:1 acetonitrile/water to give N-(4-(2-oxo-1,2,3,4-tetrahydroquinolin-6-yl)thiazol-2-yl)benzamide (0.116 g, 82%) as a beige solid. $^1$H NMR (400 MHz, DMSO-d): δ 12.73 (s, 1H), 10.19 (s, 1H), 8.12 (d, 2H, J=6.8 Hz), 7.77 (s, 1H), 7.72 (dd, 1H, J=8.4, 1.6 Hz), 7.65 (t, 1H, J=7.2 Hz), 7.55 (m, 3H), 6.90 (d, 1H, J=8.4 Hz), 2.94 (m, 2H), 2.49 (partial masked under d-DMSO, m, 2H). MS (ESI): Calcd. for C$_{19}$H$_{15}$N$_3$O$_2$S: 349, found 350 (M+1)$^+$.

Example 32

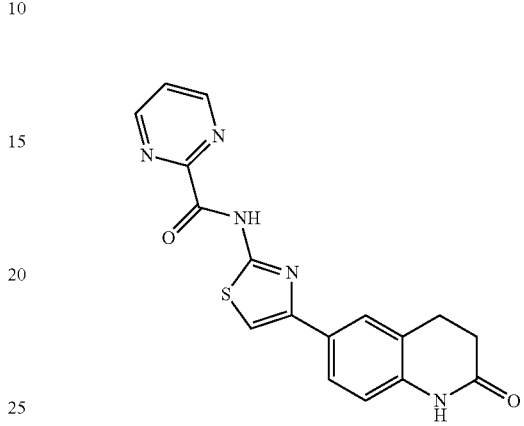

To a suspension of 6-(2-aminothiazol-4-yl)-3,4-dihydroquinolin-2(1H)-one (0.100 g, 0.408 mmol) and pyrimidine-2-carboxylic acid (0.056 g, 0.448 mmol), and pyridine (0.15 mL, 1.832 mmol) in acetonitrile (4 mL) was added propylphosphonic anhydride solution (50 wt % in ethyl acetate, 0.85 mL, 1.432 mmol). The sealed tube was heated to 50° C. for 4 days and precipitation formed. After cooling, the precipitate was collected by filtration and washed with cold 1:1 acetonitrile/water to give N-(4-(2-oxo-1,2,3,4-tetrahydroquinolin-6-yl)thiazol-2-yl)pyrimidine-2-carboxamide (0.132 g, 93%) as a greenish-brown solid. $^1$H NMR (400 MHz, DMSO-d): δ 12.39 (s, 1H), 10.19 (s, 1H), 9.06 (d, 2H, J=5.6 Hz), 7.78 (m, 2H), 7.72 (dd, 1H, J=8.8, 2.0 Hz), 7.61 9 s, 1H), 6.90 (d, 1H, J=8.4 Hz), 2.93 (m, 2H), 2.49 (partial masked under d-DMSO, m, 2H). MS (ESI): Calcd. for C$_{17}$H$_{13}$N$_5$O$_2$S: 351, found 352 (M+1)$^+$.

Example 33

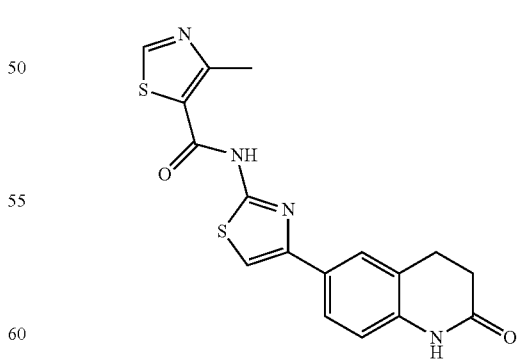

To a suspension of 6-(2-aminothiazol-4-yl)-3,4-dihydroquinolin-2(1H)-one (0.100 g, 0.408 mmol) and 4-methylthiazole-5-carboxylic acid (0.064 g, 0.448 mmol), and pyridine (0.15 mL, 1.832 mmol) in acetonitrile (4 mL) in a sealed tube was added propylphosphonic anhydride solution (50 wt % in ethyl acetate, 0.85 mL, 1.432 mmol). The sealed tube was heated to 50° C. for 4 days and the precipitation formed. After cooling, the precipitate was collected by filtration and washed with cold 1:1 acetonitrile/water to give 4-methyl-N-(4-(2-oxo-1,2,3,4-tetrahydroquinolin-6-yl)thiazol-2-yl) thiazole-5-carboxamide (0.134 g, 89%) as a biege solid. $^1$H NMR (400 MHz, DMSO-d): δ 12.71 (bs, 1H), 10.19 (s, 1H), 9.18 (s, 1H), 7.74 (s, 1H), 7.70 (dd, 1H, J=8.0, 1.6 Hz), 7.52 (bs, 1H), 6.89 (d, 1H, J=8.4 Hz), 2.93 (m, 2H), 2.68 (s, 3H), 2.49 (partial masked under d-DMSO, m, 2H). MS (ESI): Calcd. for $C_{17}H_{14}N_4O_2S_2$: 370, found 371 (M+1)$^+$.

Example 34

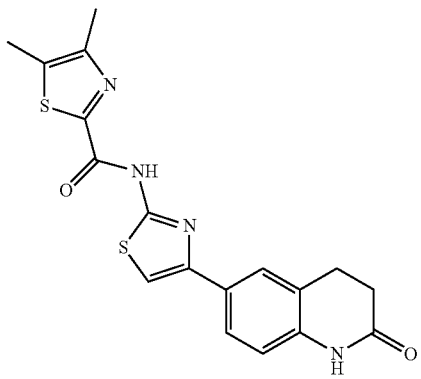 [SMILES: Cc1nc(C(=O)Nc2nc(-c3ccc4c(c3)CCC(=O)N4)cs2)sc1C]

To a suspension of 6-(2-aminothiazol-4-yl)-3,4-dihydroquinolin-2(1H)-one (0.100 g, 0.408 mmol) and 4,5-dimethythiazole-2-carboxylic (0.071 g, 0.448 mmol), and pyridine (0.15 mL, 1.832 mmol) in acetonitrile (4 mL) in a sealed was added propylphosphonic anhydride solution (50 wt % in ethyl acetate, 0.85 mL, 1.432 mmol). The sealed tube was heated to 50° C. for 4 days and the precipitation formed. After cooling, the precipitate was collected by filtration and washed with cold 1:1 acetonitrile/water to give 4,5-dimethyl-N-(4-(2-oxo-1,2,3,4-tetrahydroquinolin-6-yl) thiazol-2-yl)thiazole-2-carboxamide (0.062 g, 40%) as a biege solid. 4,5-dimethyl-N-(4-(2-oxo-1,2,3,4-tetrahydroquinolin-6-yl)thiazol-2-yl)thiazole-2-carboxamide existed as a tautomers in HPLC and $^1$H NMR (400 MHz, DMSO-d): δ 12.39 (bs, 0.5 H), 10.95 (bs, 0.5 H), 10.18 (s, 1H), 7.78-7.65 (m, 2H), 7.57 (s, 0.5 H), 7.47 (s, 0.5 H), 6.89 (d, 1H, J=8.4 Hz), 2.93 (m, 2H), 2.49 (partial masked under d-DMSO, m, 2H). MS (ESI): Calcd. For $C_{18}H_{16}N_4O_2S_2$: 384, found 385 (M+1)$^+$.

Example 34

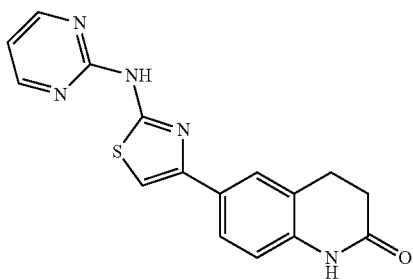 [SMILES: O=C1CCc2cc(-c3csc(Nc4ncccn4)n3)ccc2N1]

To a suspension of 6-(2-aminothiazol-4-yl)-3,4-dihydroquinolin-2(1H)-one (0.100 g, 0.408 mmol), 2-chloropyrimidine (0.047 g, 0.408 mmol), 4,5-bis(diphenylphosphino)-9,9-dimethyl-xanthene (0.045 g, 0.077 mmol), and potassium carbonate (0.197 g, 1.432 mmol) in anhydrous dioxane (4 mL) bubbling with argon in a sealed tube was added palladium(II) acetate (0.017 g, 0.073 mmol). The solution mixture was under continuous argon bubbling for additional 10 min. The sealed tube was then heated at 80° C. overnight (15 h). After cooling, the precipitate was collected by filtration and washed with cold tetrahydrofuran followed by water to give 6-(2-(pyrimidin-2-ylamino)thiazol-4-yl)-3,4-dihydroquinolin-2(1H)-one (0.126 g, 95%) as a brown solid. $^1$H NMR (400 MHz, DMSO-d): δ DMSO-d): δ 11.61 (bs, 1H), 10.15 (s, 1H), 8.57 (d, 2H, J=4.8 Hz), 7.72 (s, 1H), 7.68 (dd, 1H, J=8.4, 1.6 Hz), 7.27 (s, 1H), 6.9 (t, 1H, J=4.8 Hz), 6.87 (d, 1H, J=8.4 Hz), 2.92 (m, 2H), 2.49 (partial masked under d-DMSO, m, 2H). MS (ESI): Calcd. for $C_{16}H_{13}N_5OS$: 323, found 324 (M)$^+$.

Example 36

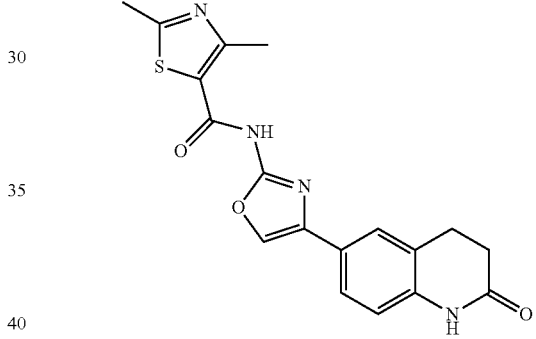

To a suspension of 6-(2-aminooxazol-4-yl)-3,4-dihydroquinolin-2(1H)-one (0.040 g, 0.175 mmol) and 2,4-dimethylthiazole-5-carboxylic acid (0.030 g, 0.192 mmol), and pyridine (0.06 mL, 0.785 mmol) in acetonitrile (2 mL) in a sealed tube was added propylphosphonic anhydride solution (50 wt % in ethyl acetate, 0.36 mL, 0.612 mmol). The sealed tube was heated to 50° C. for 5 days and the precipitation formed. After cooling, the mixture was quenched with water (10 mL) and extracted with 8:2 dichloromethane/isopropanol (2×25 mL) followed by washing once with sat. NaHCO$_3$ (100 mL). The combined organic layers were dried over anhydrous Na$_2$SO$_4$ and concentrated in vacuo. The residue was purified by pre-TLC with 95:5 dichloromethane/methanol mixture to give 2,4-dimethyl-N-(4-(2-oxo-1,2,3,4-tetrahydroquinolin-6-yl)oxazol-2-yl)thiazole-5-carboxamide (0.056 g, 87%) as a light brown solid. $^1$H NMR (400 MHz, DMSO-d): δ 10.15 (s, 1H), 8.26 (s, 1H), 7.52 (s, 1H), 7.48 (dd, 1H, J=8.0, 1.6 Hz), 6.98 (s, 1H), 6.85 (d, 1H, J=8.0 Hz), 2.88 (m, 2H), 2.62 (s, 3H), 2.53 (s, 3H), 2.44 (partial masked under d-DMSO, m, 2H). MS (ESI): Calcd. for $C_{18}H_{16}N_4O_3S$: 368, found 369 (M+1)$^+$.

Example 37

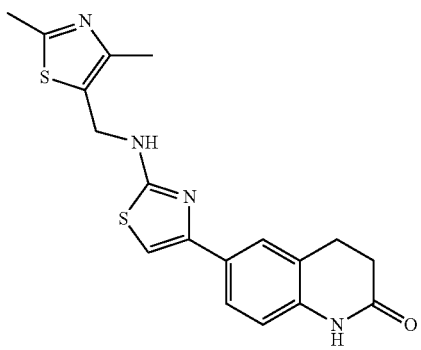 [SMILES: Cc1nc(C)c(CNc2nc(-c3ccc4c(c3)CCC(=O)N4)cs2)s1]

To a solution of 6-(2-aminothiazol-4-yl)-3,4-dihydroquinolin-2(1H)-one (0.100 g, 0.408 mmol) and 2,4-dimethylthiazole-5-carboxyaldehyde (0.063 g, 0.448 mmol) in dry dichloromethane (8 mL) with glacial acetic acid (1 mL) in a flamed dried flask. The mixture was stirred for 20 hours prior to addition of excess sodium borohydride (0.070 mg, 1.71 mmol). The reaction mixture was stirred and monitored by LCMS for completion. When completed, the mixture was quenced with water and extracted with ethyl acetate (3×20 mL). The combined organic layers were washed once with sat. NaHCO$_3$, dried over anhydrous Na$_2$SO$_4$ and concentrated in vacuo. The residue was purified by flash chromatography over silica gel using 95:5 dichloromethane/methanol to give 6-(2-(((2,4-dimethylthiazol-5-yl)methyl)amino)thiazol-4-yl)-3,4-dihydroquinolin-2(1H)-one (0.029 g, 19%) as a yellow solid. $^1$H NMR (400 MHz, DMSO-d): δ 10.12 (s, 1H), 8.08 (t, 1H, J=5.6 Hz), 7.65 (s, 1H), 7.61 (dd, 1H, J=8.0, 1.6 Hz), 6.92 (s, 1H), 6.84 (d, 1H, J=8.0 Hz), 4.55 (d, 2H, J=5.6 Hz), 2.90 (t, 2H, J=7.8 Hz), 2.52 (s, 3H), 2.45 (partial masked under d-DMSO, m, 2H), 2.35 (s, 3H). MS (ESI): Calcd. for C$_{18}$H$_{18}$N$_4$OS$_2$: 370, found 371 (M+1)$^+$.

Example 38

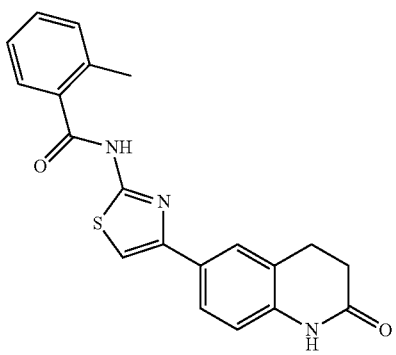 [SMILES: Cc1ccccc1C(=O)Nc1nc(-c2ccc3c(c2)CCC(=O)N3)cs1]

To a suspension of 6-(2-aminothiazol-4-yl)-3,4-dihydroquinolin-2(1H)-one (0.100 g, 0.408 mmol) and o-toluic (0.061 g, 0.448 mmol), and pyridine (0.15 mL, 1.832 mmol) in acetonitrile (4 mL) in a sealed tube was added propylphosphonic anhydride solution (50 wt % in ethyl acetate, 0.85 mL, 1.432 mmol). The sealed tube was heated to 50° C. for 14 days and the precipitation formed. After cooling, the precipitate was collected by filtration and washed with cold 1:1 acetonitrile/water to give 2-methyl-N-(4-(2-oxo-1,2,3,4-tetrahydroquinolin-6-yl)thiazol-2-yl)benzamide (0.099 g, 67%) as a beige solid. $^1$H NMR (400 MHz, DMSO-d): δ 12.61 (s, 1H), 10.18 (s, 1H), 7.74 (bs, 1H), 7.69 (dd, 1H, J=8.4, 2.0 Hz), 7.57 (dd, 1H, J=7.6, 1.6 Hz), 7.53 (s, 1H), 7.43 (ddd, 1H, J=7.6, 7.6, 1.6 Hz), 7.31 9m, 2H), 6.89 (d, 1H, J=8.0 Hz), 2.93 (m, 2H), 2.49 (partial masked under d-DMSO, m, 5H), 2.42 (s, 3H). MS (ESI): Calcd. For C$_{20}$H$_{17}$N$_3$O$_2$S: 363, found 364 (M+1)$^+$.

Example 39

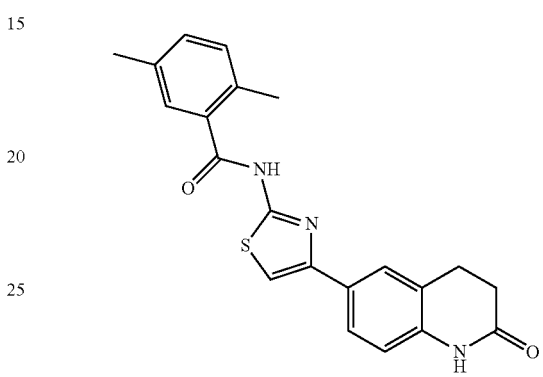

To a suspension of 6-(2-aminothiazol-4-yl)-3,4-dihydroquinolin-2(1H)-one (0.100 g, 0.408 mmol) and 2,5-dimethylbenzoic acid (0.067 g, 0.448 mmol), and pyridine (0.15 mL, 1.832 mmol) in acetonitrile (4 mL) in a sealed tube was added propylphosphonic anhydride solution (50 wt % in ethyl acetate, 0.85 mL, 1.432 mmol). The sealed tube was heated to 50° C. for 14 days and the precipitation formed. After cooling, the precipitate was collected by filtration and washed with cold 1:1 acetonitrile/water to give 2,5-dimethyl-N-(4-(2-oxo-1,2,3,4-tetrahydroquinolin-6-yl)thiazol-2-yl)benzamide (0.096 g, 62%) as a beige solid. $^1$H NMR (400 MHz, DMSO-d): δ 12.53 (s, 1H), 10.18 (s, 1H), 7.74 (bs, 1H), 7.69 (dd, 1H, J=8.4, 2.0 Hz), 7.52 (s, 1H), 7.42 (bs, 1H), 7.25-7.18 (m, 2H), 6.89 (d, 1H, J=8.0 Hz), 2.93 (m, 2H), 2.49 (partial masked under d-DMSO, m, 2H), 2.37 (s, 3H), 2.32 (s, 3H). MS (ESI): Calcd. for C$_{21}$H$_{19}$N$_3$O$_2$S: 377, found 378 (M+1)$^+$.

Example 40

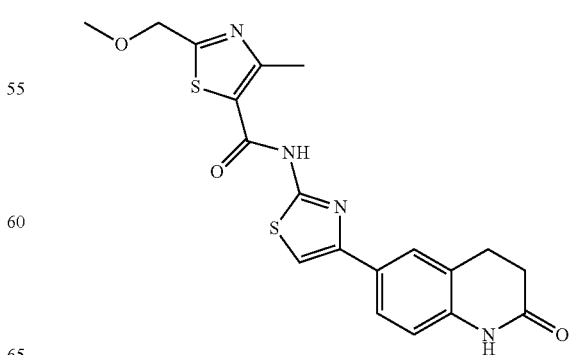

To a suspension of 6-(2-aminothiazol-4-yl)-3,4-dihydroquinolin-2(1H)-one (0.100 g, 0.408 mmol) and 2-(methoxylmethyl)-4-methyl-1,3-thiazole-5-carboxylic acid (0.084 g, 0.448 mmol), and pyridine (0.15 mL, 1.832 mmol) in acetonitrile (4 mL) in a sealed tube was added propylphosphonic anhydride solution (50 wt % in ethyl acetate, 0.85 mL, 1.432 mmol). The sealed tube was heated to 50° C. for 7 days and the precipitation formed. After cooling, the precipitate was collected by filtration and washed with cold 1:1 acetonitrile/water to give 2-(methoxymethyl)-4-methyl-N-(4-(2-oxo-1,2,3,4-tetrahydroquinolin-6-yl)thiazol-2-yl)thiazole-5-carboxamide (0.98 g, 58%) as a light brown solid. $^1$H NMR (400 MHz, DMSO-d): δ 12.65 (bs, 1H), 10.19 (s, 1H), 9.18 (s, 1H), 7.74 (s, 1H), 7.69 (dd, 1H, J=8.0, 1.6 Hz), 7.52 (bs, 1H), 6.89 (d, 1H, J=8.4 Hz), 4.72 (s, 2H), 3.45 (s, 3H), 2.93 (m, 2H), 2.64 (s, 3H), 2.49 (partial masked under d-DMSO, m, 2H). MS (ESI): Calcd. for $C_{19}H_{18}N_4O_3S_2$: 414, found 415 (M+1)$^+$.

Example 41

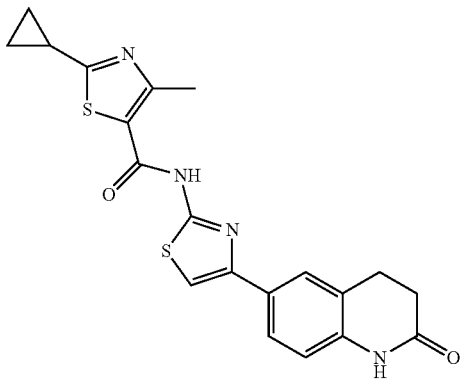 [SMILES: Cc1nc(C2CC2)sc1C(=O)Nc1nc(-c2ccc3c(c2)CCC(=O)N3)cs1]

To a suspension of 6-(2-aminothiazol-4-yl)-3,4-dihydroquinolin-2(1H)-one (0.100 g, 0.408 mmol) and 2-(cyclopropyl)-4-methyl-1,3-thiazole-5-carboxylic acid (0.082 g, 0.448 mmol), and pyridine (0.15 mL, 1.832 mmol) in acetonitrile (4 mL) in a sealed tube was added propylphosphonic anhydride solution (50 wt % in ethyl acetate, 0.85 mL, 1.432 mmol). The sealed tube was heated to 50° C. for 7 days. The reaction mixture was quenced with water and extracted with ethyl acetate (3×20 mL). The combined organic layers were washed once with sat. NaHCO$_3$, dried over anhydrous Na$_2$SO$_4$ and concentrated in vacuo. The residue was purified by flash chromatography over silica gel using 95:5 dichloromethane/methanol to give 2-cyclopropyl-4-methyl-N-(4-(2-oxo-1,2,3,4-tetrahydroquinolin-6-yl)thiazol-2-yl)thiazole-5-carboxamide (0.078 g, 46%) as an orange solid. $^1$H NMR (400 MHz, DMSO-d): δ 12.50 (bs, 1H), 10.19 (s, 1H), 7.74 (s, 1H), 7.69 (dd, 1H, J=8.4, 1.6 Hz), 7.50 (bs, 1H), 6.89 (d, 1H, J=8.4 Hz), 2.93 (m, 2H), 2.58 (s, 3H), 2.49 (partial masked under d-DMSO, m, 2H), 2.44 (m, 1H), 1.18 (m, 2H), 1.03 (m, 2H). MS (ESI): Calcd. for $C_{20}H_{18}N_4O_2S_2$: 410, found 411 (M+1)$^+$.

Example 42

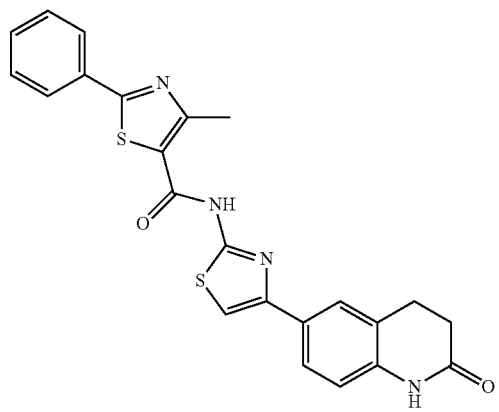 [SMILES: Cc1nc(-c2ccccc2)sc1C(=O)Nc1nc(-c2ccc3c(c2)CCC(=O)N3)cs1]

To a suspension of 6-(2-aminothiazol-4-yl)-3,4-dihydroquinolin-2(1H)-one (0.100 g, 0.408 mmol) and 4-methyl-2-phenyl-1,3-thiazole-5-carboxylic acid (0.098 g, 0.448 mmol), and pyridine (0.15 mL, 1.832 mmol) in acetonitrile (4 mL) in a sealed tube was added propylphosphonic anhydride solution (50 wt % in ethyl acetate, 0.85 mL, 1.432 mmol). The sealed tube was heated to 48.5° C. for 4 days and the precipitation formed. After cooling, the precipitate was collected by filtration and washed with cold 1:1 acetonitrile/water to give 4-methyl-N-(4-(2-oxo-1,2,3,4-tetrahydroquinolin-6-yl)thiazol-2-yl)-2-phenylthiazole-5-carboxamide (0.151 g, 83%) as a beige solid. $^1$H NMR (400 MHz, DMSO-d): δ 12.74 (bs, 1H), 10.20 (s, 1H), 7.98 (m, 2H), 7.75 (bs, 1H), 7.70 (dd, 1H, J=8.0, 1.6 Hz), 7.59-7.48 (m, 4H), 6.90 (d, 1H, J=8.4 Hz), 2.94 (m, 2H), 2.73 (s, 3H), 2.50 (masked under d-DMSO, m, 2H). MS (ESI): Calcd. for $C_{23}H_{18}N_4O_2S_2$: 446, found 447 (M+1)$^+$.

Example 43

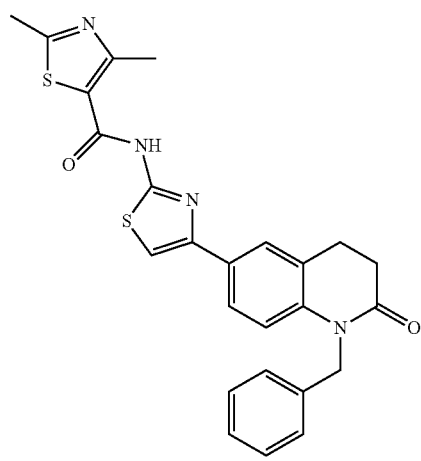 [SMILES: Cc1nc(C)c(C(=O)Nc2nc(-c3ccc4c(c3)CCC(=O)N4Cc3ccccc3)cs2)s1]

Example 44

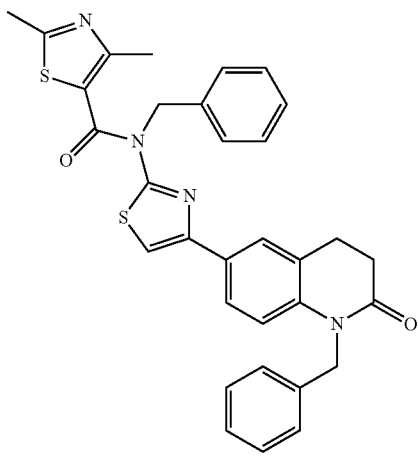 [SMILES: Cc1nc(C)c(C(=O)N(Cc2ccccc2)c2nc(-c3ccc4c(c3)CCC(=O)N4Cc3ccccc3)cs2)s1]

To a solution of 2,4-dimethyl-N-(4-(2-oxo-1,2,3,4-tetrahydroquinolin-6-yl)thiazol-2-yl)thiazole-5-carboxamide (0.100 g, 0.260 mmol) and benzylbromide (0.058 g, 0.338 mmol) in anhydrous dimethylformamide (4 mL) in a flamed dried flask under argon atmosphere at 0° C. was added sodium hydride (60% in mineral oil, 0.015 g, 0.364 mmol) was added in one portion. The reaction was stirred for 15 min at 0° C. prior warm to room temperature. The mixture was stirred overnight. After consumption of starting material, the reaction mixture was quenched with sat. ammonium chloride (25 mL) and extracted with ethyl acetate (2×25 mL). The combined organics were washed once with sat. sodium bicarbonate (50 mL) and dried over anhydrous sodium sulfate. The concentrated residue was purified by flash chromatography over silica gel using 95:5 dichloromethane/methanol to give products N-(4-(1-benzyl-2-oxo-1,2,3,4-tetrahydroquinolin-6-yl)thiazol-2-yl)-2,4-dimethylthiazole-5-carboxamide (0.021 g, 17%) and N-benzyl-N-(4-(1-benzyl-2-oxo-1,2,3,4-tetrahydroquinolin-6-yl)thiazol-2-yl)-2,4-dimethylthiazole-5-carboxamide (0.027 g, 19%) both as yellow solids.

43: $^1$H NMR (400 MHz, DMSO-d) of N-(4-(1-benzyl-2-oxo-1,2,3,4-tetrahydroquinolin-6-yl)thiazol-2-yl)-2,4-dimethylthiazole-5-carboxamide: d 12.59 (bs, 1H), 7.79 (d, 1H, J=2.0 Hz), 7.65 (dd, 1H, J=8.4, 2.0 Hz), 7.53 (bs, 1H), 7.31 (m, 2H), 7.23 (m, 2H), 7.21 (m, 1H), 6.97 (d, 1H, J=8.4 Hz), 5.18 (s, 2H), 3.01 (m, 2H), 2.75 (m, 2H), 2.66 (s, 3H), 2.60 (s, 3H). MS (ESI): Calcd. for $C_{25}H_{22}N_4O_2S_2$: 474, found 475 (M+1)$^+$.

44: $^1$H NMR (400 MHz, DMSO-d) of N-benzyl-N-(4-(1-benzyl-2-oxo-1,2,3,4-tetrahydroquinolin-6-yl)thiazol-2-yl)-2,4-dimethylthiazole-5-carboxamide: δ 7.32 (m, 2H), 7.25-7.17 (m, 7 H), 7.14 (dd, 1H, J=8.4, 2.0 Hz), 7.02 (s, 1H), 6.87 (m, 2H), 5.35 (s, 2H), 5.18 (s, 2H), 2.90 (m, 2H), 2.72 (m, 2H), 2.59 (s, 3H), 2.56 (s, 3H). MS (ESI): Calcd. for $C_{32}H_{28}N_4O_2S_2$: 564, found 565 (M+1)$^+$.

Example 45

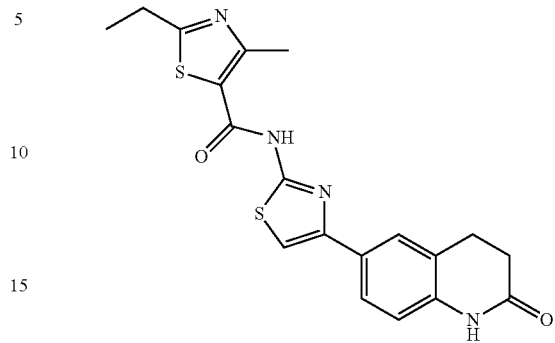

To a suspension of 6-(2-aminothiazol-4-yl)-3,4-dihydroquinolin-2(1H)-one (0.100 g, 0.408 mmol) and 2-ethyl-4-methyl-1,3-thiazole-5-carboxylic acid (0.077 g, 0.448 mmol), and pyridine (0.15 mL, 1.832 mmol) in acetonitrile (4 mL) in a sealed tube was added propylphosphonic anhydride solution (50 wt % in ethyl acetate, 0.85 mL, 1.432 mmol). The sealed tube was heated to 50° C. for 5 days and the precipitation formed. After cooling, the precipitate was collected by filtration and washed with cold 1:1 acetonitrile/water to give 2-ethyl-4-methyl-N-(4-(2-oxo-1,2,3,4-tetrahydroquinolin-6-yl)thiazol-2-yl)thiazole-5-carboxamide (0.094 g, 58%) as a beige solid. $^1$H NMR (400 MHz, DMSO-d): δ 12.56 (bs, 1H), 10.19 (s, 1H), 7.74 (s, 1H), 7.69 (dd, 1H, J=8.4, 1.6 Hz), 7.51 (bs, 1H), 6.89 (d, 1H, J=8.4 Hz), 2.99 (q, 2H, J=7.6 Hz), 2.93 (m, 2H), 2.62 (s, 3H), 2.49 (partial masked under d-DMSO, m, 2H), 1.32 (t, 3H, J=7.6 Hz). MS (ESI): Calcd. for $C_{19}H_{18}N_4O_2S_2$: 398, found 399 (M+1)$^+$.

Example 46

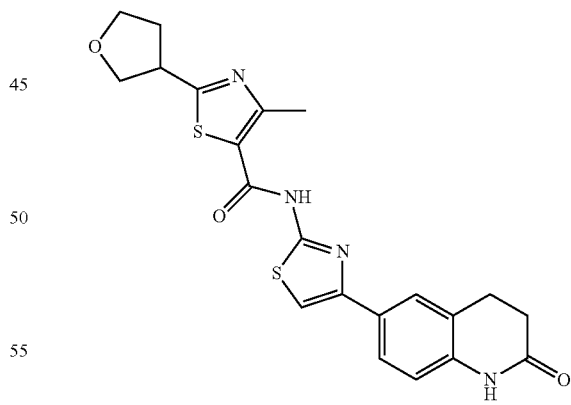

To a suspension of 6-(2-aminothiazol-4-yl)-3,4-dihydroquinolin-2(1H)-one (0.100 g, 0.408 mmol) and 4-methyl-2-(oxolan-3-yl)-1,3-thiazole-5-carboxylic acid (0.096 g, 0.448 mmol), and pyridine (0.15 mL, 1.832 mmol) in acetonitrile (4 mL) in a sealed tube was added propylphosphonic anhydride solution (50 wt % in ethyl acetate, 0.85 mL, 1.432 mmol). The sealed tube was heated to 50° C. for 5 days and the precipitation formed. After cooling, the precipitate was collected by filtration and washed with cold 1:1 acetonitrile/ water to give 4-methyl-N-(4-(2-oxo-1,2,3,4-tetrahydroquinolin-6-yl)thiazol-2-yl)-2-(tetrahydrofuran-3-yl)thiazole-5-carboxamide (0.114 g, 63%) as a light brown solid. $^1$H NMR (400 MHz, DMSO-d): δ 12.60 (bs, 1H), 10.19 (s, 1H), 7.74 (s, 1H), 7.69 (dd, 1H, J=8.4, 1.6 Hz), 7.51 (bs, 1H), 6.89 (d, 1H, J=8.4 Hz), 4.06 (dd, 1H, J=8.0, 7.2 Hz), 3.92 (m, 1H), 3.86 (m, 1H), 3.81 (m, 1H), 2.93 (m, 2H), 2.63 (s, 3H), 2.49 (partial masked under d-DMSO, m, 2H), 2.40 (m, 1H), 2.12 (m, 1H). MS (ESI): Calcd. for $C_{21}H_{20}N_4O_2S_2$: 440, found 441 $(M+1)^+$.

Example 47

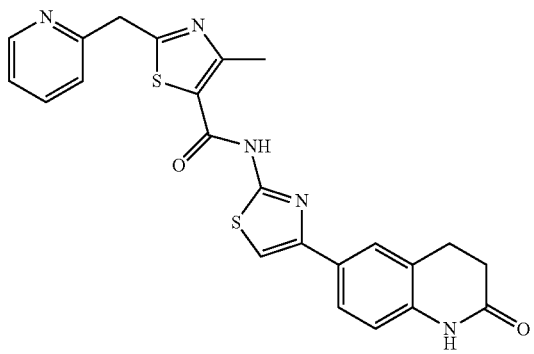 [SMILES: Cc1nc(Cc2ccccn2)sc1C(=O)Nc1nc(-c2ccc3c(c2)CCC(=O)N3)cs1]

To a suspension of 6-(2-aminothiazol-4-yl)-3,4-dihydroquinolin-2(1H)-one (0.100 g, 0.408 mmol) and 4-methyl-2-(pyridin-2-ylmethy)-1,3-thiazole-5-carboxylic acid (0.105 g, 0.448 mmol), and pyridine (0.15 mL, 1.832 mmol) in acetonitrile (4 mL) in a sealed tube was added propylphosphonic anhydride solution (50 wt % in ethyl acetate, 0.85 mL, 1.432 mmol). The sealed tube was heated to 50° C. for 5 days. The reaction mixture was quenced with water and extracted with ethyl acetate (3×20 mL). The combined organic layers were washed once with sat. NaHCO$_3$, dried over anhydrous Na$_2$SO$_4$ and concentrated in vacuo. The residue was purified by flash chromatography over silica gel using 95:5 dichloromethane/methanol to give 4-methyl-N-(4-(2-oxo-1,2,3,4-tetrahydroquinolin-6-yl)thiazol-2-yl)-2-(pyridin-2-ylmethyl)thiazole-5-carboxamide (0.096 g, 51%) as an orangy-brown solid. $^1$H NMR (400 MHz, DMSO-d): δ 12.57 (bs, 1H), 10.19 (s, 1H), 8.57 (dd, 1H, J=4.8, 0.8 Hz), 7.81 (ddd, 1H, J=8.0, 8.0, 2.0 Hz), 7.73 (s, 1H), 7.68 (dd, 1H, J=8.4, 1.6 Hz), 7.50 (bs, 1H), 7.47 (d, 1H, J=8.0 Hz), 7.33 (ddd, 1H, J=7.6, 4.8, 1.6 Hz), 6.88 (d, 1H, J=8.4 Hz), 4.50 (s, 2H), 2.92 (m, 2H), 2.61 (s, 3H), 2.48 (partial masked under d-DMSO, m, 2H). MS (ESI): Calcd. for $C_{23}H_{19}N_5O_2S_2$: 461, found 462 $(M+1)^+$.

Example 48

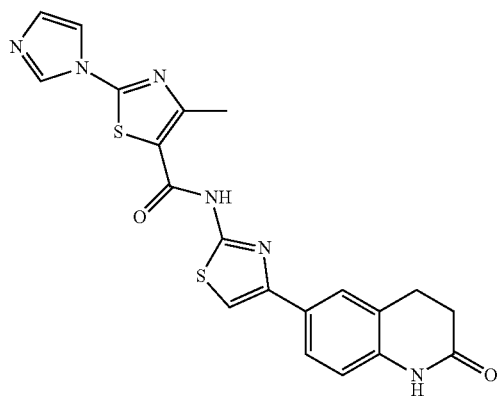 [SMILES: Cc1nc(-n2ccnc2)sc1C(=O)Nc1nc(-c2ccc3c(c2)CCC(=O)N3)cs1]

To a suspension of 6-(2-aminothiazol-4-yl)-3,4-dihydroquinolin-2(1H)-one (0.100 g, 0.408 mmol) and 2-(1H-imidazol-1-yl)-4-methythiazole-5-carboxylic acid (0.938 g, 0.448 mmol), and pyridine (0.15 mL, 1.832 mmol) in acetonitrile (4 mL) in a sealed tube was added propylphosphonic anhydride solution (50 wt % in ethyl acetate, 0.85 mL, 1.432 mmol). The sealed tube was heated to 50° C. for 5 days and the precipitation formed. After cooling, the precipitate was collected by filtration and washed with cold 1:1 acetonitrile/water to give 2-(1H-imidazol-1-yl)-4-methyl-N-(4-(2-oxo-1,2,3,4-tetrahydroquinolin-6-yl)thiazol-2-yl)thiazole-5-carboxamide (0.140 g, 79%) as a yellowish-brown solid. $^1$H NMR (400 MHz, DMSO-d): δ 12.81 (bs, 1H), 10.21 (s, 1H), 8.48 (s, 1H), 7.87 (s, 1H), 7.74 (s, 1H), 7.68 (dd, 1H, J=8.4, 1.6 Hz), 7.48 (bs, 1H), 7.21 (s, 1H), 6.90 (d, 1H, J=8.4 Hz), 2.93 (m, 2H), 2.49 (partial masked under d-DMSO, m, 2H). MS (ESI): Calcd. for $C_{20}H_{16}N_6O_2S_2$: 436, found 437 $(M+1)^+$.

Example 49

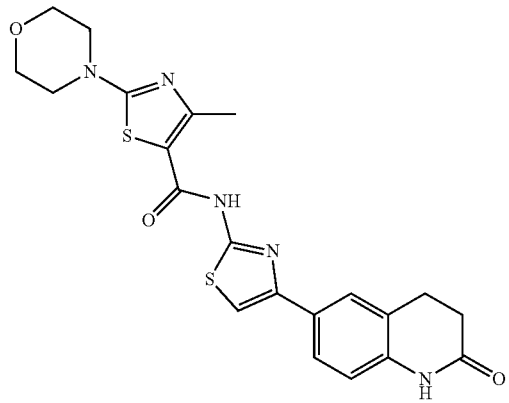 [SMILES: Cc1nc(N2CCOCC2)sc1C(=O)Nc1nc(-c2ccc3c(c2)CCC(=O)N3)cs1]

To a suspension of 6-(2-aminothiazol-4-yl)-3,4-dihydroquinolin-2(1H)-one (0.100 g, 0.408 mmol) and 4-methyl-2-morpholinothiazole-5-carboxylic acid (0.102 g, 0.448 mmol), and pyridine (0.15 mL, 1.832 mmol) in acetonitrile (4 mL) in a sealed tube was added propylphosphonic anhydride solution (50 wt % in ethyl acetate, 0.85 mL, 1.432 mmol). The sealed tube was heated to 50° C. for 5 days. The reaction mixture was quenced with sat. NaHCO$_3$ and extracted with ethyl acetate (3×20 mL). The combined organic layers were washed once with sat. NaHCO$_3$, dried over anhydrous Na$_2$SO$_4$ and concentrated in vacuo. The residue was purified by flash chromatography over silica gel using 95:5 dichloromethane/methanol to give 4-methyl-2-morpholino-N-(4-(2-oxo-1,2,3,4-tetrahydroquinolin-6-yl)thiazol-2-yl)thiazole-5-carboxamide (0.046 g, 25%) as a yellow solid. $^1$H NMR (400 MHz, DMSO-d): δ 12.03 (bs, 1H), 10.18 (s, 1H), 7.73 (s, 1H), 7.68 (dd, 1H, J=8.4, 1.6 Hz), 7.45 (bs, 1H), 6.88 (d, 1H, J=8.4 Hz), 3.72 (m, 4H), 2.47 (m, 4H), 2.48 (partial masked under d-DMSO, m, 2H). MS (ESI): Calcd. for $C_{21}H_{21}N_5O_3S_2$: 455, found 456 $(M+1)^+$.

Example 50

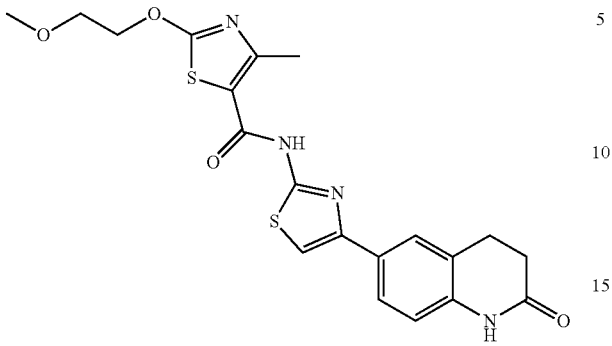

To a suspension of 6-(2-aminothiazol-4-yl)-3,4-dihydroquinolin-2(1H)-one (0.100 g, 0.408 mmol) and 2-(2-methoxyethoxyl)-4-methylthiazole-5-carboxylic acid (0.97 g, 0.448 mmol), and pyridine (0.15 mL, 1.832 mmol) in acetonitrile (4 mL) in a sealed tube was added propylphosphonic anhydride solution (50 wt % in ethyl acetate, 0.85 mL, 1.432 mmol). The sealed tube was heated to 50° C. for 5 days. The reaction mixture was quenced with sat. NaHCO$_3$ and extracted with 8:2 dichloromethane/isopropanol mixture (3×20 mL). The combined organic layers were washed once with sat. NaHCO$_3$, dried over anhydrous Na$_2$SO$_4$ and concentrated in vacuo. The residue was purified by flash chromatography over silica gel using 95:5 dichloromethane/methanol to give 2-(2-methoxyethoxy)-4-methyl-N-(4-(2-oxo-1,2,3,4-tetrahydroquinolin-6-yl)thiazol-2-yl)thiazole-5-carboxamide (0.102 g, 57%) as a white solid. $^1$H NMR (400 MHz, DMSO-d): δ 12.41 (bs, 1H), 10.19 (s, 1H), 7.73 (s, 1H), 7.68 (dd, 1H, J=8.4, 1.6 Hz), 7.48 (bs, 1H), 6.88 (d, 1H, J=8.4 Hz), 4.54 (m, 2H), 3.69 (m, 2H), 3.31 (s, 3H), 2.93 (m, 2H), 2.55 (s, 3H), 2.48 (partial masked under d-DMSO, m, 2H). MS (ESI): Calcd. for C$_{20}$H$_{20}$N$_4$O$_4$S$_2$: 444, found 445 (M+1)$^+$.

Example 51

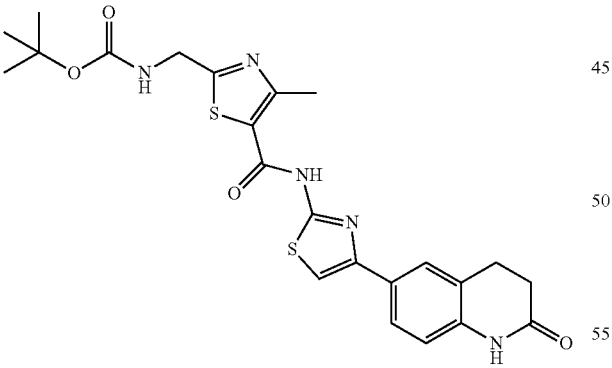

To a suspension of 6-(2-aminothiazol-4-yl)-3,4-dihydroquinolin-2(1H)-one (0.200 g, 0.816 mmol) and 4-methyl-2-({[(tert-butoxyl)carbonyl]amino}-methyl-1,3-thiazole-5-carboxylic acid (0.233 g, 0.856 mmol), and pyridine (0.30 mL, 3.670 mmol) in acetonitrile (8 mL) in a sealed tube was added propylphosphonic anhydride solution (50 wt % in ethyl acetate, 1.70 mL, 2.851 mmol). The sealed tube was heated to 50° C. for 5 days. The reaction mixture was quenced with sat. NaHCO$_3$ and extracted with 8:2 dichloromethane/isopropanol mixture (3×20 mL). The combined organic layers were washed once with sat. NaHCO$_3$, dried over anhydrous Na$_2$SO$_4$ and concentrated in vacuo. The residue was purified by flash chromatography over silica gel using 95:5 dichloromethane/methanol to give tert-butyl ((4-methyl-5-((4-(2-oxo-1,2,3,4-tetrahydroquinolin-6-yl)thiazol-2-yl)carbamoyl)thiazol-2-yl)methyl)carbamate (0.291 g, 72%) as a yellow solid. $^1$H NMR (400 MHz, DMSO-d): δ 12.61 (bs, 1H), 10.19 (s, 1H), 7.85 (m, 1H), 7.74 (s, 1H), 7.69 (dd, 1H, J=8.0, 1.6 Hz), 7.51 (bs, 1H), 6.89 (d, 1H, J=8.0 Hz), 4.38 (d, 2H, J=6.0 Hz), 2.93 (m, 2H), 2.62 (s, 3H), 2.49 (partial masked under d-DMSO, m, 2H), 1.43 (s, 9H). MS (ESI): Calcd. for C$_{23}$H$_{25}$N$_5$O$_4$S$_2$: 499, found 500 (M+1)$^+$.

Example 52

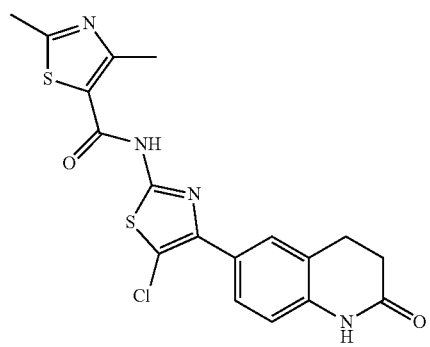 [SMILES: Cc1nc(C)c(C(=O)Nc2nc(-c3ccc4c(c3)CCC(=O)N4)c(Cl)s2)s1]

To a suspension of 6-(2-amino-5-chlorothiazol-4-yl)-3,4-dihydroquinolin-2(1H)-one hydrochloride (0.200 g, 0.633 mmol) and 2,4-dimethyl-1,3-thiazole-5-carboxylic acid (0.109 g, 0.696 mmol), and pyridine (0.28 mL, 3.481 mmol) in acetonitrile (8 mL) in a sealed tube was added propylphosphonic anhydride solution (50 wt % in ethyl acetate, 1.32 mL, 2.211 mmol). The sealed tube was heated to 50° C. for 5 days and the precipitation formed. After cooling, the precipitate was collected by filtration and washed with cold 1:1 acetonitrile/water to give N-(5-chloro-4-(2-oxo-1,2,3,4-tetrahydroquinolin-6-yl)thiazol-2-yl)-2,4-dimethylthiazole-5-carboxamide (0.098 g, 33%) as a reddish pink solid. $^1$H NMR (400 MHz, DMSO-d): δ 12.86 (bs, 1H), 10.26 (s, 1H), 7.72 (s, 1H), 7.69 (dd, 1H, J=8.4, 1.6 Hz), 6.94 (d, 1H, J=8.4 Hz), 2.94 (m, 2H), 2.68 (s, 3H), 2.61 (s, 3H), 2.49 (partial masked under d-DMSO, m, 2H). MS (ESI): Calcd. for C$_{18}$H$_{15}$ClN$_4$O$_2$S$_2$: 418, found 419 (M+1)$^+$.

Example 53

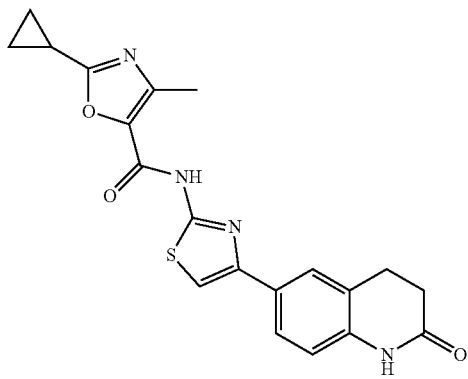 [SMILES: Cc1nc(C2CC2)oc1C(=O)Nc1nc(-c2ccc3c(c2)CCC(=O)N3)cs1]

To a suspension of 6-(2-amino-thiazol-4-yl)-3,4-dihydroquinolin-2(1H)-one hydrochloride (0.100 g, 0.408 mmol) and 2-cyclopropyl-4-methyl-1,3-oxazole-5-carboxylic acid (0.072 g, 0.428 mmol), and pyridine (0.15 mL, 1.831 mmol) in acetonitrile (4 mL) in a sealed was added propylphosphonic anhydride solution (50 wt % in ethyl acetate, 0.85 mL, 1.431 mmol). The sealed tube was heated to 50° C. for 5 days and the precipitation formed. After cooling, the precipitate was collected by filtration and washed with cold 1:1 acetonitrile/water to give 2-cyclopropyl- 4-methyl-N-(4-(2-oxo-1,2,3,4-tetrahydroquinolin-6-yl)thiazol-2-yl)oxazole-5-carboxamide (0.143 g, 89%) as a beige solid. $^1$H NMR (400 MHz, DMSO-d): δ 12.52 (bs, 1H), 10.19 (s, 1H), 7.75 (s, 1H), 7.71 (dd, 1H, J=8.4, 1.6 Hz), 7.52 (s, 1H), 6.89 (d, 1H, J=8.4 Hz), 2.93 (m, 2H), 2.49 (partial masked under d-DMSO, m, 2H), 2.39 (s, 3H), 2.14 (m, 1H), 1.25 (m, 2H), 1.12 (m, 2H). MS (ESI): Calcd. for $C_{20}H_{18}N_4O_3S$: 394, found 395 $(M+1)^+$.

Example 54

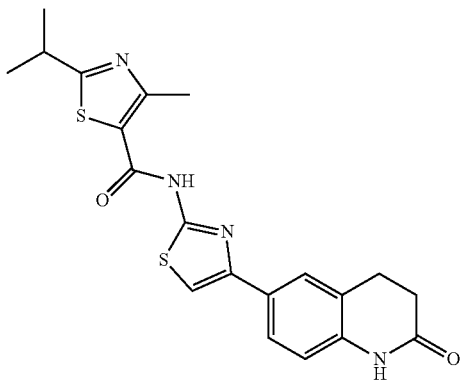 [SMILES: Cc1nc(C(C)C)sc1C(=O)Nc1nc(-c2ccc3c(c2)CCC(=O)N3)cs1]

To a suspension of 6-(2-amino-thiazol-4-yl)-3,4-dihydroquinolin-2(1H)-one hydrochloride (0.100 g, 0.408 mmol) and 4-methyl-2-(propan-2-yl)-1,3-thiazole-5-carboxylic acid (0.083 g, 0.448 mmol), and pyridine (0.15 mL, 1.831 mmol) in acetonitrile (4 mL) in a sealed tube was added propylphosphonic anhydride solution (50 wt % in ethyl acetate, 0.85 mL, 1.431 mmol). The sealed tube was heated to 50° C. for 5 days and the precipitation formed. After cooling, the precipitate was collected by filtration and washed with cold 1:1 acetonitrile/water to give 2-isopropyl-4-methyl-N-(4-(2-oxo-1,2,3,4-tetrahydroquinolin-6-yl)thiazol-2-yl)thiazole-5-carboxamide (0.104 g, 62%) as a beige solid. $^1$H NMR (400 MHz, DMSO-d): δ 12.56 (bs, 1H), 10.19 (s, 1H), 7.74 (s, 1H), 7.69 (dd, 1H, J=8.4, 1.6 Hz), 7.51 (s, 1H), 6.89 (d, 1H, J=8.4 Hz), 3.29 (m, 1H), 2.93 (m, 2H), 2.62 (s, 3H), 2.49 (partial masked under d-DMSO, m, 2H), 1.36 (s, 3H), 1.34 (s, 3H). MS (ESI): Calcd. for $C_{20}H_{20}N_4O_2S_2$: 412, found 413 $(M+1)^+$.

Example 55

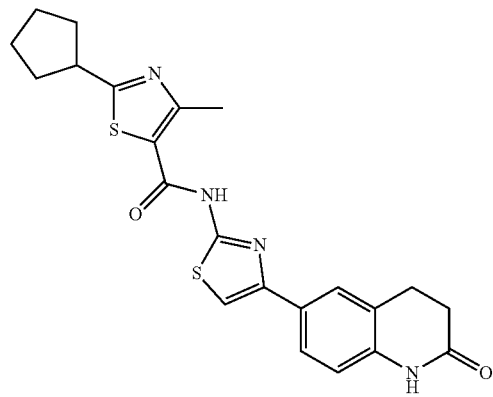 [SMILES: Cc1nc(C2CCCC2)sc1C(=O)Nc1nc(-c2ccc3c(c2)CCC(=O)N3)cs1]

To a suspension of 6-(2-amino-thiazol-4-yl)-3,4-dihydroquinolin-2(1H)-one hydrochloride (0.100 g, 0.408 mmol) and 2-cyclopentyl-4-methyl-1,3-thiazole-5-carboxylic acid (0.095 g, 0.448 mmol), and pyridine (0.15 mL, 1.831 mmol) in acetonitrile (4 mL) in a sealed tube was added propylphosphonic anhydride solution (50 wt % in ethyl acetate, 0.85 mL, 1.431 mmol). The sealed tube was heated to 50° C. for 5 days and the precipitation formed. After cooling, the precipitate was collected by filtration and washed with cold 1:1 acetonitrile/water to give 2-cyclopentyl-4-methyl-N-(4-(2-oxo-1,2,3,4-tetrahydroquinolin-6-yl)thiazol-2-yl)thiazole-5-carboxamide (0.143 g, 80%) as a beige solid. $^1$H NMR (400 MHz, DMSO-d): δ 12.53 (bs, 1H), 10.19 (s, 1H), 7.74 (s, 1H), 7.69 (dd, 1H, J=8.4, 1.6 Hz), 7.50 (bs, 1H), 6.89 (d, 1H, J=8.4 Hz), 3.44 (m, 1H), 2.93 (m, 2H), 2.62 (s, 3H), 2.49 (partial masked under d-DMSO, m, 2H), 2.12 (m, 2H), 1.77 (m, 4H), 1.67 (m, 2H). MS (ESI): Calcd. for $C_{22}H_{22}N_4O_2S_2$: 438, found 439 $(M+1)^+$.

Example 56

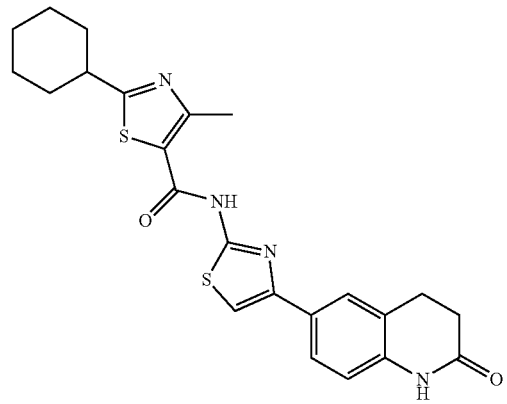 [SMILES: Cc1nc(C2CCCCC2)sc1C(=O)Nc1nc(-c2ccc3c(c2)CCC(=O)N3)cs1]

To a suspension of 6-(2-amino-thiazol-4-yl)-3,4-dihydroquinolin-2(1H)-one hydrochloride (0.100 g, 0.408 mmol) and 2-cyclohexyl-4-methyl-1,3-thiazole-5-carboxylic acid (0.101 g, 0.448 mmol), and pyridine (0.15 mL, 1.831 mmol) in acetonitrile (4 mL) the sealed tube was added propylphosphonic anhydride solution (50 wt % in ethyl acetate, 0.85 mL, 1.431 mmol). The sealed tube was heated to 50° C.

for 5 days and the precipitation formed. After cooling, the precipitate was collected by filtration and washed with cold 1:1 acetonitrile/water to give 2-cyclohexyl-4-methyl-N-(4-(2-oxo-1,2,3,4-tetrahydroquinolin-6-yl)thiazol-2-yl)thiazole-5-carboxamide (0.149 g, 81%) as a beige solid. $^1$H NMR (400 MHz, DMSO-d): δ 12.54 (bs, 1H), 10.19 (s, 1H), 7.74 (s, 1H), 7.69 (dd, 1H, J=8.4, 1.6 Hz), 7.51 (bs, 1H), 6.89 (d, 1H, J=8.4 Hz), 2.99 (m, 1H), 2.93 (m, 2H), 2.62 (s, 3H), 2.49 (partial masked under d-DMSO, m, 2H), 2.06 (m, 2H), 1.78 (m, 4H), 1.55-1.31 (m, 4H), 1.27 (m, 1H). MS (ESI): Calcd. for $C_{23}H_{24}N_4O_2S_2$: 452, found 453 (M+1)$^+$.

Example 57

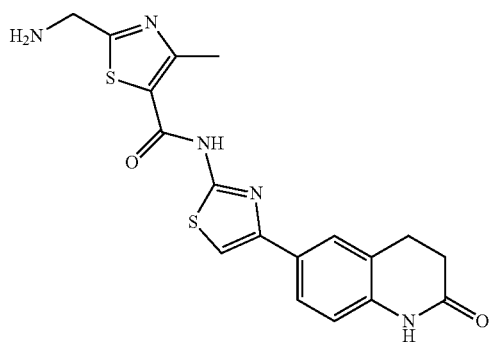 [SMILES: Cc1nc(CN)sc1C(=O)Nc1nc(-c2ccc3c(c2)CCC(=O)N3)cs1]

tert-Butyl ((4-methyl-5-((4-(2-oxo-1,2,3,4-tetrahydroquinolin-6-yl)thiazol-2-yl)carbamoyl)thiazol-2-yl)methyl)carbamate (0.100 g, 0.200 mmol) was suspended 6 mL of 4M hydrogen chloride solution in dioxane in sealed flask. The mixture was stirred for 6 hours at room temperature. The reaction mixture was concentrated in vacuo. The HCl salt was dissolved in minimum amount of methanol and quenched with sat. sodium bicarbonate. The mixture was extracted with 8:2 dichloromethane/isopropanol (6×10 mL). The combined organic layers were washed once with sat. NaHCO$_3$, dried over anhydrous Na$_2$SO$_4$ and concentrated in vacuo. to give 2-(aminomethyl)-4-methyl-N-(4-(2-oxo-1,2,3,4-tetrahydroquinolin-6-yl)thiazol-2-yl)thiazole-5-carboxamide (0.060 g, 75%) as an orange solid. $^1$H NMR (400 MHz, DMSO-d): δ acylic NH (not observed), 10.18 (s, 1H), 7.85 (m, 1H), 7.74 (s, 1H), 7.69 (dd, 1H, J=8.0, 1.6 Hz), 7.45 (s, 1H), 6.89 (d, 1H, J=8.0 Hz), 4.03 (s, 2H), 2.93 (m, 2H), 2.62 (s, 3H), 2.49 (partial masked under d-DMSO, m, 2H), 1.23 (bs, 2H). MS (ESI): Calcd. for $C_{18}H_{17}N_5O_2S_2$: 399, found 400 (M+1)$^+$.

Biological Activities of Selected Compounds

Activity of exemplary compounds according to the inventive subject matter was tested for wild type, K-ras G12D, and K-ras G12V following standard G-LISA protocol as further described below, and the IC50 (μM) results are shown in Table 1 while compound formulae are depicted in FIGS. 4A-4D.

TABLE 1

| Compound | IC$_{50}$ (μM) Wild-type | IC$_{50}$ (μM) G12D | IC$_{50}$ (μM) G12V |
|---|---|---|---|
| 4556 | | >25 μM | |
| 4562 | 0.5 μM | 10 μM | 38 μM |

TABLE 1-continued

| Compound | IC$_{50}$ (μM) Wild-type | IC$_{50}$ (μM) G12D | IC$_{50}$ (μM) G12V |
|---|---|---|---|
| 4639 | | >25 μM | |
| 4662 | | >25 μM | |
| 4663 | 7 μM | 15 μM | 32 μM |
| 4664 | | >25 μM | |
| 4665 | | >25 μM | |
| 4666 | | >25 μM | |
| 4683 | | 12 μM | |
| 4684 | | >25 μM | |
| 4685 | | >25 μM | |
| 4686 | | 11 μM | |
| 4687 | | 19 μM | |
| 4734 | | >25 μM | |
| 4735 | | >25 μM | |
| 4747 | | >25 μM | |
| 4748 | | 21 μM | |
| 4749 | | >25 μM | |
| 4800 | | >25 μM | |
| 4801 | >25 μM | 8.2 μM | 10.7 μM |
| 4802 | | >25 μM | 17 μM |
| 4803 | | >25 μM | |
| 4805 | | >25 μM | |
| 4824 | | >25 μM | |
| 4825 | | >25 μM | |
| 4826 | | >25 μM | |
| 4827 | >25 μM | >25 μM | |
| 4828 | | >25 μM | |
| 4829 | | >25 μM | |
| 4855 | | >25 μM | |
| 4856 | | >25 μM | |
| 4874 | | 16 μM | |
| 4875 | | 17 μM | |
| 4877 | 16 μM | 6 μM | 9 μM |
| 4878 | | 19 μM | >25 μM |
| 4888 | 11.3 μM | 6 μM | 14.5 μM |
| 4891 | 11.5 μM | 5 μM | 9.3 μM |
| 4892 | | 6.5 μM | |

293H cells were seeded in 6-wells at 0.6×106 cells per well and transfected next day with 5 μg of Ras wild-type, or G12C, G12D or G12V mutant DNA plasmid vector using transfection reagent Lipofectamine 3000. Next day cells were treated with 3.125-50 μM of Ras compounds for 1 hour. Wild-type transfected cells were subsequently treated with 100 ng/ml EGF for 2 minutes. Cells were washed once in ice-cold PBS, lysed in complete lysis buffer on ice, and processed by G-LISA according to Cytoskeleton protocol.

Viability assays were performed on exemplary compounds and Table 2 below lists exemplary results for selected compounds tested on wild type (Ishikawa) and various K-ras mutants (Panc1-G12D; Panc10.05-G12D; HCT116-G13D). Results are expressed in μM and corresponding structures are shown in FIGS. 4A-4D.

TABLE 2

| Compound | 72 hr Cell Viability Panc1 (G12D) | 72 hr Cell Viability Panc10.05 (G12D) | 72 hr Cell Viability Ishikawa (K-Ras wild-type) | 72 hr Cell Viability HCT116 (G13D) |
|---|---|---|---|---|
| 4562 | 6 μM | 2 μM | | |
| 4801 | 10 μM | 2 μM | | |
| 4827 | 16 μM | 4 μM | | |
| 4855 | ≥25 μM | ≥25 μM | | |
| 4856 | ≥25 μM | ≥25 μM | | |
| 4874 | 12 μM | | 3 μM | |
| 4875 | 9 μM | | 2 μM | |
| 4876 | 13 μM | | 3 μM | |
| 4877 | 5 μM | | 1.2 μM | |
| 4878 | 7 μM | | 5 μM | |
| 4888 | 9 μM | 4 μM | 5 μM | 7 μM |
| 4889 | ≥25 μM | ≥25 μM | 14 μM | 21 μM |
| 4891 | 11 μM | 4 μM | 12 μM | 13 μM |
| 4892 | 17 μM | 6 μM | 14 μM | 14 μM |
| 4893 | ≥25 μM | ≥25 μM | ≥25 μM | ≥25 μM |
| 4894 | ≥25 μM | ≥25 μM | ≥25 μM | ≥25 μM |
| 4895 | ≥25 μM | ≥25 μM | ≥25 μM | ≥25 μM |
| 4896 | ≥25 μM | ≥25 μM | 19 μM | 22 μM |

Cells are counted and seeded at 1000 cells/36 ul medium/well into 384-well microplates. Cells are returned to 37° C. CO2 incubator for 18 hr. Drug is made as 200× in DMSO and diluted into medium to 10×. To each well is added 4 ul 10× drug, and plates are returned to the incubator. Final assay DMSO concentration is 0.5%. After 72 hr, 8 ul CellTiterBlue (Promega) is added to each well. After 3 hr, fluorescence (Ex550/Em590) is determined on the Victor Plate Reader (Perkin Elmer). Assay range is determined by DMSO control (100% viability) and 100 uM tamoxifen (0% viability). GI50 values are calculated using Graphpad Prism.

In-cell phosphorylation assays for Erk and Akt were performed on various of the compounds and exemplary results are shown in Table 3 below using Panc1 and Panc10.05 cell lines for G12D K-ras mutants. Results are expressed in μM and corresponding structures are shown in FIGS. 4A-4D.

Cells are seeded in complete medium into black sided, clear-bottom 384-well microplates at 3000 cells/27 ul/well. Plates are returned to 37° C. CO2 incubator for 18 hr. Drug is made as 200× in DMSO and diluted into medium to 10×. To each well is added 4 ul 10× test article or controls, and plates are returned to the incubator. Final assay DMSO concentration is 0.5%. After one hour, cells are fixed in formaldehyde, rinsed & permeabilized with triton X-100, and blocked with BSA/Goat serum blocking solution. Primary phospho-Akt and phospho-ERK antibodies are added and plates are incubated overnight at 4° C. Plates are rinsed with Tween-20 wash buffer and secondary antibody (Goat anti-rabbit, Thermofisher) is added. After 2 hours, plates are rinsed in Tween-20 wash buffer, and then PBS. Plates are imaged on the Celigo (Nexcelom) and cellular fluorescence is quantitated. Full inhibition of phospho-Akt is achieved with 1 uM BEZ235 (Sellekchem), while full inhibition of

TABLE 3

| Compound | In-Cell Western Erk phosporylation Panc1 (G12D) | In-Cell Western Akt phosporylation Panc1 (G12D) | In-Cell Western Erk phosporylation Panc10.05 (G12D) | In-Cell Western Akt phosporylation Panc10.05 (G12D) |
|---|---|---|---|---|
| 4562 | 5 μM | 8 μM | 4 μM | 22 μM |
| 4801 | 5 μM | 13 μM | 7 μM | 25 μM |
| 4827 | 9 μM | 22 μM | 17 μM | >25 μM |
| 4855 | >25 μM | >25 μM | >25 μM | >25 μM |
| 4856 | 7 μM | >25 μM | 19 μM | >25 μM |
| 4874 | >25 μM | 25 μM | 14 μM | >25 μM |
| 4875 | 24 μM | 33 μM | >25 μM | >25 μM |
| 4876 | 9 μM | 20 μM | 17 μM | >25 μM |
| 4877 | 3 μM | 7 μM | 3 μM | 17 μM |
| 4878 | 19 μM | 26 μM | 13 μM | >25 μM |
| 4888 | 4 μM | 5 μM | 2 μM | 3 μM |
| 4889 | >25 μM | >25 μM | >25 μM | >25 μM |
| 4891 | 2 μM | 7 μM | 2 μM | 3 μM |
| 4892 | 5 μM | 12 μM | 2 μM | 6 μM |
| 4893 | >25 μM | >25 μM | >25 μM | >25 μM |
| 4894 | >25 μM | >25 μM | >25 μM | >25 μM |
| 4895 | >25 μM | >25 μM | >25 μM | >25 μM |
| 4896 | 8 μM | 14 μM | 8 μM | 12 μM | phospho-ERK is achieved with 1 uM MEK Inhibitor II Calbiochem). EC50 values are calculated using Graphpad Prism.

Selected compounds were also tested for selective binding to wild type and mutant forms of K-ras in the active and non-active state using surface plasmon resonance, and exemplary results are shown in Table 4.

diffusion coefficients in label-free biosensing, John G. Quinn, Analytical Biochemistry (2011)). Buffer blanks were injected for double referencing purposes. Data processing and model fitting were performed using Qdat.

In-cell selectivity of the compounds presented herein against a specific K-ras mutant form can also be tested as shown in the following exemplary experiment. 293H cells

TABLE 4

| Compound | SPR Assay Wild-type (GDP) | SPR Assay Wild-type (GTP) | SPR Assay G12D (GDP) | SPR Assay G12D (GTP) | SPR Assay G12V (GTP) |
|---|---|---|---|---|---|
| 4556 | $Kd = 43 \pm \mu M$<br>$Rmax = 44.6 \pm 2$<br>$Res(SD) = 4\%$ | No binding/fit | $Kd = 151 \pm 4 \mu M$<br>$Rmax = 63 \pm 1$<br>$Res(SD) = 2\%$ | No binding/fit | $Kd = 19.3 \pm 7 \mu M$<br>$Rmax = 1100 \pm 3$<br>$Res(SD) = 2.2\%$ |
| 4562 | No binding/fit | No binding/fit | $Kd = 111 \pm 2 \mu M$<br>$Rmax = 66.0 \pm 0.9$<br>$Res(SD) = 2.1\%$ | No binding/fit | $Kd = 10$ mM<br>$Rmax = 300000$ |
| 4639 |  | $Kd = 6.4 \pm 0.1 \mu M$<br>$Rmax = 14.6 \pm 0.1$<br>$Res(SD) = 10.9\%$ |  |  |  |
| 4663 |  |  |  |  | No binding/fit |
| 4664 |  |  |  | $Kd = 4.8 \pm .04 \mu M$<br>$Rmax = 8.73$<br>$Res(SD) = 9.1\%$ | $Kd = 36.8 \pm 0.7 \mu M$<br>$Rmax = 143 \pm 1$<br>$Res(SD) = 7\%$ |
| 4686 |  |  |  |  | $Kd = 11.4 \pm 0.1 \mu M$<br>$Rmax = 94.2 \pm 0.2$<br>$Res(SD) = 6\%$ |
| 4687 |  |  |  |  | $Kd = 6.6 \pm 0.1 \mu M$<br>$Rmax = 72.6 \pm 0.1$<br>$Res(SD) = 8.8\%$ |
| 4729 |  |  |  |  | $Kd = 5.8 \pm 0.1 \mu M$<br>$Rmax = 73.3 \pm 0.1$<br>$Res(SD) = 10.8\%$ |
| 4734 |  |  |  |  | $Kd = 9.07 \pm .1 \mu M$<br>$Rmax = 79.0 \pm 0.1$<br>$Res(SD) = 6\%$ |
| 4735 |  |  |  |  | $Kd = 43 \pm 1 \mu M$<br>$Rmax = 203 \pm 3$<br>$Res(SD) = 6.8\%$ |
| 4747 |  |  |  |  | $Kd = 10.05 \pm .1 \mu M$<br>$Rmax = 85.3 \pm 0.1$<br>$Res(SD) = 5\%$ |
| 4749 |  |  |  |  | $Kd = 6.08 \pm .1 \mu M$<br>$Rmax = 75.9 \pm 0.1$<br>$Res(SD) = 10\%$ |
| 4800 |  |  |  | $Kd = 27.2 \pm 1 \mu M$<br>$Rmax = 389 \pm 1$<br>$Res(SD) = 10\%$ | $Kd = 15.2 \pm .2 \mu M$<br>$Rmax = 57.1 \pm 0.2$<br>$Res(SD) = 12\%$ |
| 4801 |  |  |  |  | $Kd = 11.1 \pm .09 \mu M$<br>$Rmax = 73.3 \pm 0.1$<br>$Res(SD) = 6.8\%$ |
| 4805 |  |  |  | $Kd = 570 \pm 20 \mu M$<br>$Rmax = 219 \pm 5$<br>$Res(SD) = 0.6\%$ | $Kd = 12.1 \pm 1 \mu M$<br>$Rmax = 100.3 \pm 0.2$<br>$Res(SD) = 7.5\%$ |
| 4827 |  | $Kd = 7 \pm 6$ mM<br>$Rmax = 2 \pm 2e3$<br>$Res(SD) = 3.7\%$ |  |  | $Kd = 14.3 \pm .1 \mu M$<br>$Rmax = 79.2 \pm 0.1$<br>$Res(SD) = 6.3\%$ |

The running buffer in all surface plasmon resonance experiments was 10 mM HEPES pH 7.4, 150 mM NaCl, 0.1% (v/v) Tween-20, 1 mM MgCl2, 8% DMSO. Experiments were carried out on the SensiQ Pioneer optical biosensor. The flow rate was set at 50 μL/min and the temperature was 25° C. kRAS protein was immobilized to the Nickel-NTA charged surface of the SensiQ HisCap chip (sensiqtech.com) giving a yield of 4000 RU. Small molecules were prepared in 100% DMSO and further diluted to 8% DMSO in running buffer. The small molecules were injected using the Taylor diffusion gradient injection mode (OneStep®, see e.g., Evaluation of Taylor dispersion injections: Determining kinetic/affinity interaction constants and were seeded in 6-wells and transfected next day with 5 μg of Ras wild-type, or G12C, G12D or G12V mutant DNA plasmid vector. Next day cells were treated with 3.125-50 μM of Ras compounds for 1 hour. Wild-type transfected cells were subsequently treated with 100 ng/ml EGF for 2 minutes. Cells were washed once in ice-cold PBS, lysed in complete lysis buffer on ice, and processed by G-LISA according to Cytoskeleton protocol. FIG. 1 depicts exemplary results. As is readily apparent, the tested compound A0837 (identical with 4562 of FIGS. 4A-4D) had pronounced selectivity towards the G12D mutant form and exhibited also a lower $IC_{50}$ as compared to the wild type.

Figure 2:
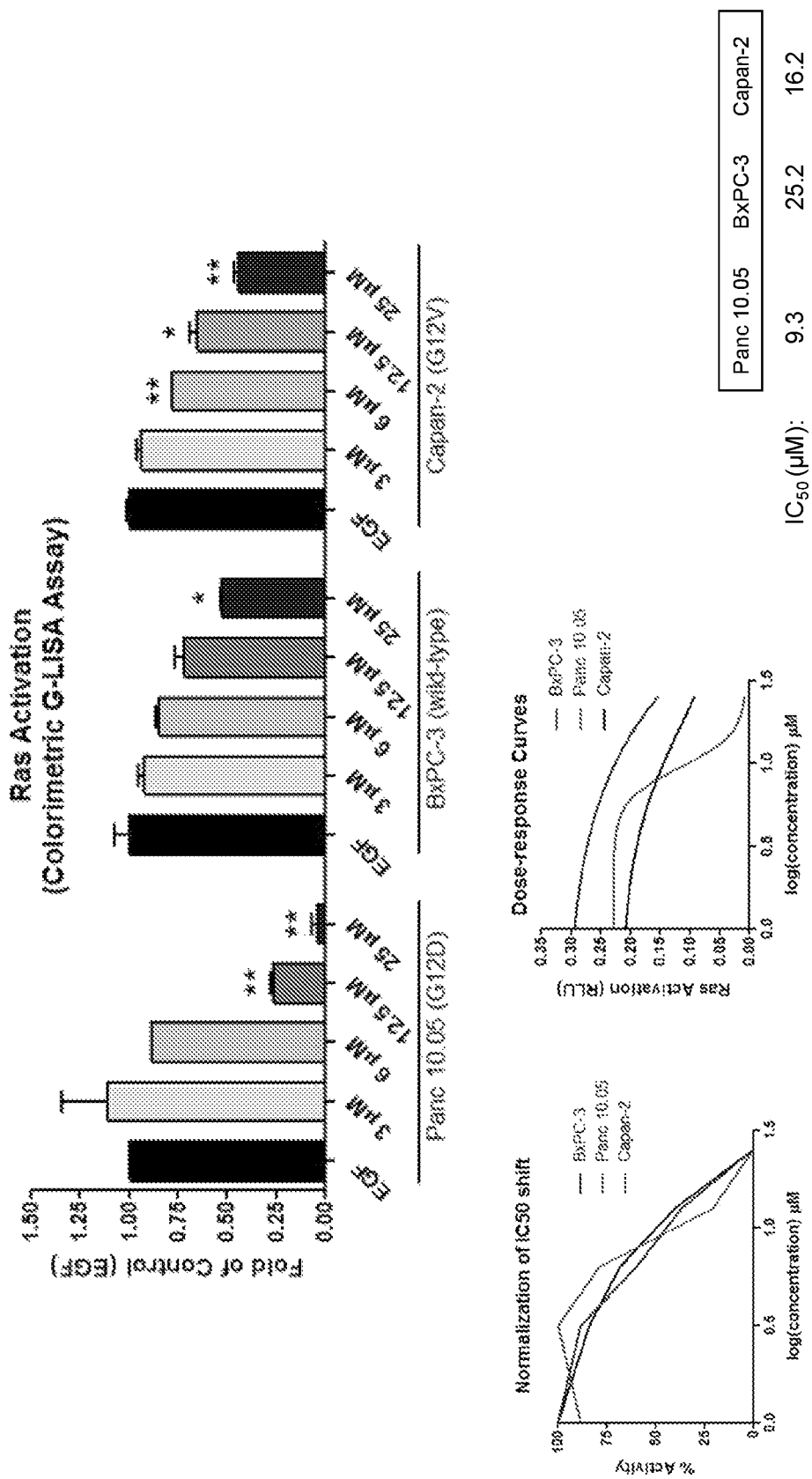
FIG. 2 depicts graphs illustrating Ras inhibition in various cancer cells using G-LISA assay.

To verify the results in specific cancer cell lines, cancer cell lines BxPC-3 (K-Ras wild-type), Panc10.05 (K-Ras G12D mutant), and Capan-2 (K-Ras G12V) were treated with 3.1 to 25 µM of Ras compound A0837 for 1 hour before stimulation with 100 ng/ml EGF for 2 minutes. Cells were washed once in ice-cold PBS, lysed in complete lysis buffer on ice, and processed by G-LISA according to Cytoskeleton protocol. As can be clearly seen in FIG. 2, the tested compound had clear selectivity towards K-ras mutant G12D, which is consistent with the other results presented above.

Figure 3:
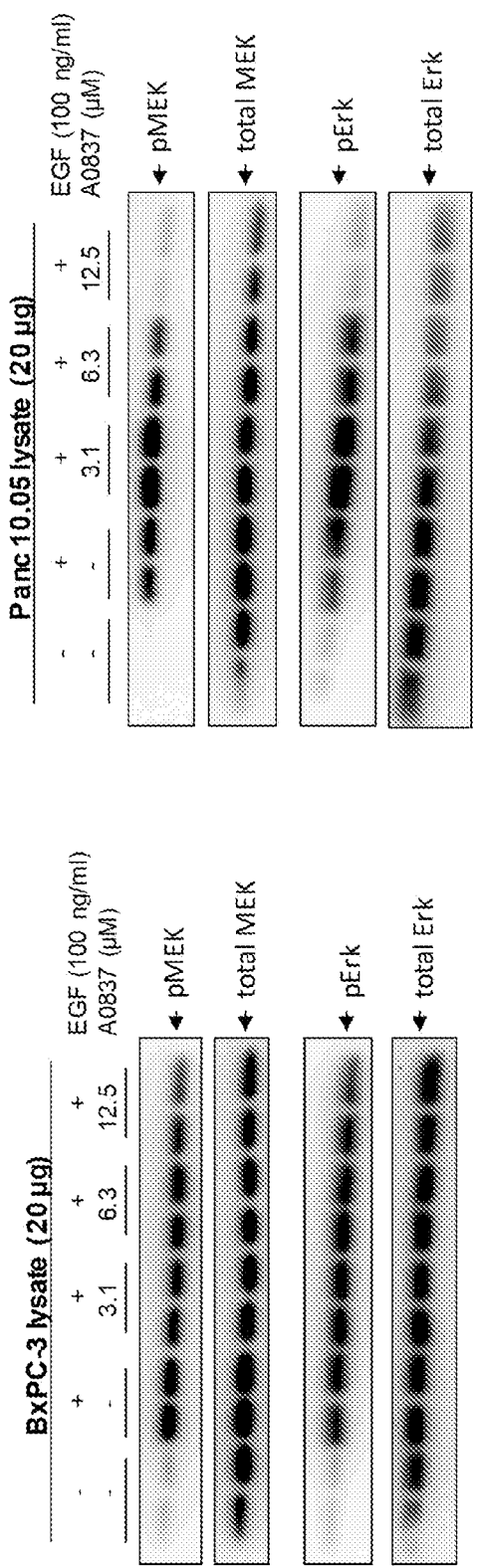
FIG. 3 shows autoradiographs for inhibition of downstream signaling as evidenced by phosphorylation of MEK and Erk in wild type and K-ras mutant (G12D) cells.
Figure 4A:
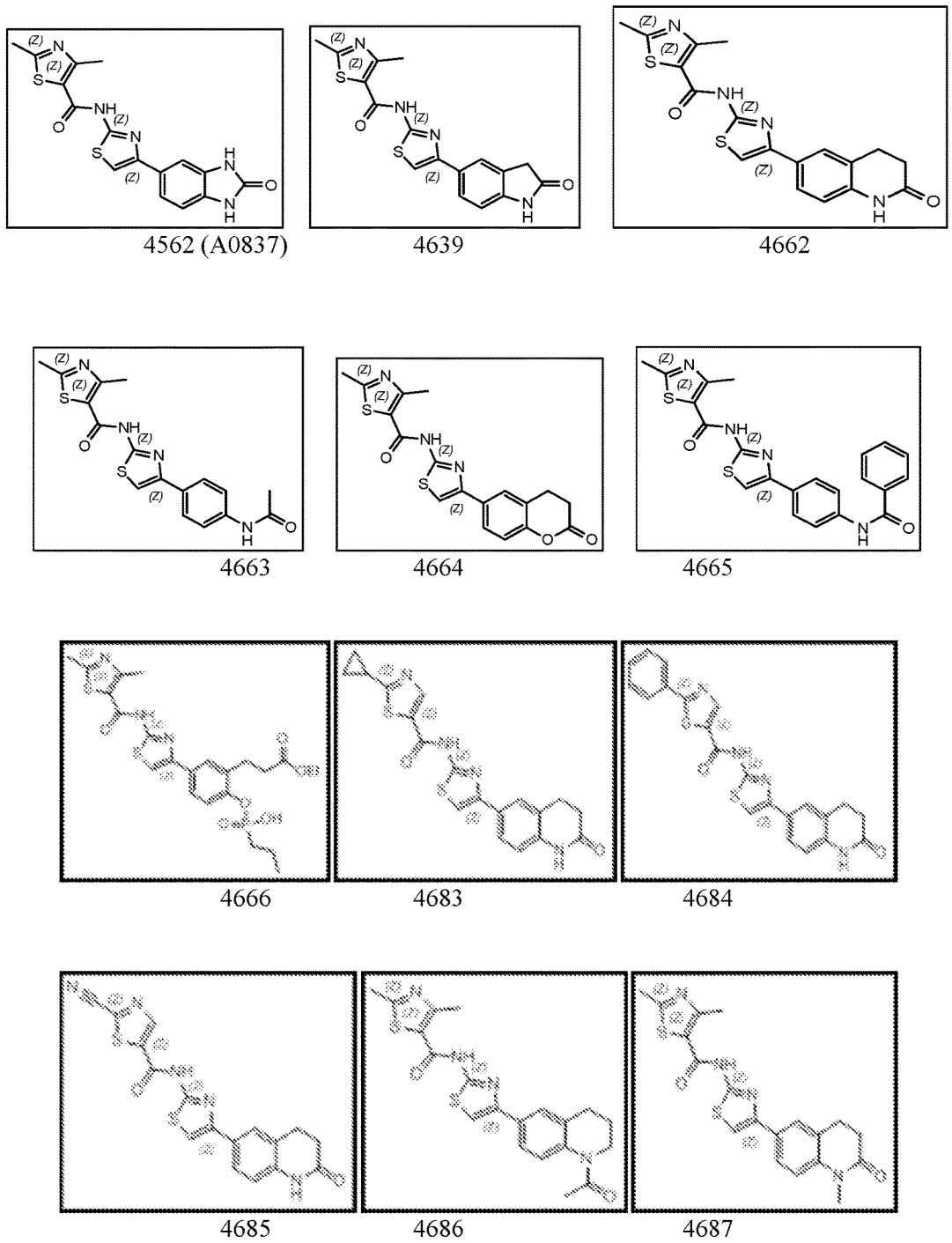
FIGS. 4A-4D show selected compounds used in testing for K-Ras inhibition.
Figure 4B:
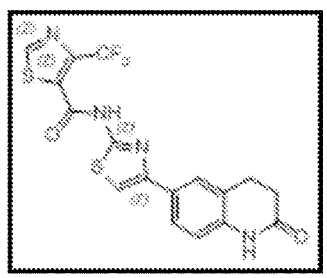
Figure 4B:
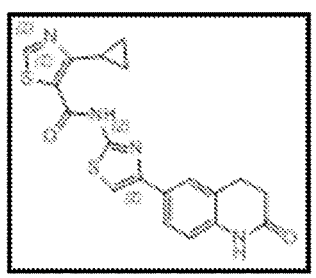
Figure 4B:
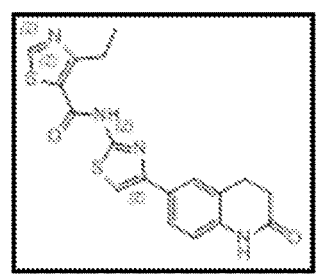
Figure 4B:
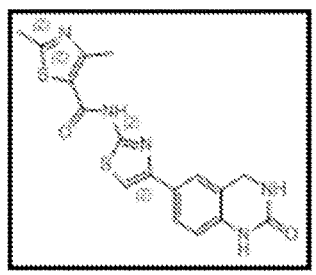
Figure 4B:
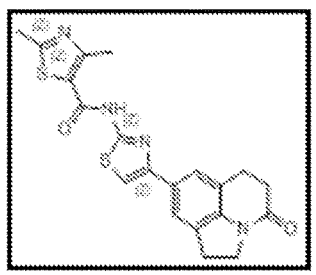
Figure 4B:
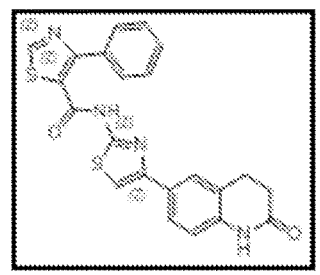
Figure 4B:
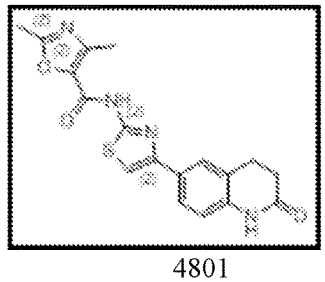
Figure 4B:
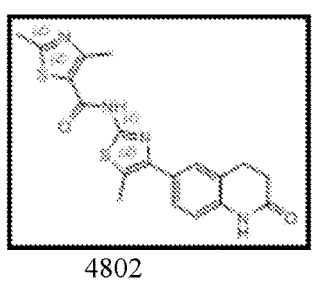
Figure 4B:
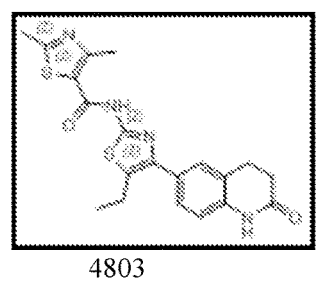
Figure 4B:
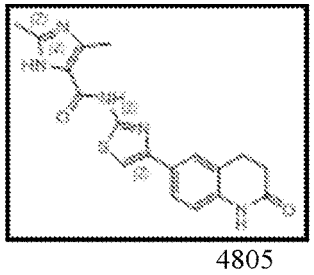
Figure 4B:
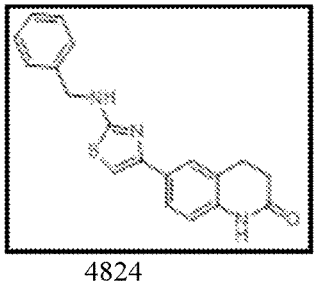
Figure 4B:
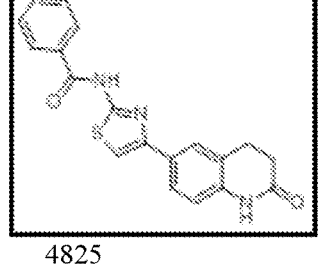
Figure 4C:
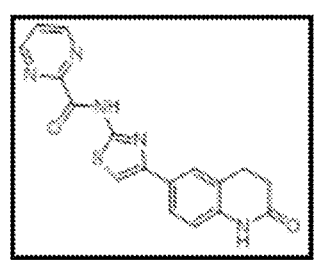
Figure 4C:
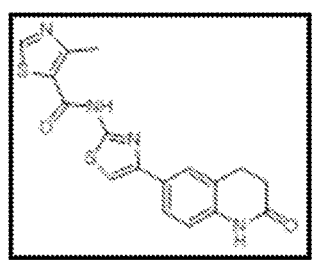
Figure 4C:
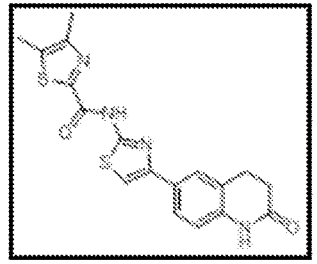
Figure 4C:
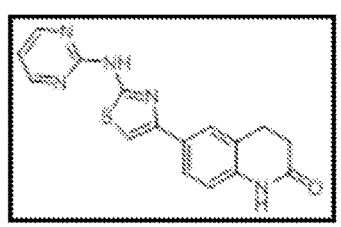
Figure 4C:
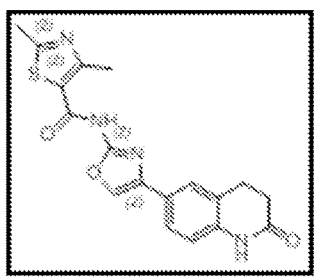
Figure 4C:
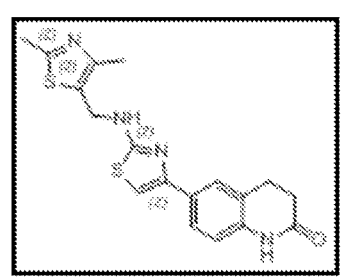
Figure 4C:
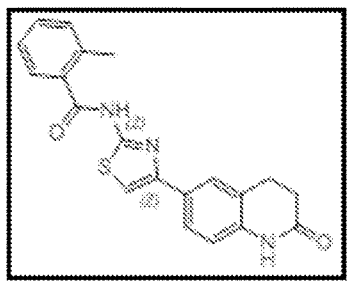
Figure 4C:
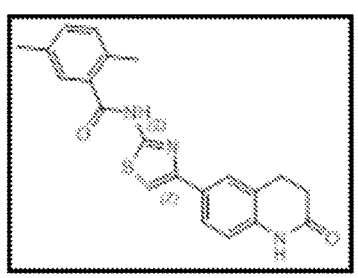
Figure 4C:
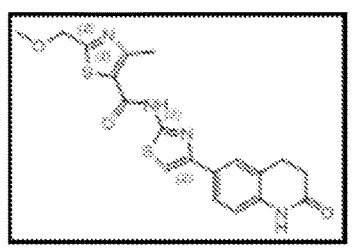
Figure 4C:
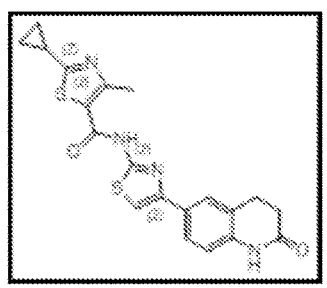
Figure 4C:
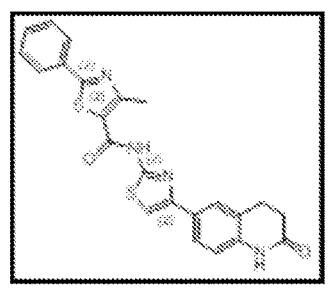
Figure 4C:
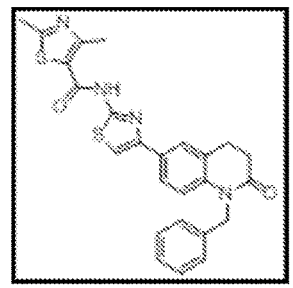
Figure 4D:
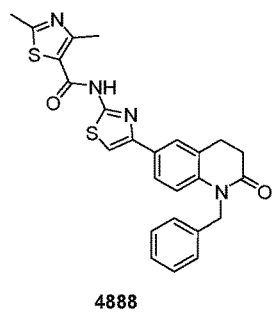
Figure 4D:
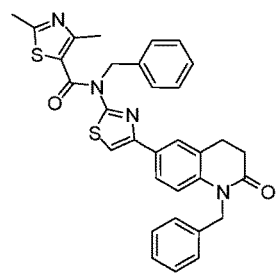
Figure 4D:
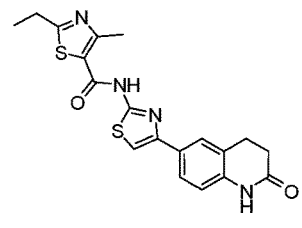
Figure 4D:
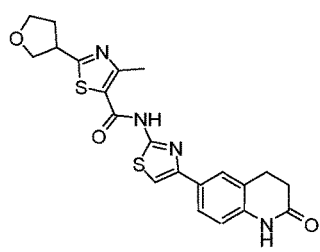
Figure 4D:
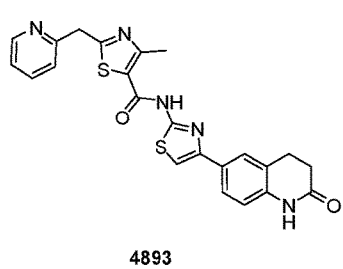
Figure 4D:
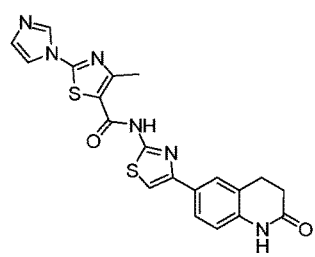
Figure 4D:
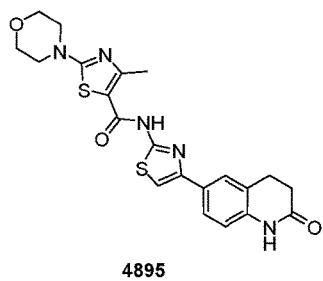
Figure 4D:
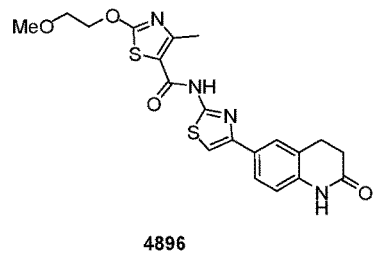

The effect of contemplated compounds on cell signaling was tested in wild type and K-ras G12D mutant cells as follows: Cancer cell lines BxPC-3 (K-Ras wild-type), and Panc10.05 (K-Ras G12D mutant) were serum-starved 0/N before treatment with 3.1 to 25 µM of Ras compound A0837 for 1 hour before stimulation with 100 ng/ml EGF for 5 minutes. Cells were washed once in ice-cold PBS, lysed in complete lysis buffer on ice, and processed by SDS-PAGE under reducing conditions for the detection of pMEK and pErk. Membranes were stripped and re-probed for total MEK/Erk. FIG. 3 shows the results of such experiment, establishing that the tested compound inhibited signaling downstream of Ras in the mutant cell line but not in the K-Ras wild type cell line.

In still further experiments, the inventors tested selected compounds in a G-LISA assay to compare $IC_{50}$ values for wild-type and various mutant K-Ras (G12D, G12V) using the following general protocol: 293H cells were seeded in 6-wells at 0.6×106 cells per well and transfected next day with 5 µg of Ras wild-type, or G12C, G12D or G12V mutant DNA plasmid vector using transfection reagent Lipofectamine 3000. Next day cells were treated with 3.125-50 µM of Ras compounds for 1 hour. Wild-type transfected cells were subsequently treated with 100 ng/ml EGF for 2 minutes. Cells were washed once in ice-cold PBS, lysed in complete lysis buffer on ice, and processed by G-LISA according to Cytoskeleton protocol.

Table 5 provides typical results in µM for the selected compounds tested, and the corresponding structures are shown in FIGS. 4A-4D. As can be seen, certain of the tested compounds had preferential/selective inhibition favoring G12D over wild-type and/or other mutant forms. N/A is result not available

| Compound | G-LISA (wild type) | G-LISA (G12D) | G-LISA (G12V) |
|---|---|---|---|
| A0837/4562 | 0.5 | 7-13 | 38 |
| 4639 | n/a | >25 | n/a |
| 4662 | n/a | >25 | n/a |
| 4663 | 7 | >25 | 32 |
| 4664 | n/a | >25 | n/a |
| 4665 | n/a | >25 | n/a |
| 4666 | n/a | >25 | n/a |
| 4683 | n/a | 11.89 | n/a |
| 4684 | n/a | >25 | n/a |
| 4685 | n/a | >25 | n/a |
| 4686 | n/a | 11 | n/a |
| 4687 | n/a | 19 | n/a |
| 4734 | n/a | >25 | n/a |
| 4735 | n/a | >25 | n/a |
| 4747 | n/a | >25 | n/a |
| 4748 | n/a | 21 | n/a |
| 4749 | n/a | 36 | n/a |
| 4800 | n/a | >25 | n/a |
| 4801 | 25.7 | 8.2 | 10.7 |
| 4802 | n/a | 27 | 17 |
| 4803 | n/a | 71 | n/a |
| 4805 | 7 | 187 | n/a |
| 4824 | n/a | >25 | n/a |
| 4825 | n/a | >25 | n/a |
| 4826 | n/a | >25 | n/a |
| 2827 | >25 | 36.6 | n/a |
| 4828 | n/a | >25 | n/a |
| 4829 | n/a | >25 | n/a |
| 4874 | n/a | 16 | n/a |
| 4875 | n/a | 17 | n/a |
| 4877 | 16 | 6 | 9 |
| 4878 | n/a | 19 | >25 |
| 4888 | 11.3 | 6 | 14.5 |

Figure 5:
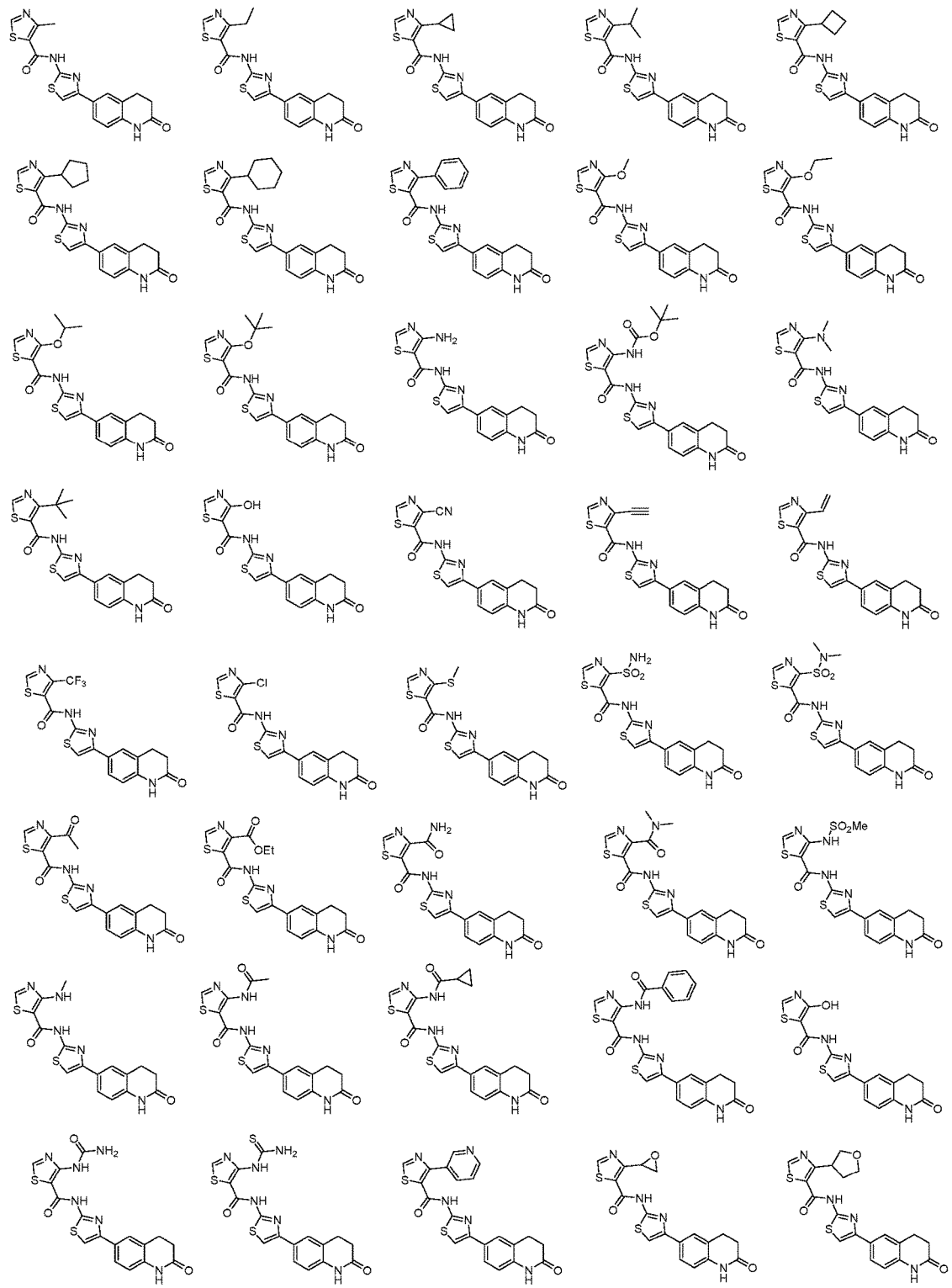
FIGS. 5-73 depict additional exemplary compounds according to the inventive subject matter.
Figure 6:
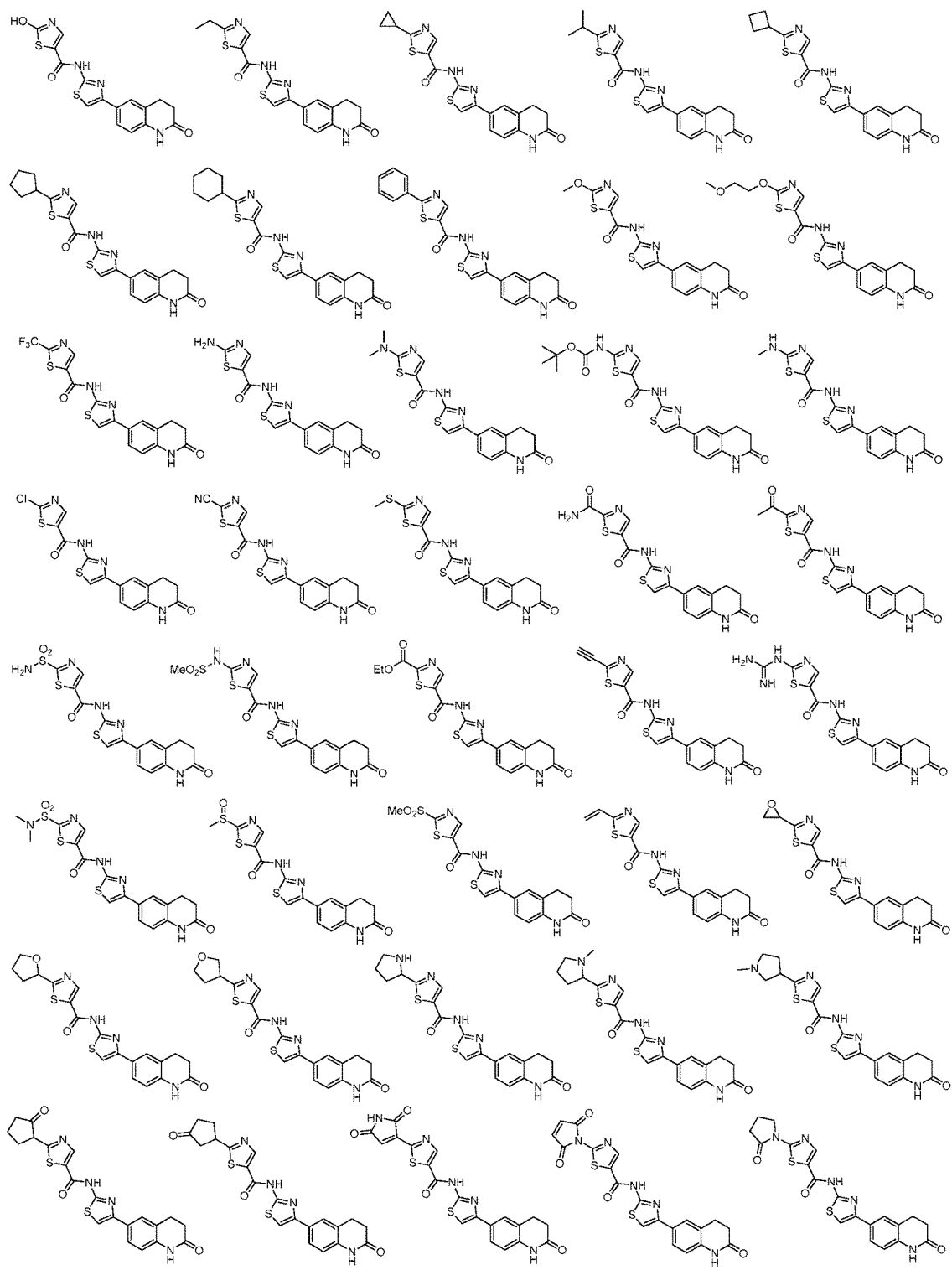
Figure 7:
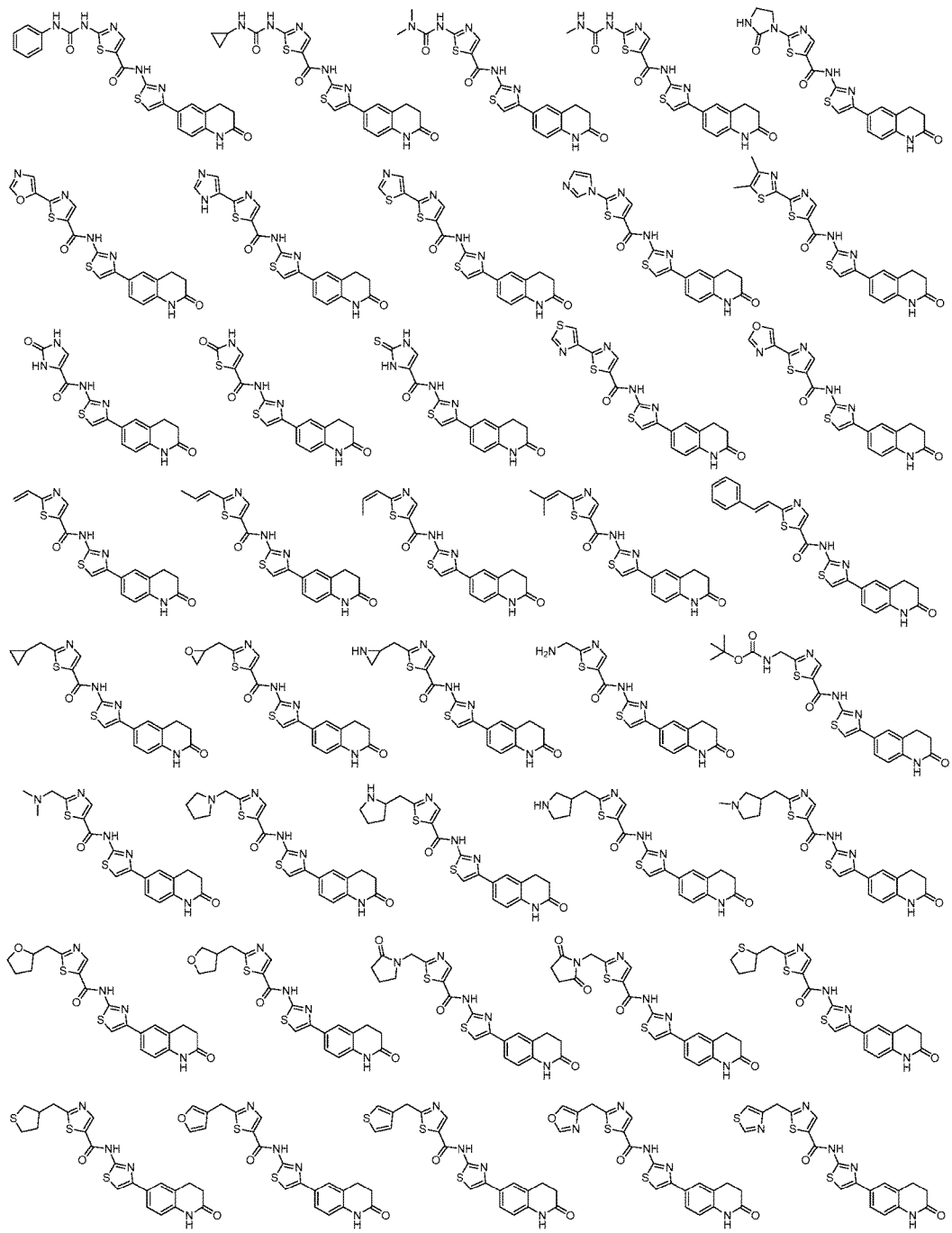
Figure 8:
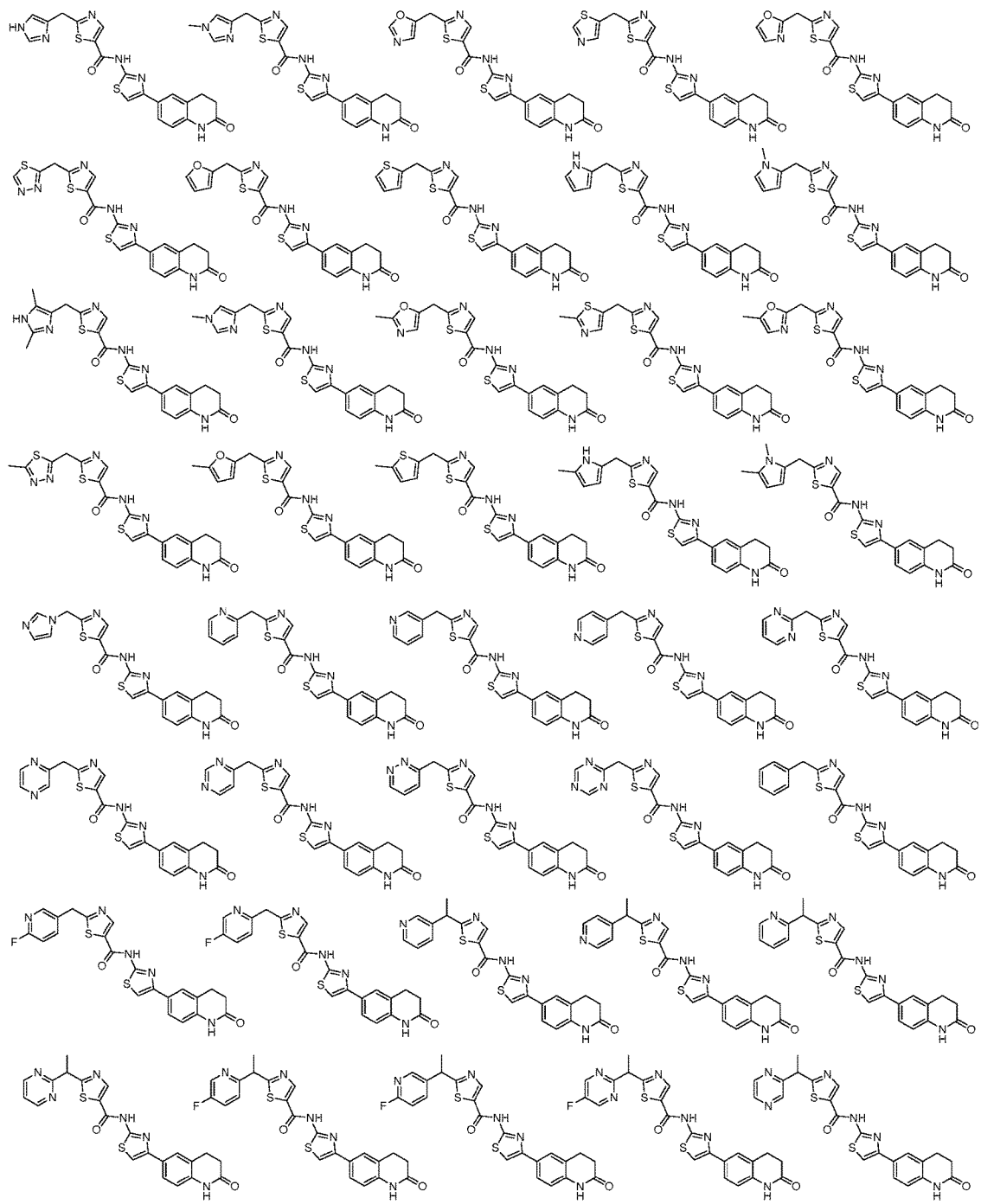
Figure 9:
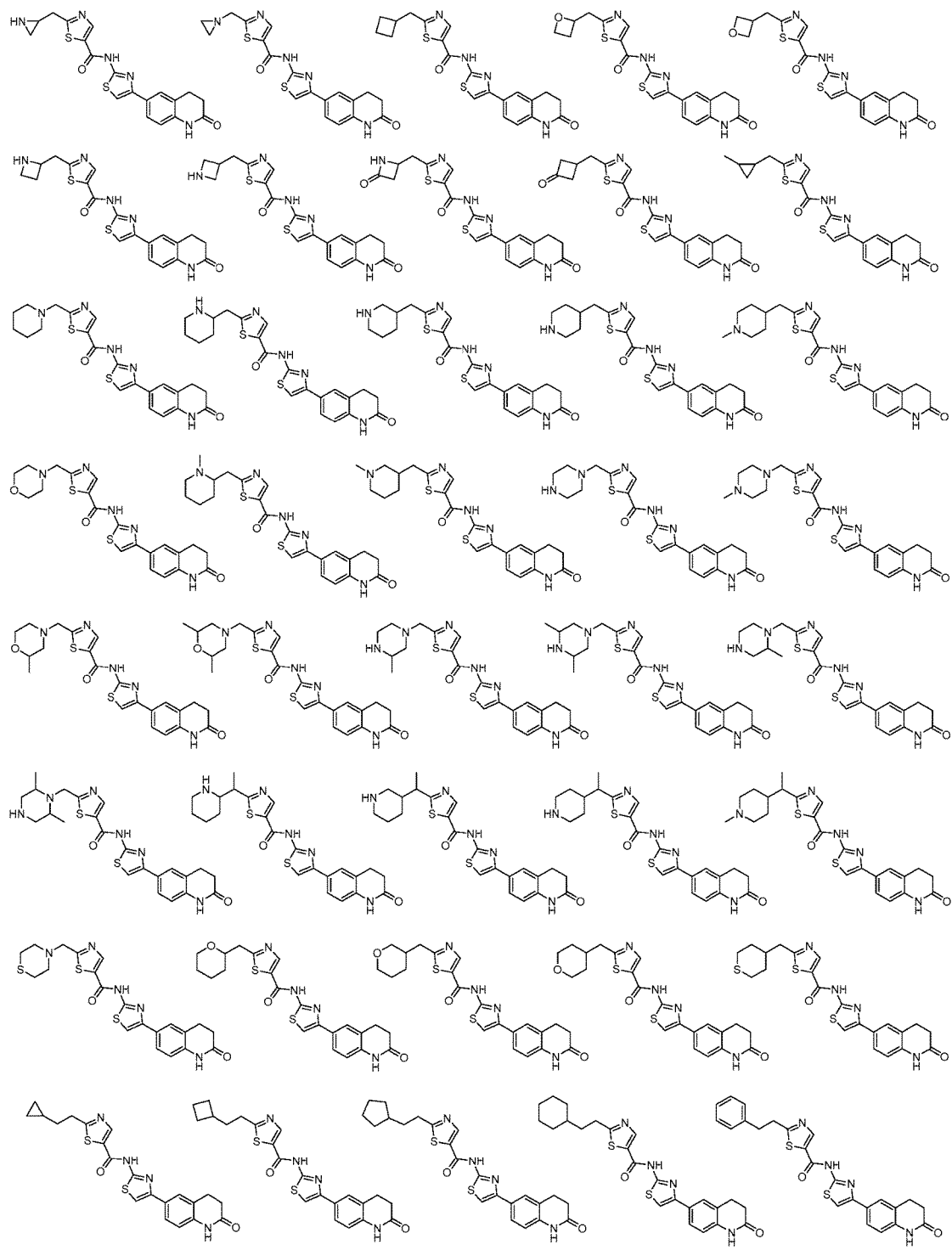
Figure 10:
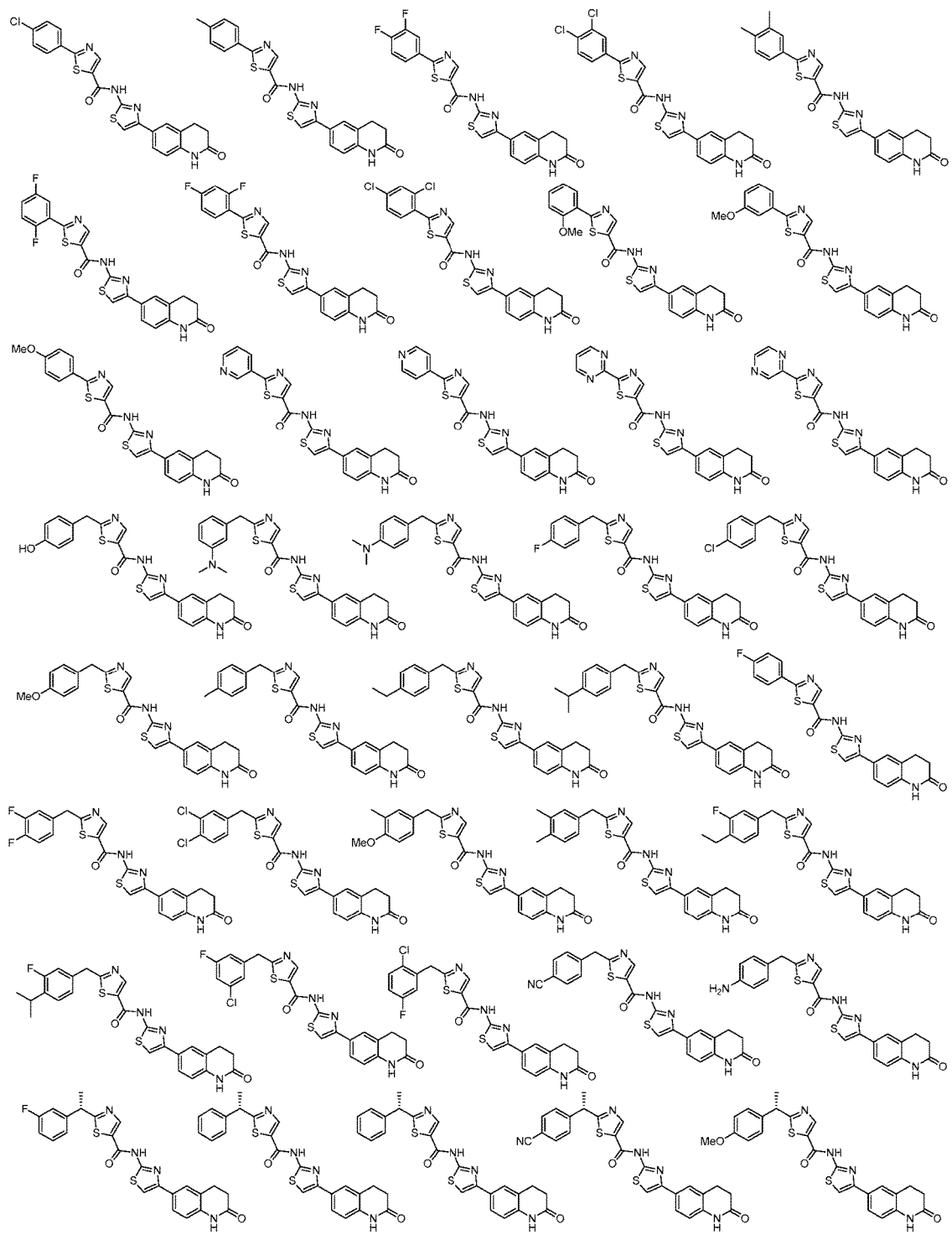
Figure 11:
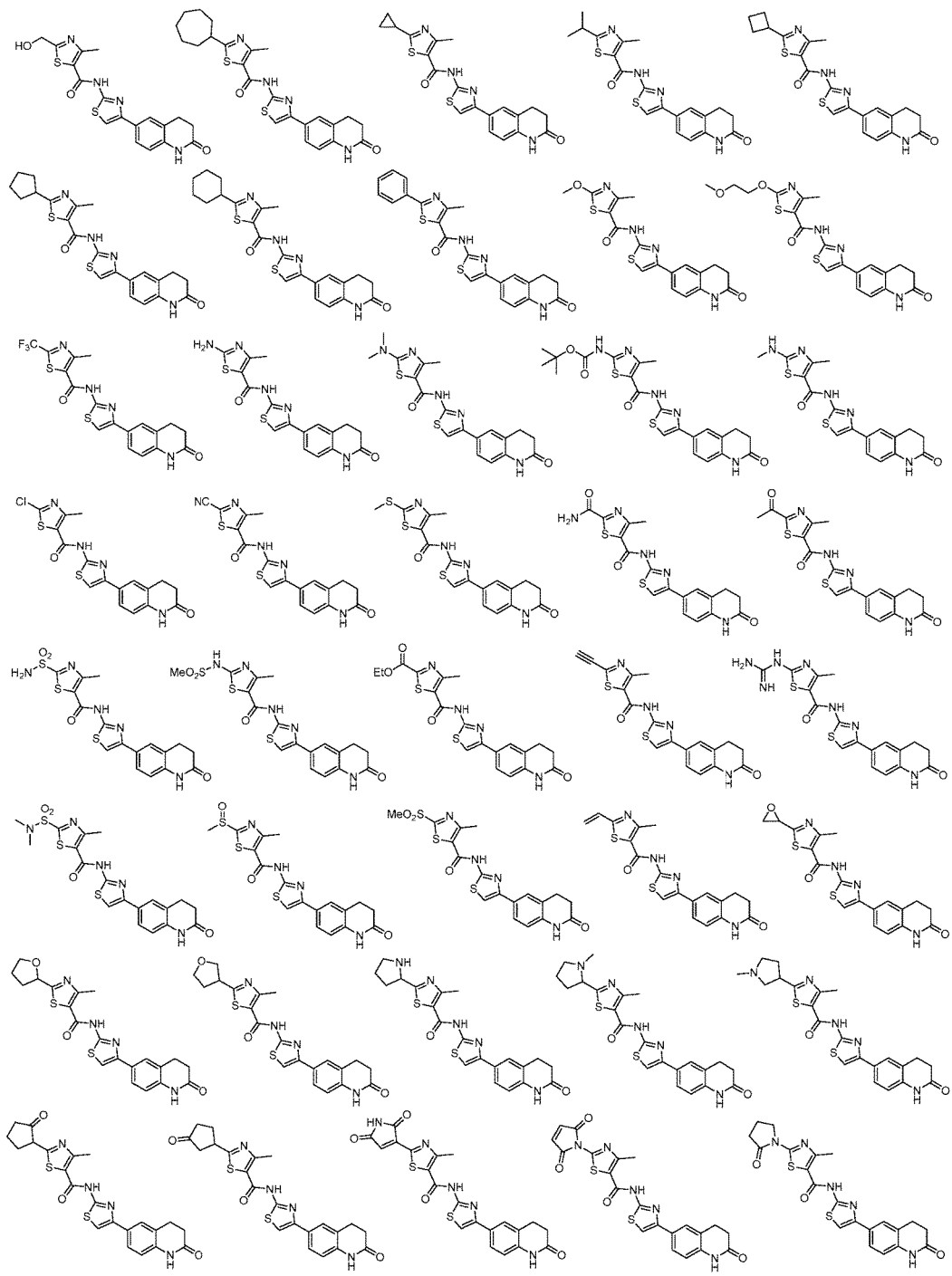
Figure 12:
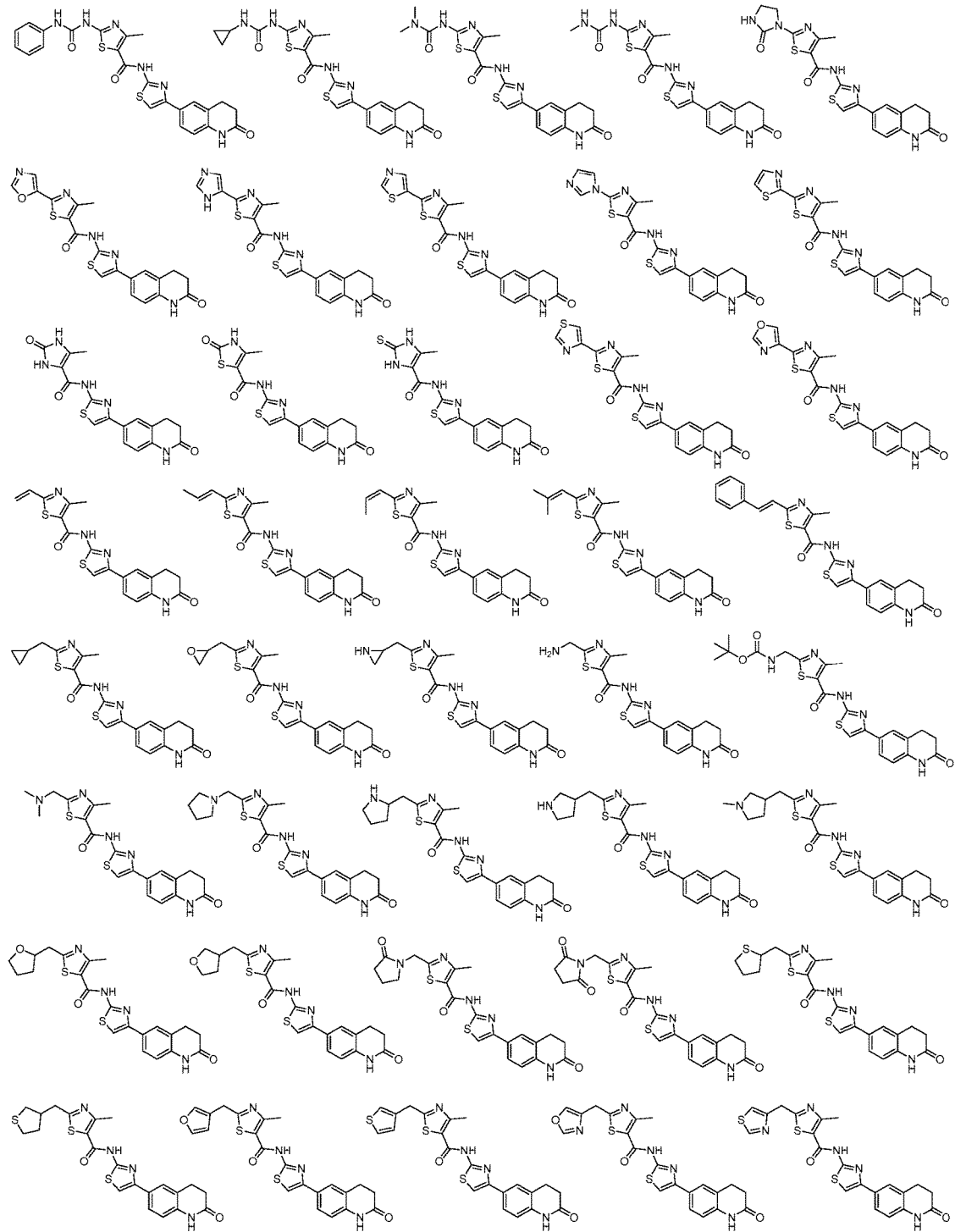
Figure 13:
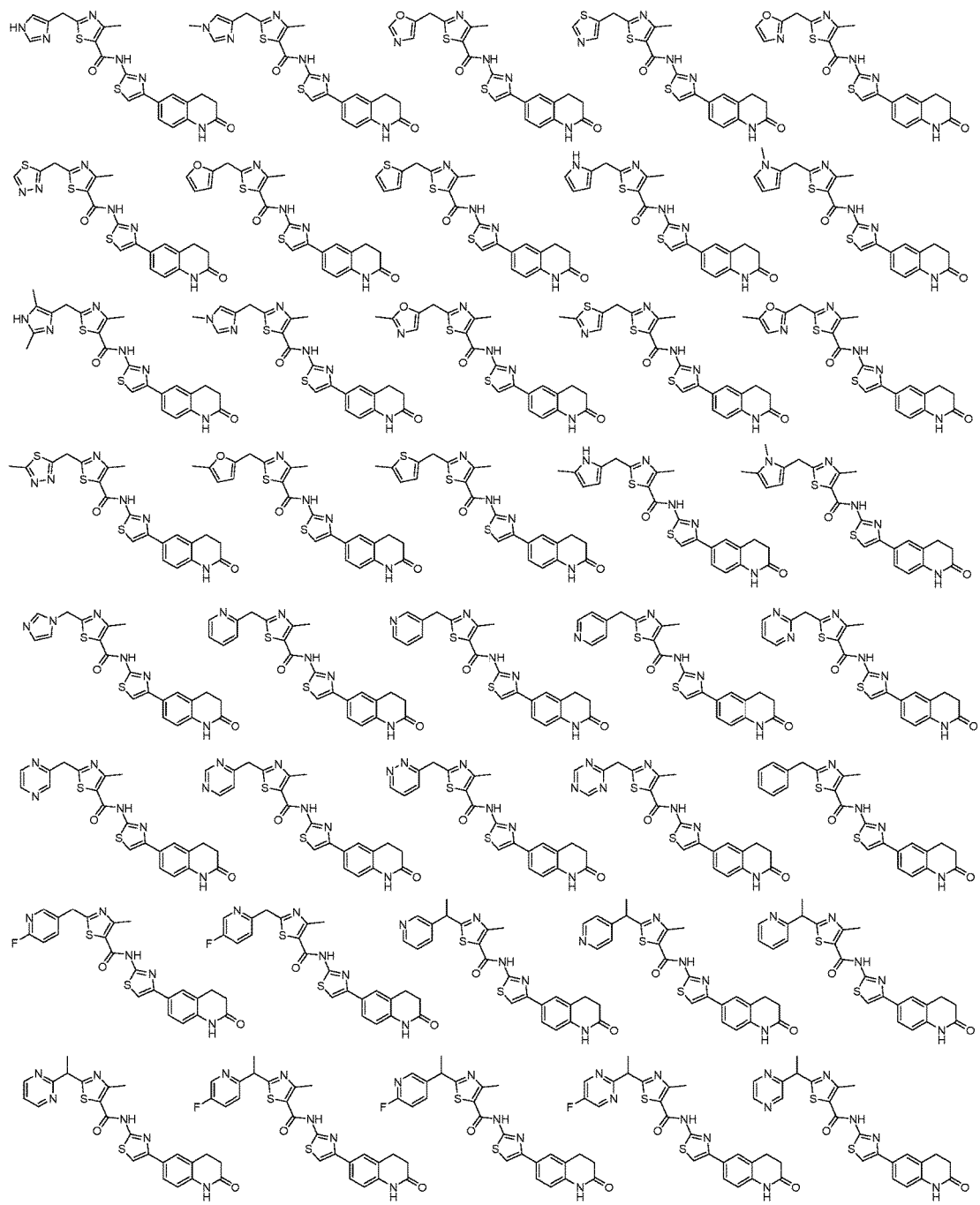
Figure 14:
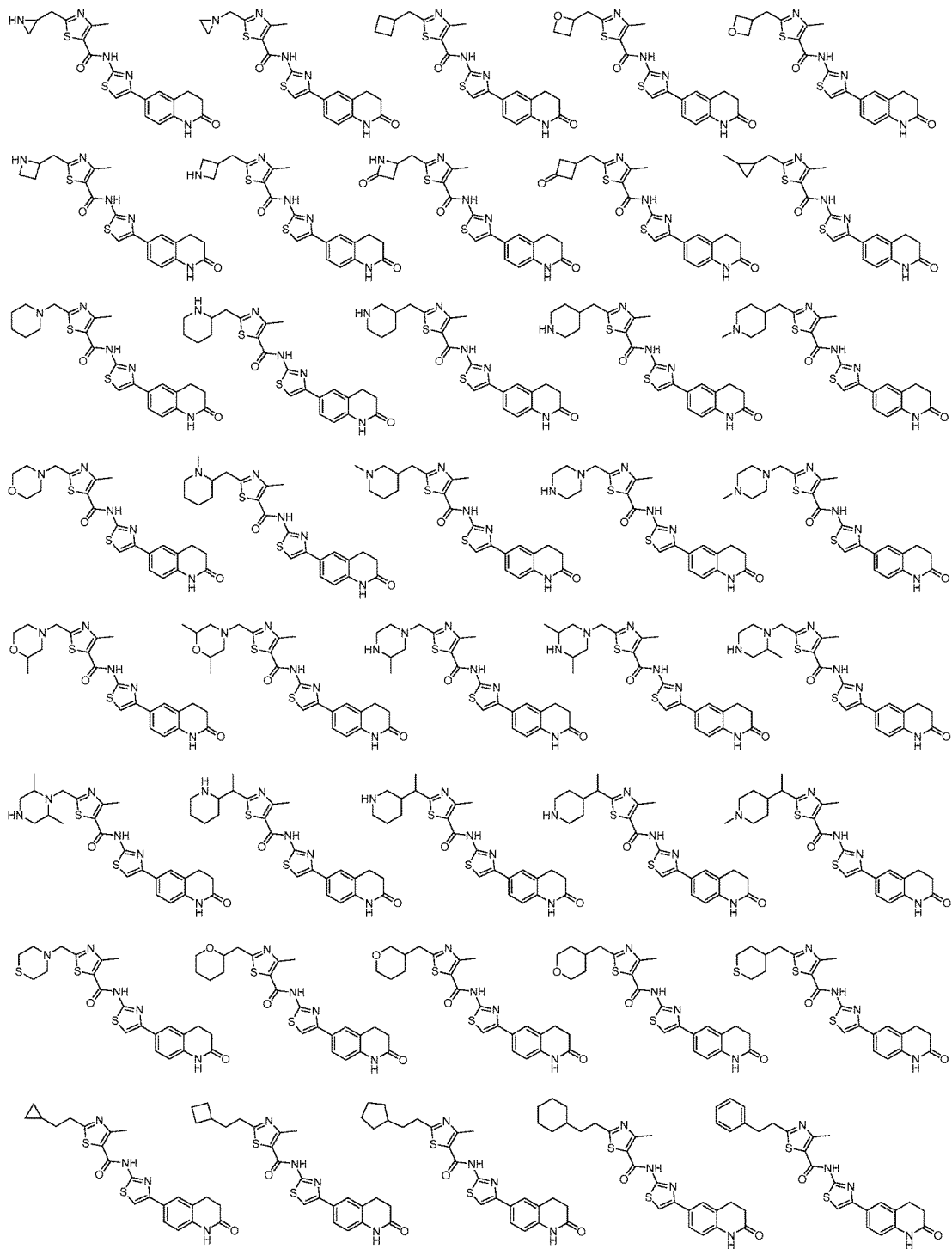
Figure 15:
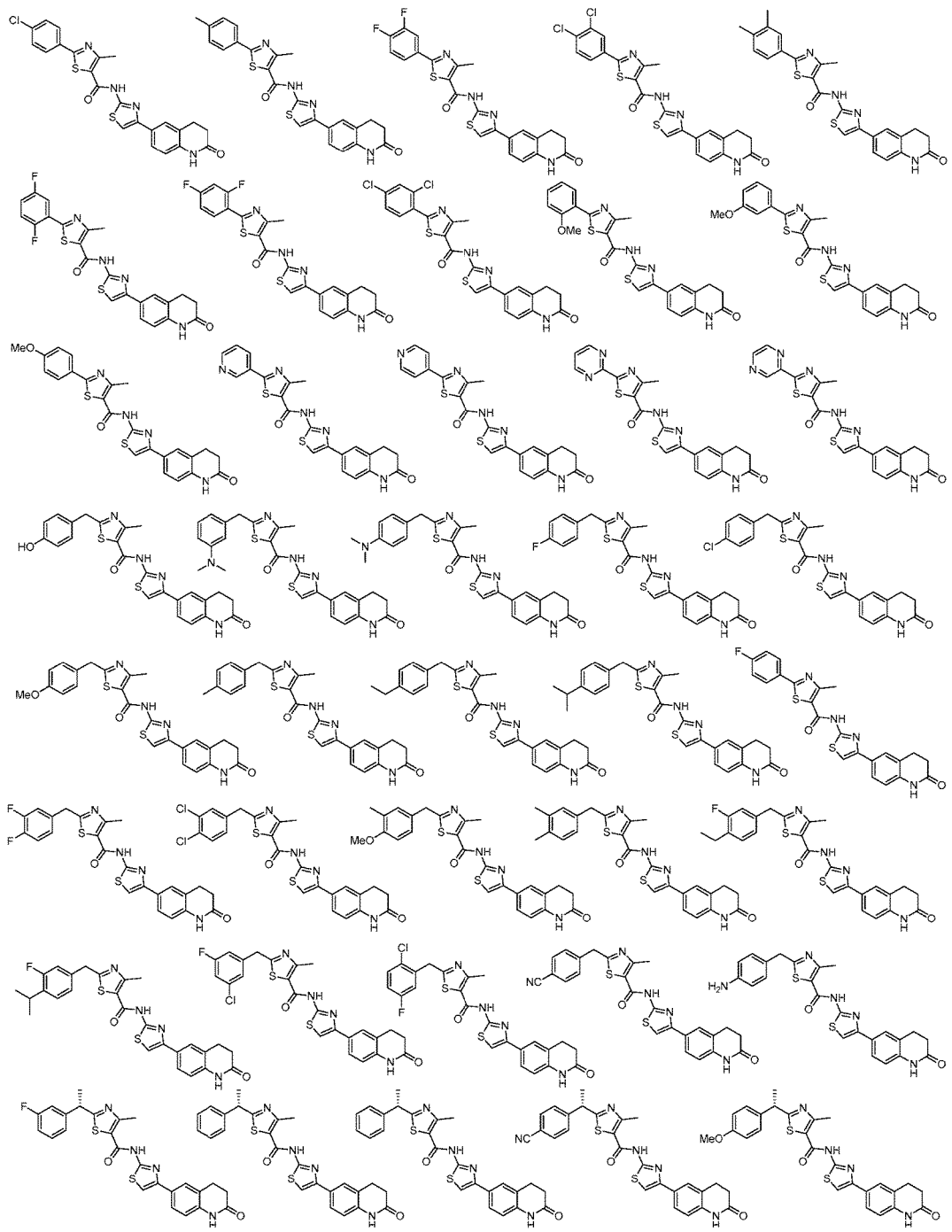
Figure 16:
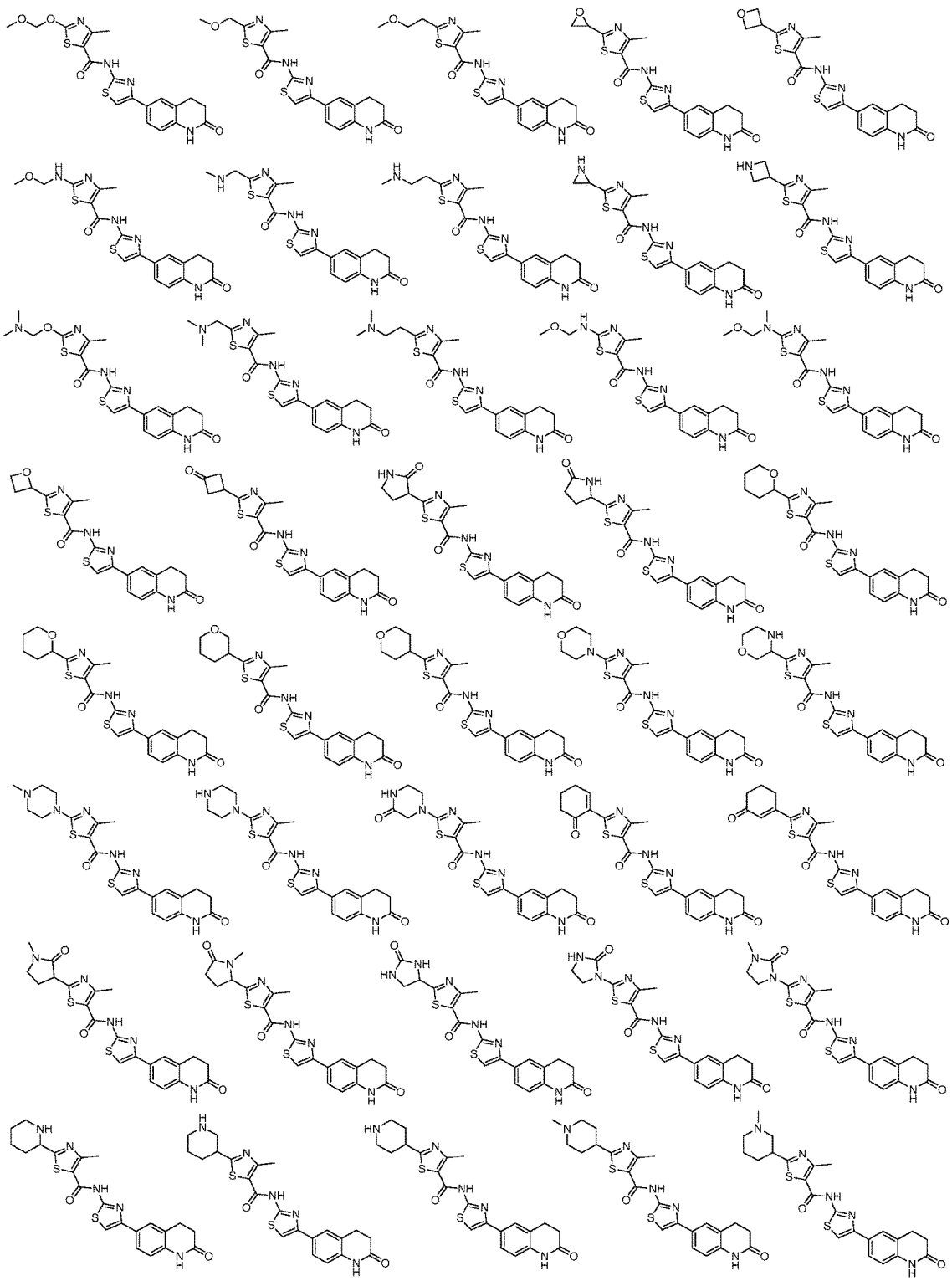
Figure 17:
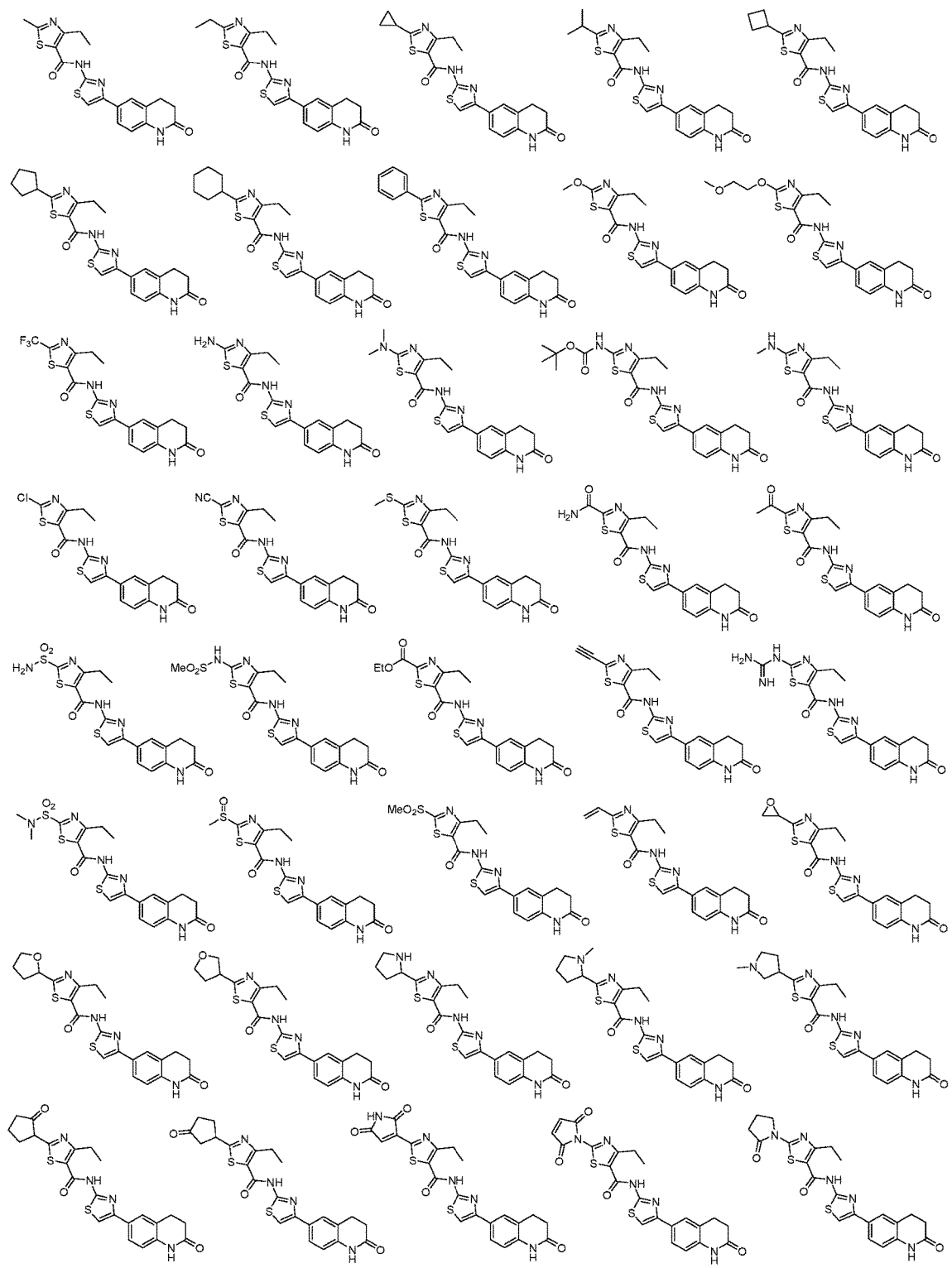
Figure 18:
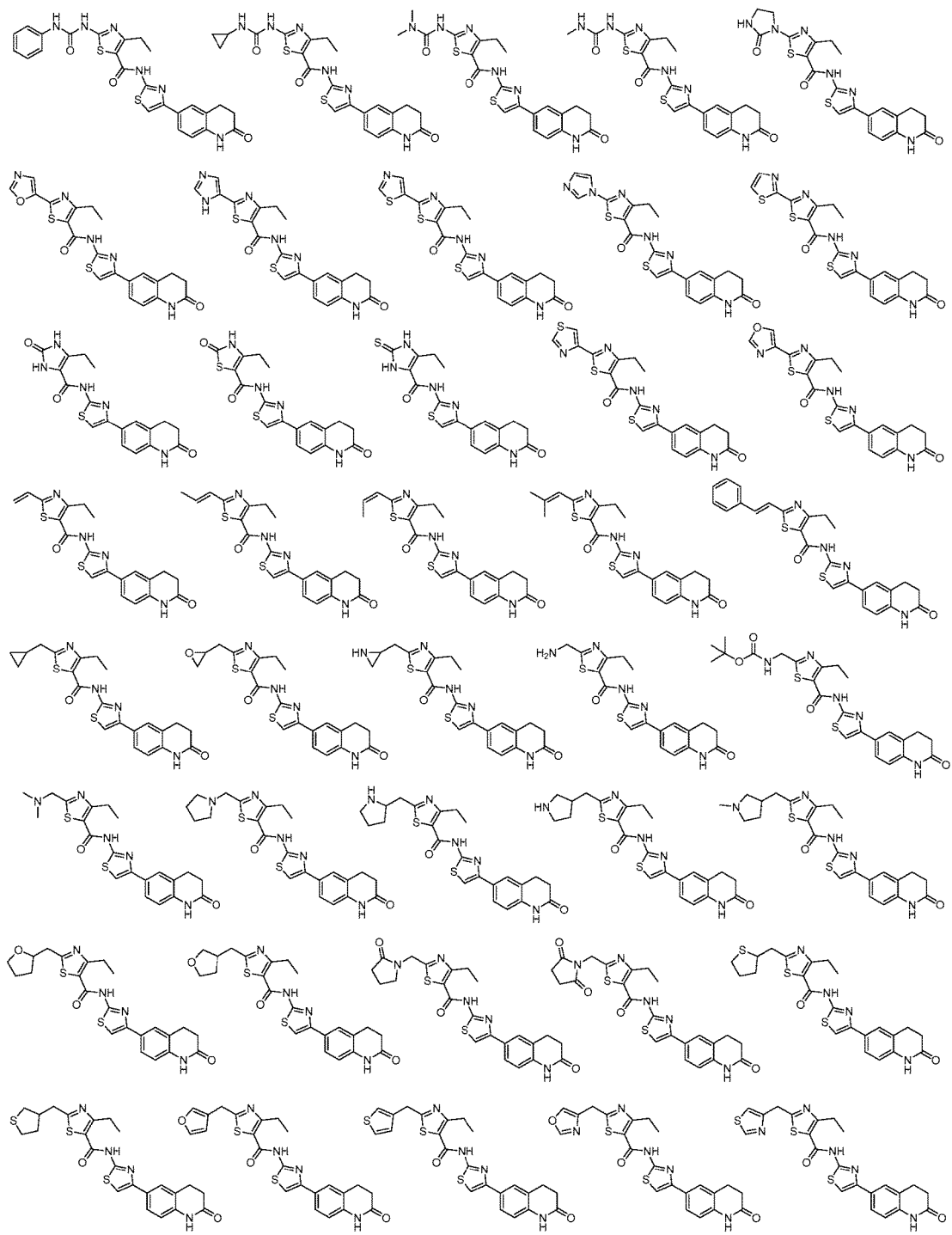
Figure 19:
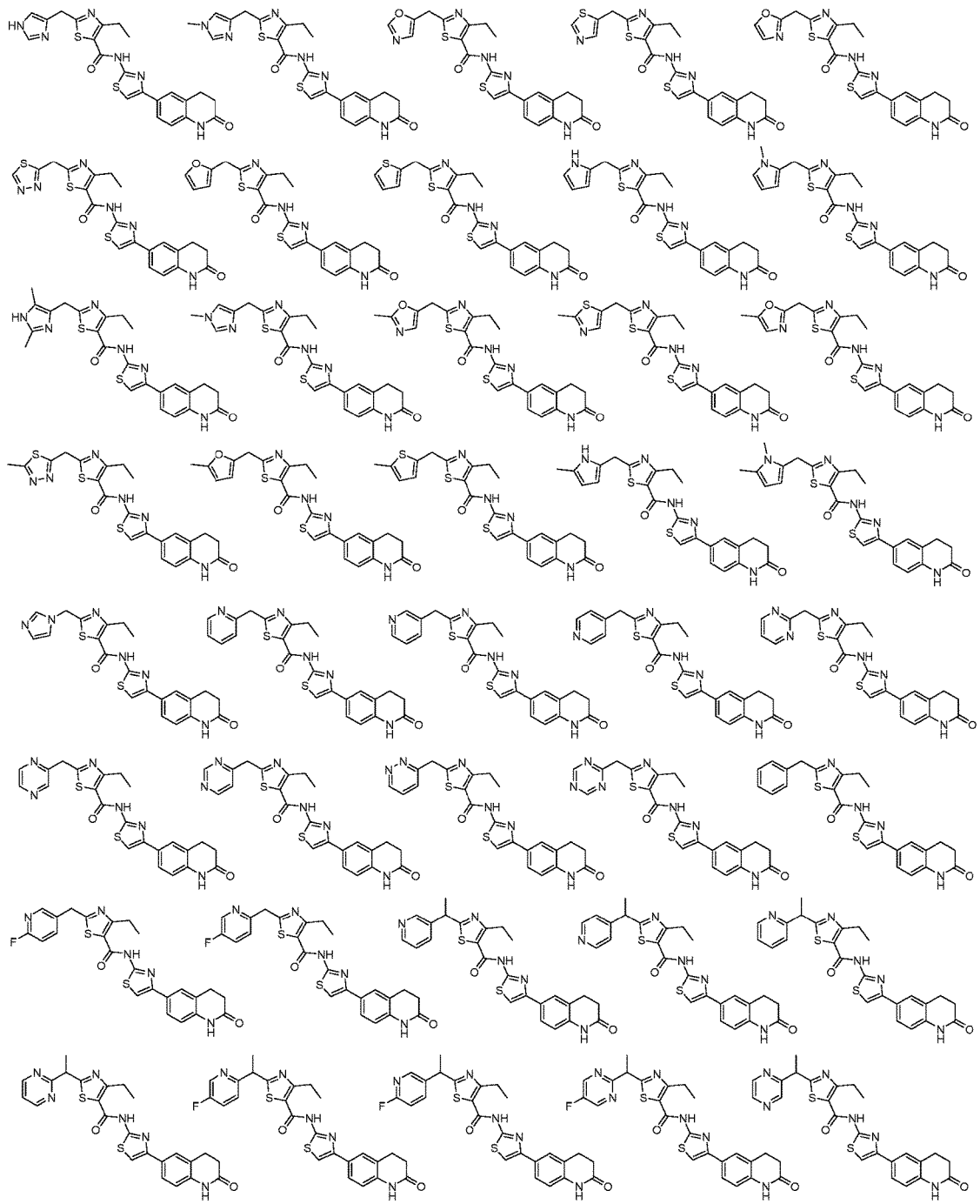
Figure 20:
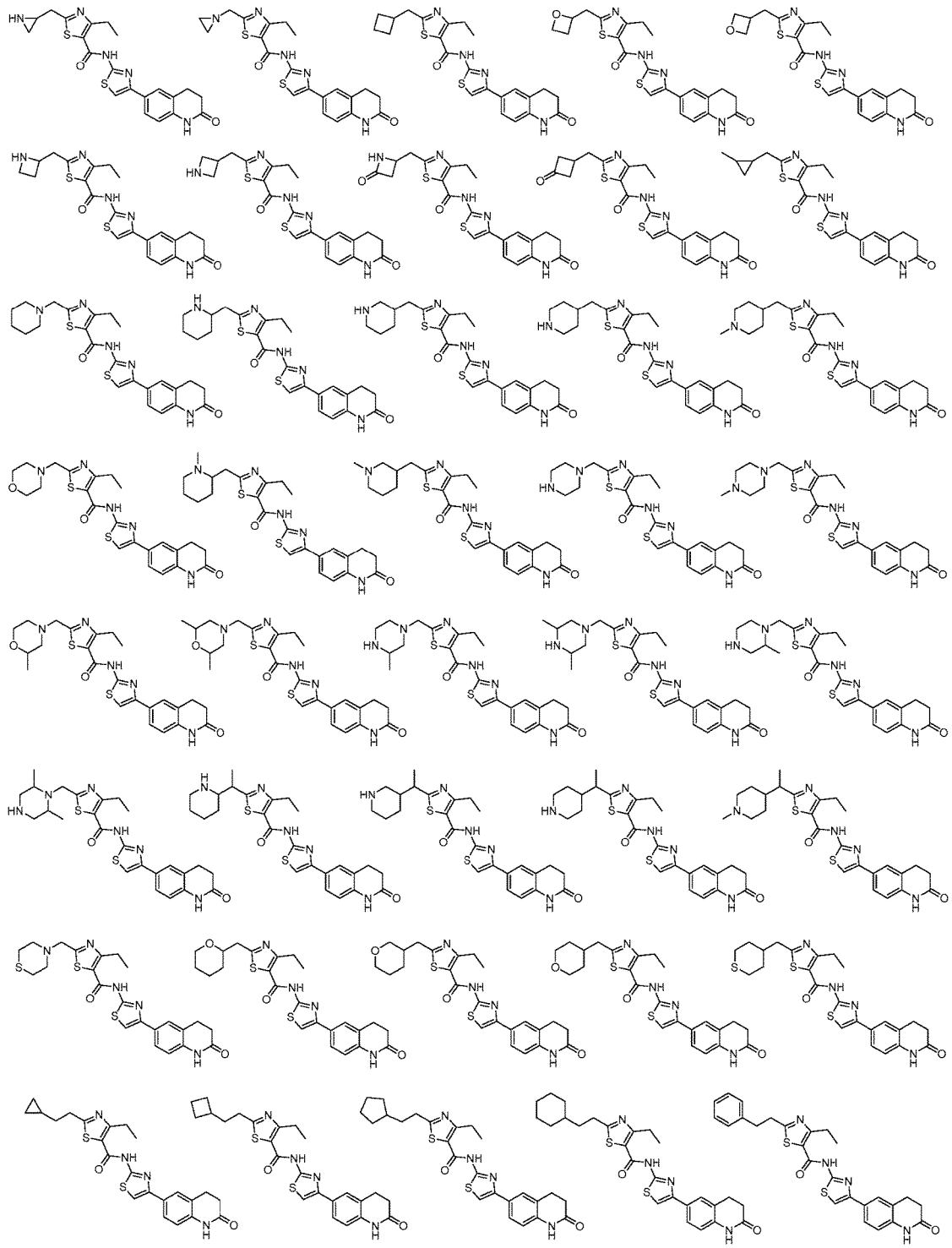
Figure 21:
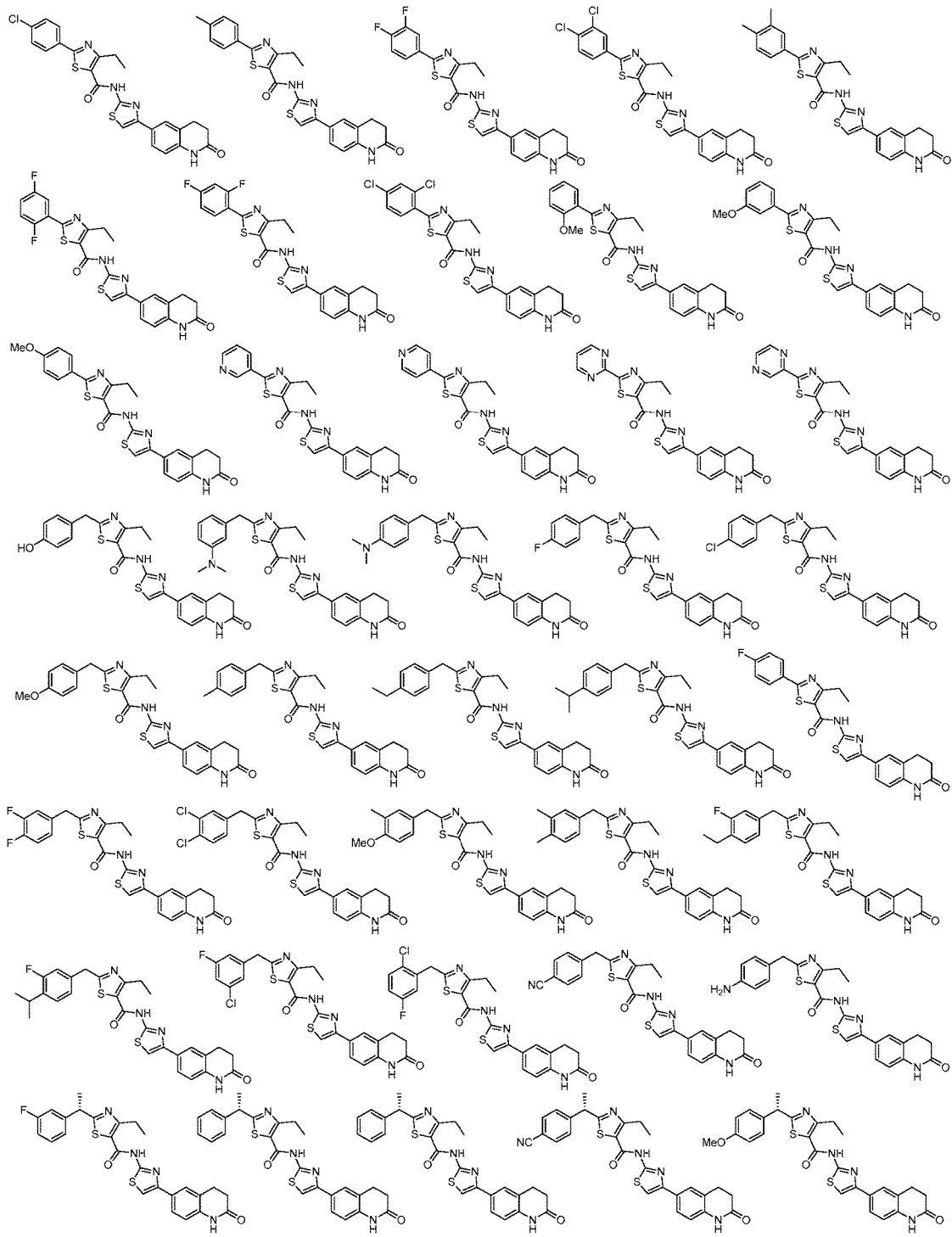
Figure 22:
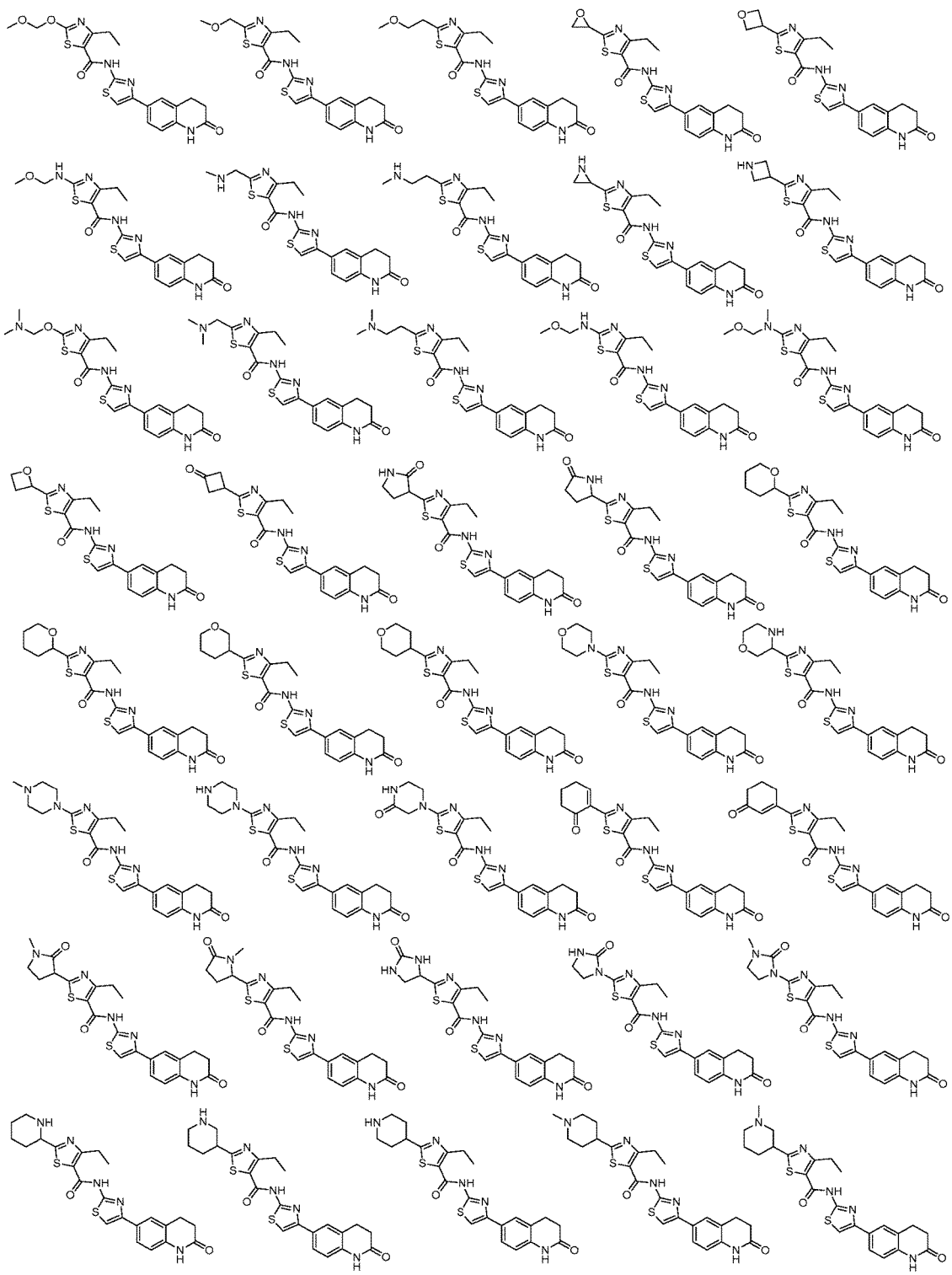
Figure 23:
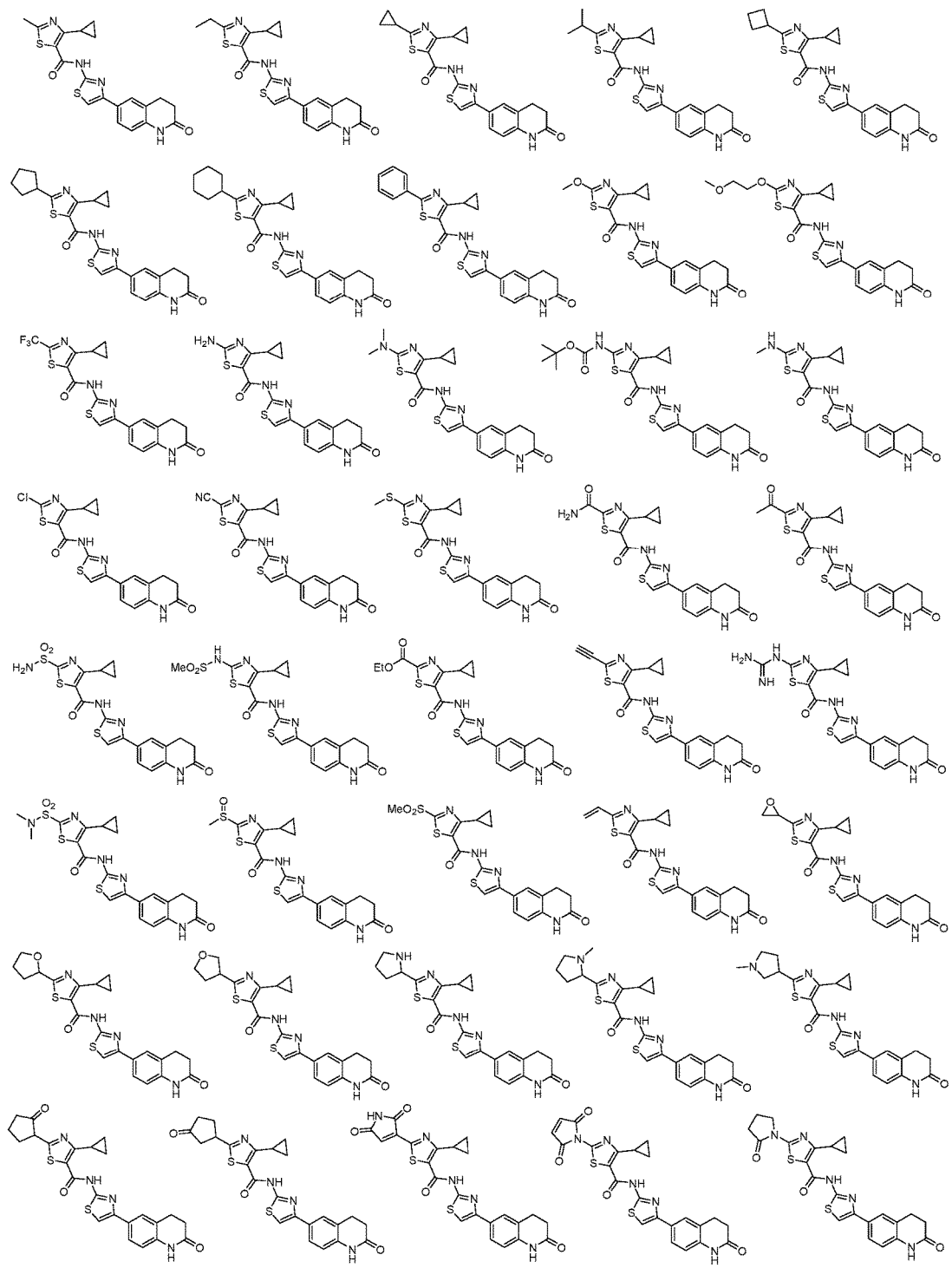
Figure 24:
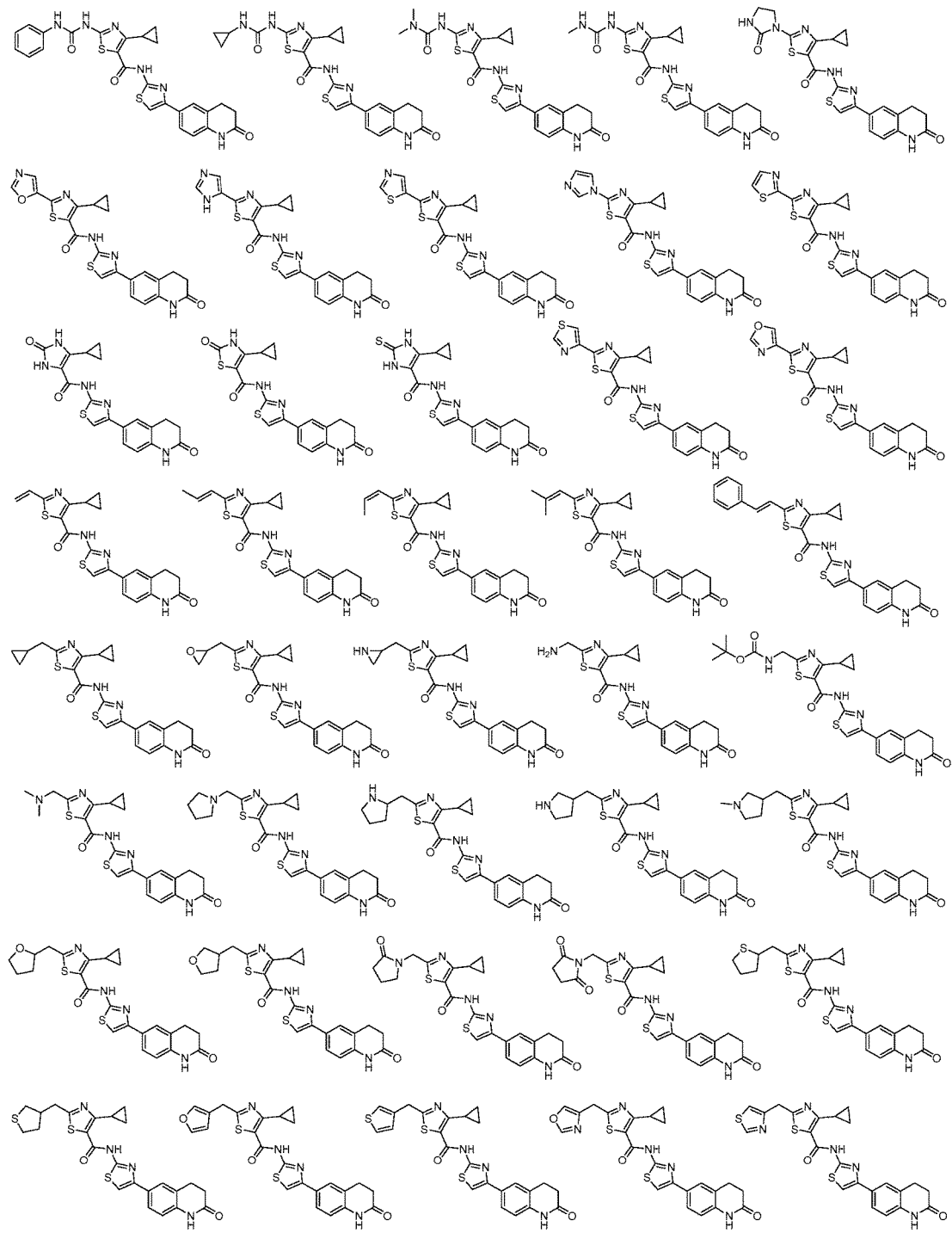
Figure 25:
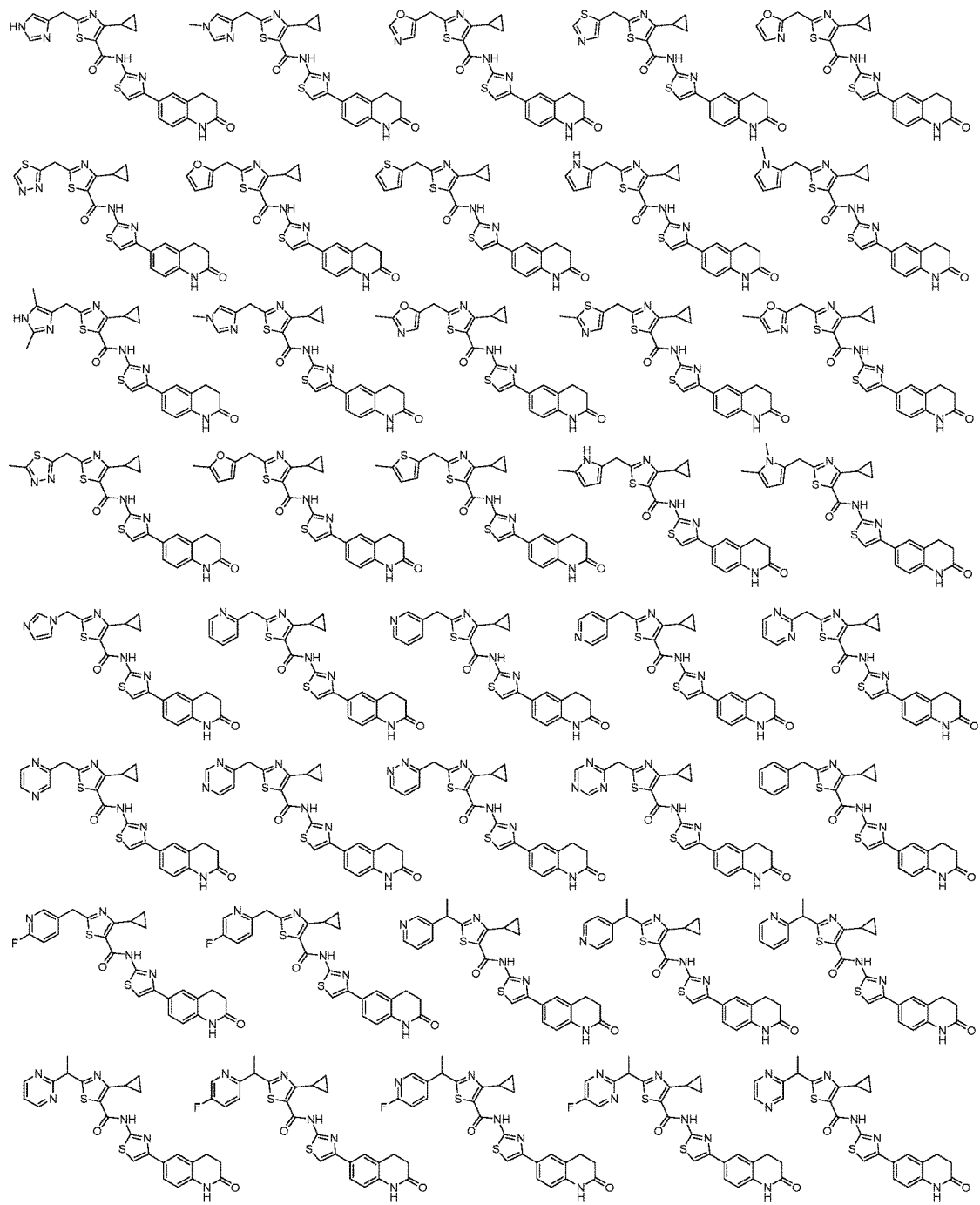
Figure 26:
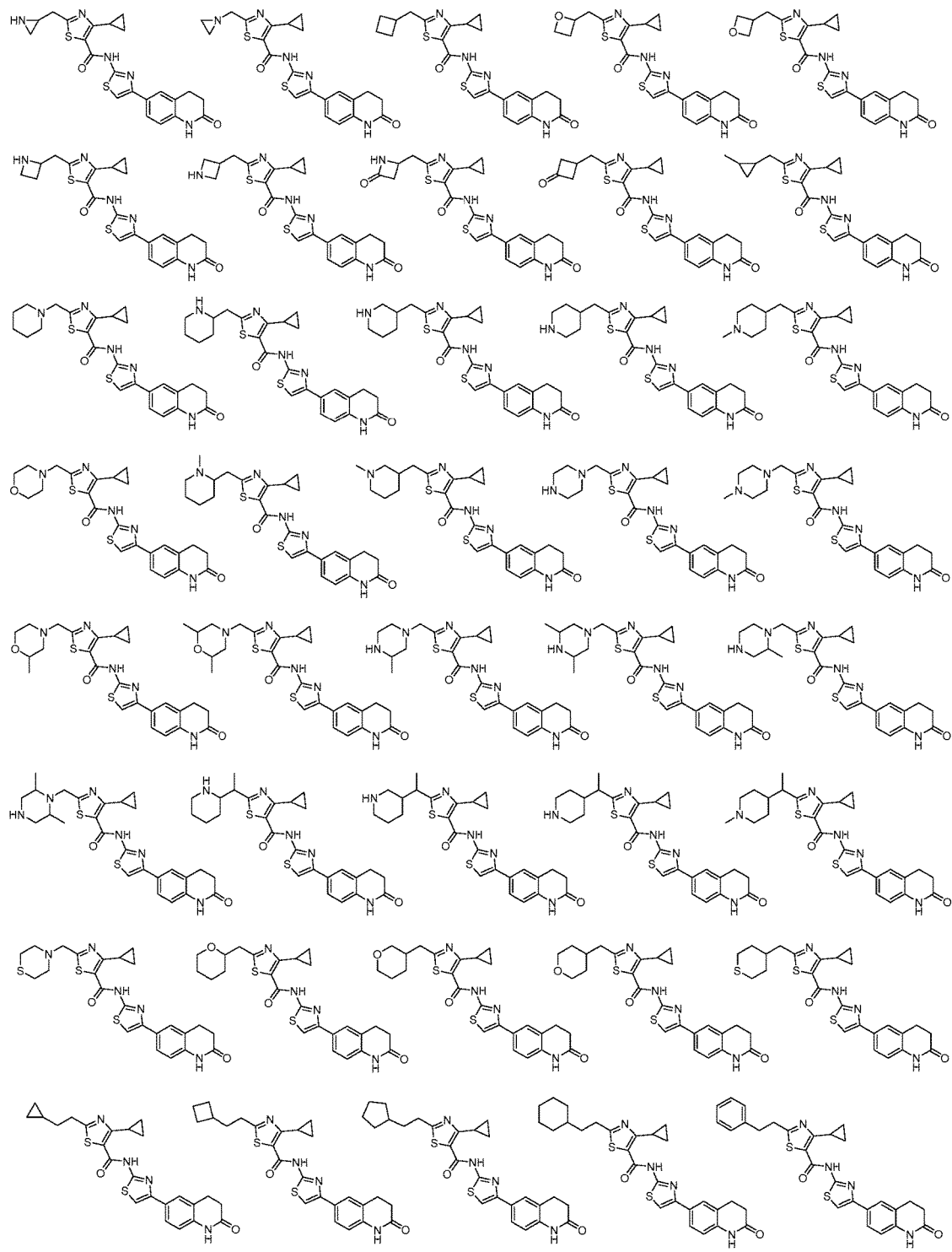
Figure 27:
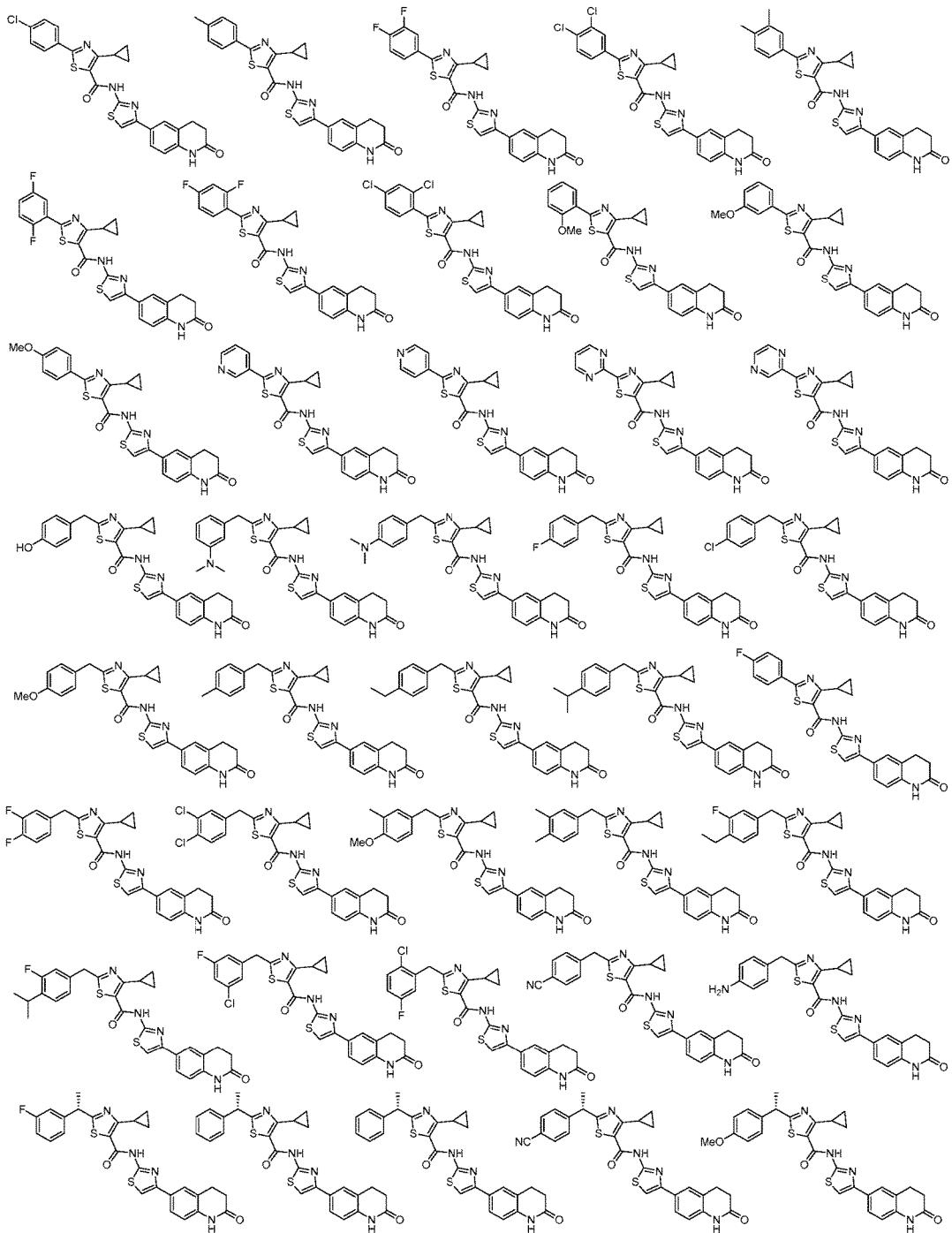
Figure 28:
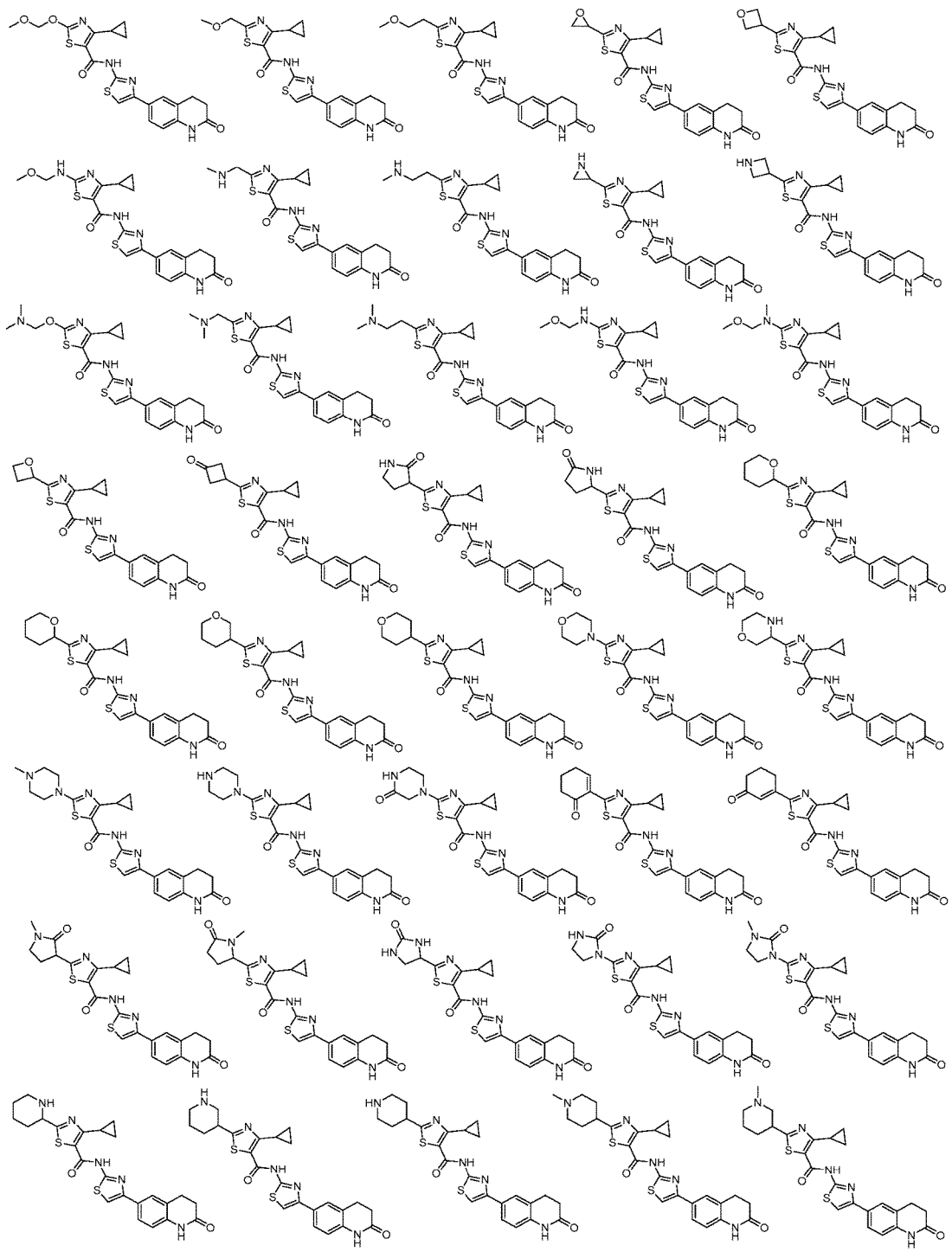
Figure 29:
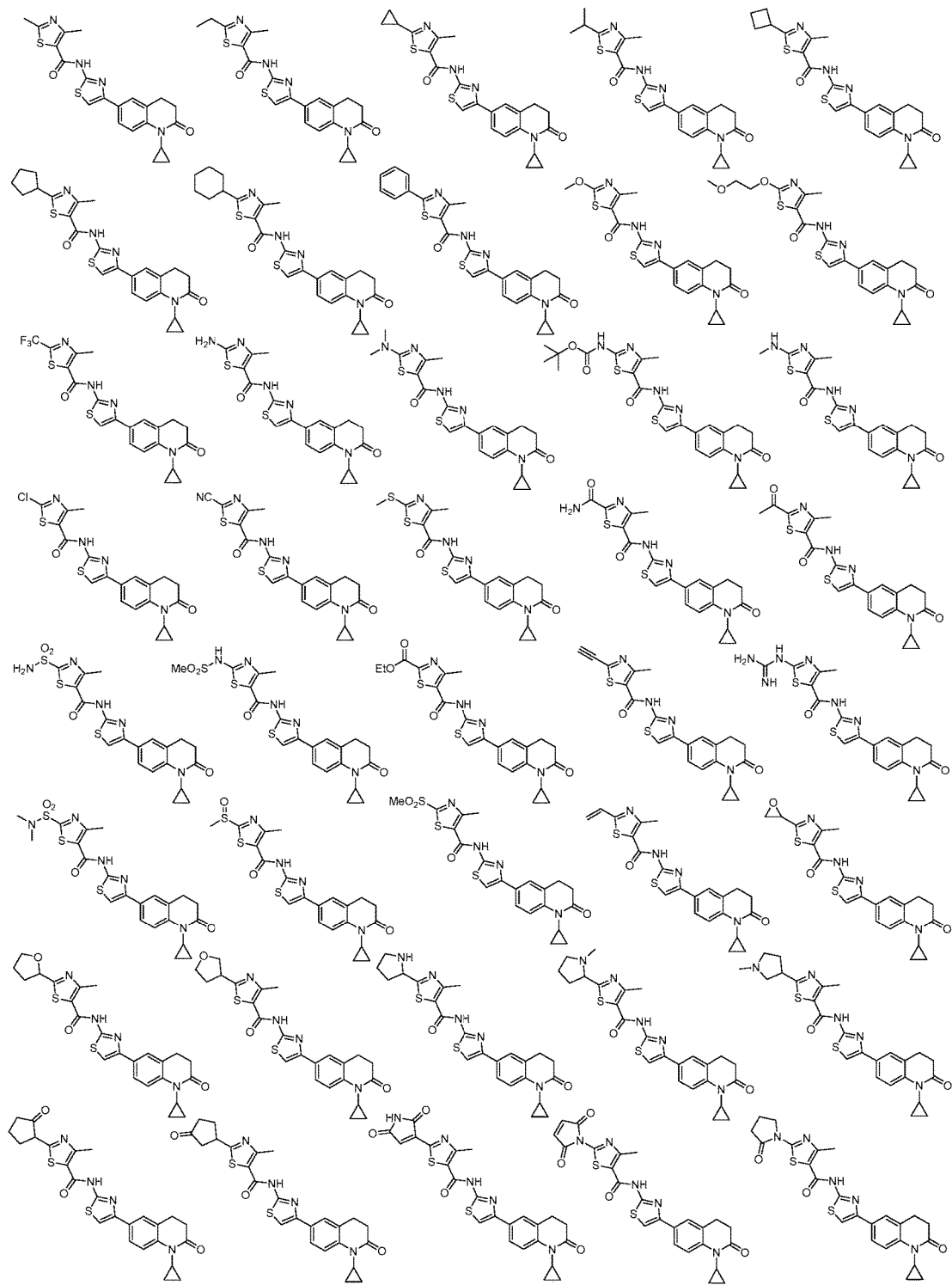
Figure 30:
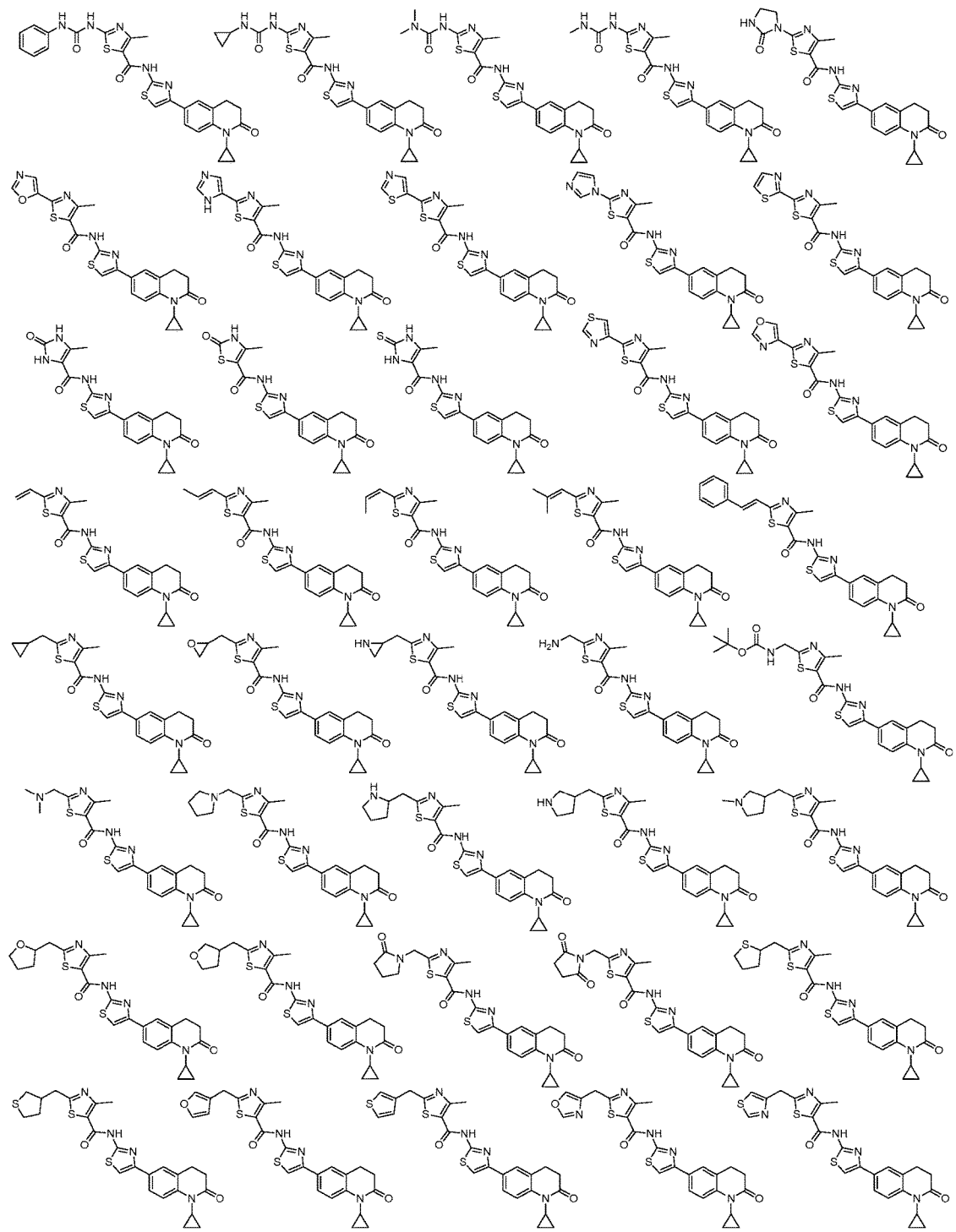
Figure 31:
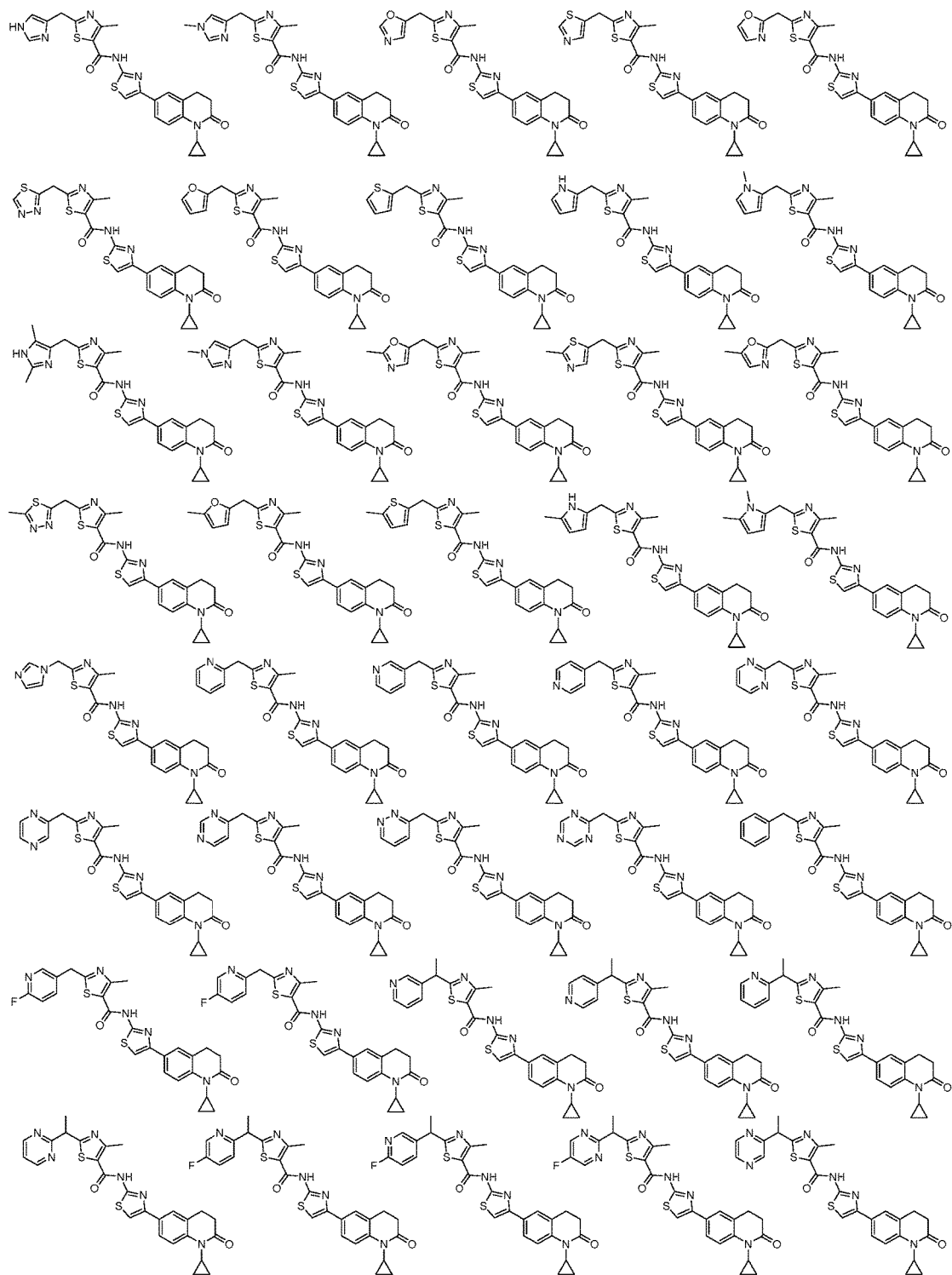
Figure 32:
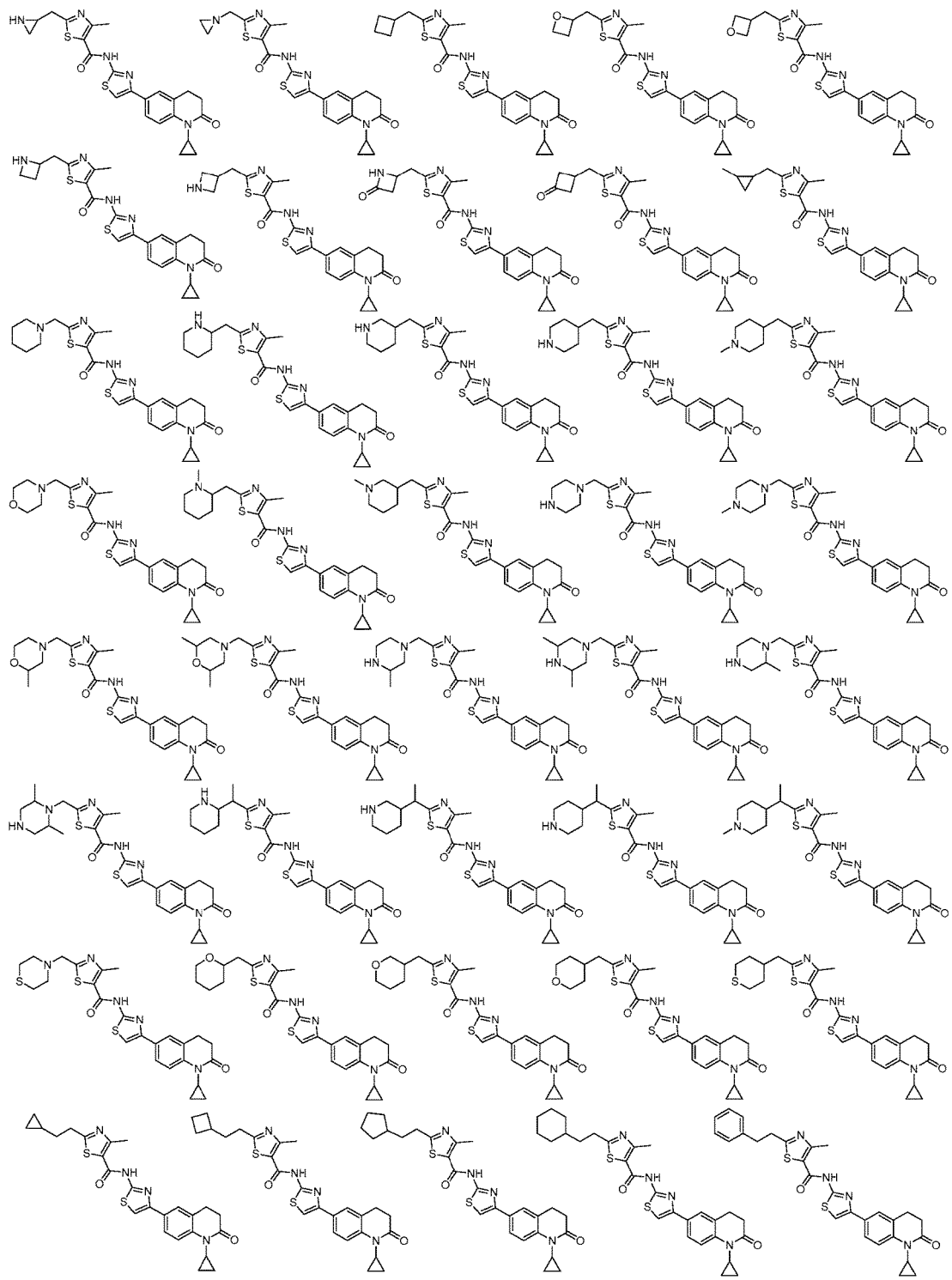
Figure 33:
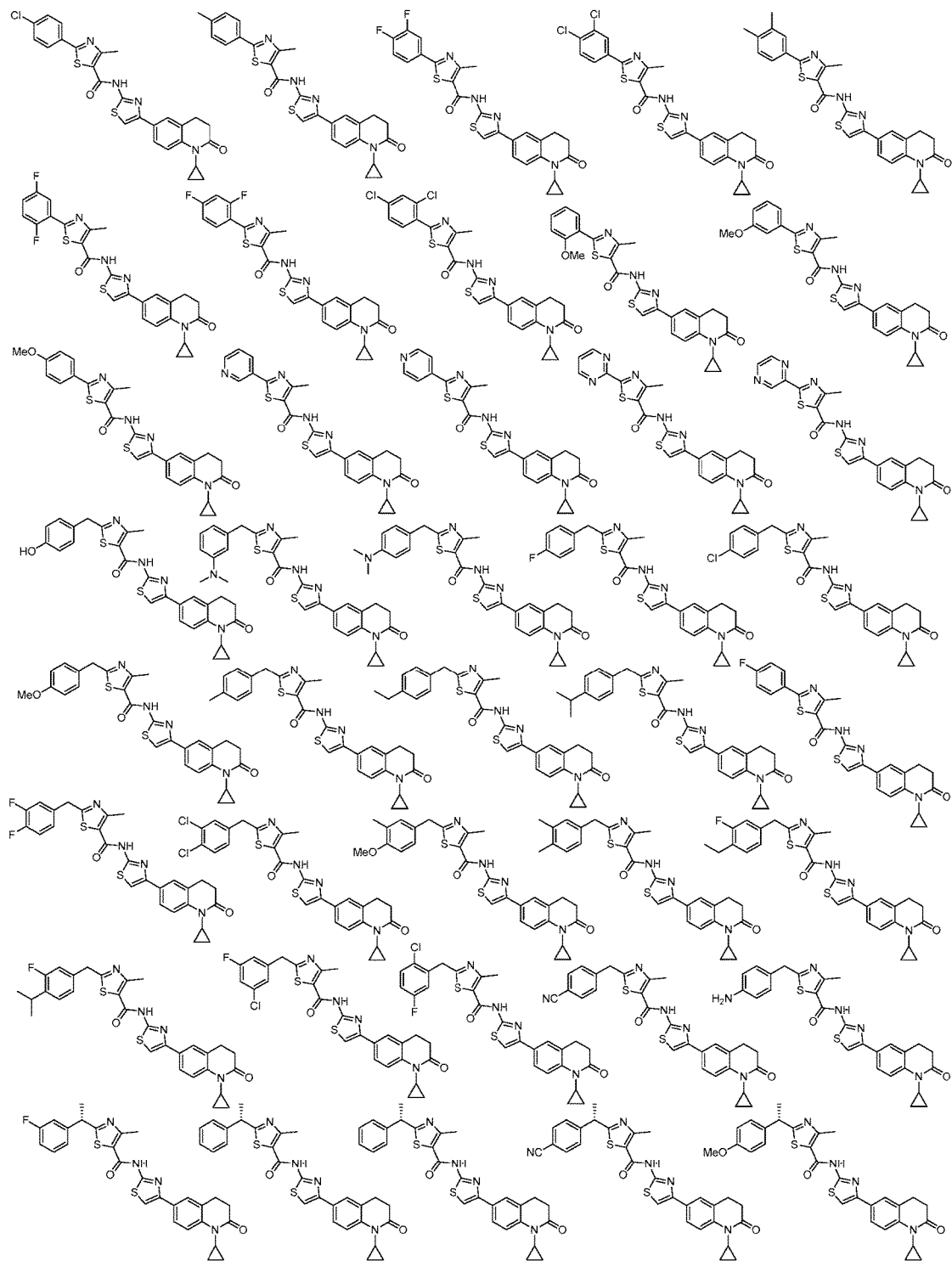
Figure 34:
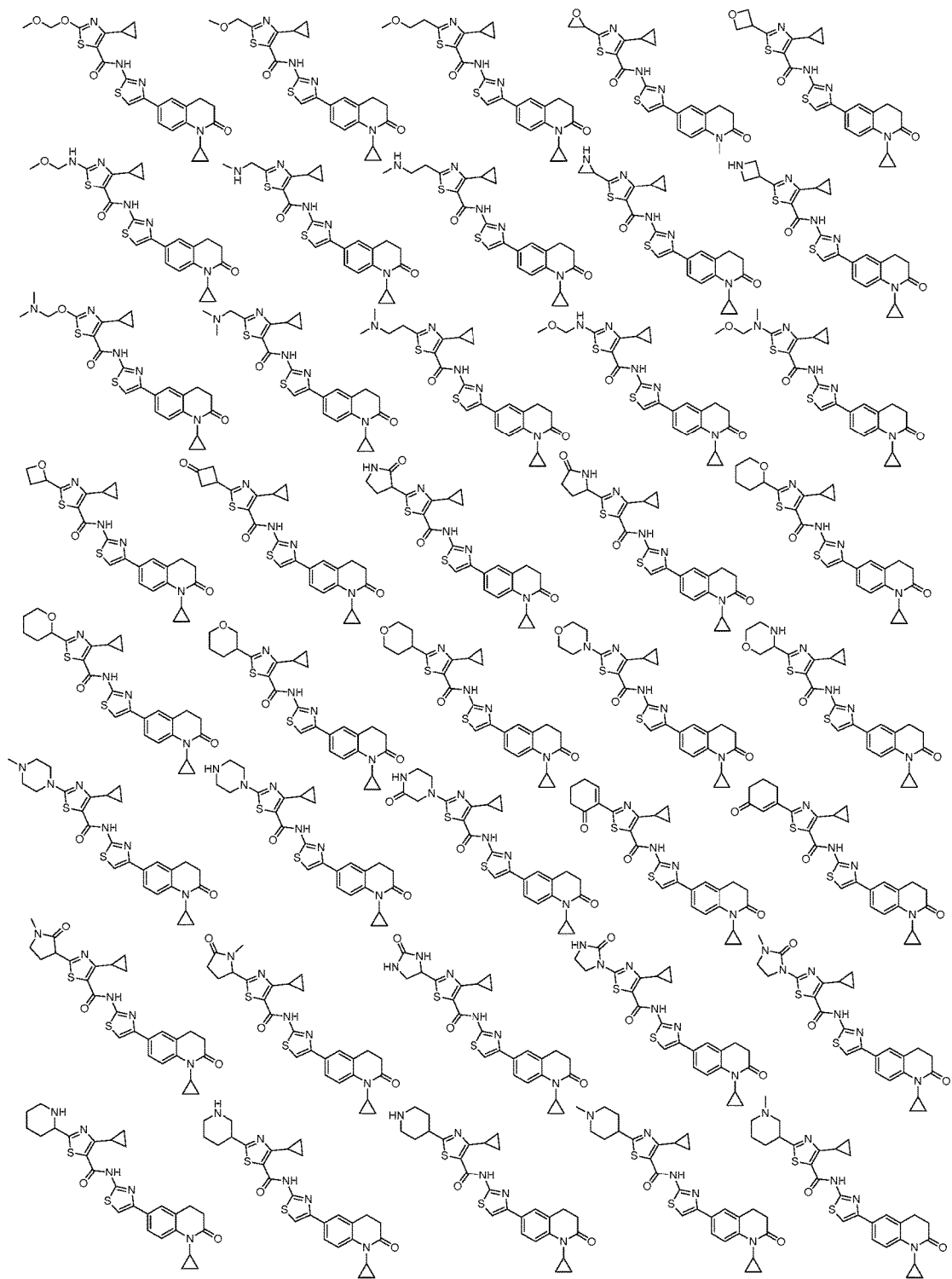
Figure 35:
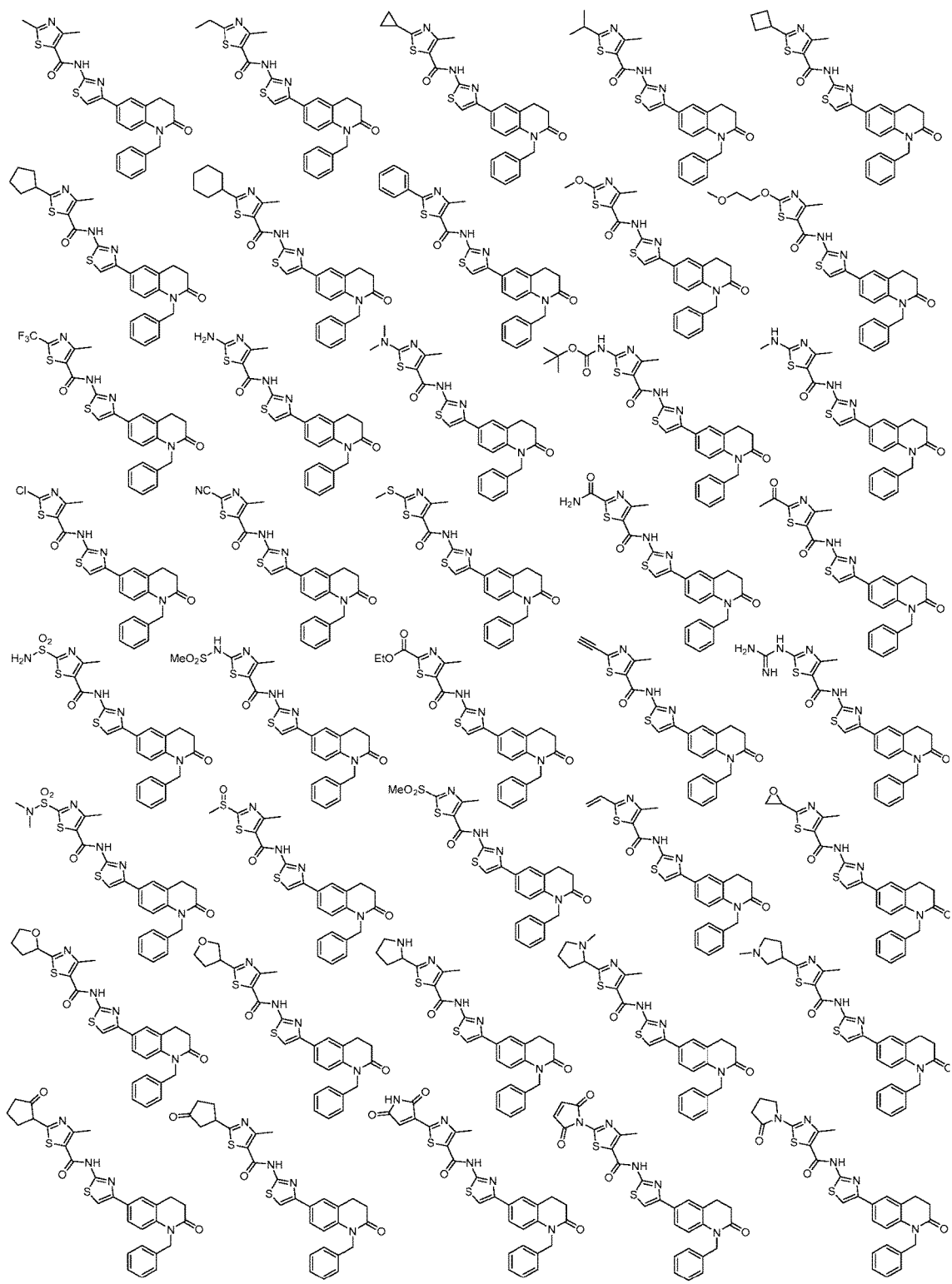
Figure 36:
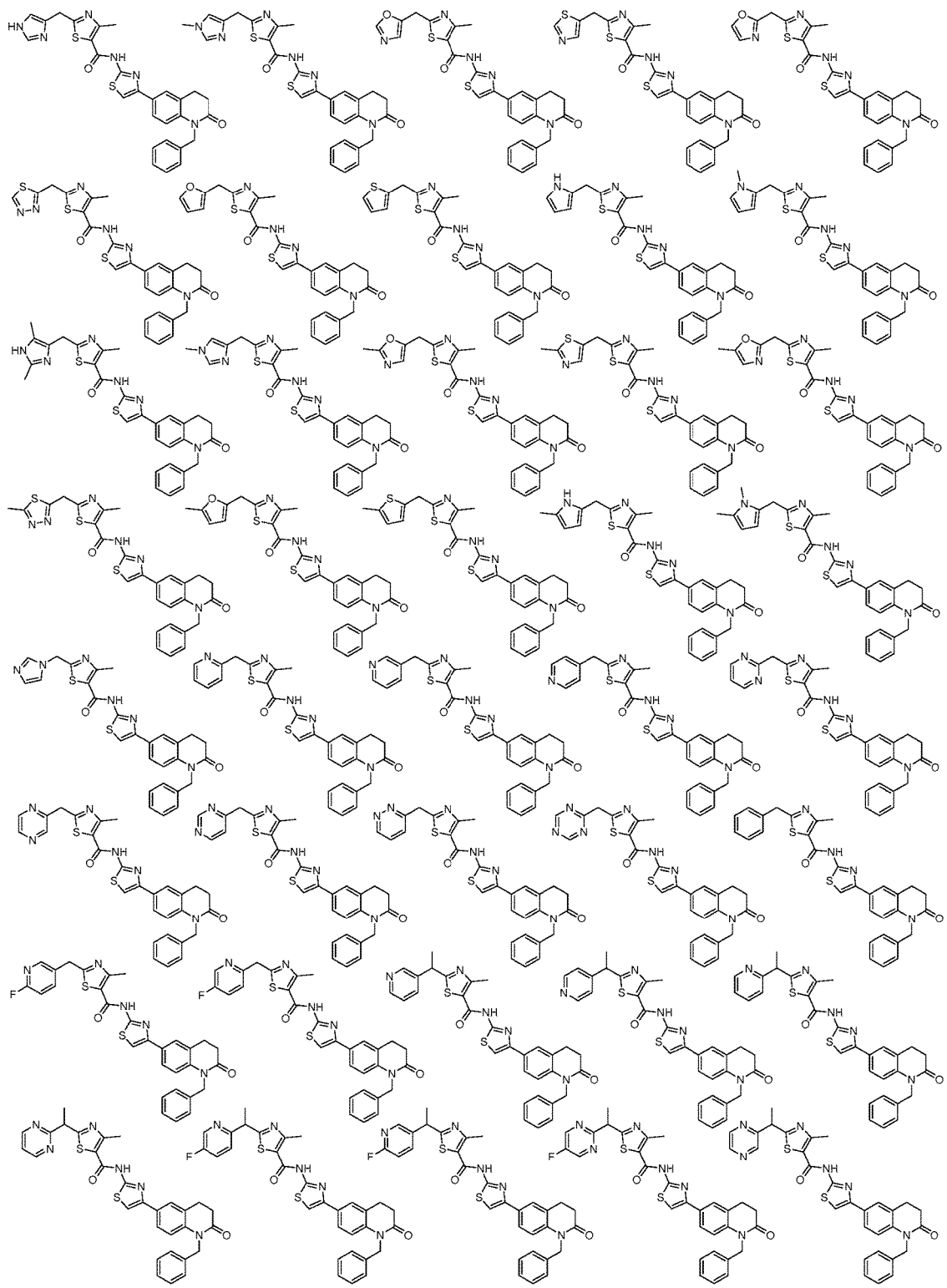
Figure 37:
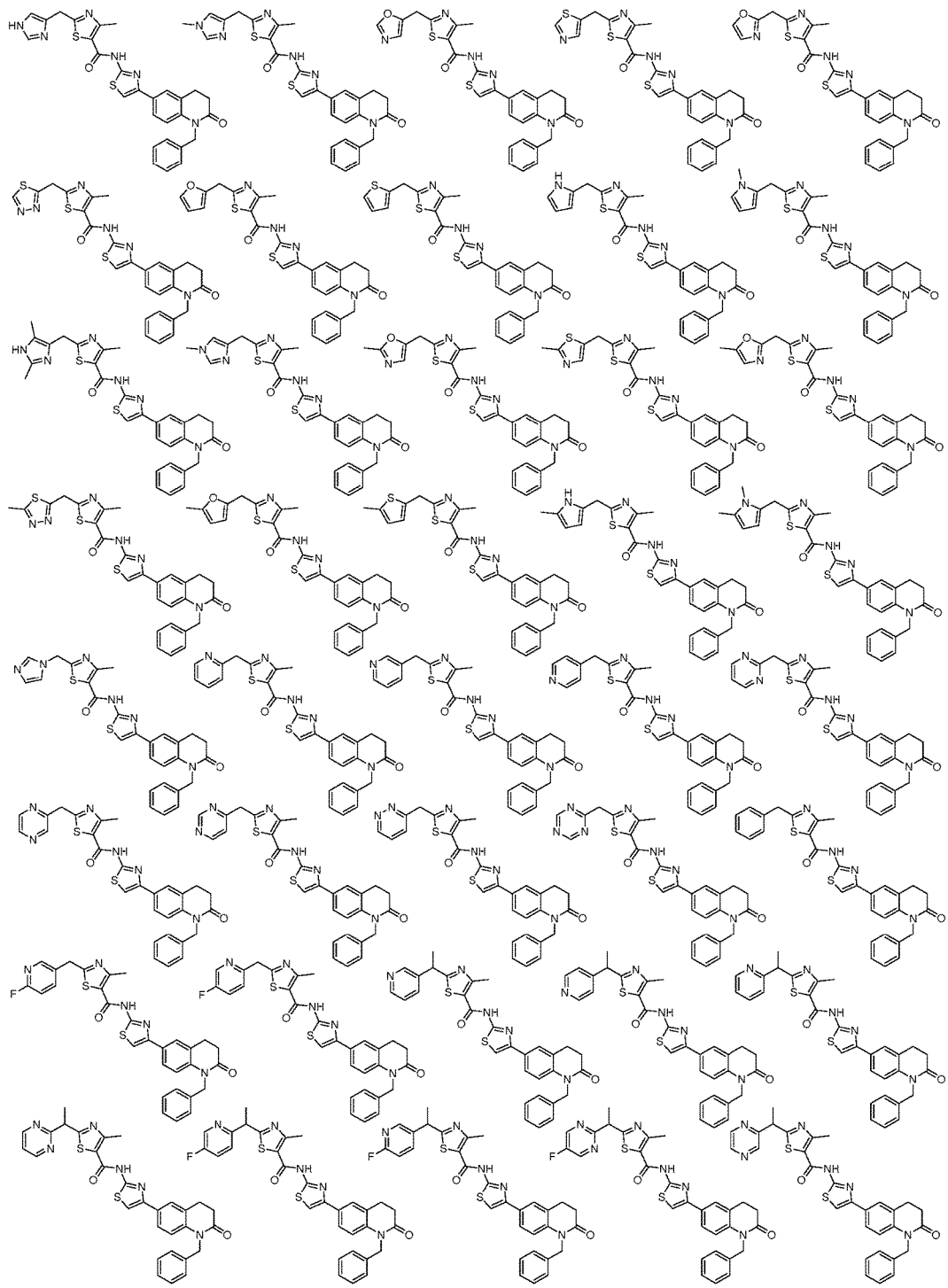
Figure 38:
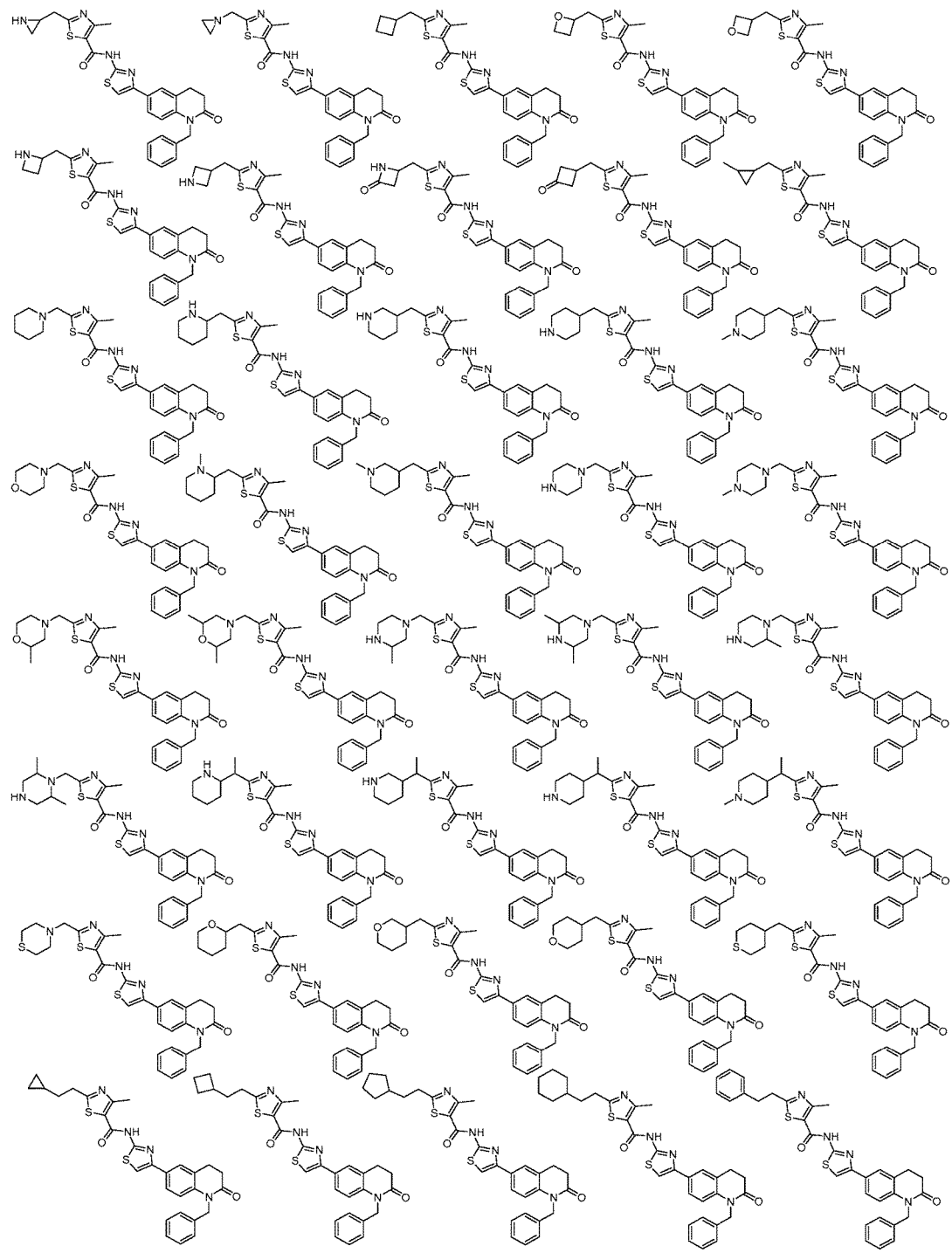
Figure 39:
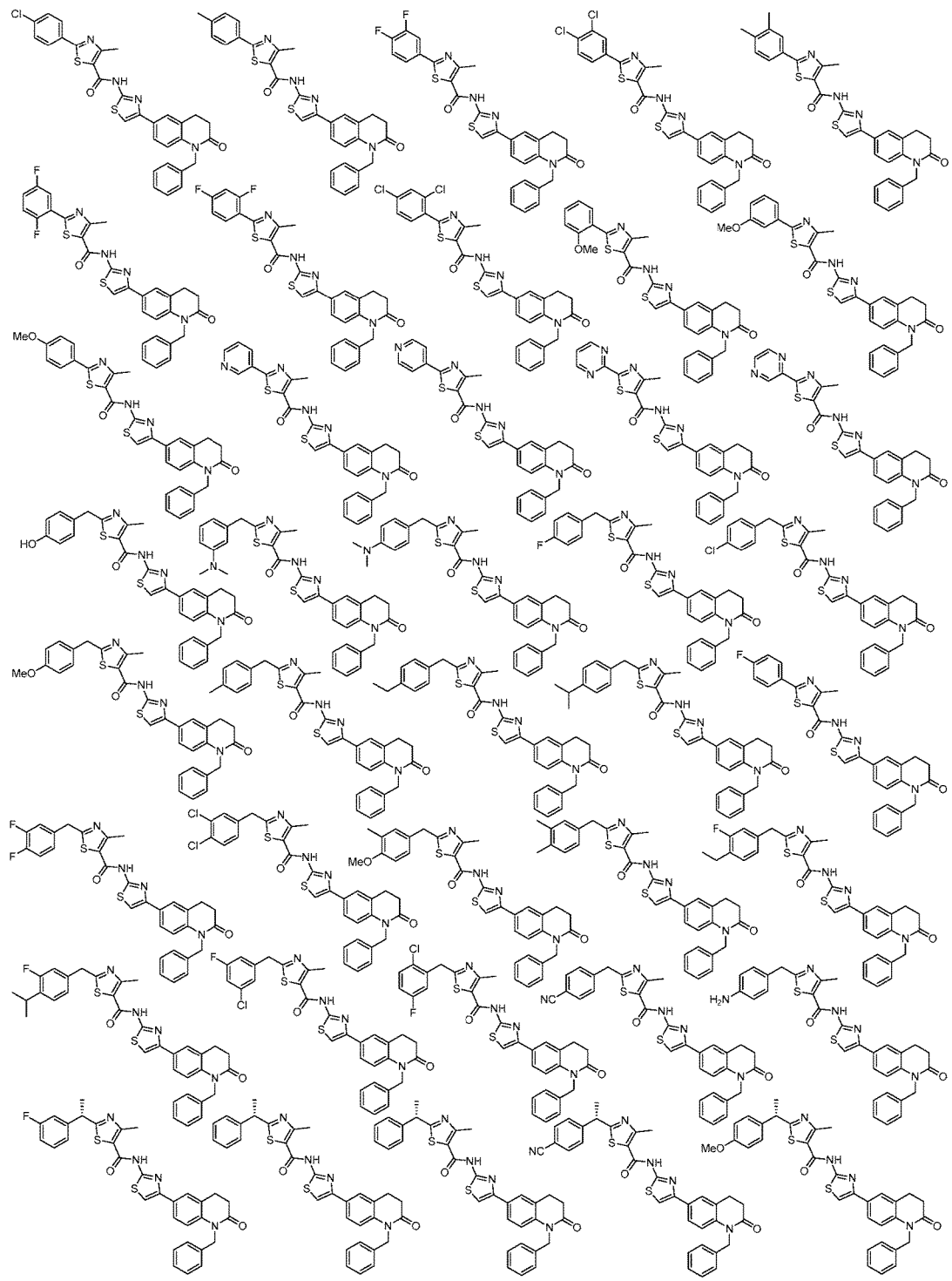
Figure 40:
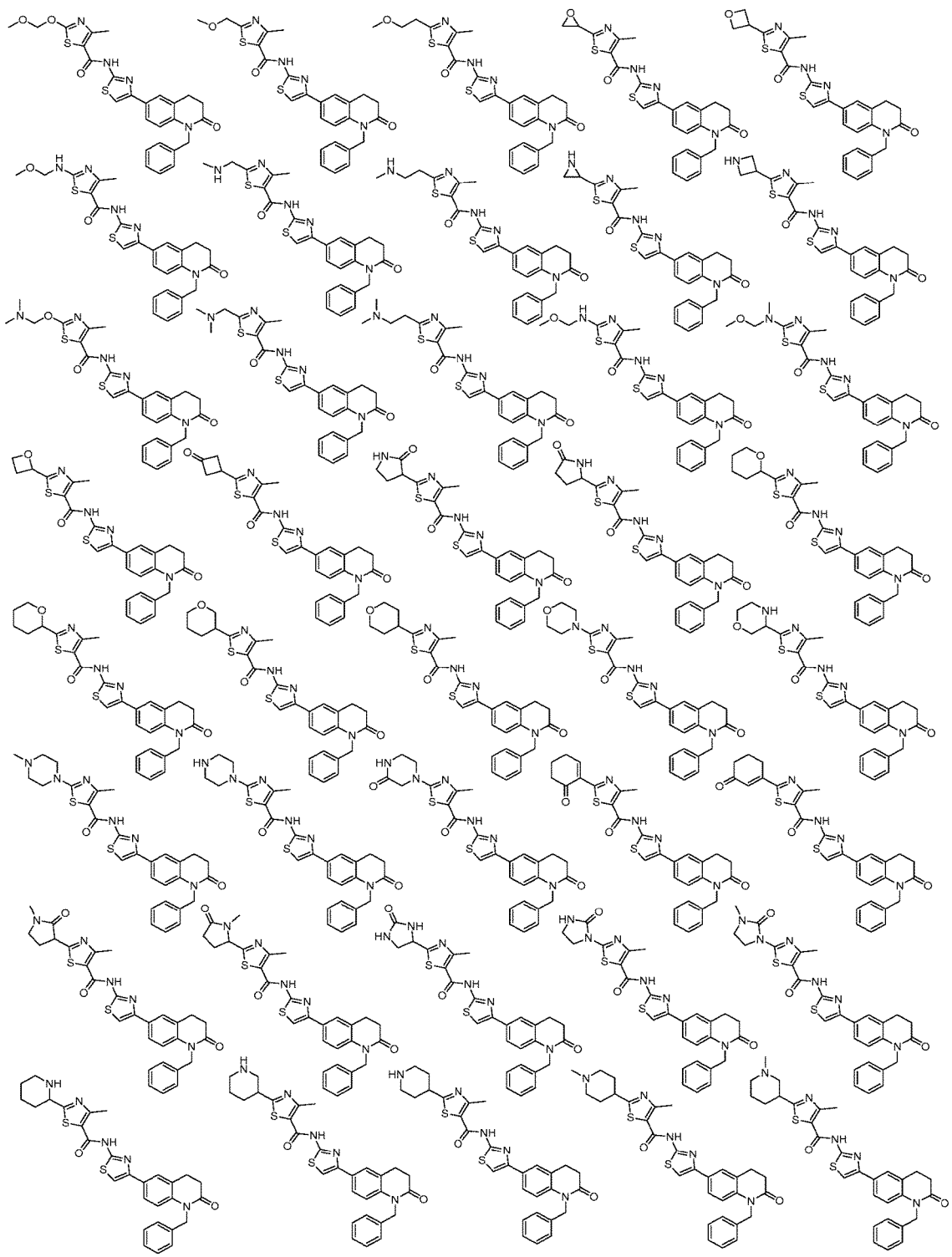
Figure 41:
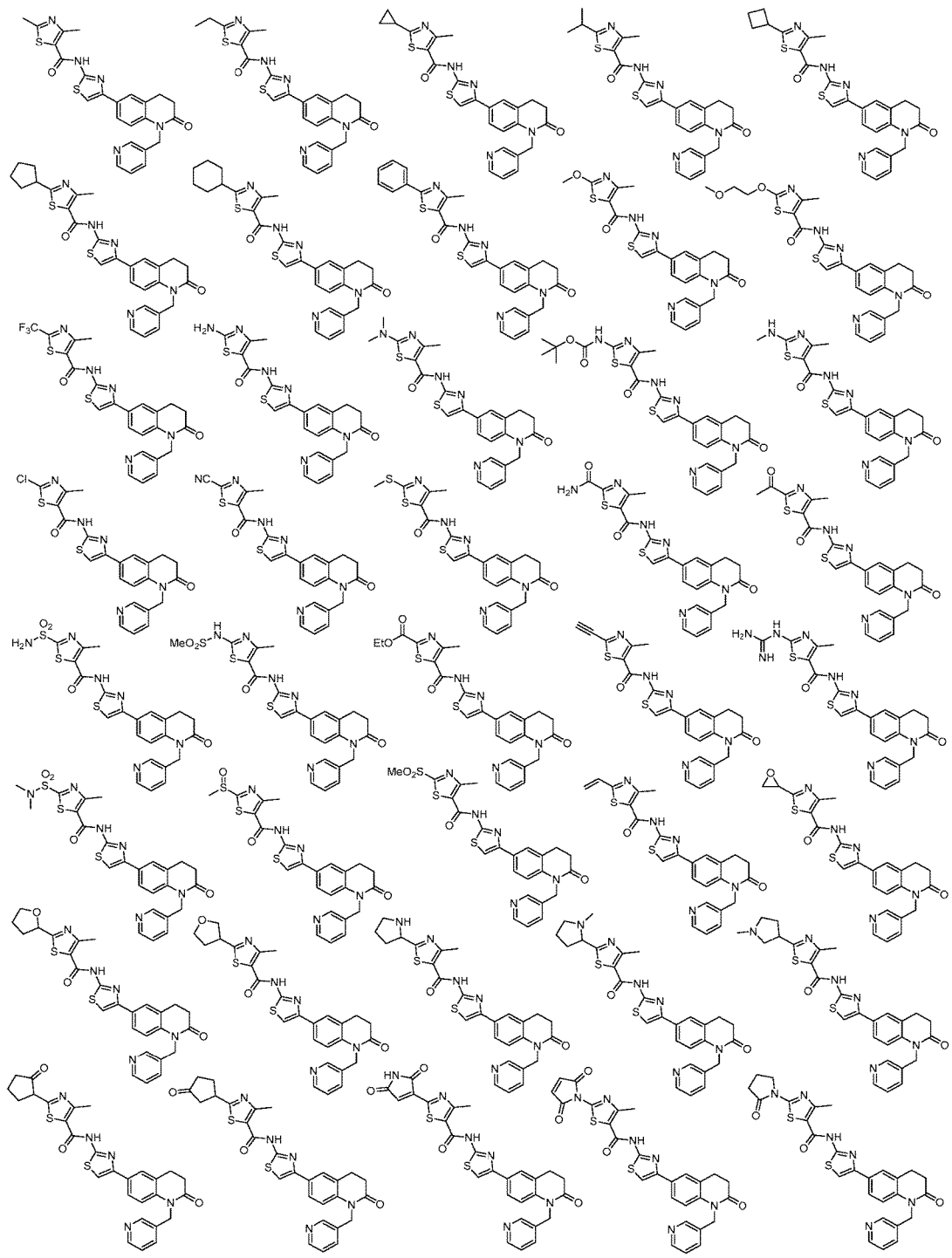
Figure 42:
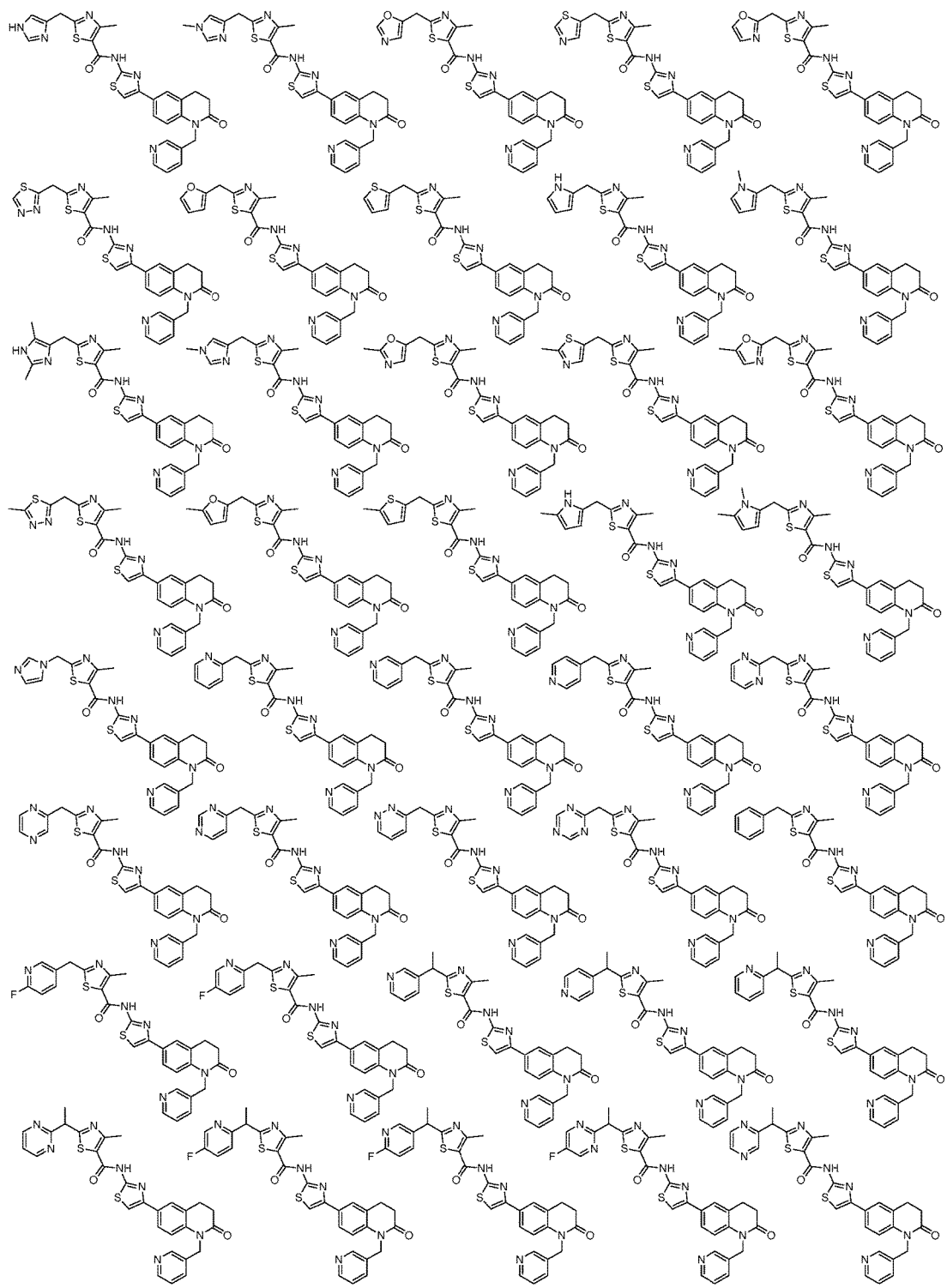
Figure 43:
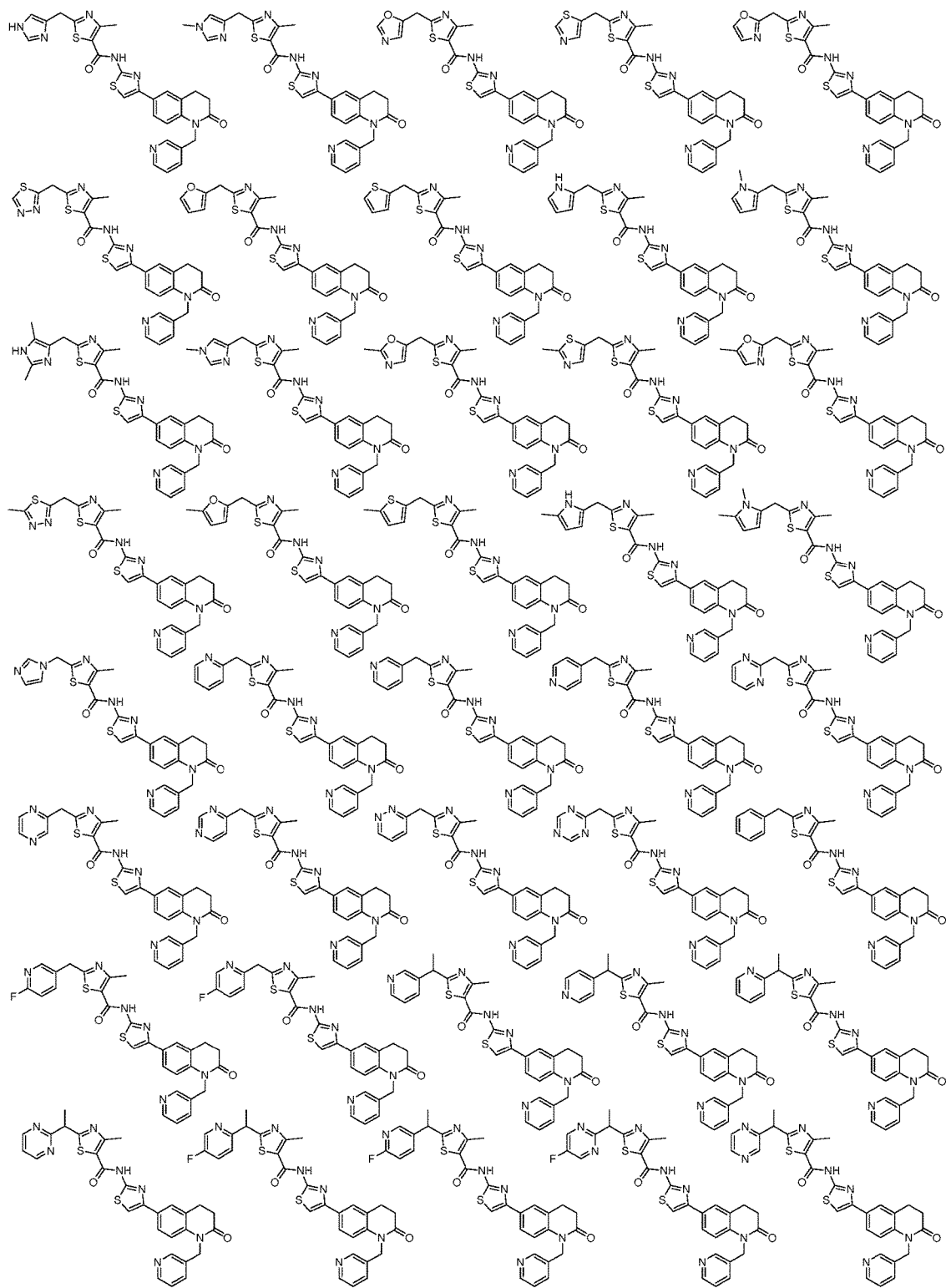
Figure 44:
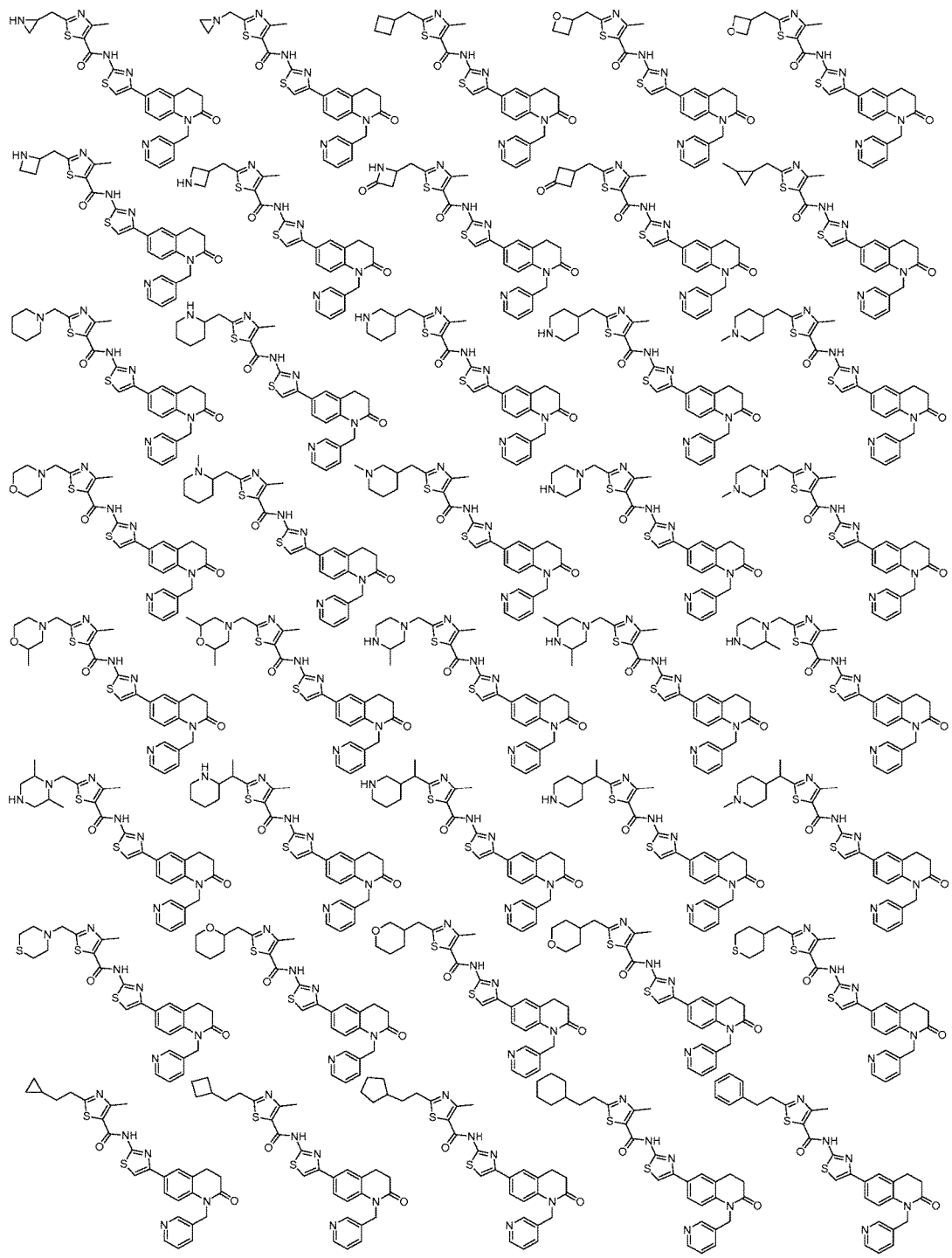
Figure 45:
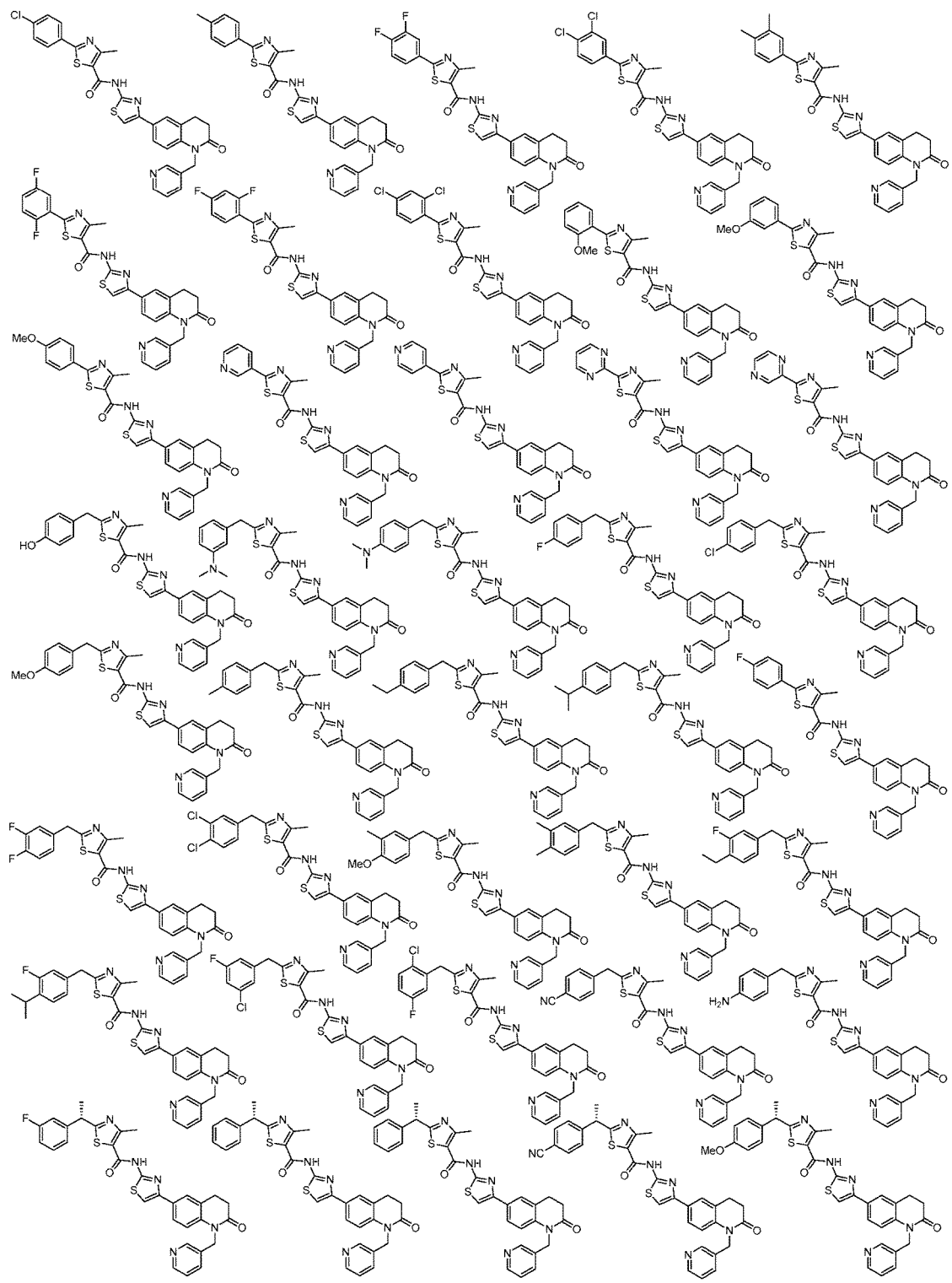
Figure 46:
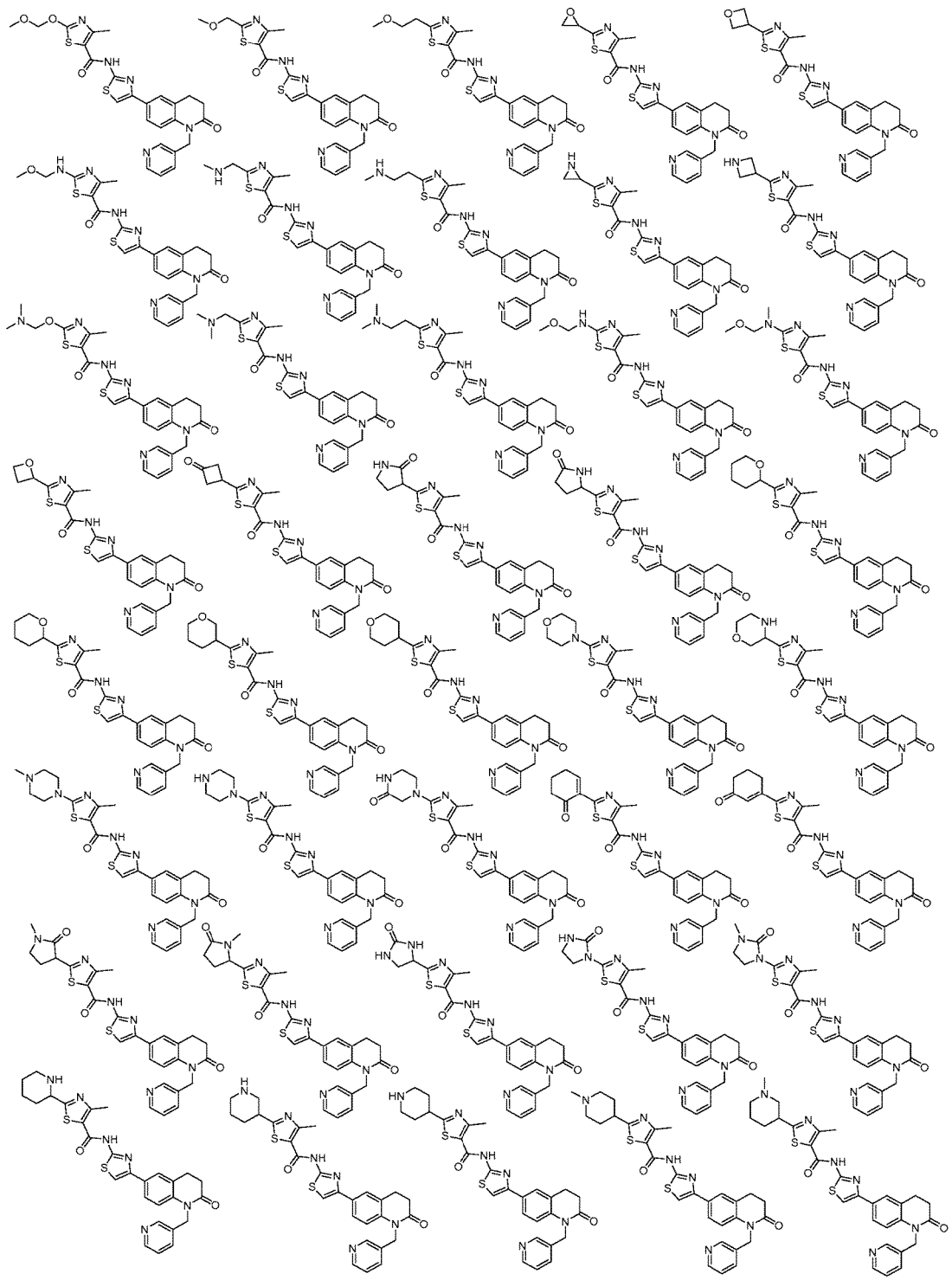
Figure 47:
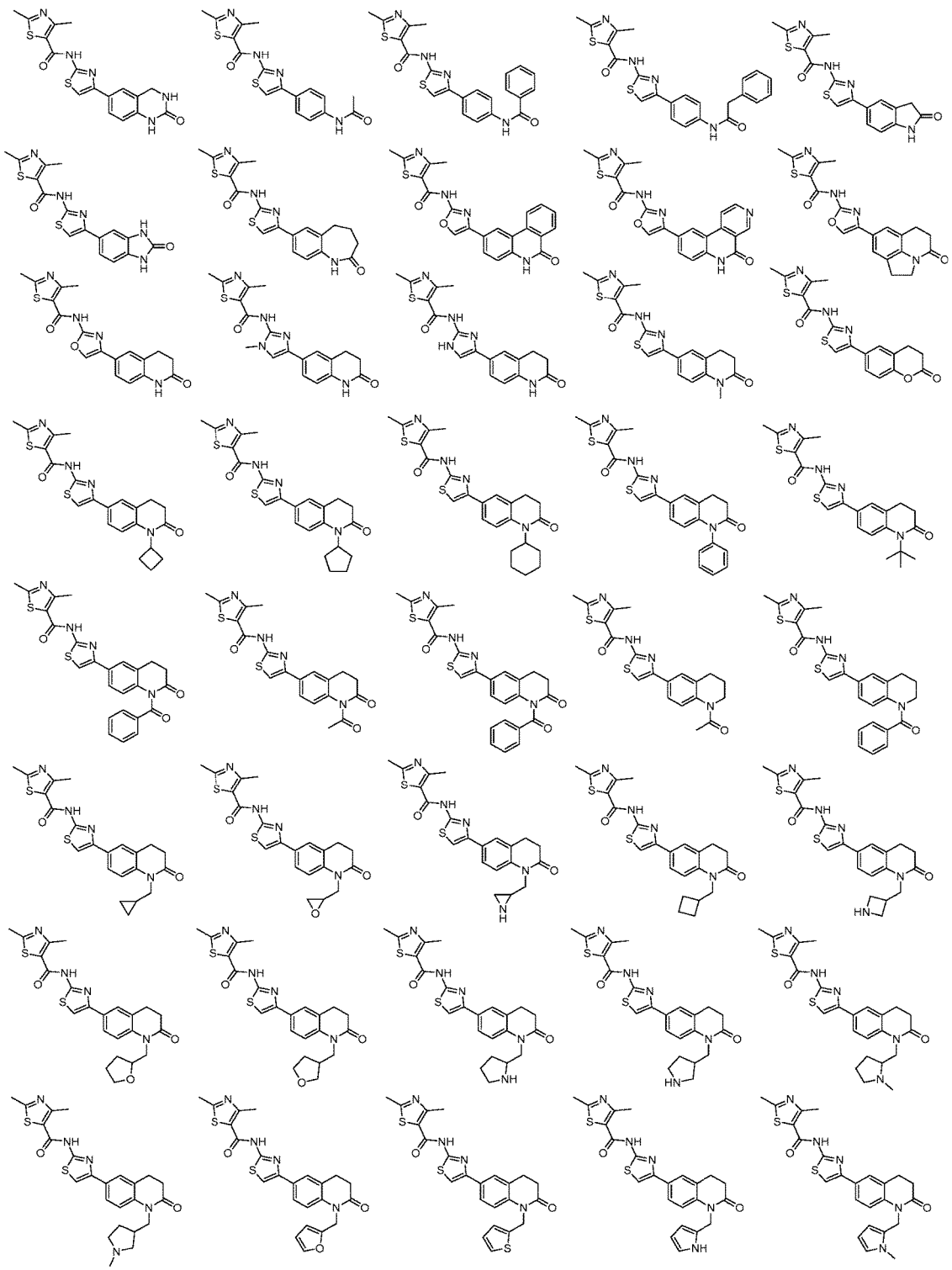
Figure 48:
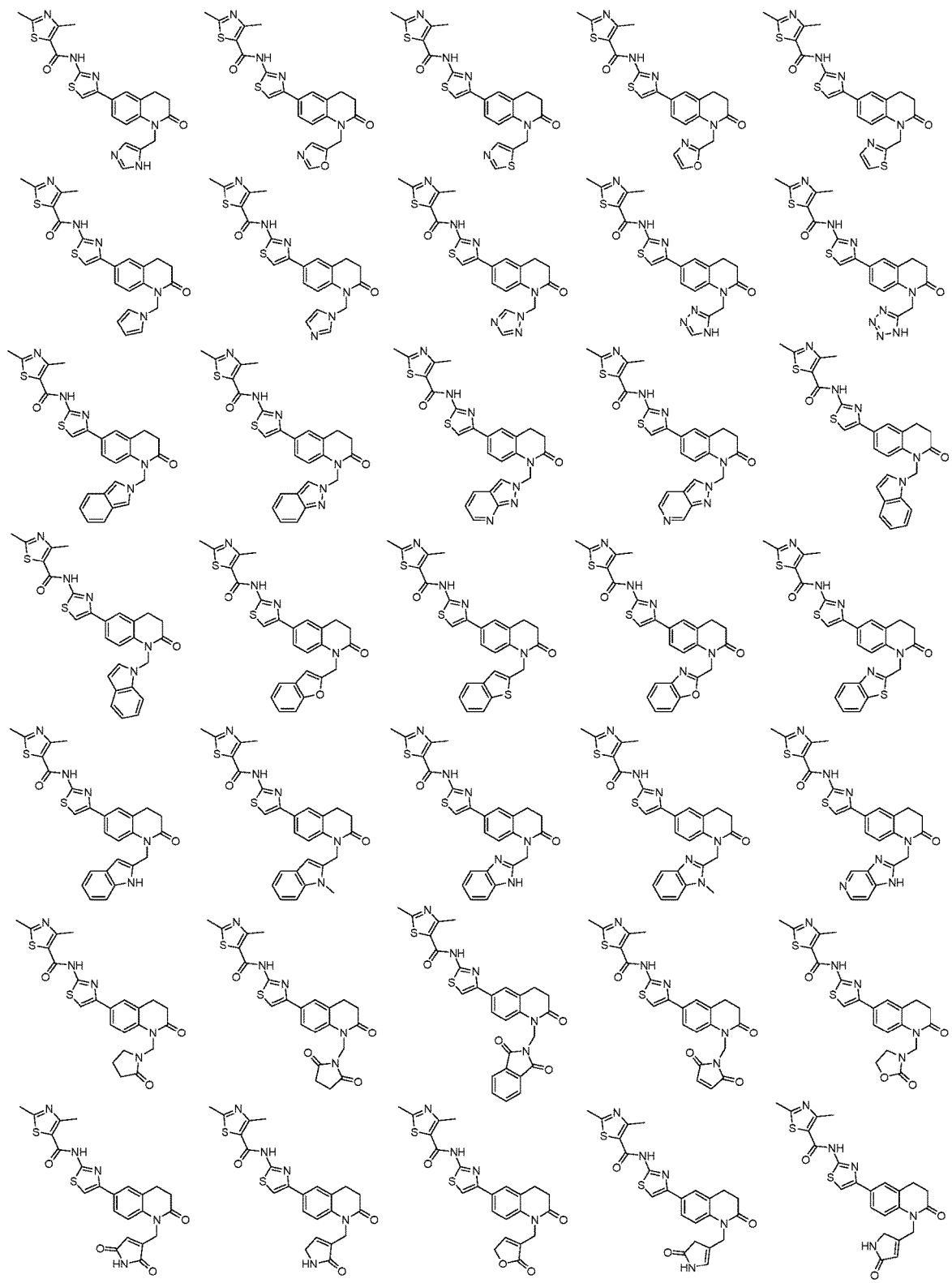
Figure 49:
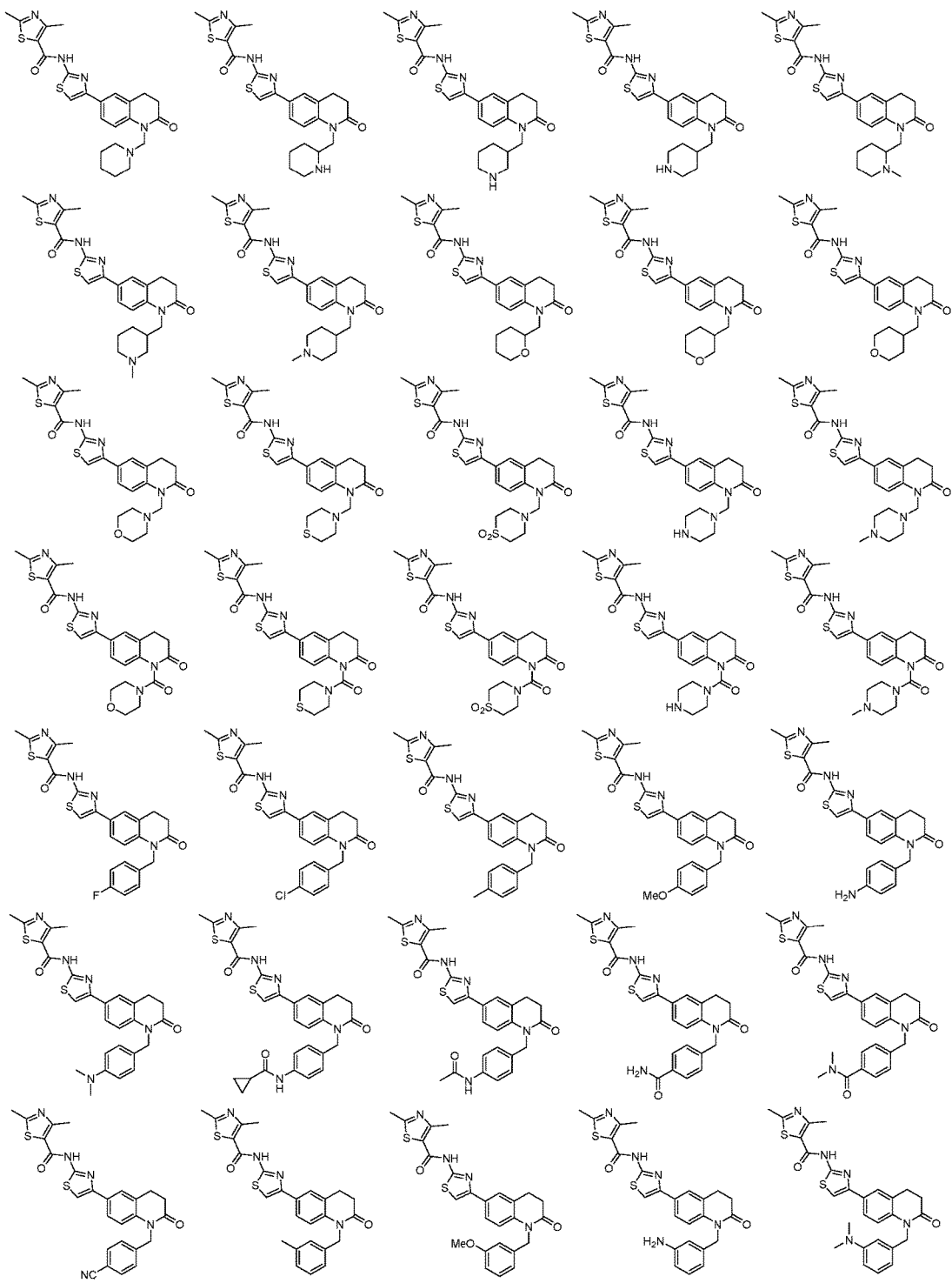
Figure 50:
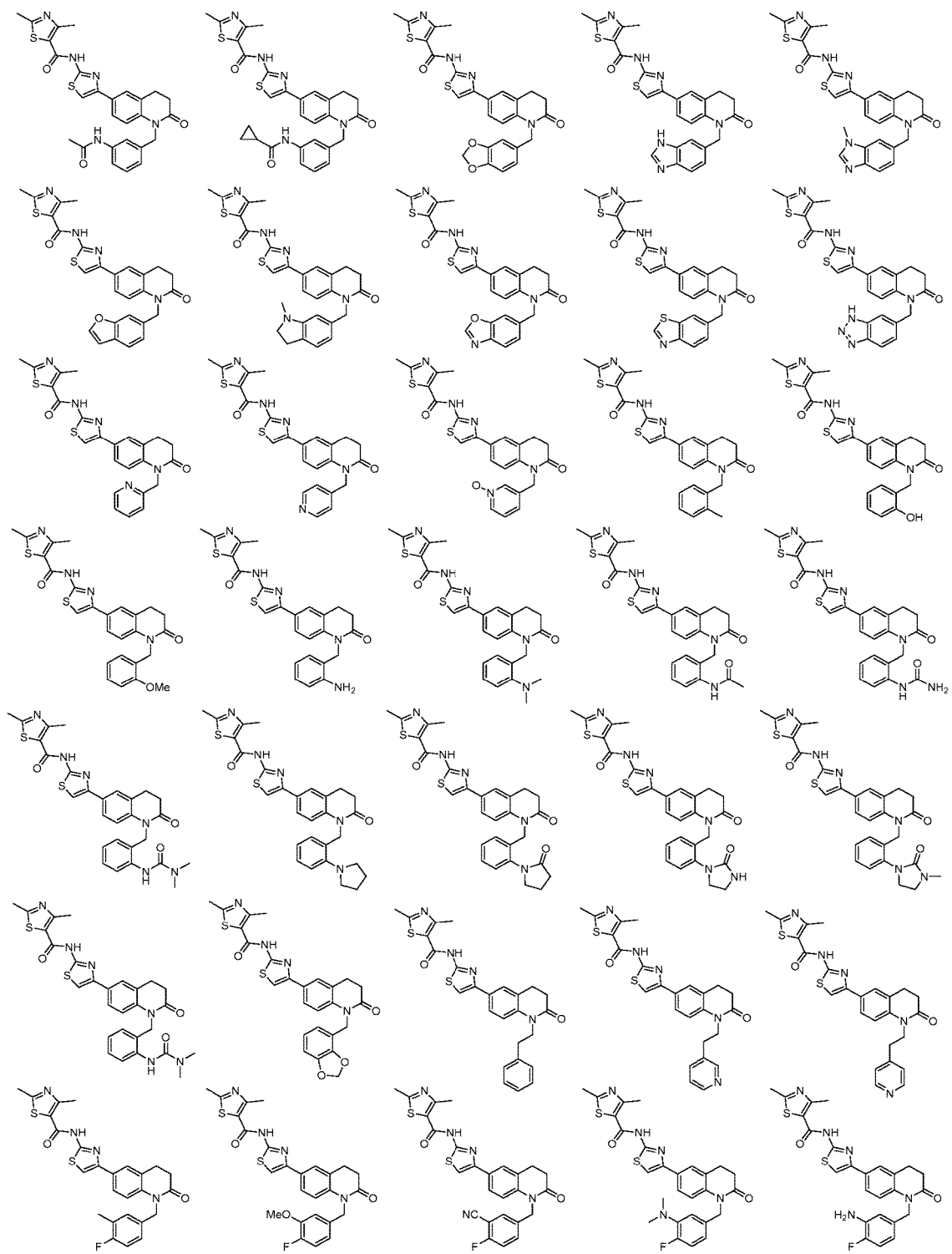
Figure 51:
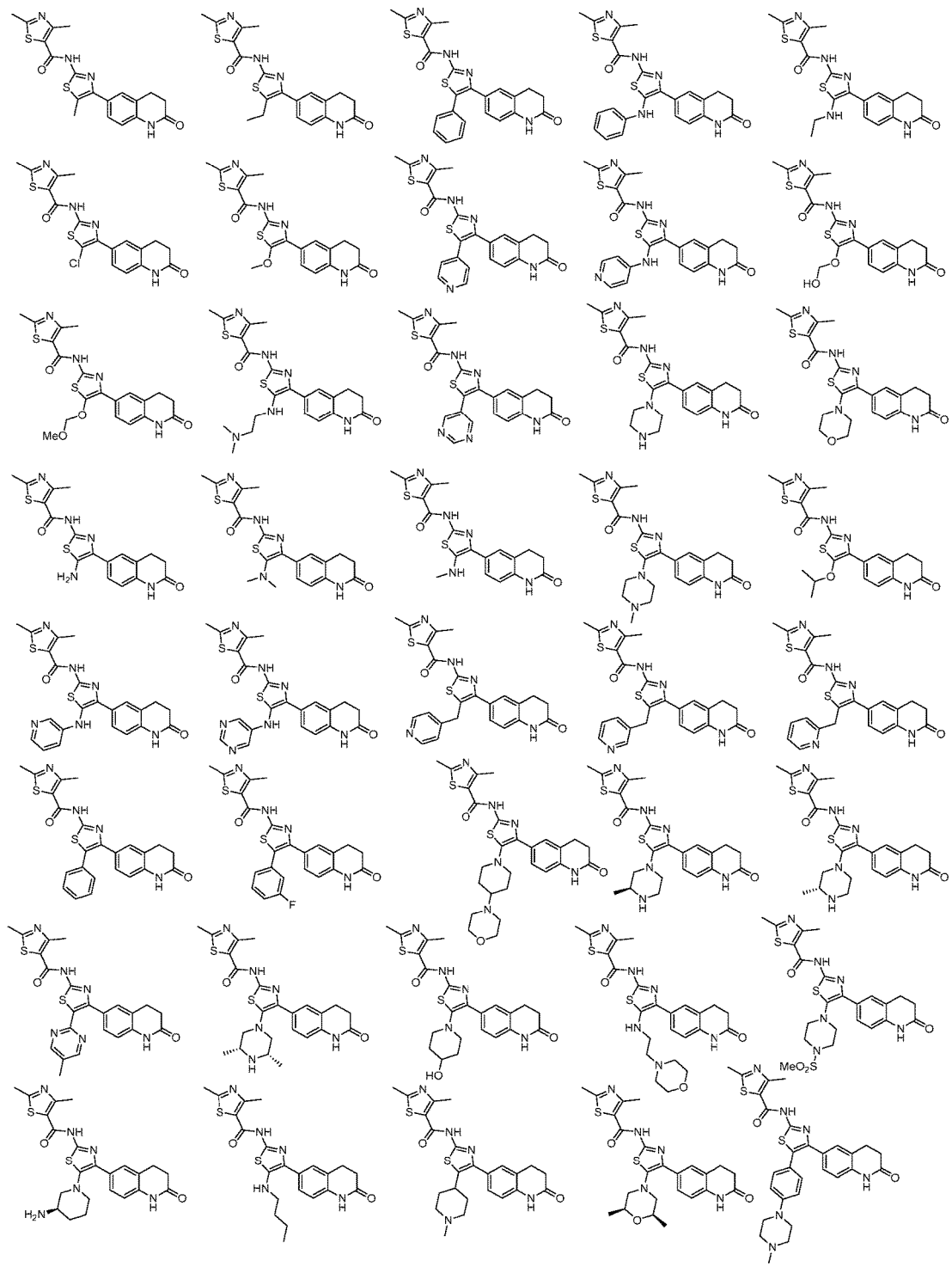
Figure 52:
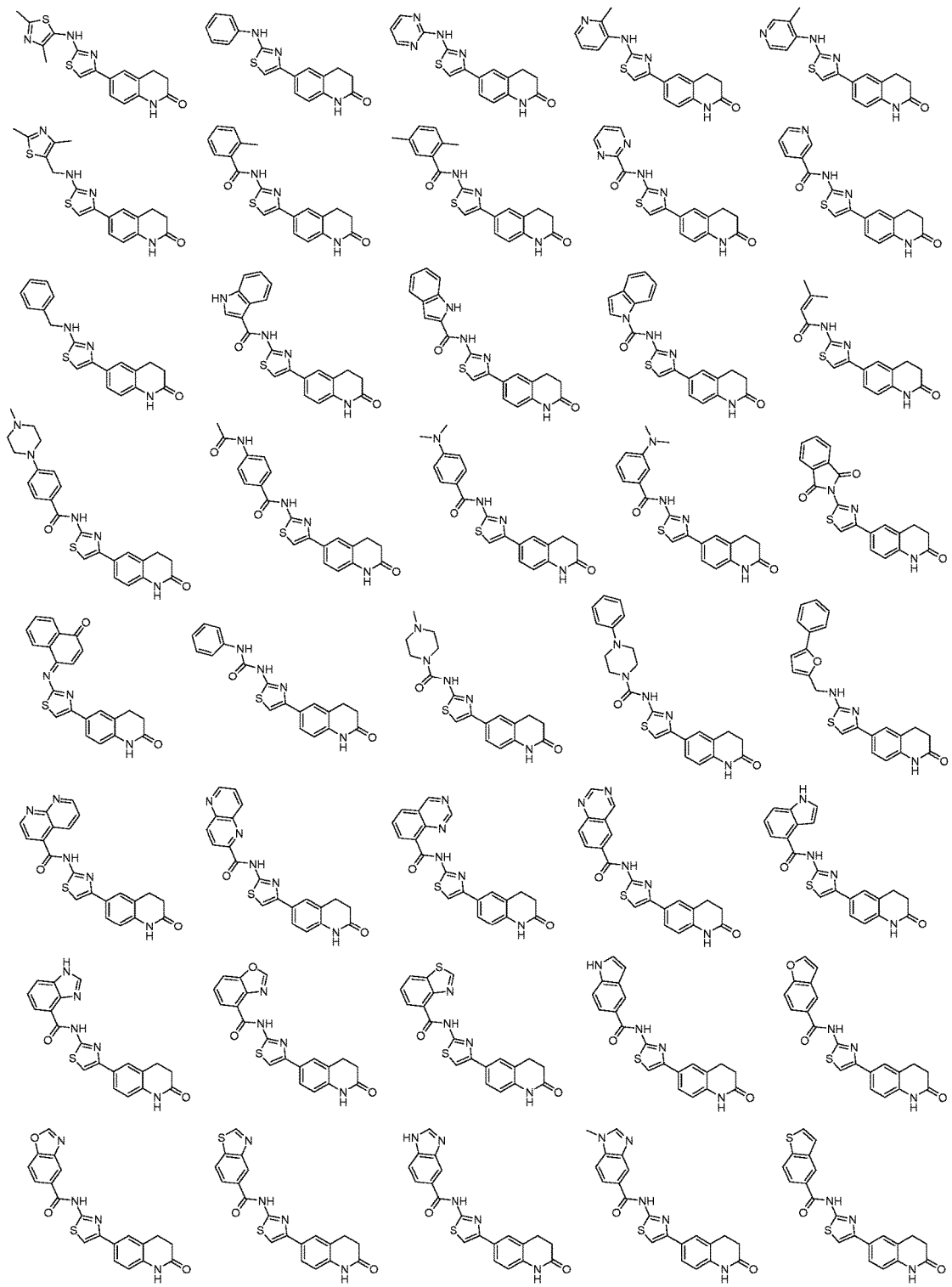
Figure 53:
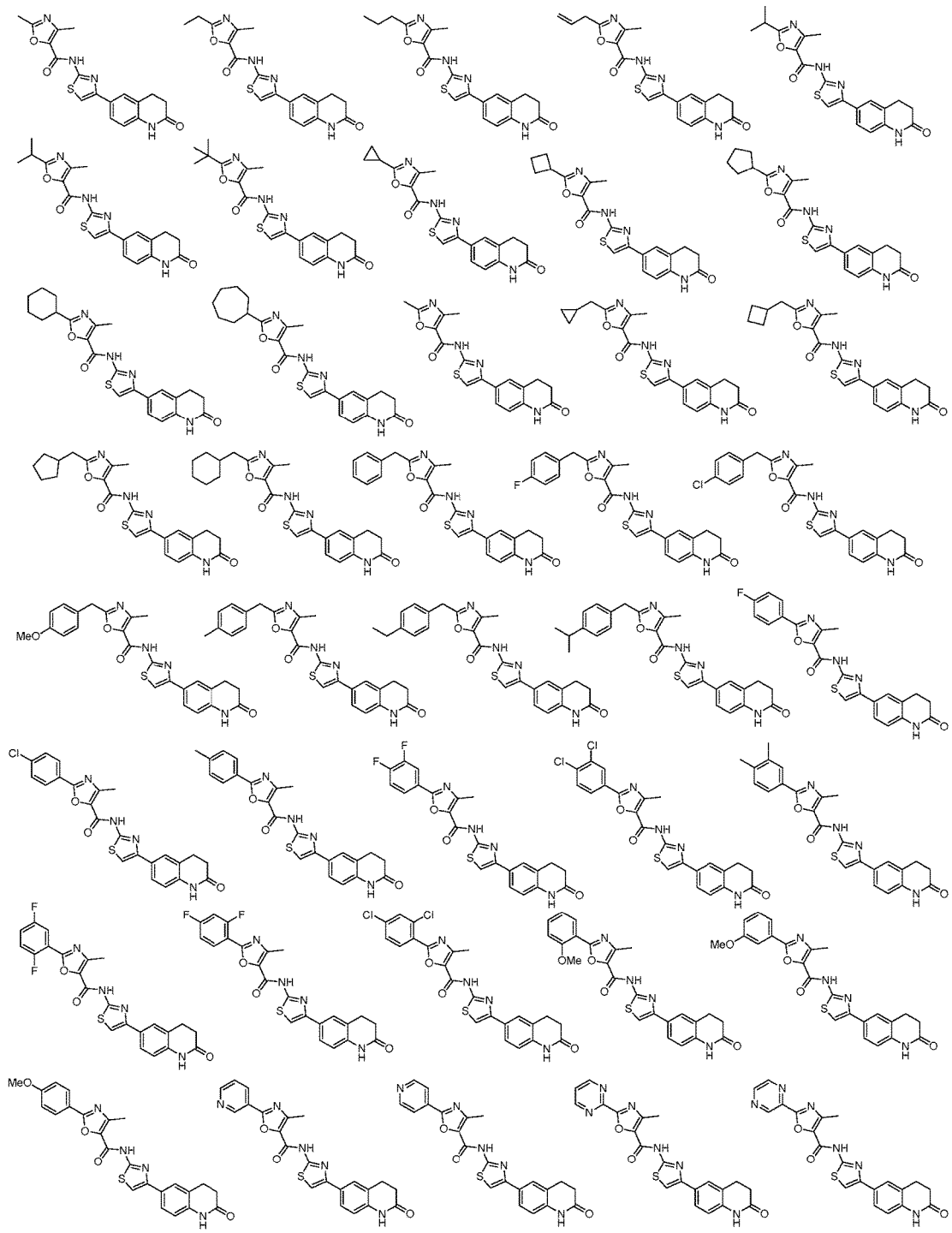
Figure 54:
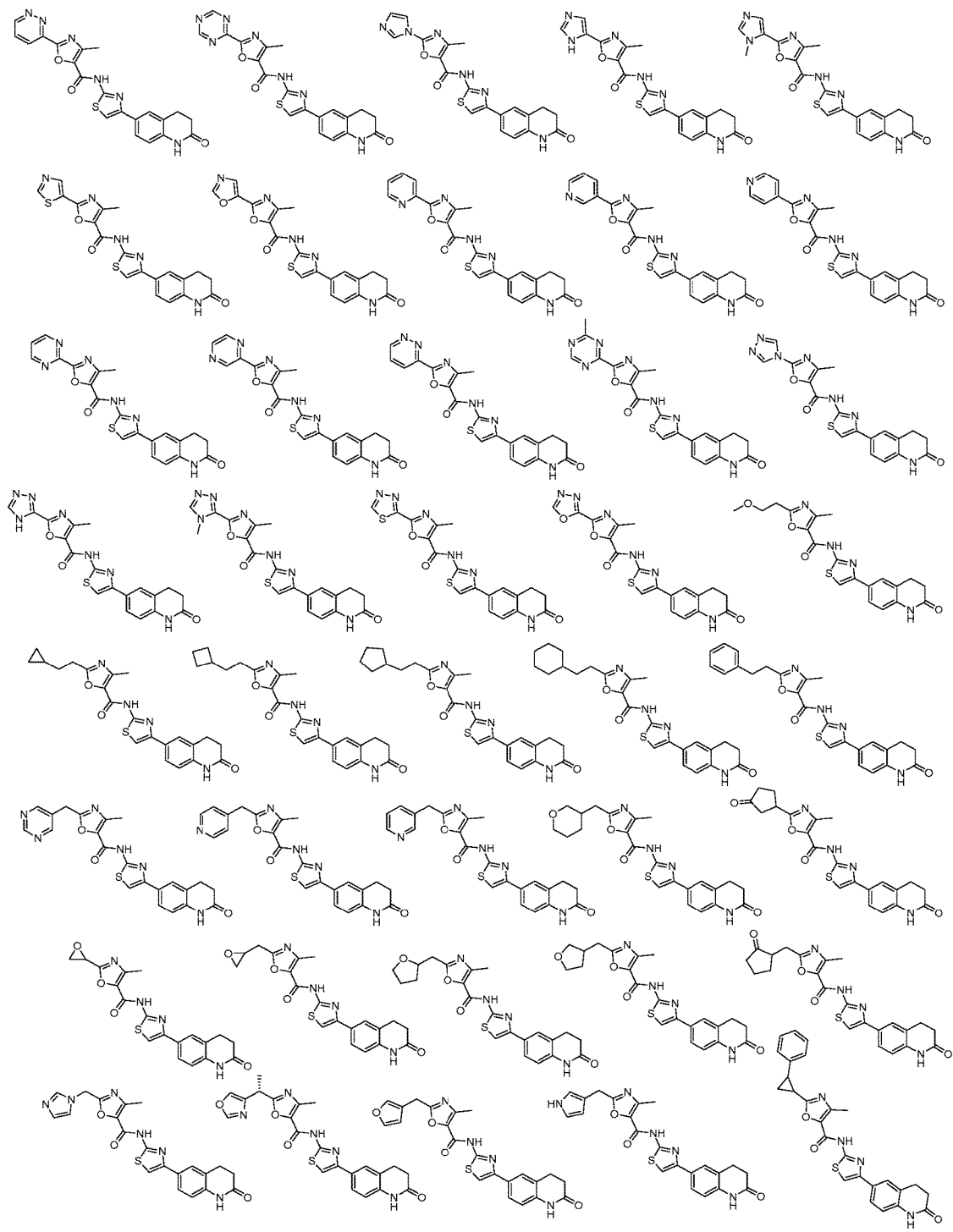
Figure 55:
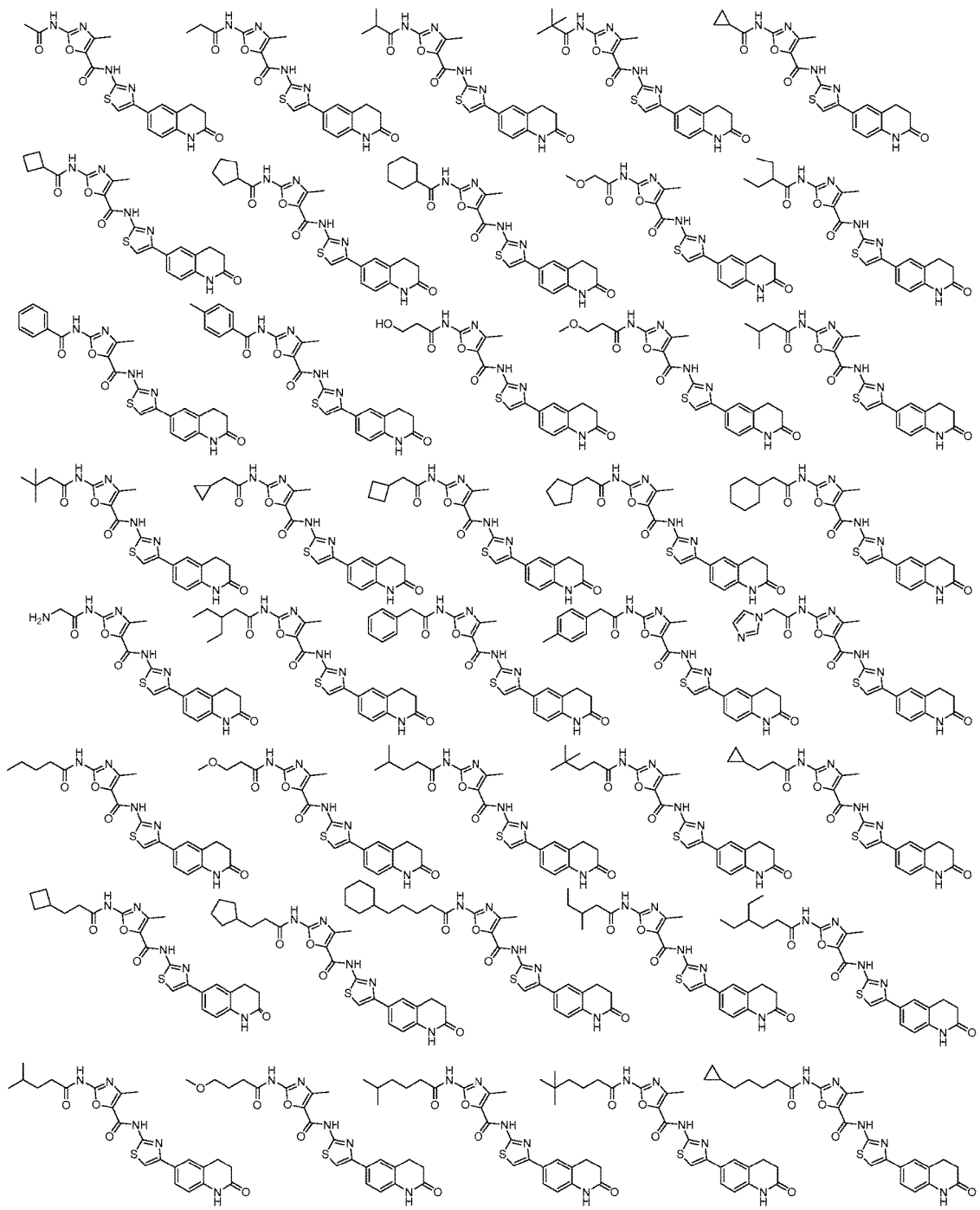
Figure 56:
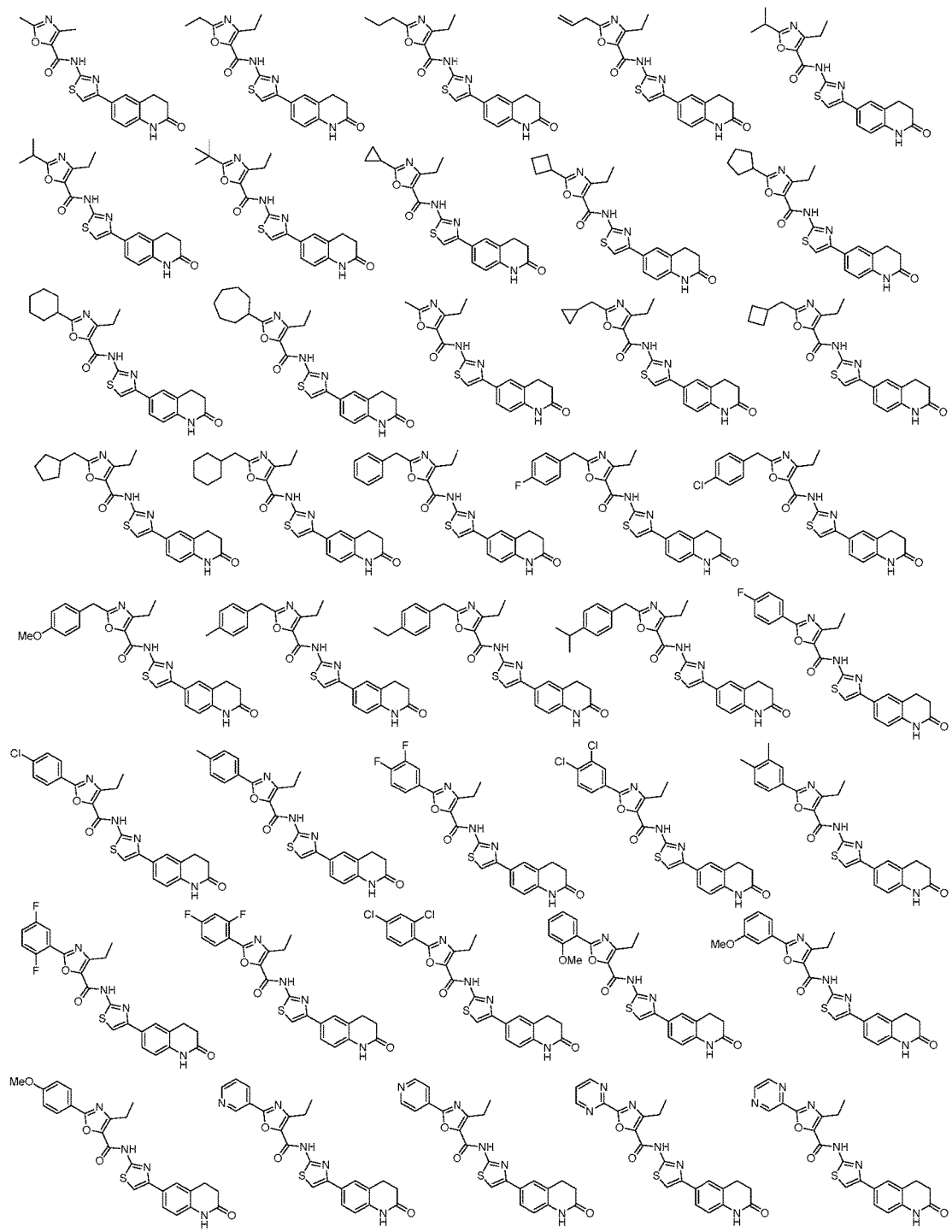
Figure 57:
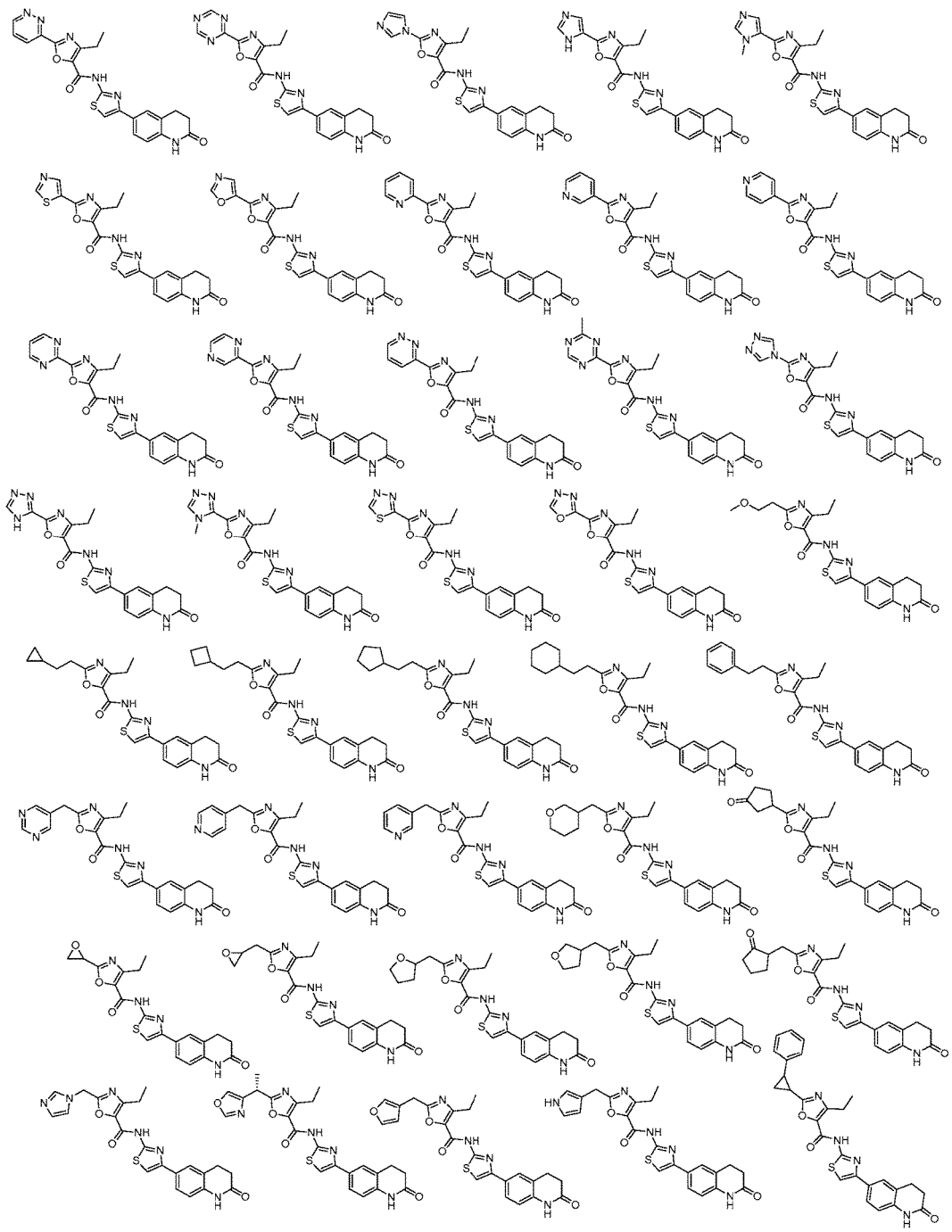
Figure 58:
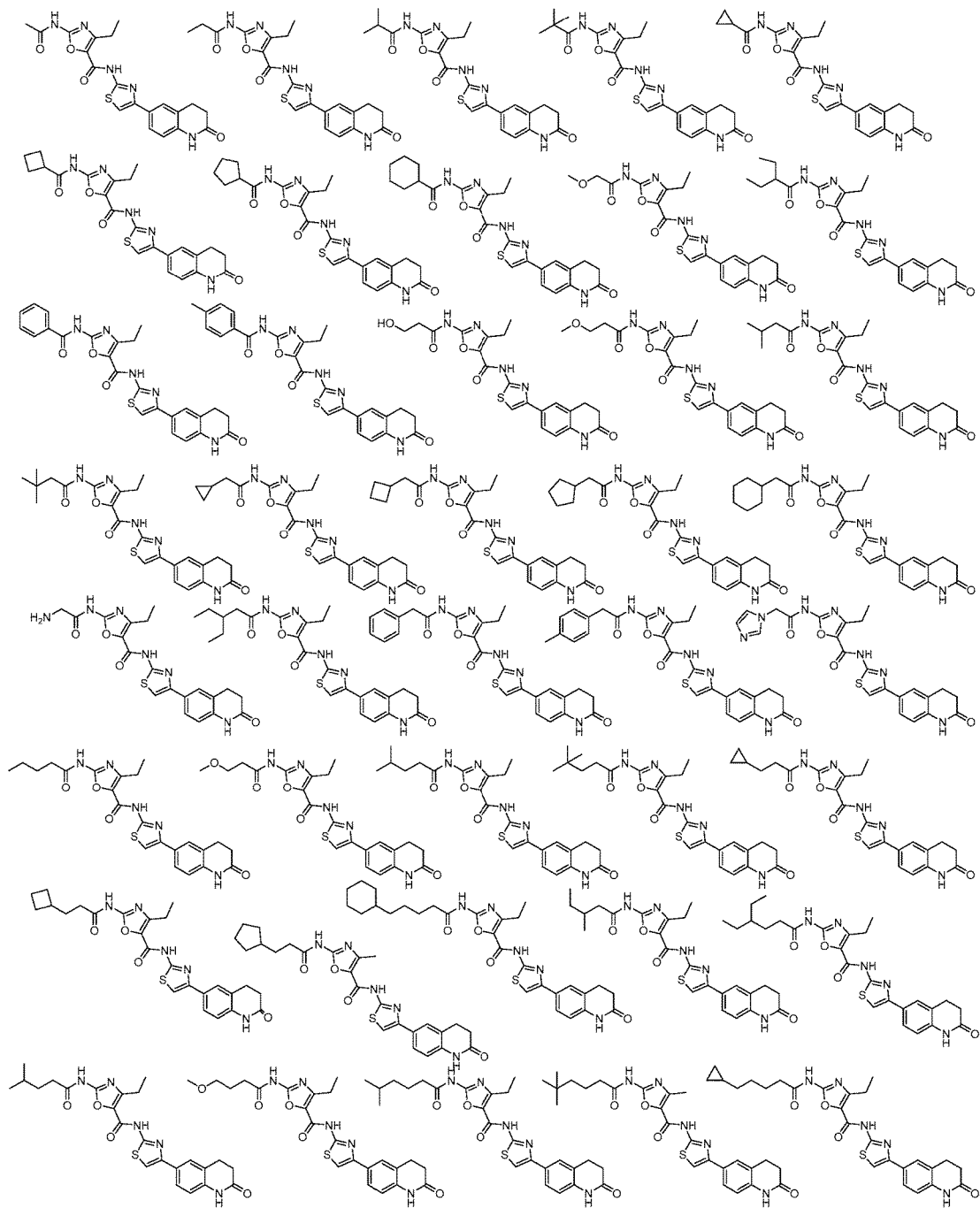
Figure 59:
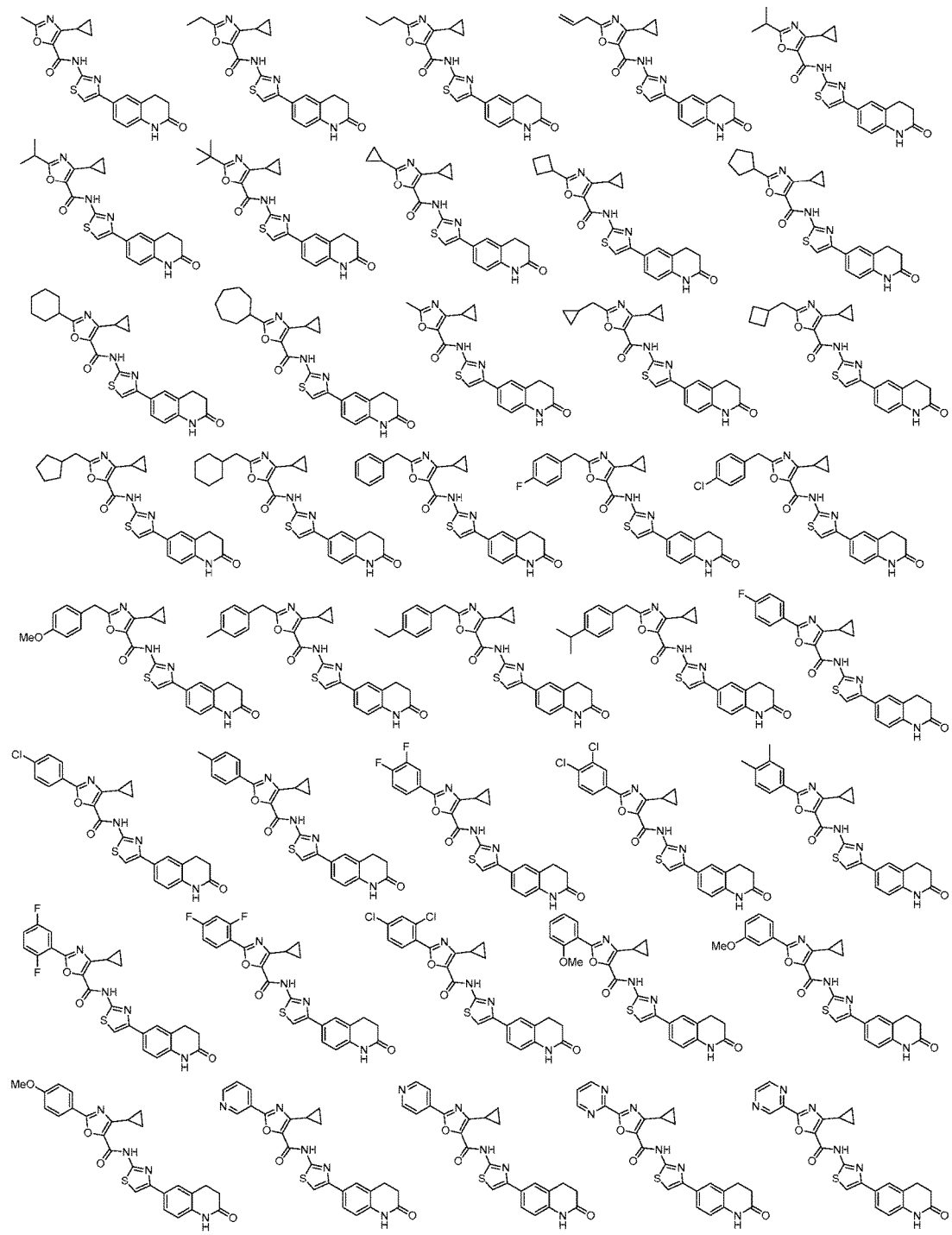
Figure 60:
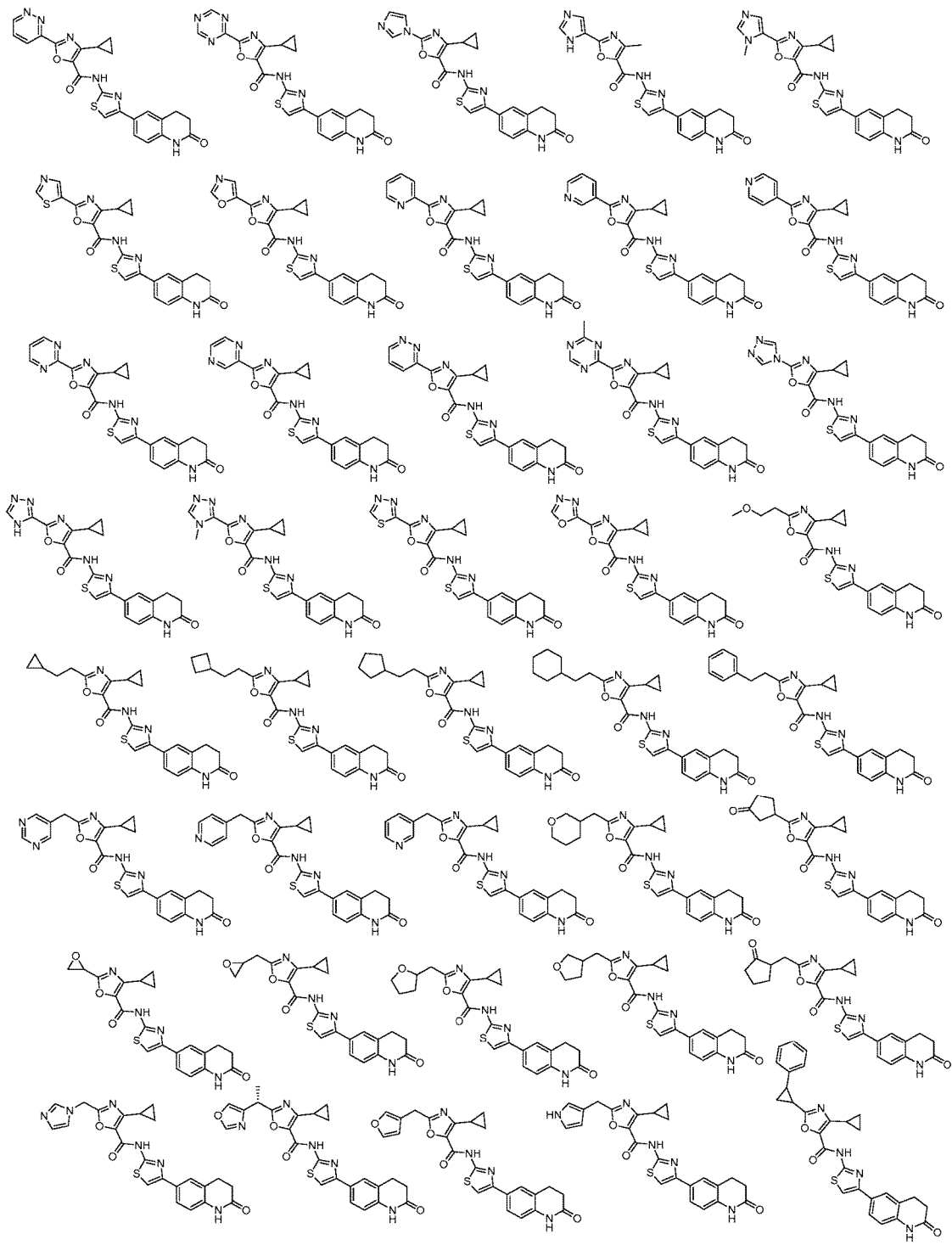
Figure 61:
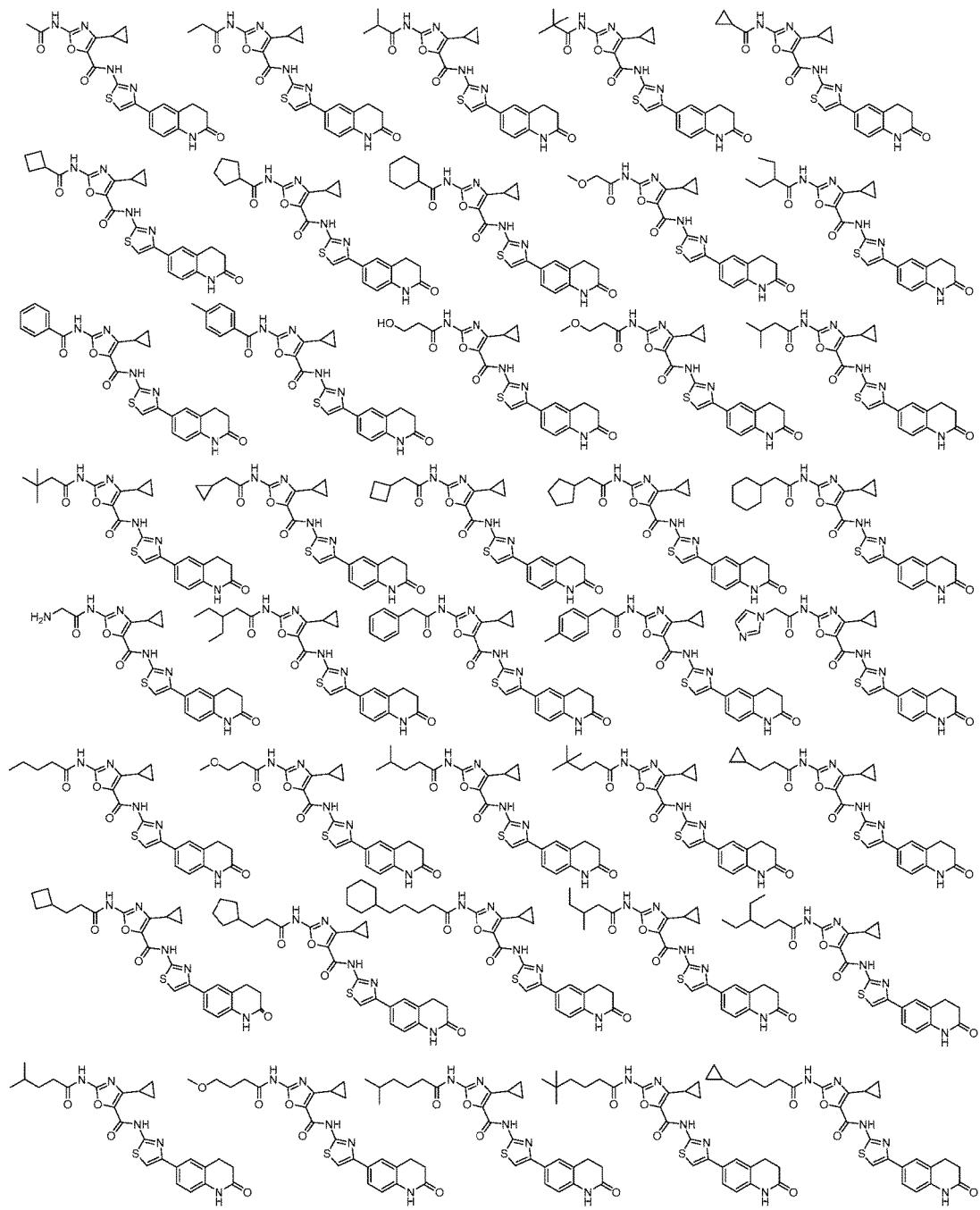
Figure 62:
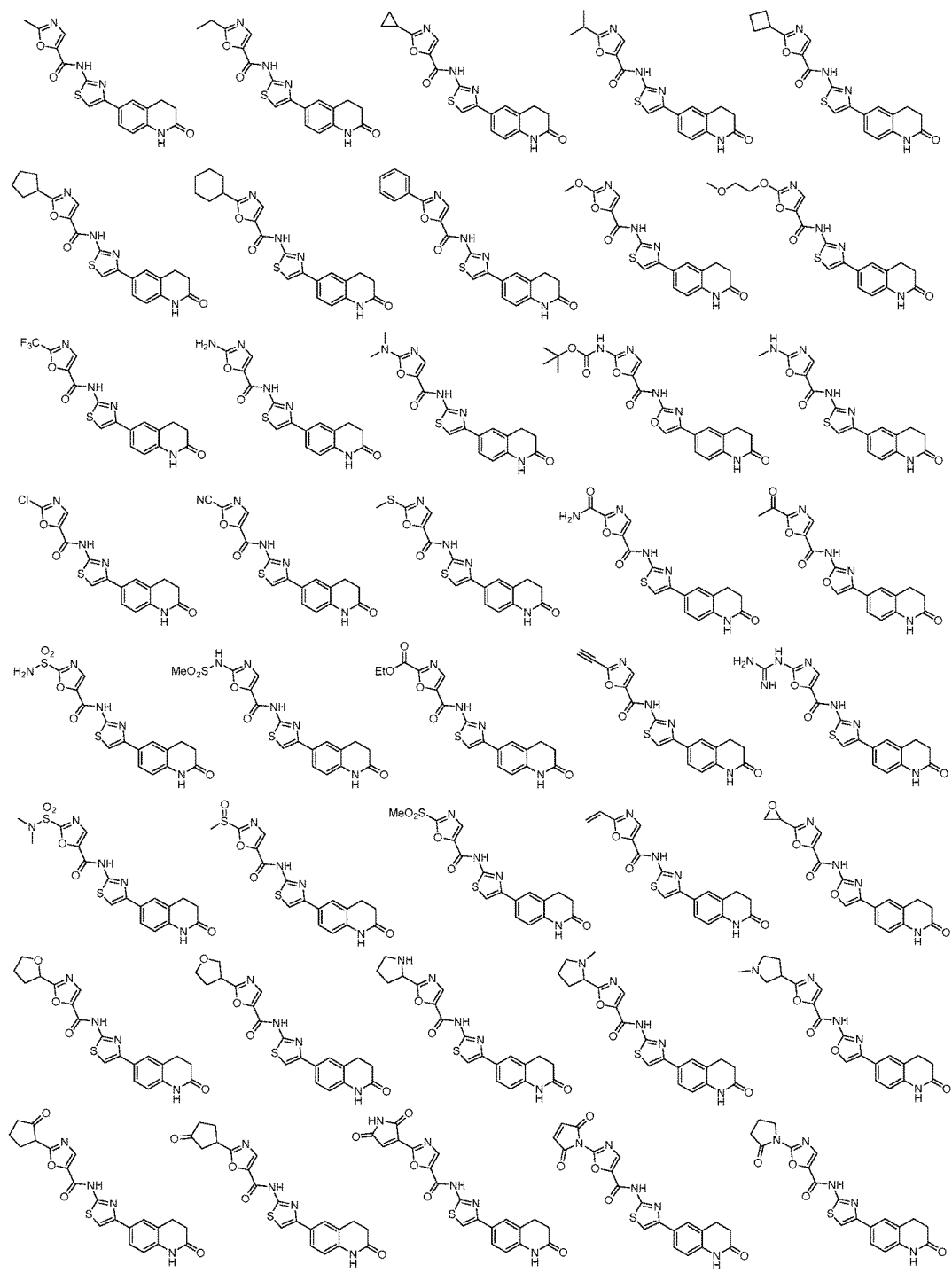
Figure 63:
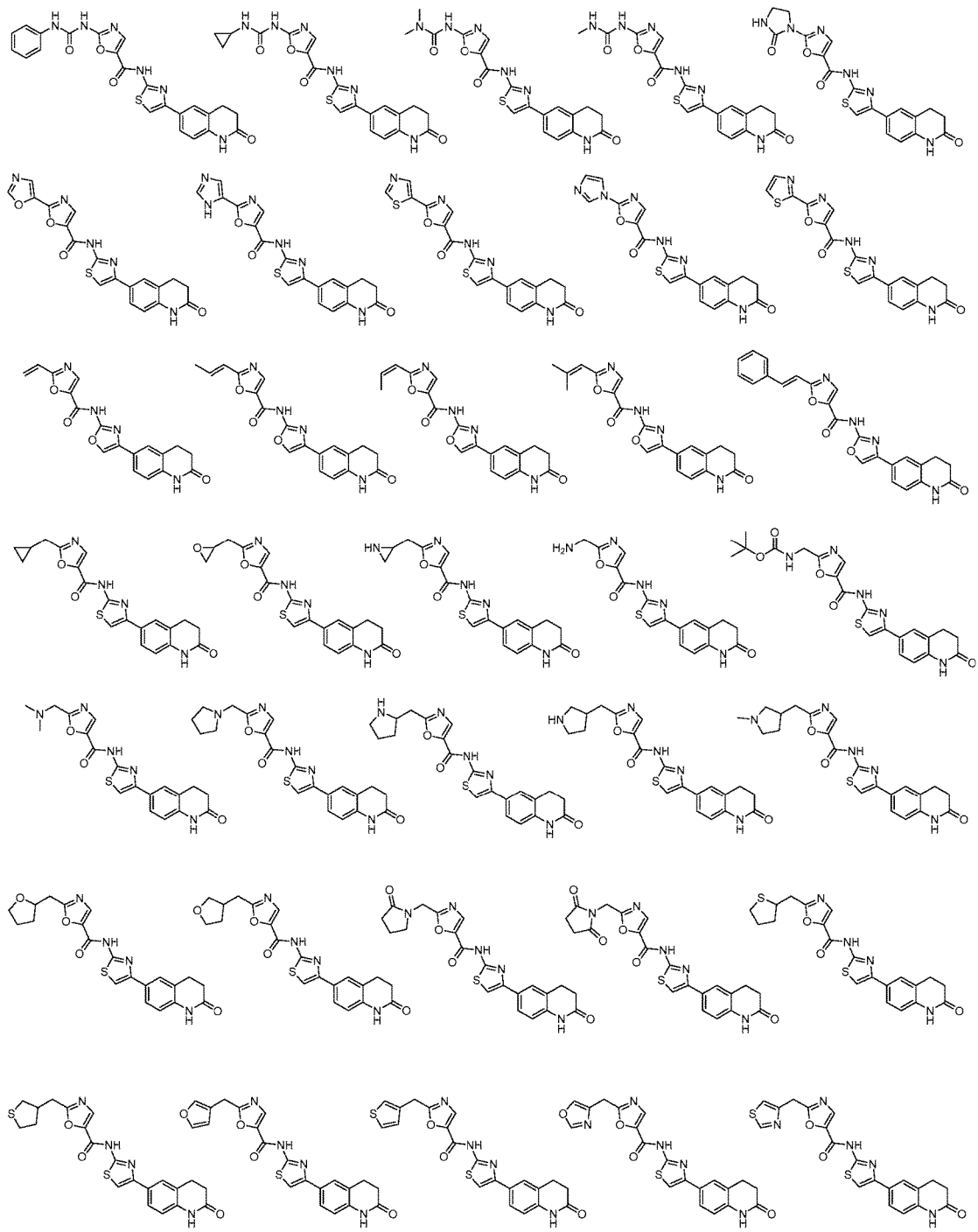
Figure 64:
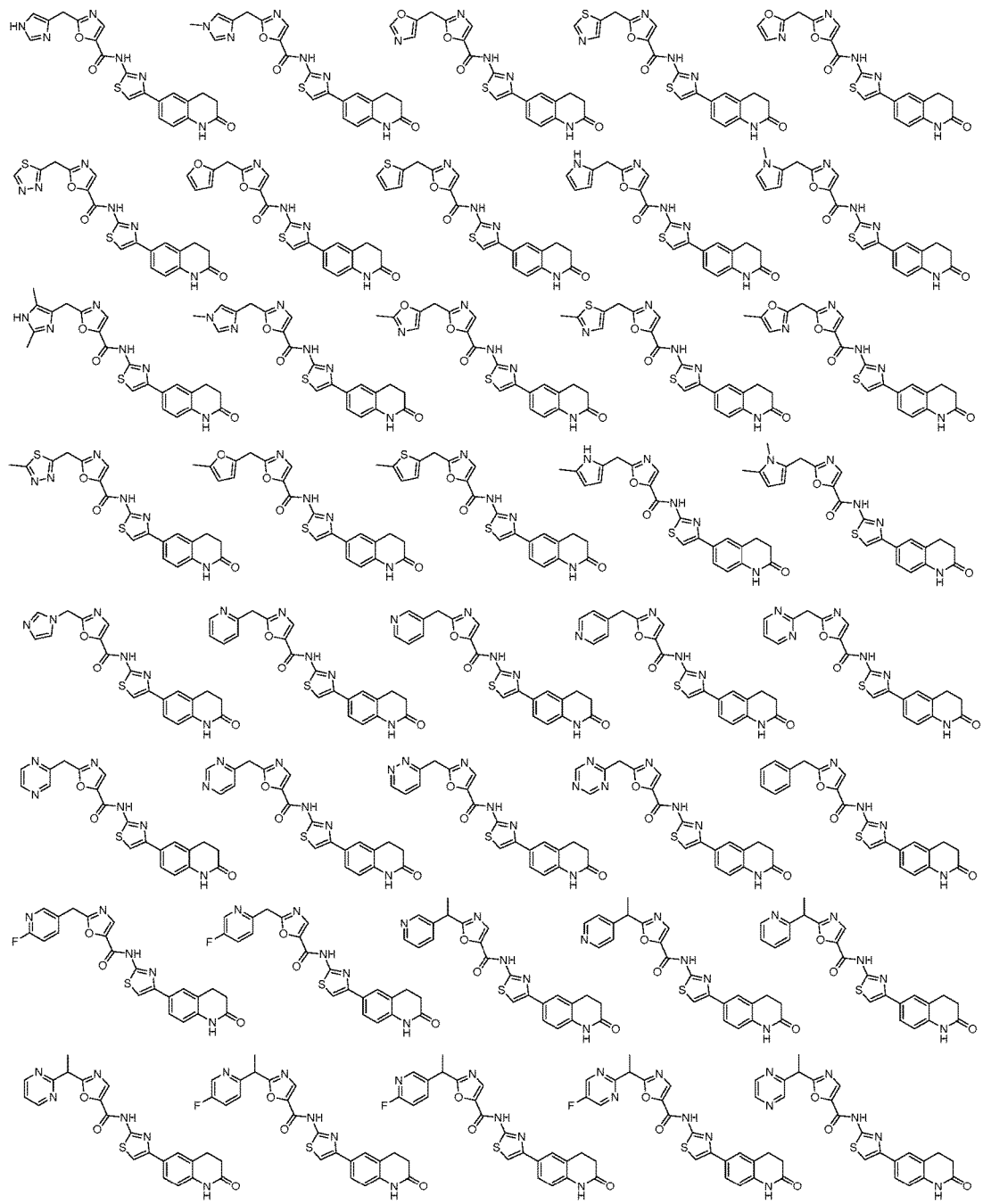
Figure 65:
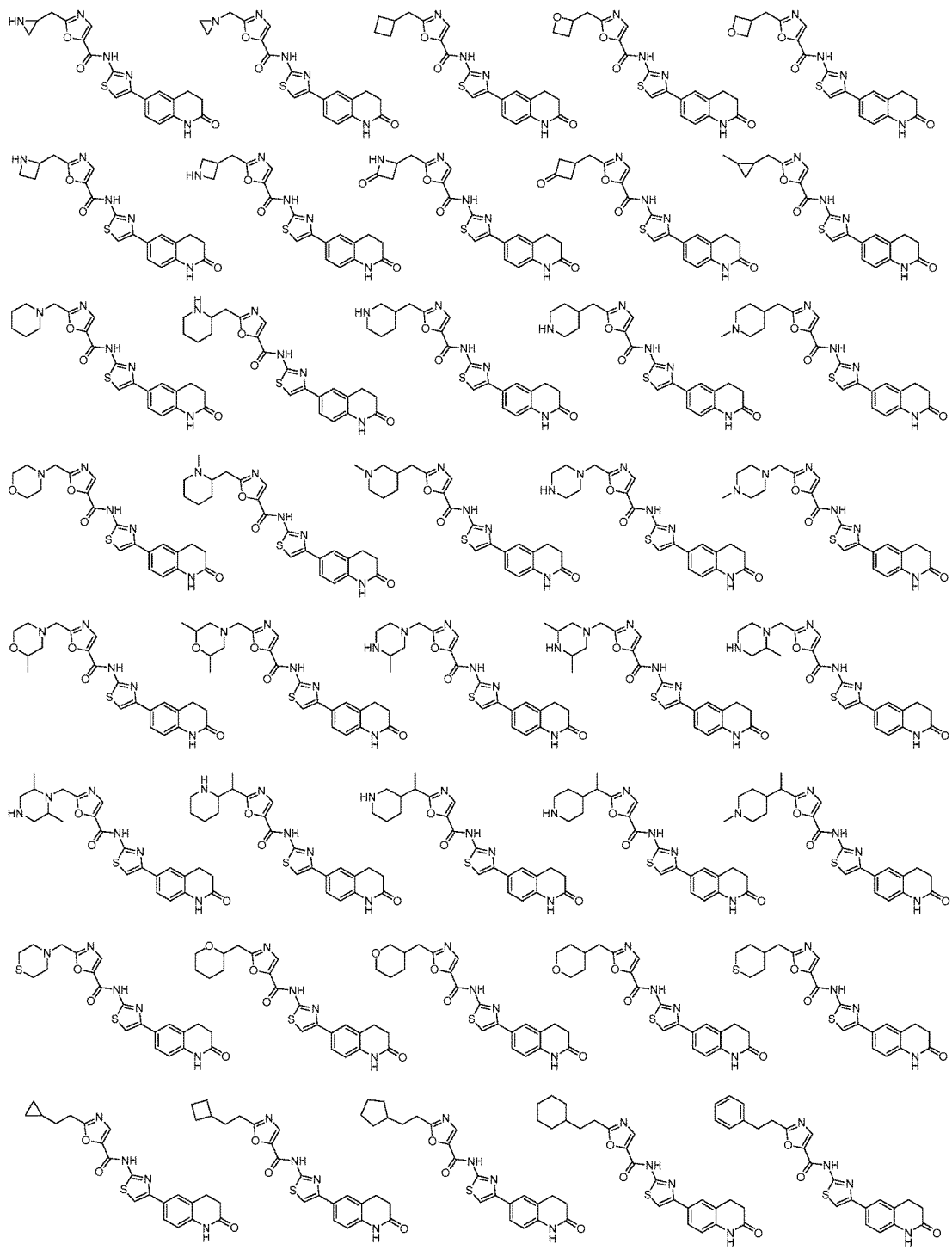
Figure 66:
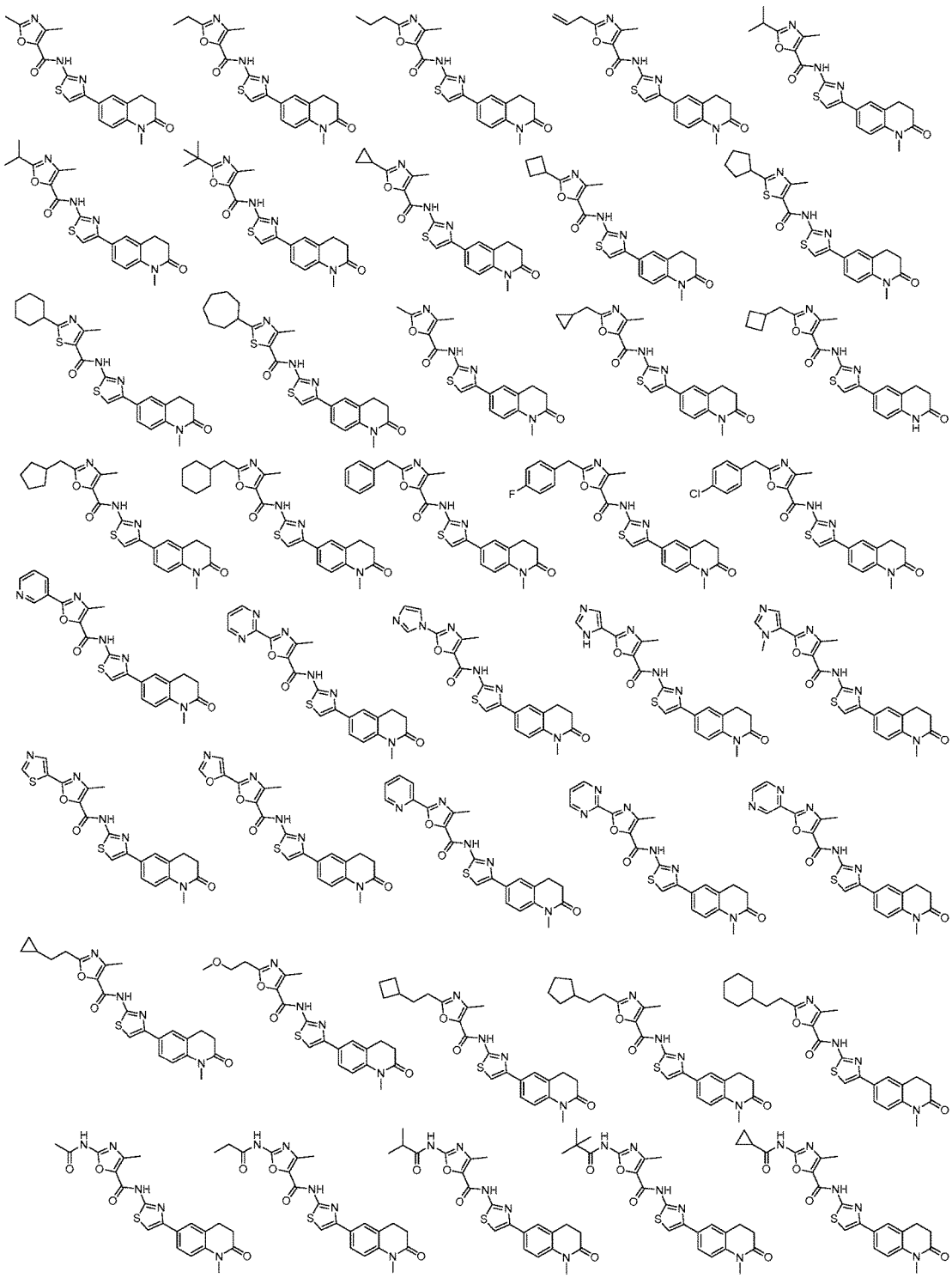
Figure 67:
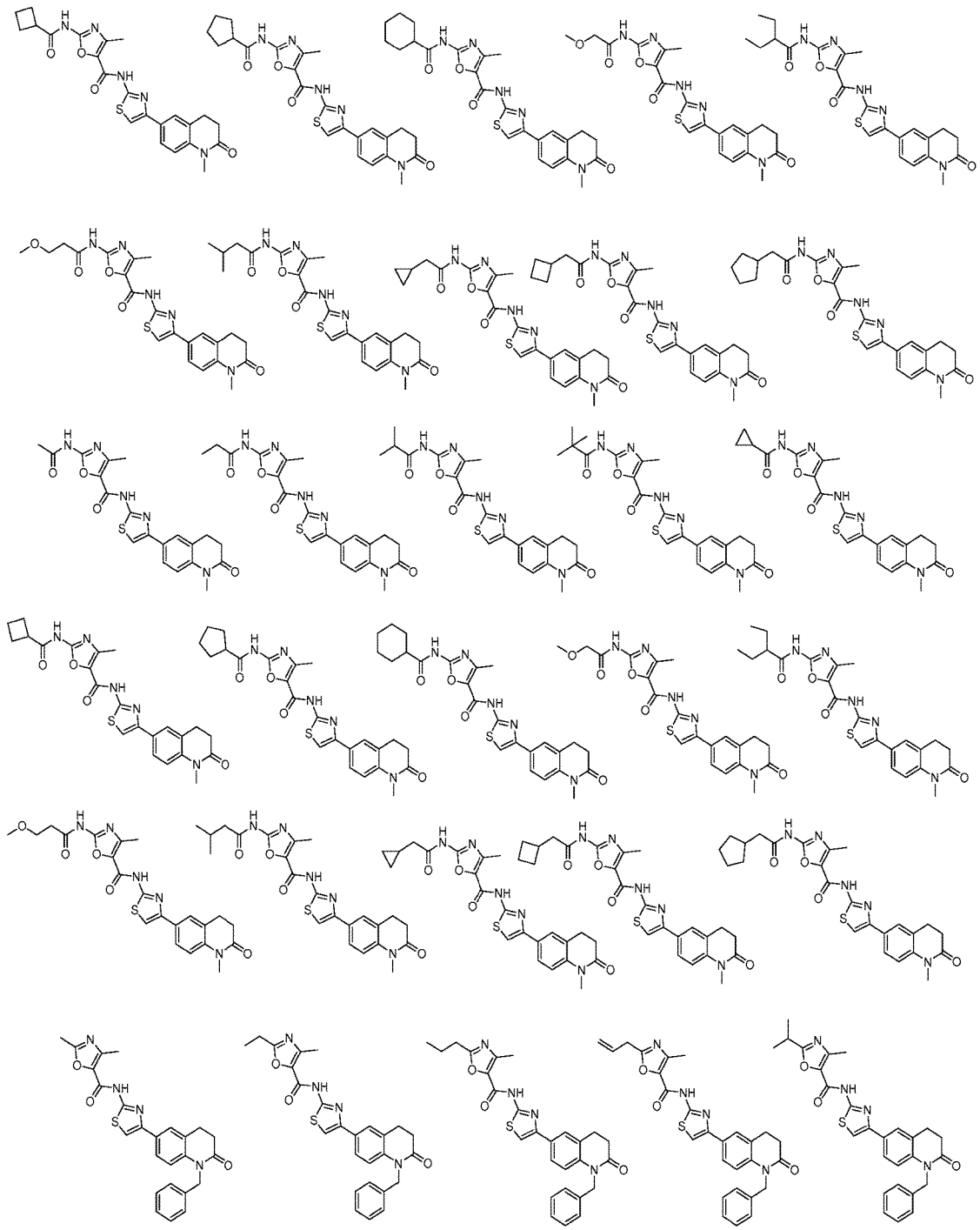
Figure 68:
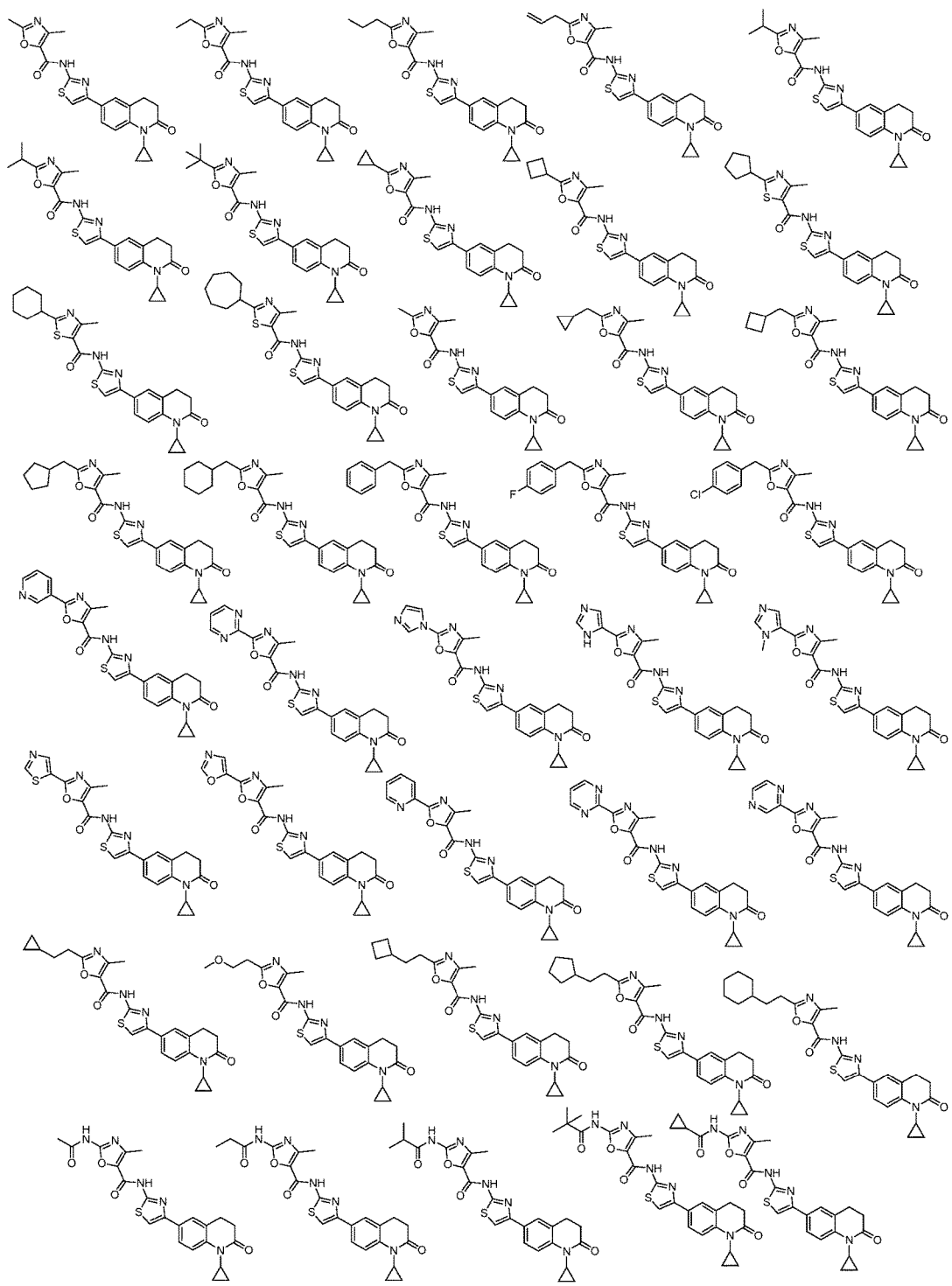
Figure 69:
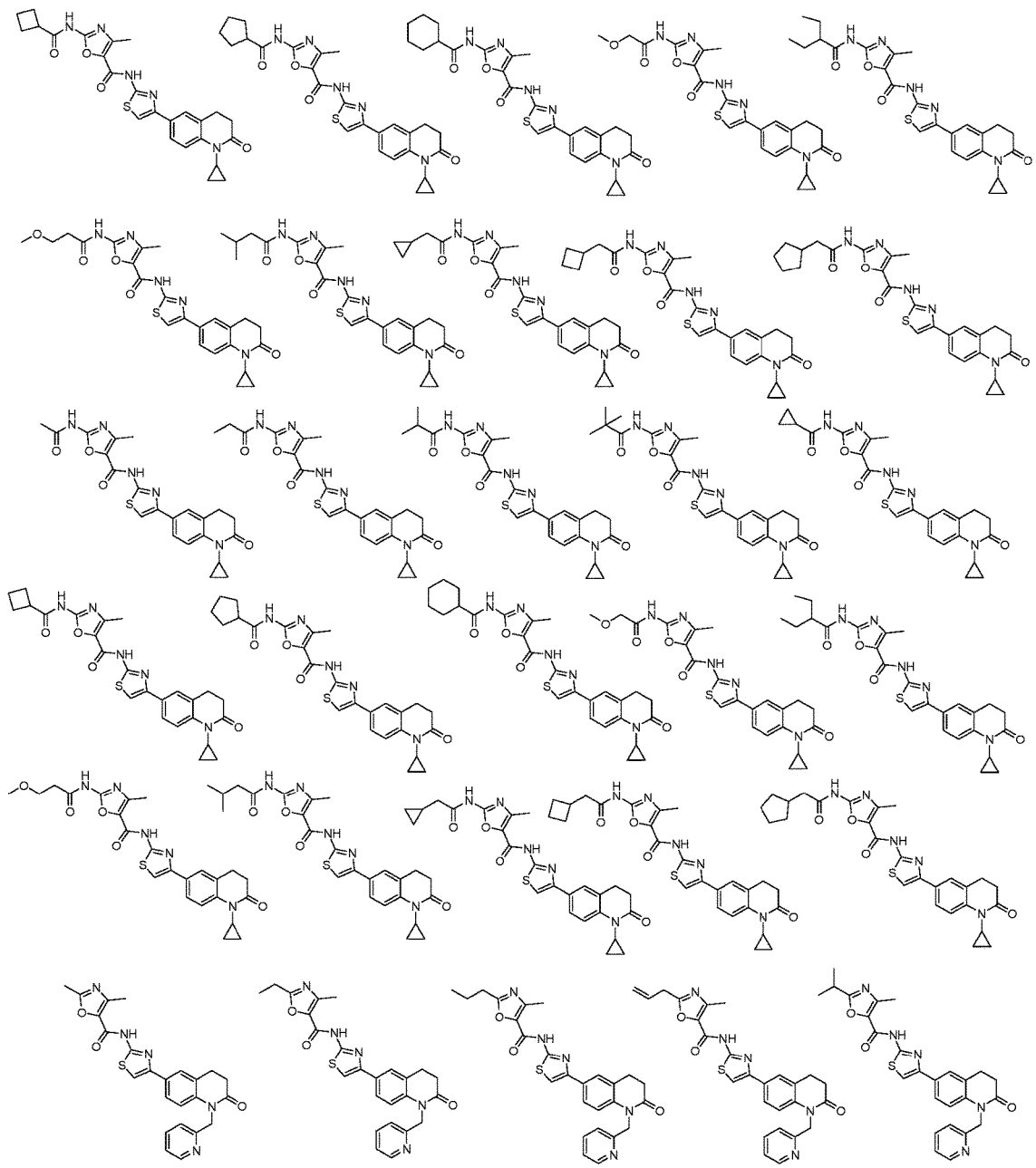
Figure 70:
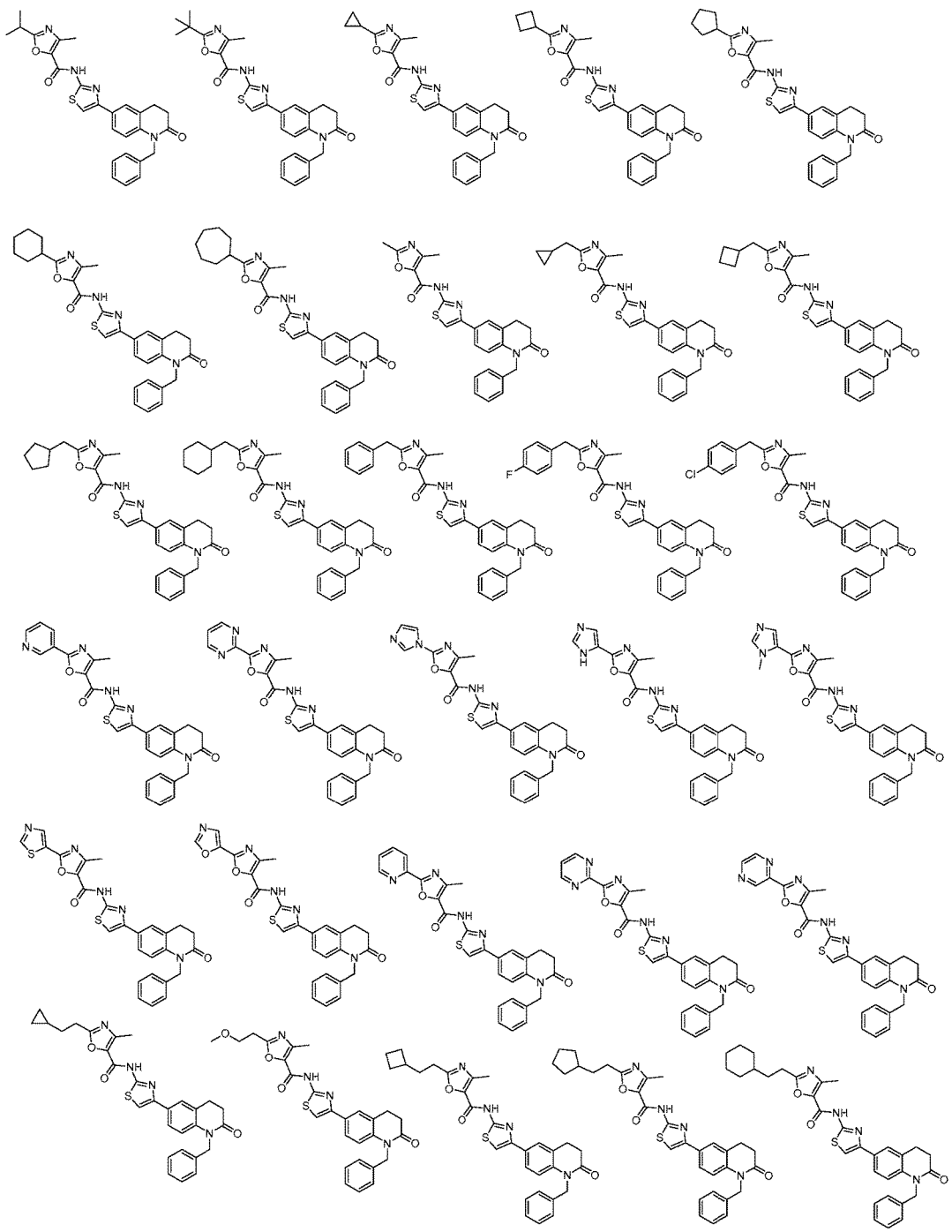
Figure 71:
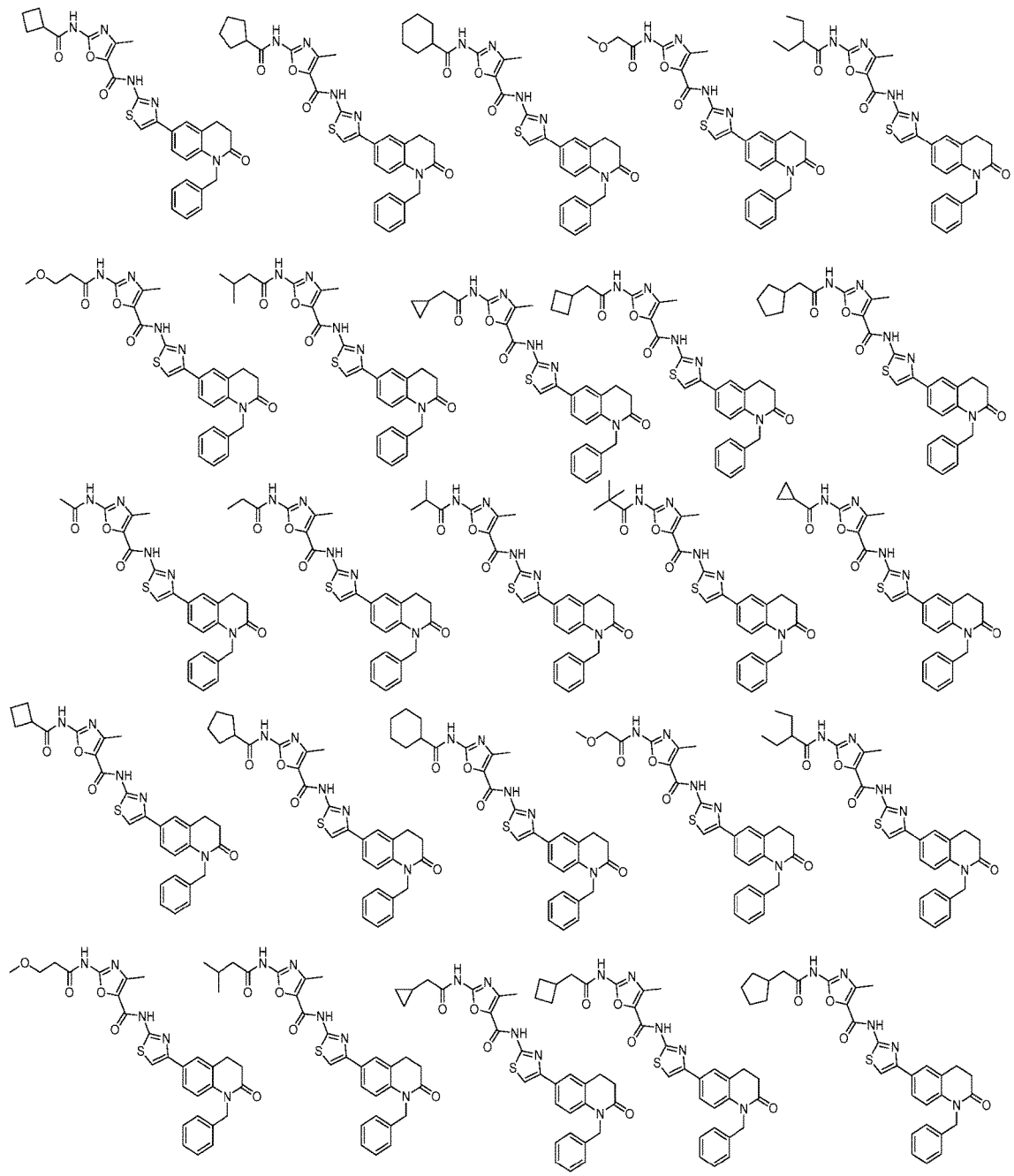
Figure 72:
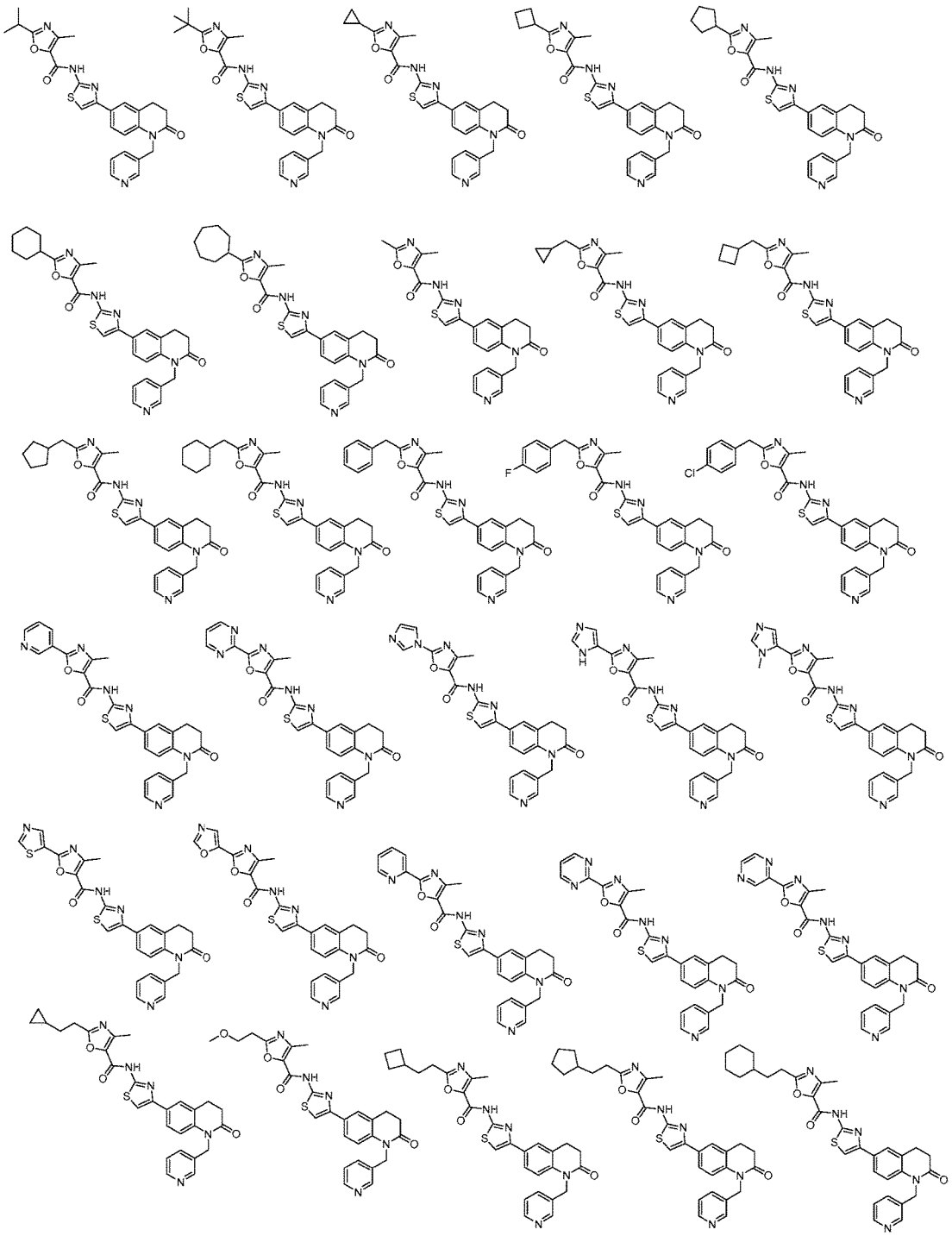
Figure 73:
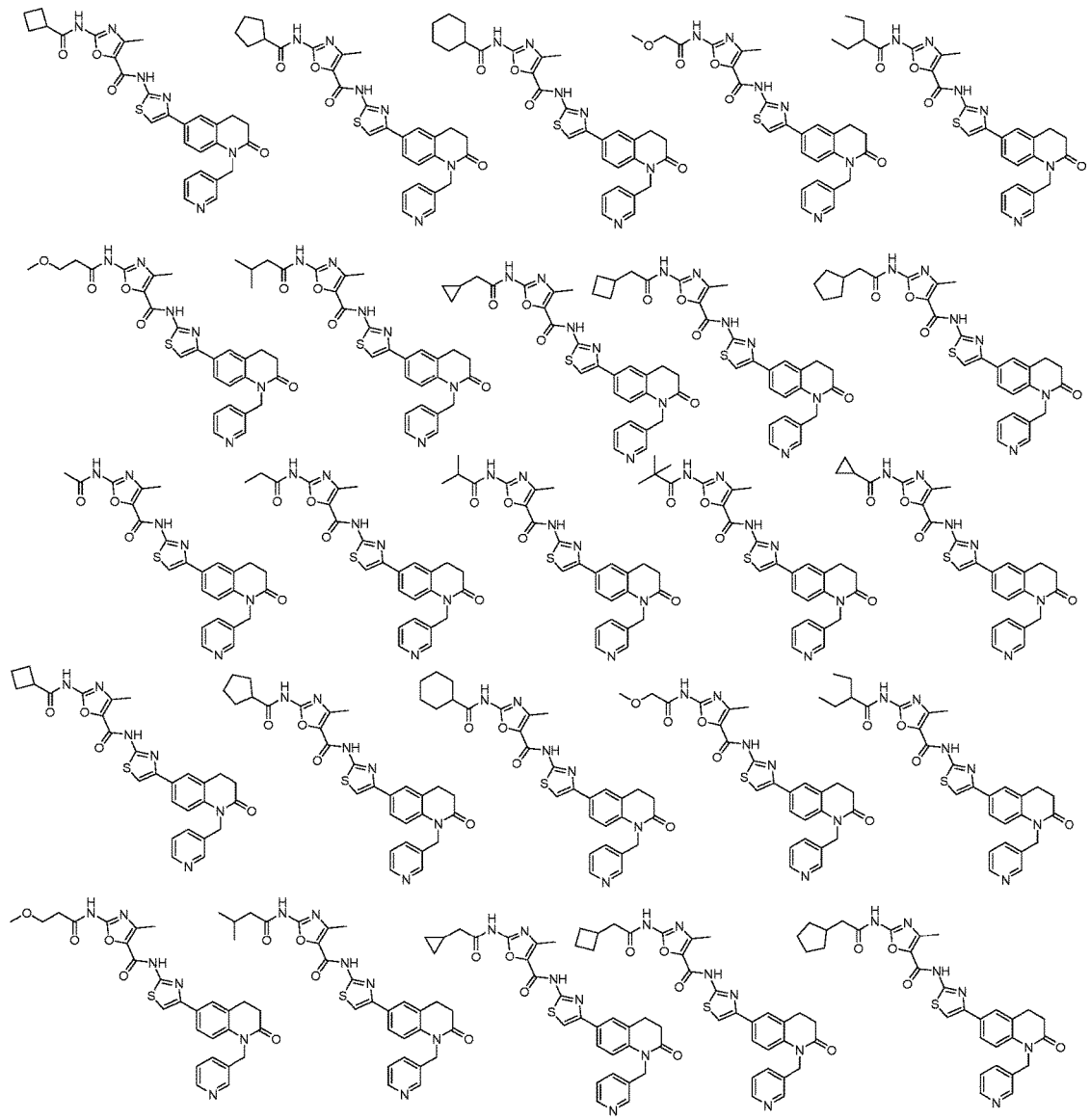

FIGS. 5-73 depict further exemplary compounds according to the inventive subject matter, which can be prepared according to the general synthetic pathways as discussed above.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A compound or a pharmaceutically acceptable salt thereof selected from the group consisting of:
- 2,4-dimethyl-N-(4-(2-oxo-2,3-dihydro-1H-benzo[d]imidazol-5-yl)thiazol-2-yl)thiazole-5-carboxamide, or a pharmaceutically acceptable salt thereof;
- N-(4-(4-benzamidophenyl)thiazol-2-yl)-2,4-dimethylthiazole-5-carboxamide, or a pharmaceutically acceptable salt thereof;
- 2,4-dimethyl-N-(4-(2-oxochroman-6-yl)thiazol-2-yl)thiazole-5-carboxamide, or a pharmaceutically acceptable salt thereof;
- 2-cyclopropyl-N-(4-(2-oxo-1,2,3,4-tetrahydroquinolin-6-yl)thiazol-2-yl)thiazole-5-carboxamide, or a pharmaceutically acceptable salt thereof;
- N-(4-(2-oxo-1,2,3,4-tetrahydroquinolin-6-yl)thiazol-2-yl)-2-phenylthiazole-5-carboxamide, or a pharmaceutically acceptable salt thereof;
- N-(4-(1-acetyl-1,2,3,4-tetrahydroquinolin-6-yl)thiazol-2-yl)-2,4-dimethylthiazole-5-carboxamide, or a pharmaceutically acceptable salt thereof;
- 2,4-dimethyl-N-(4-(1-methyl-2-oxo-1,2,3,4-tetrahydroquinolin-6-yl)thiazol-2-yl)thiazole-5-carboxamide, or a pharmaceutically acceptable salt thereof;
- 4-cyclopropyl-N-(4-(2-oxo-1,2,3,4-tetrahydroquinolin-6-yl)thiazol-2-yl)thiazole-5-carboxamide, or a pharmaceutically acceptable salt thereof;
- N-(4-(2-oxo-1,2,3,4-tetrahydroquinolin-6-yl)thiazol-2-yl)-4-(trifluoromethyl)thiazole-5-carboxamide, or a pharmaceutically acceptable salt thereof;
- 4-ethyl-N-(4-(2-oxo-1,2,3,4-tetrahydroquinolin-6-yl)thiazol-2-yl)thiazole-5-carboxamide, or a pharmaceutically acceptable salt thereof;
- 2,4-dimethyl-N-(4-(2-oxo-1,2,3,4-tetrahydroquinazolin-6-yl)thiazol-2-yl)thiazole-5-carboxamide, or a pharmaceutically acceptable salt thereof;
- N-(4-(2-oxo-1,2,3,4-tetrahydroquinolin-6-yl)thiazol-2-yl)-4-phenylthiazole-5-carboxamide, or a pharmaceutically acceptable salt thereof;
- 2,4-dimethyl-N-(5-methyl-4-(2-oxo-1,2,3,4-tetrahydroquinolin-6-yl)thiazol-2-yl)thiazole-5-carboxamide, or a pharmaceutically acceptable salt thereof;
- N-(5-ethyl-4-(2-oxo-1,2,3,4-tetrahydroquinolin-6-yl)thiazol-2-yl)-2,4-dimethylthiazole-5-carboxamide, or a pharmaceutically acceptable salt thereof;
- 2-(methoxymethyl)-4-methyl-N-(4-(2-oxo-1,2,3,4-tetrahydroquinolin-6-yl)thiazol-2-yl)thiazole-5-carboxamide, or a pharmaceutically acceptable salt thereof;
- 2-cyclopropyl-4-methyl-N-(4-(2-oxo-1,2,3,4-tetrahydroquinolin-6-yl)thiazol-2-yl)thiazole-5-carboxamide, or a pharmaceutically acceptable salt thereof;
- 4-methyl-N-(4-(2-oxo-1,2,3,4-tetrahydroquinolin-6-yl)thiazol-2-yl)-2-phenylthiazole-5-carboxamide, or a pharmaceutically acceptable salt thereof;
- N-(4-(1-benzyl-2-oxo-1,2,3,4-tetrahydroquinolin-6-yl)thiazol-2-yl)-2,4-dimethylthiazole-5-carboxamide, or a pharmaceutically acceptable salt thereof;
- 4-methyl-N-(4-(2-oxo-1,2,3,4-tetrahydroquinolin-6-yl)thiazol-2-yl)-2-(tetrahydrofuran-3-yl)thiazole-5-carboxamide, or a pharmaceutically acceptable salt thereof;
- 4-methyl-N-(4-(2-oxo-1,2,3,4-tetrahydroquinolin-6-yl)thiazol-2-yl)-2-(pyridin-2-ylmethyl)thiazole-5-carboxamide, or a pharmaceutically acceptable salt thereof;
- 2-(1H-imidazol-1-yl)-4-methyl-N-(4-(2-oxo-1,2,3,4-tetrahydroquinolin-6-yl)thiazol-2-yl)thiazole-5-carboxamide, or a pharmaceutically acceptable salt thereof;
- 4-methyl-2-morpholino-N-(4-(2-oxo-1,2,3,4-tetrahydroquinolin-6-yl)thiazol-2-yl)thiazole-5-carboxamide, or a pharmaceutically acceptable salt thereof; and
- 2-(2-methoxyethoxy)-4-methyl-N-(4-(2-oxo-1,2,3,4-tetrahydroquinolin-6-yl)thiazol-2-yl)thiazole-5-carboxamide, or a pharmaceutically acceptable salt thereof.

2. The compound or pharmaceutically acceptable salt of claim 1, wherein the compound is 2-cyclopropyl-4-methyl-N-(4-(2-oxo-1,2,3,4-tetrahydroquinolin-6-yl)thiazol-2-yl)thiazole-5-carboxamide, or a pharmaceutically acceptable salt thereof.

3. The compound or pharmaceutically acceptable salt of claim 1, wherein the compound is 4-methyl-N-(4-(2-oxo-1,2,3,4-tetrahydroquinolin-6-yl)thiazol-2-yl)-2-phenylthiazole-5-carboxamide, or a pharmaceutically acceptable salt thereof.

4. The compound or pharmaceutically acceptable salt of claim 1, wherein the compound is 4-methyl-N-(4-(2-oxo-1,2,3,4-tetrahydroquinolin-6-yl)thiazol-2-yl)-2-(tetrahydrofuran-3-yl)thiazole-5-carboxamide, or a pharmaceutically acceptable salt thereof.

5. A pharmaceutical composition comprising a pharmaceutically acceptable carrier and the compound or pharmaceutically acceptable salt of claim 1.

6. A compound according to Formula IV,

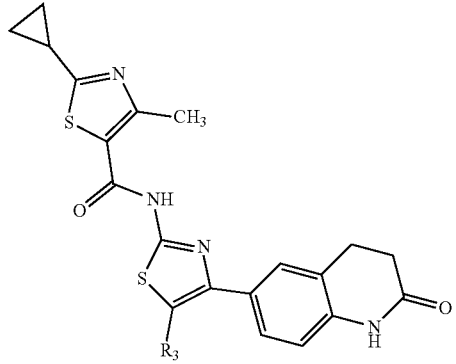

Formula IV wherein R3 is selected from the group consisting of H, methyl, and halogen;
or a pharmaceutically acceptable salt of the compound of Formula IV.

7. A pharmaceutical composition comprising a pharmaceutically acceptable carrier and the compound or pharmaceutically acceptable salt of claim 6.

* * * * *